United States Patent
Avila et al.

(10) Patent No.: US 12,252,504 B2
(45) Date of Patent: Mar. 18, 2025

(54) OLIGOSACCHARIDE-PROTEIN CONJUGATES

(71) Applicant: Genzyme Corporation, Cambridge, MA (US)

(72) Inventors: Luis Z. Avila, Arlington, MA (US); Clark Q. Pan, Sudbury, MA (US); Patrick Finn, Weymouth, MA (US); John Harrahy, Medway, MA (US); Qun Zhou, Ashland, MA (US); Yunxiang Zhu, Wayland, MA (US); Paul A. Konowicz, Maynard, MA (US); Duncan E. Paterson, Zurich (CH); Andreas Peer, Basel (CH); Joseph P. Kutzko, Southborough, MA (US); Michael R. Reardon, North Attleboro, MA (US); James E. Stefano, Hopkinton, MA (US); Xiaoyang Zheng, Newton, MA (US); Robert J. Miller, E. Bridgewater, MA (US); Lauren Young, Hampton, NH (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/671,249

(22) Filed: Feb. 14, 2022

(65) Prior Publication Data

US 2022/0242899 A1 Aug. 4, 2022

Related U.S. Application Data

(60) Continuation of application No. 16/581,148, filed on Sep. 24, 2019, now Pat. No. 11,279,725, which is a division of application No. 15/288,486, filed on Oct. 7, 2016, now Pat. No. 10,464,962, which is a continuation of application No. 14/445,941, filed on Jul. 29, 2014, now Pat. No. 9,493,498, which is a continuation of application No. 13/140,272, filed as application No. PCT/US2009/067775 on Dec. 11, 2009, now Pat. No. 8,835,614.

(60) Provisional application No. 61/122,851, filed on Dec. 16, 2008.

(51) Int. Cl.
C07H 15/04 (2006.01)
A61K 38/46 (2006.01)
A61K 47/61 (2017.01)

(52) U.S. Cl.
CPC ............. *C07H 15/04* (2013.01); *A61K 47/61* (2017.08); *A61K 38/46* (2013.01)

(58) Field of Classification Search
None
See application file for complete search history.

(56) References Cited

U.S. PATENT DOCUMENTS

| | | |
|---|---|---|
| 4,671,958 A | 6/1987 | Rodwell et al. |
| 4,701,521 A | 10/1987 | Ryser et al. |
| 4,749,570 A | 6/1988 | Poznansky |
| 4,867,973 A | 9/1989 | Goers et al. |
| 5,153,312 A | 10/1992 | Porro |
| 5,179,023 A | 1/1993 | Calhoun et al. |
| 5,206,370 A | 4/1993 | Schwartz et al. |
| 5,212,298 A | 5/1993 | Rademacher et al. |
| 5,236,838 A | 8/1993 | Rasmussen et al. |
| 5,280,113 A | 1/1994 | Rademacher et al. |
| 5,306,492 A | 4/1994 | Porro |
| 5,312,903 A | 5/1994 | Lina et al. |
| 5,324,663 A | 6/1994 | Lowe |
| 5,420,285 A | 5/1995 | Schwartz et al. |
| 5,521,290 A | 5/1996 | Sivam et al. |
| 5,549,892 A | 8/1996 | Friedman et al. |
| 5,650,096 A | 7/1997 | Harris et al. |
| 5,658,567 A | 8/1997 | Calhoun et al. |
| 5,670,488 A | 9/1997 | Gregory et al. |
| 5,691,154 A | 11/1997 | Callstrom et al. |
| 5,719,131 A | 2/1998 | Harris et al. |
| 5,747,471 A | 5/1998 | Siegel et al. |
| 5,753,520 A | 5/1998 | Schwartz et al. |
| 5,767,099 A | 6/1998 | Harris et al. |
| 5,783,565 A | 7/1998 | Lee et al. |
| 5,834,266 A | 11/1998 | Crabtree et al. |
| 5,840,702 A | 11/1998 | Bedwell |
| 5,840,710 A | 11/1998 | Lee et al. |
| 5,846,728 A | 12/1998 | Haralambidis et al. |
| 5,851,991 A | 12/1998 | Lee et al. |
| 5,863,990 A | 1/1999 | Papisov |

(Continued)

FOREIGN PATENT DOCUMENTS

EP 0384769 A2 8/1990
EP 1197222 A2 * 4/2002 ............. A61K 38/27

(Continued)

OTHER PUBLICATIONS

JP 2007224052A ,machine translation, published Sep. 6, 2007. (Year: 2007).*

(Continued)

*Primary Examiner* — Layla D Berry
(74) *Attorney, Agent, or Firm* — MORRISON & FOERSTER LLP

(57) ABSTRACT

Provided herein are conjugates comprising a protein and an oligosaccharide of one of Formulae I-VI. Also provided herein are pharmaceutical compositions comprising such conjugates. Further provided herein are methods of treating a lysosomal storage disorder in a mammal by administration of an oligosaccharide-glycoprotein conjugate.

5 Claims, 35 Drawing Sheets

(56) References Cited

U.S. PATENT DOCUMENTS

| | | |
|---|---|---|
| 5,910,487 A | 6/1999 | Yew et al. |
| 5,912,239 A | 6/1999 | Siegel et al. |
| 5,916,911 A | 6/1999 | Shayman et al. |
| 5,925,628 A | 7/1999 | Lee et al. |
| 5,935,936 A | 8/1999 | Fasbender et al. |
| 5,939,401 A | 8/1999 | Marshall et al. |
| 5,942,634 A | 8/1999 | Siegel et al. |
| 5,945,442 A | 8/1999 | Shayman et al. |
| 5,948,767 A | 9/1999 | Scheule et al. |
| 5,948,925 A | 9/1999 | Keynes et al. |
| 5,952,370 A | 9/1999 | Shayman et al. |
| 5,968,502 A | 10/1999 | Treco et al. |
| 6,022,874 A | 2/2000 | Wheeler |
| 6,030,995 A | 2/2000 | Shayman et al. |
| 6,040,332 A | 3/2000 | Shayman et al. |
| 6,051,598 A | 4/2000 | Shayman et al. |
| 6,066,626 A | 5/2000 | Yew et al. |
| 6,071,890 A | 6/2000 | Scheule et al. |
| 6,118,045 A | 9/2000 | Reuser et al. |
| 6,156,547 A | 12/2000 | Roth |
| 6,251,858 B1 | 6/2001 | Monsigny et al. |
| 6,287,857 B1 | 9/2001 | O'Riordan et al. |
| 6,399,575 B1 | 6/2002 | Smith et al. |
| 6,461,609 B1 | 10/2002 | Calhoun et al. |
| 6,465,488 B1 | 10/2002 | Butter et al. |
| 6,472,506 B1 | 10/2002 | Moreau et al. |
| 6,492,332 B1 | 12/2002 | Demopulos et al. |
| 6,495,570 B2 | 12/2002 | Jacob et al. |
| 6,534,300 B1 | 3/2003 | Canfield |
| 6,537,785 B1 | 3/2003 | Canfield |
| 6,541,669 B1 | 4/2003 | Moran et al. |
| 6,562,316 B1 | 5/2003 | Edwards et al. |
| 6,569,451 B1 | 5/2003 | Li et al. |
| 6,573,337 B1 | 6/2003 | Toth et al. |
| 6,610,703 B1 | 8/2003 | Jacob et al. |
| 6,642,038 B1 | 11/2003 | Canfield |
| 6,660,749 B2 | 12/2003 | Butters et al. |
| 6,670,165 B2 | 12/2003 | Canfield |
| 6,676,963 B1 | 1/2004 | Lanza et al. |
| 6,696,059 B2 | 2/2004 | Jacob et al. |
| 6,703,488 B1 | 3/2004 | Burton et al. |
| 6,723,843 B2 | 4/2004 | Toth et al. |
| 6,749,865 B2 | 6/2004 | Calias et al. |
| 6,770,468 B1 | 8/2004 | Canfield |
| 6,800,273 B2 | 10/2004 | Rajopadhye et al. |
| 6,800,472 B2 | 10/2004 | Canfield et al. |
| 6,828,135 B2 | 12/2004 | Canfield |
| 6,861,242 B2 | 3/2005 | Canfield |
| 6,905,856 B2 | 6/2005 | Canfield et al. |
| 7,001,994 B2 | 2/2006 | Zhu |
| 7,011,831 B2 | 3/2006 | Calhoun et al. |
| 7,019,131 B2 | 3/2006 | Wong et al. |
| 7,067,127 B2 | 6/2006 | Canfield |
| 7,141,676 B1 | 11/2006 | Wilbur et al. |
| 7,160,517 B2 | 1/2007 | Seeberger et al. |
| 7,176,185 B2 | 2/2007 | Hilfinger et al. |
| 7,232,805 B2 | 6/2007 | Weinshenker et al. |
| 7,312,324 B2 | 12/2007 | Souza et al. |
| 7,341,720 B2 | 3/2008 | Stefano |
| 7,723,296 B2 | 5/2010 | Zhu |
| 7,786,277 B2 | 8/2010 | Zhu |
| 7,910,545 B2 | 3/2011 | Meeker et al. |
| 8,124,073 B2 | 2/2012 | Stefano |
| 8,168,587 B2 | 5/2012 | Meeker et al. |
| 8,835,614 B2 | 9/2014 | Avila et al. |
| 9,493,498 B2 | 11/2016 | Avila et al. |
| 10,363,291 B2 | 7/2019 | Zhu |
| 10,792,342 B2 | 10/2020 | Zhu |
| 10,907,142 B2 | 2/2021 | Zhu |
| 10,973,887 B2 | 4/2021 | Zhu |
| 11,279,725 B2 | 3/2022 | Roberts et al. |
| 2001/0031741 A1 | 10/2001 | Ziegler et al. |
| 2001/0044453 A1 | 11/2001 | Jacob et al. |
| 2002/0025550 A1 | 2/2002 | Canfield |
| 2002/0095135 A1 | 7/2002 | Meeker et al. |
| 2002/0127213 A1 | 9/2002 | Jacob et al. |
| 2002/0137125 A1 | 9/2002 | Zhu |
| 2002/0142985 A1 | 10/2002 | Dwek et al. |
| 2003/0017139 A1 | 1/2003 | Souza et al. |
| 2003/0050299 A1 | 3/2003 | Hirth et al. |
| 2003/0082176 A1 | 5/2003 | Lebowitz et al. |
| 2003/0087868 A1 | 5/2003 | Yew et al. |
| 2003/0119088 A1 | 6/2003 | Canfield et al. |
| 2003/0153768 A1 | 8/2003 | Hirth |
| 2004/0006008 A1 | 1/2004 | Lebowitz et al. |
| 2004/0014652 A1 | 1/2004 | Trouet et al. |
| 2004/0132640 A1 | 7/2004 | Defrees et al. |
| 2004/0204379 A1 | 10/2004 | Cheng et al. |
| 2005/0003486 A1 | 1/2005 | Canfield et al. |
| 2005/0026823 A1 | 2/2005 | Zankel et al. |
| 2005/0048047 A1 | 3/2005 | Kakkis |
| 2005/0058634 A1 | 3/2005 | Zhu |
| 2005/0075305 A1 | 4/2005 | Dwek et al. |
| 2005/0169941 A1 | 8/2005 | Lees |
| 2005/0169968 A1 | 8/2005 | Elmaleh et al. |
| 2005/0222244 A1 | 10/2005 | Siegel et al. |
| 2005/0267094 A1 | 12/2005 | Shayman et al. |
| 2005/0281805 A1 | 12/2005 | Lebowitz et al. |
| 2006/0051317 A1 | 3/2006 | Batrakova et al. |
| 2006/0074107 A1 | 4/2006 | Butters et al. |
| 2006/0281145 A1 | 12/2006 | Zhu |
| 2007/0178081 A1 | 8/2007 | Fan |
| 2008/0226658 A1 | 9/2008 | Stefano |
| 2010/0047225 A1 | 2/2010 | Zhu et al. |
| 2010/0173385 A1 | 7/2010 | Zhu |
| 2011/0142818 A1 | 6/2011 | Meeker et al. |
| 2012/0141507 A1 | 6/2012 | Stefano |
| 2012/0183502 A1 | 7/2012 | Meeker et al. |
| 2017/0014520 A1 | 1/2017 | Zhu et al. |
| 2017/0042979 A1 | 2/2017 | Stefano et al. |
| 2018/0002365 A1 | 1/2018 | Avila et al. |
| 2018/0085436 A1 | 3/2018 | Zhu et al. |
| 2019/0054154 A1 | 2/2019 | Stefano |
| 2020/0010825 A1 | 1/2020 | Zhu et al. |
| 2020/0147184 A1 | 5/2020 | Zhu et al. |
| 2022/0204963 A1 | 6/2022 | Zhu et al. |

FOREIGN PATENT DOCUMENTS

| | | |
|---|---|---|
| EP | 1171128 B1 | 6/2003 |
| EP | 2889043 A2 | 7/2015 |
| JP | S59-36691 A | 2/1984 |
| JP | 2005535280 A | 11/2005 |
| JP | 2010/516257 A | 5/2010 |
| JP | 2012512313 A | 5/2012 |
| JP | 2019112444 A | 7/2019 |
| WO | WO-92/16555 A1 | 10/1992 |
| WO | WO-97/09441 A2 | 3/1997 |
| WO | WO-97/34623 A1 | 9/1997 |
| WO | WO-98/11206 A2 | 3/1998 |
| WO | WO-99/41399 A1 | 8/1999 |
| WO | WO-99/41400 A1 | 8/1999 |
| WO | WO-99/57296 A1 | 11/1999 |
| WO | WO-00/62779 A1 | 10/2000 |
| WO | WO-00/62780 A1 | 10/2000 |
| WO | WO-01/60412 A2 | 8/2001 |
| WO | WO-01/90139 A2 | 11/2001 |
| WO | WO-02/07671 A2 | 1/2002 |
| WO | WO-02/057445 A1 | 7/2002 |
| WO | WO-03/031464 A2 | 4/2003 |
| WO | 2003046150 A2 | 6/2003 |
| WO | WO-03/057179 A2 | 7/2003 |
| WO | WO-2005/002515 A2 | 1/2005 |
| WO | WO-2005/014035 A2 | 2/2005 |
| WO | WO-2005/016973 A1 | 2/2005 |
| WO | WO-2005/034909 A2 | 4/2005 |
| WO | WO-2005/077093 A2 | 8/2005 |
| WO | WO-2005/094874 A1 | 10/2005 |
| WO | 2007084737 A2 | 7/2007 |
| WO | WO-2008/029281 A2 | 3/2008 |
| WO | WO-2008/089339 A2 | 7/2008 |
| WO | WO-2008/089339 A3 | 7/2008 |
| WO | WO-2008/089403 A2 | 7/2008 |

(56) References Cited

FOREIGN PATENT DOCUMENTS

| WO | WO-2008/089403 A3 | 7/2008 |
|---|---|---|
| WO | WO-2010/075010 A2 | 7/2010 |
| WO | WO-2010/075010 A3 | 7/2010 |

OTHER PUBLICATIONS

A Guide to IUPAC Nomenclature of Organic Compounds (Recommendations 1993). "Specific Classes of Compounds R-5,6,6 Nitrogenous derivatives of carbonyl compounds" Blackwell scientific publications, (online), (retrieved on Nov. 16, 2009). Retrieved from the internet <URL http://www.acdlabs.com/iupac/nomenclature> (6 pages).
Abe et al. (Feb. 2000). "Glycosphingolipid depletion in fabry disease lymphoblasts with potent inhibitors of glucosylceramide synthase," Kidney Intl. 57:446-454.
Abe et al. (Jun. 1, 2000). "Reduction of globotriaosylceramide in Fabry disease mice by substrate deprivation," J. Clin. Invest. 105(11):1563-1571.
Abraham et al. (1993). "Heparin-binding EGF-like growth factor: characterization of rat and mouse cDNA clones, protein domain conservation across species, and transcript expression in tissues," Biochem. Biophys. Res. Commun. 190(1):125-133.
Advanced Drug Delivery Reviews. Table of Contents, vol. 53, Iss. 2 (Dec. 17, 2001).
Advanced Drug Delivery Reviews. Table of Contents, vol. 54, Iss. 4 (Jun. 17, 2002).
Advanced Drug Delivery Reviews. Table of Contents, vol. 55, Iss. 2 (Feb. 10, 2003).
Advanced Drug Delivery Reviews. Table of Contents, vol. 56, Iss. 4 (Mar. 3, 2004).
Advanced Drug Delivery Reviews. Table of Contents, vol. 57, Iss. 4 (Feb. 28, 2005).
Amalfitano et al. (Aug. 1999). "Systemic correction of the muscle disorder glycogen storage disease type II after hepatic targeting of a modified adenovirus vector encoding human acid-alpha-glucosidase," PNAS 96:8861-8866.
Andersson et al. (2000). "N-butyldeoxygalactonojirimycin: a more selective inhibitor of glycosphingolipid biosynthesis than N-butyldeoxynojirimycin, in vitro and in vivo," Biochem. Pharmacol. 59:821-829.
Arakatsu et al. (1966). "Immunochemical studies on dextrans. V. Specificity and cross-reactivity with dextrans of the antibodies formed in rabbits to isomaltonic and isomaltotrionic acids coupled to bovine serum albumin," J. Immunol. 97(6):858-866.
Ashwell et al. (1982). "Carbohydrate-specific receptors of the liver," Ann. Rev. Biochem. 51:531-534.
Ashwell et al. (1972). "Carbohydrate Antigens: coupling of carbohydrates to proteins by a mixed anhydride reaction," Meth. in Enzymology, vol. XXVII, Complete Carbohydrates, Part B, pp. 219-222.
Avigad et al. (1962). "The D-galactose oxidase of Polyporus circinatus," J. Biol. Chem. 237:2736-2743.
Baba et al. (1988). "Preparation and application of a pentamannosyl monophosphate-bovine serum albumin conjugate," Carbohydr. Res. 177:163-172.
Balaji et al. (Aug. 1994). "Molecular dynamics simulations of high-mannose oligosaccharides," Glycobiology 4(4):497-515.
Barbon et al. (Sep. 2005). "AAV8-mediated hepatic expression of acid sphingomyelinase corrects the metabolic defect in the visceral organs of a mouse model of Niemann-Pick disease," Mol. Ther. 12(3):431-440.
Barton et al. (1991). "Replacement therapy for inherited enzyme deficiency—macrophage-targeted glucocerebrosidase for Gaucher's disease," N. Engl. J. Med. 324:1464-1470.
Bayer et al. (1987). "Enzyme-based detection of glycoproteins on blot transfers using avidin-biotin technology," Anal. Biochem. 161:123-131.

Bayer et al. (1988). "Biocytin hydrazide—a selective label for sialic acids, galactose, and other sugars in glycoconjugates using avidin-biotin technology," Anal. Biochem. 170:271-281.
Beesley et al. (2001). "Mutational analysis of 85 mucopolysaccharidosis type I families: frequency of known mutations, identification of 17 novel mutations and in vitro expression of missense mutations," Hum. Genet. 109:503-511.
Berge et al. (1977). "Pharmaceutical salts," J. Pharm. Sci. 66:1-19.
Bernstein et al. (1980). "A general synthesis of model glycoproteins: coupling of alkenyl glycosides to proteins, using reductive ozonolysis followed by reductive amination with sodium cyanoborohydride," Carb. Res. 78:C1-C3.
Beutler et al. (1996). "Gaucher disease: four families with previously undescribed mutations," Proc. Assoc. Am. Physicians 108:179-184.
Bielicki et al. (1999). "Advantages of using same species enzyme for replacement therapy in a feline model of mucopolysaccharidosis type VI," J. Biol. Chem. 274(51):36335-36343.
Bijvoet et al. (1998). "Generalized glycogen storage and cardiomegaly in a knockout mouse model of Pompe disease," Hum. Mol. Genet. 7(1):53-62.
Bijvoet et al. (1999). "Human acid α-glucosidase from rabbit milk has therapeutic effect in mice with glycogen storage disease type II," Hum. Mol. Genet. 8(12):2145-2153.
Bodamer et al. (1997). "Dietary treatment in late-onset acid maltase deficiency," Eur. J. Pediatr. 156(Suppl. 1):S39-S42.
Bond et al. (1997). "Structure of a human lysosomal sulfatase," Structure 15:277-289.
Bongiorno et al. (2003). "Fabry disease: enzyme replacement therapy," J. Eur. Acad. Dermatol. Venereol. 17:676-679.
Bou-Gharios et al. (1993). "Lysosomal storage diseases: mechanisms of enzyme replacement therapy," Histochem. 25(9):593-605.
Bowie et al. (1990). "Deciphering the message in protein sequences: tolerance to amino acid substitutions," Science 247:1306-1310.
Brady et al. (2001). "Enzyme replacement therapy in Fabry disease," J. Inherit. Metab. Dis. 24(Suppl. 2):18-24.
Branco et al. (1999). "Selective deletion of antigen-specific, activated T cells by a humanized MAB to CD2 (MEDI-507) is mediated by NK cells," Transpl. 68(10):1588-1596.
Branden et al. (1999). Introduction to Protein Structure, 2nd edition, Garland Publishing, Inc., New York: 1999; pp. 358-366.
Braslawsky et al. (1991). "Adriamycin(hydrazone)-antibody conjugates require internalization and intracellular acid hydrolysis for antitumor activity," Cancer Immunol. Immunother. 33(6):367-374.
Bretthauer et al. (1973). "Characterization of a phosphorylated pentasaccharide isolated from Hansenula holstii NRRL Y-2448 phosphomannan," Biochem. 12(7):1251-1256.
Brooks et al. (2001). "Glycosidase active site mutations in human alpha-L-iduronidase," Glycobiol. 11(9):741-750.
Brooks et al. (1999). "Immune response to enzyme replacement therapy in lysosomal storage disorder patients and animal models," Mol. Genet. Metabol. 68:268-275.
Brooks et al. (1991). "A specific fluorogenic assay for N-acetylgalactosamine-4-sulphatase activity using immunoads," J. Inher. Metab. Dis. 14:5-12.
Buechner et al. (2008). "Central nervous system involvement in Anderson-Fabry disease: a clinical and MRI retrospective study," J. Neurol. Neurosurg. Psychiatry 79(11):1249-1254.
Byers et al. (1997). "Effect of enzyme replacement therapy on bone formation in a feline model of mucopolysaccharidosis type VI," Bone 21(5):425-431.
Caliceti et al. (2003). "Pharmacokinetic and biodistribution properties of poly(ethylene glycol)-protein conjugates," Adv. Drug Deliv. Rev. 55(10):1261-1277.
Casares et al. (2001). "Antigen-specific downregulation of T cells by doxorubicin delivered through a recombinant MHC II-peptide chimera," Nat. Biotechnol. 19:142-147.
Cavallaro et al. (2004). "Glycosylated macromolecular conjugates of antiviral drugs with a polyaspartamide," J. Drug. Targeting 12(9-10):593-605.
Chaudhari et al. (1972). "Coupling of amino acids and amino sugars with cyanuric chloride (2,4,6-trichloro-s-triazine)," Can. J. Chem. 50(13):1987-1991.

(56) References Cited

OTHER PUBLICATIONS

Chen et al. (2000). "Purification and characterization of human α-galactosidase a expressed in insect cells using a baculovirus vector," Protein Expr. Purif. 20:228-236.

Chen et al. (2000). "Towards a molecular therapy for glycogen storage disease type II (Pompe disease)," Mol. Med. Today 6(6):245-251.

Chen (1998). "Glycogen storage diseases," in Harrison's principles of internal medicine, Fauci et al. (eds.); McGraw-Hill, 14 edition, pp. 2176-2182.

Christensen, M.K. et al. (1994). "Synthesis of Glycosylated Peptide Templates Containing 6'-O-Phosphorylated Mannose Disaccharides and Their Binding to the Cation-Independent Mannose 6-Phosphate Receptor," Journal of the Chemical Society Perkin Transactions 1(10):1299-1310.

Civallero et al. (2006). "Twelve different enzyme assays on dried-blood filter paper samples for detection of patients with selected inherited lysosomal storage diseases," Clin. Chim. Acta 372:98-102.

Cleary et al. (1995). "The presenting features of mucopolysaccharidosis type IH (Hurler syndrome)," Acta Paediatr. 84:337-339.

Colville et al. (1996). "Early presentation in the mucopolysaccharide disorders," Child care, Health and Development 22(1):31-36.

Cox et al. (Apr. 2000). "Novel oral treatment of Gaucher's disease with N-butyldeoxynojirimycin (OGT 918) to decrease substrate biosynthesis," Lancet 355:1481-1485.

Crawley et al. (1996). "Enzyme replacement therapy in a feline model of Maroteaux-Lamy syndrome," J. Clin. Invest. 97(8):1864-1873.

Crich et al. (1998). "Direct chemical synthesis of β-mannopyranosides and other glycosides via glycosyl trillates," Tetrahedron 54:8321-8348.

Czartoryska et al. (2000). "Changes in serum chitotriosidase activity with cessation of replacement enzyme (cerebrosidase) administration in Gaucher disease," Clin. Biochem. 33(2):147-149.

Czartoryska et al. (1998). "Serum chitotriosidase activity in Gaucher patients on enzyme replacement therapy (ERT)," Clin. Biochem. 31(5):417-420.

Daniele et al. (2002). "Uptake of recombinant iduronate-2-sulfatase into neuronal and glial cells in vitro," Biochim. Biophys. Acta 1588:203-209.

Davis et al. (1999). "Glycoprotein synthesis: from glycobiological tools to tailor-made catalysts," Synlett 9:1495-1507.

Davis (1999). "Recent developments in glycoconjugates," J. Chem. Soc. Perkin Trans. 1 1:3215-3237.

Davis (2002). "Synthesis of glycoproteins," Chem. Rev. 102:579-601.

Day et al. (2003). "Induction of antigen-specific CTL responses using antigens conjugated to short peptide vectors," J. Immunol. 170:1498-1503.

Demeule et al. (2002). "High transcytosis of melanotransferrin (P97) across the blood-brain barrier," J. Neurochem. 83:924-933.

Den Tandt et al. (1996). "Marked increase of methylumbelliferyl-tetra-N-acetylchitotetraoside hydrolase activity in plasma from Gaucher disease patients," J. Inherit. Metab. Dis. 19:344-350.

Deonarain (1998). "Ligand-targeted receptor mediated vectors for gene delivery," Exp. Opin. Ther. Patents 8(1):53-69.

Derossi et al. (1998). "Trojan peptides: the penetratin system for intracellular delivery," Trends Cell Biol. 8:84-87.

Desnick et al. (1979). "Enzyme therapy in Fabry disease: differential in vivo plasma clearance and metabolic effectiveness of plasma and splenic α-galactosidase A isozymes," PNAS 76(10):5326-5330.

Desnick et al. (2003). "Fabry disease, an under-recognized multisystemic disorder: expert recommendations for diagnosis, management, and enzyme replacement therapy," Ann. Int. Med. 138:338-346.

Desnick (1995). α-galactosidase A deficiency: Fabry disease in the metabolic and molecular bases of inherited disease, 7th edition, Scriver et al. (eds.), McGraw-Hill, New York, pp. 2741-2784.

Di Francesco et al. (1997). "In vitro correction of iduronate-2-sulfatase deficiency by adenovirus-mediated gene transfer," Gene Ther. 4(5):442-448.

Distler et al. (1991). "The binding specificity of high and low molecular weight phosphomannosyl receptors from bovine testes: Inhibition studies with chemically synthesized 6-O-phosphorylated oligomannosides," J. Biol. Chem. 266(22):21687-21692.

Dodelson De Kremer et al. (1997). "Actividad de la chitotriosidasa plasmatica en pacientes Argentinos con enfermedad de Gaucher Diversas lisosomopatias y en otras metabolopaties geneticas," Medicina (Buenos Aires) 57:677-684. (English Summary on p. 683).

Downing et al. (2006). "Synthesis of enzymatically active human alpha-L-iduronidase in *Arabidopsis* cgl (complex glycan-deficient) seeds" Plant Biotechnol. 4(2):169-181.

Dubowchik et al. (2002). "Cathepsin B-labile dipeptide linkers for lysosomal release of doxorubicin from internalizing immunoconjugates: model studies of enzymatic drug release and antigen-specific in vitro anticancer activity," Bioconjugate Chem. 13:855-869.

Duffels et al. (2000). "Synthesis of high-mannose type neoglycolipids: active targeting of liposomes to macrophages in gene therapy," Chem. Eur. J. 6(8):1416-1430.

Duncan et al. (1983). "A new reagent which may be used to introduce sulfhydryl groups into proteins, and its use in the preparation of conjugates for immunoassay," Anal. Biochem. 132:68-73.

Durand et al. (1997). "Active-site motifs of lysosomal acid hydrolases: invariant features of clan GH-A glycosyl hydrolases deduced from hydrophobic cluster analysis," Glycobiology 7(2)277-284.

Dvir et al. (2003). "X-ray structure of human acid-β-glucosidase, the defective enzyme in Gaucher disease," EMBO Reports 4(7):1-6.

El Sayed, H. et al. (Jul. 1, 1982). "Stereoselective Syntheses of 1,2-cis- and 1,2-trans-D-mannopyranosides," *Carbohydrate Research* 105(1):33-43.

Elliot et al. (1997). "Intercellular trafficking and protein delivery by a herpesvirus structural protein," Cell 88:223-233.

Elstein et al. (Oct. 2007). "Oral maintenance clinical trial with miglustat for type I Gaucher disease: switch from or combination with intravenous enzyme replacement," Blood 110(7):2296-2301.

Eng et al. (Jul. 2001). "Safety and efficacy of recombinant human alpha-galactosidase A-replacement therapy in Fabry's disease," N. Engl. J. Med. 345(1):9-16.

Eto et al. (2004). "Treatment of lysosomal storage disorders: cell therapy and gene therapy," J. Inherit. Metab. Dis. 27:411-415.

Etrych et al. (2001). "New HPMA copolymers containing doxorubicin bound via pH-sensitive linkage: synthesis and preliminary in vitro and in vivo biological properties," J. Controlled Release 73:89-102.

European Patent Application No. 06740572.0 Summons to attend oral proceeding at the European Patent Office, dated Mar. 30, 2011.

Fawell et al. (Jan. 1994). "Tat-mediated delivery of heterologous proteins into cells," PNAS 91:664-668.

Felice et al. (1995). "Clinical variability in adult-onset acid maltase deficiency: report of affected sibs and review of the literature," Medicine (Baltimore) 74(3):131-135.

Fellgiebel et al. (Sep. 2006). "CNS manifestations of Fabry's disease," Lancet Neurol. 5(9):791-795.

Fielder et al. (1970). "An immunogenic polysaccharide-protein conju-gate," J. Immunol. 105(1):265-267.

Final Office Action mailed on Jun. 9, 2017, for U.S. Appl. No. 13/433,822, filed Mar. 29, 2012, 14 pages.

Final Office Action mailed on May 5, 2016, for U.S. Appl. No. 13/433,822, filed Mar. 29, 2012, 15 pages.

Final Office Action mailed on Jul. 8, 2014, for U.S. Appl. No. 13/433,822, filed Mar. 29, 2012, 12 pages.

Final Office Action mailed on Jan. 26, 2016, for U.S. Appl. No. 14/272,960, filed May 8, 2014, 6 pages.

Final Office Action mailed on Oct. 23, 2012, for U.S. Appl. No. 12/523,631, filed Aug. 20, 2009, 14 pages.

Final Office Action mailed on Jul. 19, 2016, for U.S. Appl. No. 14/463,955, filed Aug. 20, 2014, 5 pages.

Flomen et al. (Jan. 1993). "Determination of the organisation of coding sequences within the iduronate sulphate sulphatase (IDS) gene," Hum. Mol. Genet. 2(1):5-10.

(56) References Cited

OTHER PUBLICATIONS

Freireich et al. (1966). "Quantitative comparison of toxicity of anticancer agents in mouse, rat, hamster, dog, monkey, and man," Cancer Chemother. Rep. 50(4):219-244.
Friden et al. (1996). "Characterization, receptor mapping and blood-brain barrier transcytosis of antibodies to the human transferrin receptor," J. Pharmacol. Exp. Ther. 278(3):1491-1498.
Fujita et al. (1992). "Targeted delivery of human recombinant superoxide dismutase by chemical modification with mono- and polysaccharide derivatives," J. Pharmacol. Exp. Ther. 263(3):971-978.
Funhoff et al. (2005). "PEG shielded polymeric double-layered micelles for gene delivery," J. Control Release 102(3):711-724.
Furbish et al. (1981). "Uptake and distribution of placental glucocerebrosidase in rat hepatic cells and effects of sequential deglycosylation," Biochim. Biophys. Acta 673:425-434.
Gahmberg et al. (1992). "Cell surface carbohydrate in cell adhesion. Sperm cells and leukocytes bind to their target cells through specific oligosaccharide ligands," APMIS Suppl 27:39-52.
Gahmberg et al. (1994). "Nonmetabolic radiolabeling and tagging of glycoconjugates," Methods Enzymol. 230:32-44.
Gaillard et al. (2005). "Targeted delivery across the blood-brain barrier," Expert Opin. Drug Deliv. 2(2):299-309.
Garman et al. (Sep.-Oct. 2002). "Structural basis of Fabry disease," Mol. Genet. Metab. 77(1-2):3-11.
Garman et al. (2004). "The molecular defect leading to Fabry disease: structure of human α-galactosidase," J. Mol. Biol. 337:319-335.
Gaziev et al. (2000). "Chronic graft-versus-host disease: is there an alternative to the conventional treatment?" Bone Marrow Transplant 25(7):689-696.
GenBank Accession No. AI587087, tr53e08.x1 NCI_CGAP_Pan1 Homo sapiens cDNA clone IMAGE:2222008 3-similar to gb:X59960 Sphingomyelin Phosphodiesterase Precursor (Human); mRNA sequence (1997).
GenBank Accession No. NM_000152, "Homo sapiens glucosidase, alpha; acid (GAA), transcript variant 1, mRNA" (2006).
GenBank Accession No. X05790, "Human mRNA for alpha-galactosidase A (EC 3.2.1-22)" (1987).
Genzyme Corp. Prescribing information for Fabrazyme® (Nov. 2006) (available online at http://www.fabrazyme.com/hcp/pi/fz_us_hc_pi_pdf).
Geoghegan et al. (1992). "Site-directed conjugation of nonpeptide groups to peptides and proteins via periodate oxidation of a 2-amino alcohol. Application to modification at N-terminal serine," Bioconjugate Chem. 3:138-146.
Ghose et al. (1983). "Preparation of antibody-linked cytotoxic agents," Meth. Enzymol. 93:280-333.
Giugliani et al. (2007). "Management guidelines for mucopolysaccharidosis VI," Pediatrics 120(2):405-418.
Gottschalk et al. (1994). "Folate receptor mediated DNA delivery into tumor cells: potosomal disruption results in enhanced gene expression," Gene Ther. 1(3):185-191.
Grabowski et al. (1995). "Enzyme therapy in type 1 Gaucher disease: comparative efficacy of mannose-terminated glucocerebrosidase from natural and recombinant sources," Ann. Intern. Med. 122(1):33-39.
Grady (Saturday, May 27, 2000). "Cell transplamts offer hope for severe cases of diabetes," The New York Times, pp. A1 and A11.
Gray (1974). "The direct coupling of oligosaccharides to proteins and derivatized gels," Arch. Biochem. Biophys. 163(1):426-428.
Gregoriadis et al. (Jan. 1993). "Polysialic acids: potential in drug delivery," FEBS 315(3):271-276.
Gregoriadis et al. (1999). "Polysialylated proteins. An approach to improving enzyme stability and half-life in the blood circulation," S.T.P. Pharma Sci. 9(1):61-66.
Grewal (1994). "Stroke in Fabry's disease," J. Neurol. 241:153-156.
Grindley, B.T. (1998). "Applications of tin-containing intermediates to carbohydrate chemistry", Advances in Carbohydrate Chem. & Biochem. 53:17-142.
Guffon et al. (1998). "Follow-up of nine patients with Hurler syndrome after bone marrow transplantation," J. Pediatr. 133(1):119-125.
Gullingsrud et al. (1998). "Ocular abnormalities in the mucopolysaccharidoses after bone marrow transplantation. Longer follow-up," Ophthalmology 105(6):1099-1105.
Gummert et al. (1999). "Newer immunosuppressive drugs: a review," 10:1366-1380.
Guo et al. (1995). "Elevated plasma chitotriosidase activity in various lysosomal storage disorders," J. Inherit Metab. Dis. 18:717-722.
Hagihara et al. (2006). "Exploration of oligosaccharide-protein interactions in glycoprotein quality control by synthetic approaches," Chem. Rec. 6(6):290-302.
Hamann et al. (2002). "An anti-CD33 antibody-calicheamicin conjugate for treatment of acute myeloid leukemia. Choice of linker," Bioconjug. Chem. 13:40-46.
Hara et al. (1994). "Mutation analysis of a Sandhoff disease patient in the Maronite community in Cyprus," Hum. Genet. 94:136-140.
Helenius et al. (Mar. 2001). "Intracellular functions of N-linked glycans," Science 291(5512):2364-2369.
Hembrough et al. (2004). "Identification and characterization of a very low density lipoprotein receptor-binding peptide from tissue factor pathway inhibitor that has antitumor and antiangiogenic activity," Blood 103(9):3374-3380.
Heng et al. (2001). "Synthesis of a mannotetraose—the repeating unit of the cell-wall mannans of Microsporum gypseum and related species of Trychophyton," J. Carb. Chem. 20(3-4):285-296.
Henry (1999). "Cyclosporine and tacrolimus (FK506): A comparison of efficacy and safety profiles," Clin. Transplant 13:209-220.
Hers (1965). "Inborn lysosomal diseases," Gastroenterology 48(5):625-633.
Himmelspach et al. (1971). "Use of 1-(m-aminophenyl)flavazoles for the preparation of immunogens with oligosaccharide determinant groups," Eur. J. Immunol. 1(2):106-112.
Hinman et al. (1993). "Preparation and characterization of monoclonal antibody conjugates of the calicheamicins: a novel and potent family of antitumor antibiotics," Cancer Res. 53:3336-3342.
Hirschhorn (1995). "Glycogen storage disease type II: acid α-glucosidase (acid maltase) deficiency" in the metabolic and molecular bases of inherited disease, 7th edition, Scriver et al. (eds.), McGraw-Hill, New York, Ch. 77, pp. 2443-2464.
Hodosi et al. (1997). "A fundamentally new, simple, sterospecific synthesis of oligosaccharides containing the β-mannopyranosyl and β-Rhamnopyranosyl linkage," J. Am. Chem. Soc. 119:2335-2336.
Hodosi et al. (1998). "Glycosylation via locked anomeric configuration: stereospecific synthesis of oligosaccharides containing the β-D-mannopyranosyl and β-L-rhamnopyranosyl linkage," Carbohydr. Res. 308:63-75.
Hoefsloot et al. (1990). "Characterization of the human lysosomal α-glucosidase gene," Biochem. J. 272:493-497.
Hoefsloot et al. (1988). "Primary structure and processing of lysosomal α-glucosidase; homology with the intestinal sucrase-isomaltase complex," EMBO J. 7:1697-1704.
Hojo et al. (2000). "Recent progress in the solid-phase synthesis of glycopeptide," Current Prot. Peptide Sci. 1:23-48.
Hollak et al. (1994). "Marked elevation of plasma chitotriosidase activity. A novel hallmark of Gaucher disease," J. Clin. Invest. 93(3):1288-1292.
Hong et al. (2000). : Immunosuppressive agents in organ transplantation: past, present, and future, Semin. Nephrol. 20(2):108-125.
Horinouchi et al. (1995). "Acid sphingomyelinase deficient mice: a model of types A and B Niemann-Pick disease," Nat. Genet. 10:288-293.
Ideguchi et al. (2000). "Local adenovirus-mediated CTLA4-immunoglobulin expression suppresses the immune responses to adenovirus vectors in the brain," Neuroscience 95(1):217-226.
International Search Report and Written Opinion issued in international patent application No. PCT/US2006/012698, date of mailing: Nov. 10, 2006.
International Search Report issued in international patent application No. PCT/US2001/19579, date of mailing: Aug. 28, 2002.

(56) References Cited

OTHER PUBLICATIONS

International Search Report and Written Opinion issued in international patent application No. PCT/US2008/051429, date of mailing: Oct. 7, 2008.
International Search Report and Written Opinion issued in international patent application No. PCT/US2008/051327, date of mailing: Jul. 10, 2008.
International Search Report and Written Opinion issued in international patent application No. PCT/US2009/067775, date of mailing: Nov. 17, 2010.
Ioannou et al. (2001). "Fabry disease: preclinical studies demonstrate the effectiveness of alpha-galactosidase A replacement in enzyme-deficient mice," Am. J. Hum. Genet. 68:14-25.
Ioannou et al. (1996). "Fabry disease: enzyme replacement therapy in α-galactosidase a deficient mice," Am. J. Hum. Genet. 59(4 Suppl.):A15, Abstr. 71.
Ioannou et al. (Dec. 1992). "Overexpression of human alpha-galactosidase A results in its intracellular aggregation, crystallization in lysosomes, and selective secretion," J. Cell Biol. 119(5):1137-1150.
Ito et al. (2000). "Induction of CTL responses by simultaneous administration of liposomal peptide vaccine with anti-CD40 and anti-CTLA-4 mAb," J. Immunol. 164:1230-1235.
Itoh et al. (1995). Synthesis of alkyl β-mannosides from mannobiose by aspergillus niger β-mannosidase, J. Fermentation & Bioengin. 80(5):510-512.
Jeyakumar et al. (May 1999). "Delayed symptom onset and increased life expectancy in Sandhoff disease mice treated with N-butyldeoxynojirimycin," PNAS 96:6388-6393.
Jeyakumar et al. (Jan. 2001). "Enhanced survival in Sandhoff disease mice receiving a combination of substrate deprivation therapy and bone marrow transplantation," Blood 97(1):327-329.
Jeyakumar et al. (2002). "Glycosphingolipid lysosomal storage diseases: therapy and pathogenesis," Neuropathol. Appl. Neurobiol. 28:343-357.
Kakavanos et al. (2003). "Immune tolerance after long-term enzyme-replacement therapy among patients who have mucopolysaccharidosis I," Lancet 361:1608-1613.
Kakkis et al. (1996). "Long-term and high-dose trials of enzyme replacement therapy in the canine model of mucopolysaccharidosis I," Biochem. Mol. Med. 58(2):156-167.
Kakkis et al. (1994). "Overexpression of the human lysosomal enzyme alpha-L-iduronidase in Chinese hamster ovary cells," Prot. Express. Purif. 5:225-232.
Kakkis et al. (2004). "Successful induction of immune tolerance to enzyme replacement therapy in canine mucopolysaccharidosis I," PNAS 101(3):829-834.
Kamada et al. (Apr. 2003). "Synthesis of a poly(vinylpyrrolidone-co-dimethyl maleic anhydride) co-polymer and its application for renal drug targeting," Nat. Biotechnol. 21:399-404.
Kaneko et al. (1991). "New hydrazone derivatives of adriamycin and their immunoconjugates—a correlation between acid stability and cytotoxicity," Bioconjugate Chem. 2(3):133-141.
Kaye et al. (Sep. 1990). "A single amino acid substitution results in a retinoblastoma protein defective in phosphorylation and oncoprotein binding," PNAS 87:6922-6926.
Keeling et al. (2001). "Gentamicin-mediated suppression of Hurler syndrome stop mutations restores a low level of α-L-iduronidase activity and reduces lysosomal glycosaminoglycan accumulation," Hum. Molec. Genet. 10(3):291-299.
Kelly et al. (1996). "Primary structure of bovine adenosine deaminase," J. Pharm. Biomed. Analysis 14:1513-1519.
Kikuchi et al., "Clinical and Metabolic Correction of Pompe Disease by Enzyme Therapy in Acid Maltase deficient Quail" J. Clin. Invest. 101(4):827-833 (1998).
Kim et al., "Mutational spectrum of the iduronate 2 sulfatase gene in 25 unrelated Korean Hunter syndrome patients: Identification of 13 novel mutations" Hum. Mutat. 21:499-450 (2003).
Kim et al., J. "Stereoselective direct glycosylation with anomeric hydroxyl sugars by activation with phthalic anhydride and trifluoromethanesulfonic anhydride involving glycosyl phthalate intermediates." J. Am. Chem. Soc. 130:8537-8547 (2008).
Kim et al., "Identification of Novel SNPs in the Interleukin 6 Receptor Gene (IL6R)" Hum. Mutat. 21:450-451 (2003). Online citation: Mutation in Brief #601, 5 pp., http://onlinelibrary.wiley.com/doi/10.2002/humu.9130/pdf.
King et al., "Preparation of Protein Conjugates via Intermolecular Hydrazone Linkage" Biochemistry 25:5774-5779 (1986).
King et al., "Monoclonal Antibody Conjugates of Doxorubicin Prepared with Branched Linkers: A Novel Method for Increasing the Potency of Doxorubicin Immunoconjugates" Bioconjugate Chem. 10:279-288 (1999).
Kleinhammer et al., "Synthesis and immunological properties of an artificial antigen with the repeating oligosaccharide unit of *Salmonella* Illinois as haptenic group" Eur. J. Immunol. 3:834-838 (1973).
Ko et al., "Atypical Fabry's Disease, An Oligosymptomatic Variant" Arch. Pathol. Lab. Med. 120:86-89 (1996).
Kolodny et al., "Storage Diseases of the Reticuloendothelial System" in Nathan and Oski's Hematology of Infancy and Childhood, 5th Edition. vol. 2. David G. Nathan and Stuart H. Orkin (Eds.) W.B. Saunders Co.: 1998; Ch 38, pp. 1461-1507.
Kolonin et al., "Reversal of obesity by targeted ablation of adipose tissue" Nature Med. 10:625-632 (2004).
Kornfeld et al., The Biogenesis of Lysosomes Annu. Rev: Cell Biol. 5:483-525 (1989).
Kralovec et al., "Synthesis of site-specific methotrexate-IgG conjugates. Comparison of stability and antihumor activity with active ester-based conjugates" Cancer Immunol. Immunother,. 29:293-302 (1989).
Kurlberg et al., "Blockade of the B7-CD26 Pathway by CTLA4-Ig Counteracts Rejection and Prolongs Survival in Small Bowel Transplantation" Scand. J. Immunol. 51:224-230 (2000).
Lanciotti et al., "Targeting Adenoviral Vectors Using Heterofunctional Polyethylene Glycol FGF2 Conjugates" Mol. Ther. 8(1):99-107 (2003).
Lansmann et al., "Human acid sphingomyelinase. Assignment of the disulfide bond pattern" Eur. J. Biochem. 270:1076-1088 (2003).
Lebowitz et al., "Glycosylation-independent targeting enhances enzyme delivery to lysosomes and decreases storage in mucopolysaccharidosis type VII mice" PNAS 101(9):3083-3088 (Mar. 2004).
Lecolley et al., "A new approach to bioconjugates for proteins and peptides (pegylation■) utilising living radical polymerisation" Chem. Commun. 18:2026-2027 (2004).
Lee et al., "2-Imino-2-Methoxyethyl 1-Thioglycosides: New Reagents for Attaching Sugars to Proteins" Biochemistry 15(18):3956-3963 (1976).
Lee et al., "A Biochemical and Pharmacological Comparison of Enzyme Replacement Therapies for the Glycolipid Storage Disorder Fabry Disease" Glycobiology 13(4):305-313 (2003).
Lee et al., "Improved Inhibitors of Glucosylceramide Synthase" J. Biol. Chem. 274(21):14662-14669 (May 21, 1999).
Lee et al., "Receptor mediated uptake of peptides that bind the human transferrin receptor" Eur. J. Biochem. 268:2004-2012 (2001).
Lee et al., "N-Terminal Site-Specific Mono-PEGylation of Epidermal Growth Factor" Pharm. Res. 20(5):818-825 (May 2003).
Lees et al., "Versatile and efficient synthesis of protein-polysaccharide conjugate vaccines using aminooxy reagents and oxime chemistry" Vaccine 24:716-729 (2006).
Lemieux et al., "The Properties of a 'Synthetic' Antigen Related to the Human Blood-Group Lewis a" J. Am. Chem. Soc. 97(14):4076-4083 (1975).
Leonard et al., "Cytokine Receptor Signaling Pathways" J. Allergy Clin. Immunol. 105:877-888 (2000).
Li et al., "Isolation and Characterization of Mannose 6-Phosphate/Insulin-Like Growth Factor II Receptor from Bovine Serum" Glycobiol. 1(5):511-517 (1991).
Li et al., "Direct Multiplex Assay of Lysosomal Enzymes in Dried Blood Spots for Newborn Screening" Clin. Chem. 50(10):1785-1796 (2004).
Liou et al., "Analyses of Variant Acid β■Glucosidases. Effects of Gaucher Disease Mutations" J. Biol. Chem. 281(7):4242-4253 (Feb. 2006).

(56) References Cited

OTHER PUBLICATIONS

Lisi et al., "Enzyme Therapy. I. Polyethylene Glycol:β-Glucuronidase Conjugates as Potential Therapeutic Agents in Acid Mucopolysaccharidosis" J. Appl. Biochem. 4:19-33 (1982).
Litjens et al., "An N-acetylgalactosamine-4-sulfatase mutation (Δ G228) results in a severe Maroteaux-Lamy phenotype" Hum. Mut. 1(5):397-402 (1992).
Lovering et al., "Mechanistic and Structural Analysis of a Family 31 a-Glycosidase and Its glycosyl-enzyme Intermediate" J. Biol. Chem. 280(3):2105-2115 (2005).
Macdermott et al.,"Anderson-Fabry disease: clinical manifestations and impact of disease in a cohort of 98 hemizygous males" J. Med. Genet. 38:750-760 (2001).
Mann et al., "Endocytosis and targeting of exogenous HIV-1 Tat protein" EMBO J. 10(7):1733-1739 (1991).
Marinova-Mutafchieva et al., "A Comparative Study Into the Mechanisms of Action of Anti-Tumor Necrosis Factor α. Anti CD4, and Combined Anti-Tumor Necrosis Factor α/anti-CD4 Treatment in Early Collagen-Induced Arthritis" Arthritis Rheum. 43(3):638-644 (Mar. 2000).
Marshall et al., "Improved management of lysosomal glucosylceramide levels in a mouse model of type 1 Gaucher disease using enzyme and substrate reduction therapy" J. Inherit. Metab. Dis. 33:281-289 (2010).
Marshall et al., "Demonstration of Feasibility of In Vivo Gene Therapy for Gaucher Disease Using a Chemically Induced Mouse Model" Mol. Ther. 6(2):179-189 (Aug. 2002).
Martiniuk et al., "Isolation of a cDNA for human acid α-glucosidase and detection of genetic heterogeneity for mRNA, in three α-glucosidase-deficient patients" Proc. Natl. Acad. Sci. USA 83:9641-9644 (1986).
Masson et al., "Fabry Disease: A Review" Joint Bone Spine 71:381-383 (2004).
Masterson et al., "Hip Dysplasia in Hurler's Syndrome: Orthopaedic Management After Bone Marrow Transplantation" J. Pediatr. Ortho. 16:731-733 (1996).
Matsuura et al., "Human α-Galactosidase A: Characterization of the N-Linked Oligosaccharides on the Intracellular and Secreted Glycoforms Overexpressed by Chinese Hamster Ovary Cells" Glycobiology 8(4):329-339 (1998).
Matsuzawa et al., "Fabry disease: correlation between structural changes in α-galactosidase, and clinical and biochemical phenotypes" Hum. Genet. 117:317-328 (2005).
Mayer et al., "Synthesis of Labeled Glycosyl Phosphatidyl Inositol (GPI) Anchors" Eur. J. Org. Chem. 1999(10):2563-2571 (1999).
Mayes et al., "Differential assay for lysosomal α-galactosidases in human tissues and its application to Fabry's disease" Clin. Chem. Acta 112:247-251 (1981).
Mcbroom et al., "Carbohydrate Antigens■Coupling of Carbohydrates to Proteins by Diazonium and Phenylisothiocyanate Reactions" Methods in Enzymology, vol. XXVIII, Complete Carbohydrates, Part B, pp. 212-219 (1972).
Mceachern et al., "AAV8-Mediated Expression of Glucocerebrosidase Ameliorates the Storage Pathology in the Visceral Organs of a Mouse Model of Gaucher Disease" J. Gene Med. 8:719-729 (2000).
Mcgovern, "Lysosomal Storage Diseases" in Harrison's Principles of Internal Medicine, Fauci et al., (Eds.), pp. 2169-2176 (McGraw-Hill, 14th ed., 1998).
Mcvie-Wylie et al., "Biochemical and pharmacological characterization of different recombinant acid α-glucosidase preparations evaluated for the treatment of Pompe disease" Mol. Genet. Metab. 94:448-455 (2008).
Medin et al., "Correction in trans for Fabry disease: Expression, secretion and uptake of α-galactosidase A in patient-derived cells driven by a high-titer recombinant retroviral vector." Proc. Natl. Acad. Sci. USA 93:7917-7922 (1996).
Mehta et al., (Eds.), "Fabry Disease, Perspectives from 5 years of FOS. Oxford, United Kingdom: Oxford PharmaGenesis" Ltd., 2006; Table of Contents, pp. vii-x.

Menander-Huber et al., "Orgotein, the Drug Version of Bovine Cu—Zn Superoxide Dismutase II. A Summary Account of Clinical Trials in Man and Animals" in Superoxide and Superoxide Dismutases. A.M. Michelson et al., (eds.), Academic Press, 1977; pp. 537-549.
Mendez et al., The Vascular Dementia of Fabry's Disease Dement. Geriatr. Cogn. Disord. 8:252-257 (1997).
Michelson et al., "Production of Superoxide by Metal Ions" in Superoxide and Superoxide Dismutases A.M. Michelson et al., (eds.), Academic Press, 1977; pp. 77-86.
Miller et al., "Genetic Studies of the lac Repressor" J. Mol. Biol. 131:191-222 (1979).
Minko et al., "Molecular Targeting of Drug Delivery Systems to Cancer" Current Drug Targets 5:389-406 (2004).
Mistry et al., "A Practical Approach to Diagnosis and Management of Gaucher's Disease" Bailliére's Clin. Haematol. 10(4):817-839 (1997).
Mitchell et al., "Polyarginine enters cells more efficiently than other polycationic homopolymers" J. Peptide Res. 56:318-325 (2000).
Mizukami et al., "Systemic inflammation in glucocerebrosidase-deficient mice with minimal glucosylceramide storage" J. Clin. Invest. 109:1215-1221 (2002).
Moczar et al., "Preparation of N-Acetylglucosamine Derivatives of Proteins" FEBS Letters 50(3):300-302 (l975).
Moder "New Medications for Use in Patients with Rheumatoid Arthritis" Ann. Allergy Asthma Immunol. 84:280-287 (2000).
Molema et al., "Neoglycoproteins as Carriers for , Antiviral Drugs: Synthesis of Analysis of Protein-Drug Conjugates" J. Med. Chem. 34:1137-1141 (1991).
Montalvo et al., "Glycogenosis type II: identification and expression of three novel mutations in the acid a glucosidase gene causing the infantile form of the disease" Mol. Genet. Metab. 81:203-208 (2004).
Moore et al., "The Cerebral Vasculopathy of Fabry Disease" J. Neurol. Sci. 257:258-263 (2007).
Morales, "Gaucher's Disease: A Review" Ann. Pharmacother. 30:381-388 (1996).
Moreland et al., "Lysosomal Acid α-Glucosidase Consists of Four Different Peptides Processed from a Single Chain Precursor" J. Biol. Chem. 280(8):6780-6791 (2005).
Munier-Lehmann et al., "Re-expression of the Mannose 6-Phosphate Receptors in Receptor-deficient Fibroblasts" J. Biol. Chem. 271(25):15166-15174 (1996).
Munavu, R. M. et al. (1976). "Selective Formation of 2 Esters of Some Methyl α-D-Hexopyranosis via Dibutylstannylene Derivatives", J. Org. Chem. 41(10):1832-1836.
Murunganandam et al., "Selection of phage-displayed llama single-domain antibodies that transmigrate across human blood-brain barrier endothelium" FASEB J.■16:240-242(2002).
Murray et al., "Cellular and Tissue Distribution of Intravenously Administered Agalsidase Alfa" Author manuscript [online]: http://www.ncbi.nlm.nih.gov/pmc/articles/PMC1839873/pdf/nihms19304.pdf. Final publication in: Mol. Genet. Metab. 90(3):307-312 (2007).
Mutsaers et al., "Determination of the structure of the carbohydrate chains of acid α-glucosidase from human placenta" Biochim. Biophys. Acta 911:244-251 (1987).
Nakao, "An Atypical Variant of Fabry's Disease in Men with Left Ventricular Hypertrophy" N..Engl. J. Med. 333:288-293 (1995).
Neufeld et al., "The Mucopolysaccharidoses" in the Metabolic and Molecular Bases of Inherited Diseases, 7th Edition, Scriver et al., (Eds.) McGraw-Hill, New York: 1995; Ch. 78, pp. 2465-2494.
Neufeld, "Lysosomal Storage Diseases" Annu. Rev. Biochem. 60:257-280 (1991).
Nevins, "Overview of New Immunosuppressive Therapies" Curr. Opin. Pediatr. 12:146-150 (2000).
Nicolaou et al., "New Synthetic Technology for the Stereocontrolled Construction of 1,1'-Disaccharides and 1,1':1",2-Trisaccharides. Synthesis of the FG Ring System of Everninomicin 13,384-1" J. Am. Chem. Soc. 119:9057-9056 (1997).
Nicolaou, K.C. et al. (1999). "Total Synthesis of Everninomicin 13,384-1—Part 2: Synthesis of the FGHA2 Fragment", Angew Chem. Int. Ed. 38(22):3340-3345.

(56) References Cited

OTHER PUBLICATIONS

Nieman et al., "Family 39 α-L-iduronidases and β-D-xylosidases react through similar glycosyl-enzyme intermediates: identification of the human iduronidase nucleophile" Biochemistry 42(26):8054-8065 (Jul. 2003).
Non-Final Office Action mailed on Apr. 9, 2014, for U.S. Appl. No. 13/354,855, filed Jan. 20, 2012, 11 pages.
Non-Final Office Action mailed on Feb. 19, 2016, for U.S. Appl. No. 14/534,328, filed Nov. 6, 2014, 5 pages.
Non-Final Office Action mailed on Nov. 16, 2016, for U.S. Appl. No. 13/433,822, filed Mar. 29, 2012, 17 pages.
Non-Final Office Action mailed on Oct. 16, 2015, for U.S. Appl. No. 13/433,822, filed Mar. 29, 2012, 22 pages.
Non-Final Office Action mailed on Dec. 23, 2013, for U.S. Appl. No. 13/433,822, filed Mar. 29, 2012, 24 pages.
Non-Final Office Action mailed on May 22, 2015, for U.S. Appl. No. 14/272,960, filed May 8, 2014, 7 pages.
Non-Final Office Action mailed on Oct. 25, 2013, for U.S. Appl. No. 12/523,631, filed Aug. 20, 2009, 7 pages.
Non-Final Office Action mailed on Feb. 21, 2012, for U.S. Appl. No. 12/523,631, filed Aug. 20, 2009, 9 pages.
Non-Final Office Action mailed on Mar. 23, 2016, for U.S. Appl. No. 14/463,955, filed Aug. 20, 2014, 7 pages.
Non-Final Office Action mailed on Oct. 22, 2013, for U.S. Appl. No. 13/768,266, filed Feb. 15, 2013, 6 pages.
Notice of Allowance mailed on Aug. 8, 2014, for U.S. Appl. No. 13/354,855, filed Jan. 20, 2012, 8 pages.
Notice of Allowance mailed on Jul. 14, 2016, for U.S. Appl. No. 14/534,328, filed Nov. 6, 2014, 7 pages.
Notice of Allowance mailed on Jun. 30, 2016, for U.S. Appl. No. 14/272,960, filed May 8, 2014, 5 pages.
Notice of Allowance mailed on Jun. 9, 2016, for U.S. Appl. No. 14/272,960, filed May 8, 2014, 7 pages.
Notice of Allowance mailed on Feb. 10, 2014, for U.S. Appl. No. 12/523,631, filed Aug. 20, 2009, 7 pages.
Notice of Allowance mailed on Feb. 22, 2017, for U.S. Appl. No. 14/463,955, filed Aug. 20, 2014, 8 pages.
Notice of Allowance mailed on Jun. 3, 2014, for U.S. Appl. No. 13/768,266, filed Feb. 15, 2013, 8 pages.
Notice of Allowance mailed on Nov. 16, 2012, for U.S. Appl. No. 12/642,383, filed Dec. 18, 2009, 11 pages.
O'Connor et al., "Enzyme Replacement Therapy for Murine Mucopolysaccharidosis Type VII Leads to Improvements in Behavior and Auditory Function" J. Clin. Invest. 101(7):1394-1400 (1998).
Oberholzer et al., "Cytokine Signaling-Regulation of the Immune Response in Normal and Critically Ill States" Crit. Care. Med. 28(4 Suppl.):N3-N12 (2000).
Office Action issued in U.S. Appl. No. 11/762,689, mailed Sep. 25, 2008.
Office Action issued in U.S. Appl. No. 11/762,689, mailed Jun. 1, 2009.
Office Action issued in U.S. Appl. No. 11/762,689, mailed Jan. 19, 2010.
Office Action issued in U.S. Appl. No. 11/762,689, mailed Jul. 22, 2010.
Office Action issued in U.S. Appl. No. 11/762,689: Notice of Allowance, mailed Nov. 12, 2010.
Office Action issued in U.S. Appl. No. 13/033,344, mailed Aug. 17, 2011.
Office Action issued in U.S. Appl. No. 13/033,344: Notice of Allowance, mailed Dec. 30, 2011.
Office Action issued in U.S. Appl. No. 09/884,526, mailed May 29, 2003.
Office Action issued in U.S. Appl. No. 09/884,526, mailed Feb. 18, 2004.
Office Action issued m U.S. Appl. No. 09/884,526, mailed Aug. 25, 2004.
Office Action issued in U.S. Appl. No. 09/884,526, mailed Jan. 31, 2005.
Office Action issued in U.S. Appl. No. 09/884,526, mailed Aug. 10, 2005.
Office Action issued in U.S. Appl. No. 09/884,526, mailed Mar. 6, 2006.
Office Action issued in U.S. Appl. No. 09/884,526, mailed Oct. 17, 2006.
Office Action issued in U.S. Appl. No. 10/051,711, mailed Sep. 30, 2003.
Office Action issued in U.S. Appl. No. 10/051,711, mailed Apr. 16, 2004.
Office Action issued in U.S. Appl. No. 10/051,711, mailed Jan. 12, 2005.
Office Action issued in U.S. Appl. No. 10/051,711: Notice of Allowance, mailed Jun. 14, 2005.
Office Action issued in U.S. Appl. No. 10/758,773, mailed Jun. 1, 2007.
Office Action issued in U.S. Appl. No. 10/758,773, mailed Feb. 12, 2008.
Office Action issued in U.S. Appl. No. 10/758,773, mailed Sep. 26, 2008.
Office Action issued in U.S. Appl. No. 10/758,773, mailed May 18, 2009.
Office Action issued in U.S. Appl. No. 10/943,893, mailed Feb. 28, 2007.
Office Action issued in U.S. Appl. No. 10/943,893, mailed Sep. 20, 2007.
Office Action issued in U.S. Appl. No. 10/943,893, mailed Jan. 30, 2008.
Office Action issued in U.S. Appl. No. 10/943,893, mailed Sep. 25, 2007.
Office Action issued in U.S. Appl. No. 10/943,893, mailed, Dec. 17, 2008.
Office Action issued in U.S. Appl. No. 10/943,893, mailed, Feb. 24, 2009.
Office Action issued in U.S. Appl. No. 10/943,893: Notice of Allowance, mailed Jun. 15, 2009.
Office Action issued in U.S. Appl. No. 10/943,893: Notice of Allowance, mailed Sep. 25, 2009.
Office Action issued in U.S. Appl. No. 11/264,255, mailed Oct. 12, 2007.
Office Action issued in U.S. Appl. No. 11/264,255, mailed Jun. 25, 2008.
Office Action issued in U.S. Appl. No. 11/398,949, mailed Jan. 31, 2007.
Office Action issued in U.S. Appl. No. 11/398,949: Notice of Allowance, mailed Oct. 10, 2007.
Office Action issued in U.S. Appl. No. 11/970,907, mailed Jun. 17, 2010.
Office Action issued in U.S. Appl. No. 11/970,907, mailed Dec. 8, 2010.
Office Action issued in U.S. Appl. No. 11/970,907: Notice of Allowance, mailed May 27, 2011.
Office Action issued in U.S. Appl. No. 11/970,907: Notice of Allowance, mailed Oct. 26, 2011.
Office Action issued in U.S. Appl. No. 12/237,113, mailed Nov. 19, 2009.
Office Action issued in U.S. Appl. No. 12/237,113: Notice of Allowance, mailed May 3, 2010.
Office Action issued in U.S. Appl. No. 12/523,631, mailed Feb. 21, 2012.
Office Action issued in U.S. Appl. No. 12/642,383, mailed Mar. 13, 2012.
Ohkuma et al., "Fluorescence probe measurement of the intraiysosomal pH in living cells and the perturbation of pH by various agents" Proc. Natl. Acad. Sci. USA 75(7):3327-3331 (1978).
Ohshim.a et al., "α-Galactosidase A deficient mice: A model of Fabry disease" Proc. Natl. Acad. Sci. USA 94:2540-2544 (Mar. 1997).
Okumiya et al., "Two Novel Mutations in the α-Galactosidase Gene in Japanese Classical Hemizygotes with Fabry Disease" Jpn. J. Human Genet. 41:313-321 (1996).

(56) References Cited

OTHER PUBLICATIONS

Olson et al., "Structure of uPAR, plasminogen, and sugar-binding sites of the 300 kDa mannose 6-phosphate receptor" EMBO J. 23:2019-2028 (2004).
Olson et al., "Structure Basis for Recognition of Phosphorylated High Mannose Oligosaccharides by the Cation-dependent Mannose 6-Phosphate Receptor" J. Biol. Chem. 274(42):29889-29886 (Oct. 1999).
Olson et al., "Twists and Turns of the Cation-dependent Mannose 6-Phosphate Receptor" J. Biol. Chem., 277(12):10156-10161 (Mar. 22, 2002).
Olson et al., "The N-terminal Carbohydrate Recognition Site of the Cation-independent Mannose 6-Phosphate Receptor" J. Biol. Chem. 279(32):34000-34009 (Aug. 2004).
Orr et al., "Synthetic Concanavalin A Receptors and Erythrocyte Agglutination" Nature 272:722-725 (1978).
O'Shannessy et al., "A Novel Procedure for Labeling Immunoglobulins by Conjugation to Oligosaccharide Moieties" Immunol. Lett. 8:274-277 (1984).
O'Shannessy et al., "Specific Conjugation Reactions of the Oligosaccharide Moieties of Immunoglobulins." J. Applied Biochem. 7:347-355 (1985).
Oshima et al., "Cloning, Sequencing, and Expression of cDNA for Human β-Glucuronidase" Proc. Natl. Acad. Sci. USA 84:685-689 (Feb. 1987).
Overkleeft et al., "Generation of Specific Deoxynojirimycin-type Inhibitors of the Non-Lysosomal Glucosylceramidase". J. Biol. Chem. 273(41):26522-26527 (Oct. 9, 1998).
Paladin Labs Inc., "Conditional Approval of Replagal" (agalsidase alfa): Fact Sheet Health Canada, Drugs and Health Products, Feb. 6, 2004, 4 pages. Available online at http://www.hc.sc.gc.ca/dhp-mps/prodpharma/notices-avis/conditions/replagal_fs_fd_066304-eng.php.
Papisov et al., "Hydrophilic Polyals: Biomimetic Biodegradable Stealth Materials for Pharmacology and Bioengineering" Abstract, 226th American Chemical Society National Meeting, New York, NY, Sep. 7-11, 2003, 3 pages.
Papisov et al., "Semisynthetic Hydrophilic Polyals" Biomacromolecules 6:2659-2670 (2005).
Papisov, "Acyclic polyacetais from polysaccharides" ACS Symposium Series 786:301-314 (2001).
Parolis et al., "The Extracellular Polysaccharide of Pichia (Hansenula) holstil NRRL Y-2448: The Phosphorylated Side Chains" Carbohydr. Res. 309:77-87 (1998).
Pastores et al., "Current and Emerging Therapies for the Lysosomal Storage Disorders" Expert Opin. Emerging Drugs 10(4):891-902 (2005).
Pastores et al., "Enzyme Therapy in Gaucher Disease Type 1: Dosage Efficacy and Adverse Effects in 33 Patients Treated for 6 to 24 Months" Blood 82(2):408-416 (1993).
Pekari et al., "Synthesis of the fully phosphorylated GPI anchor pseudohexasaccharide of Toxoplasma gondii" J. Org. Chem. 66:7432-7442 (2001).
Peltola et. al., "Characterization of a Point Mutation in Aspartyiglucosaminidase Gene: Evidence for a Readthrough of a Translational Stop Codon" Hum. Molec. Genet. 3(12):2237-2242 (1994).
Peters et al., "Hurler Syndrome: Past, Present and Future" J. Pediatr. 133(1):7-9 (1998).
Peters et al., "Hurler Syndrome: II. Outcome of HLA-Genotypically Identical Sibling and HLA-Haploidentical Related Donor Bone Marrow Transplantation in Fifty-Four Children" Blood 91(7):2601-2608 (1998).
Peters et. alt., "Phylogenetic Conservation of Arylsulfatases. cDNA Cloning and Expression of Human Arylsulfatase B" J. Biol. Chem. 265(6):3374-3381 (Feb. 1990).
Platt et al., "Prevention of Lysosomal Storage in Tay-Sachs Mice Treated with N-Butyldeoxynojirimycin" Science 276:428-431 (Apr. 1997).
Ponce et al., "Enzyme Therapy in Gaucher Disease Type 1: Effect of Neutralizing Antibodies to Acid β-Glucosidase" Blood 90(1):43-48 (Jul. 1997).
Ponticelu et al., "Promising New Agents in the Prevention of Transplant Rejection" Drugs R&D 1:55-60 (Jan. 1999).
Potter et al., "Review—The Use of Immunosuppressive Agents to Prevent Neutralizing Antibodies Against a Transgene Product" Ann. NY Acad. Sci. 875:159-174 (1999).
Poznansky et al., "α-1,4-Glucosidase-albumin polymers: in vitro properties and advantages for enzyme replacement therapy" Can. J. Physiol. Pharmacol. 58:322-325 (1980).
Poznansky et al., "Insulin Carrier Potential for Enzyme and Drug Therapy" Science 223:1304-1306 (1984).
Prince et al., "Lipoprotein Receptor Binding, Cellular Uptake, and Lysosomal Delivery of Fusions between the Receptor-associated Protein (RAP) and α-L-Iduronidase or Acid α-Glucosidase" J. Biol. Chem. 279(33):35037-35046 (Aug. 2004).
Przepiorka et al., "A Phase II Study of BTI-322, a Monoclonal Anti-CD2 Antibody, for Treatment of Steroid-Resistant Acute Graft-Versus■Host Disease" Blood 92(11):4066-4071 (Dec. 1998).
Qi et al., "Effect of Tacrollmus (FK506) and Sirolimus (Rapamycin) Mono- and Combination Therapy in Prolongation of Renal Allograft Survival in the Monkey" Transplantation 69(7):1275-1283 (Apr. 2000).
Qiu et al., "Activation of Human Acid Sphingomyelinase through Modification or Deletion of C-terminal Cysteine" J. Biol. Chem. 278(35):32744-32752 (Aug. 2003).
Raben et al., "Enzyme Replacement Therapy in the Mouse Model of Pompe Disease" Mol. Genet. Metab. 60: 159-169 (2003).
Raben et al., "Glycogen Stored in Skeletal but Not in Cardiac Muscle in Acid α-Glucosidase Mutant (Pompe) Mice is Highly Resistant to Transgene-Encoded Human Enzyme" Mol. Ther. 6(5):601-608 (Nov. 2002).
Raben et al., "Targeted Disruption of the Acid α-Glucosidase Gene in Mice Causes an illness with Critical Features of Both Infantile and Adult Human Glycogen Storage Disease Type II" J. Biol. Chem. 273(30):19086-19092 (Jul. 1998).
Raben et al., "Replacing Acid α-Glucosidase in Pompe Disease: Recombinant and Transgenic Enzymes Are Equipotent, but Neither Completely Clears Glycogen from Type II Muscle Fibers" Mol. Ther. 11:46-56 (2005).
Rempel et al., "A homology model for human α-L-iduronidase: insights into human disease" Mol. Genet. Metab. 85:28-37 (2005).
Restriction Requirement mailed on Dec. 20, 2013, for U.S. Appl. No. 13/354,855, filed Jan. 20, 2012, 9 pages.
Restriction Requirement mailed on Nov. 27, 2015, for U.S. Appl. No. 14/534,328, filed Nov. 6, 2014, 8 pages.
Restriction Requirement mailed on Sep. 1, 2009, for U.S. Appl. No. 11/970,907, filed Jan. 8, 2008, 11 pages.
Restriction Requirement mailed on Aug. 8, 2006, for U.S. Appl. No. 11/398,949, filed Apr. 5, 2006, 14 pages.
Restriction Requirement mailed on Apr. 10, 2013, for U.S. Appl. No. 13/433,822, filed Mar. 29, 2012, 6 pages.
Restriction Requirement mailed on Apr. 21, 2008, for U.S. Appl. No. 11/762,689, filed Jun. 13, 2007, 7 pages.
Restriction Requirement mailed on Oct. 28, 2011, for U.S. Appl. No. 12/523,631, filed Aug. 20, 2009, 7 pages.
Reuser et al., "Glycogenosis Type II (Acid Maltase Deficiency)" Muscle & Nerve. Suppl. 3:S61-S69 (1995).
Reuser et al., "Uptake and Stability of Human and Bovine Acid α-Glucosidase in Cultured Fibroblasts and Skeletal Muscle Cells from Glycogenosis Type II Patients" Exp. Cell Res. 155(1):178-189 (1984).
Rodriguez et al., "Aminooxy-, Hydrazide-, and Thiosemicarbazide-Functionalized Saccharides: Versatile Reagents for Glycoconjugate Synthesis" J. Org. Chem. 63:7134-7135 (1998).
Rodriguez et al., "A Strategy for the Chemoselective Synthesis of O-linked Glycopeptides with Native Sugar-Peptide Linkages" J. Am. Chem. 119(4):9905-9906 (1997).
Rodwell et al., "Site-specific covalent modification of monoclonal antibodies: In vitro and in vivo evaluations" Proc. Natl. Acad. Sci. USA 83:2632-2636 (1986).

(56) References Cited

OTHER PUBLICATIONS

Romanczuk et al., "Modification of an Adenoviral Vector with Biologically Selected Peptides: A Novel Strategy for Gene Delivery to Cells of Choice" Hum. Gene Ther. 10:2615-2626 (Nov. 1999).
Rosenthal et al., "Enzyme Replacement Therapy for Gaucher Disease: Skeletal Responses to Macrophage-targeted Glucocerebrosidase" Pediatrics 96(4):629-637 (1995).
Roussele et al., "New Advances in the Transport of Doxorubicin through the Blood-Brain Barrier by a Peptide Vector-Mediated Strategy" Mol. Pharmacol. 57:679-686 (2000).
Rubinstein et al., "Recent Advances in Cytokines, Cytokine Receptors and Signal Transduction" Cytokine & Growth Factor Rev. 9(2):175-181 (1996).
Rudinger, "Characteristics of the amino acids as components of a peptide hormone sequence" in Peptide Hormones, J.A. Parsons (ed.) Baltimore, MD: Univ. Park Press, 1976; pp. 1-7.
Ryan et al., "Clinical Outcomes and Insulin Secretion after Islet Transplantation with the Edmonton Protocol" Diabetes 50:710-719 (Apr. 2001).
Sakuraba et al., "Identification of Point Mutations in the α-Galactosidase A Gene in Classical and Atypical Hemizygotes with Fabry Disease" Am. J. Hum. Genet. 47:784-789 (1990).
Sands et al., "Murine Mucopolysaccharidosis Type VII: Long Term Therapeutic Effects of Enzyme Replacement and Enzyme Replacement Followed by Bone Marrow Transplantation" J. Clin. Invest. 99(7):1596-1605 (Apr. 1997).
Scaravilli et al., "Enzyme Replacement in Grafted Nerve of Twitcher Mouse" Nature 305(5936):713-715 (Oct. 20, 1983).
Schiffmann et al., "Enzyme Replacement Therapy in Fabry Disease a Randomized Controlled Trial" JAMA 285(21 ):2743-2749 (Jun. 2001 1-.
Schiffmann et al., "Infusion of α-galactosidase A reduces tissue globotriaosylceramide storage in patients with Fabry disease" PNAS 97(1):365-370 (Jan. 2000).
Schnyder et al., "Targeting of skeletal muscle in vitro using biotinylated immunoliposomes" Biochem. J. 377:61-67 (2004).
Schuchman et al., "Human arylsulfatase B: Mopac cloning nucleotide sequence of a full-length cDNA and regions of amino acid identity with arylsulfases A and C" Genomics 6(1)149-168(1990).
Schwartz et al., "Preparation of Hydrazine-Modified Proteins and Their Use for the Synthesis of Tc-Protein Conjugates" Bioconjugate Chem. 2:333-336 (1991).
Schwarze et al., "In Vivo Protein Transduction: Delivery of a Biologically Active Protein into the Mouse" Science 285:1569-1572 (Sep. 1999).
Scott et al., "Structure and sequence of the human α-L-iduronidase gene" Genomics 13:1311-1313 (Aug. 1992).
Scott et al., "Human α-L-iduronidase: cDNA isolation and expression" Proc. Natl. Acad. Sci. USA 88:9695-9699 (Nov. 1991).
Scott et al., "Molecular genetics of mucopolysaccharidosis type I: diagnostic clinical and biological implications" Hum. Mutat. 6(4):268-302 (1995).
Scriver et al., (eds.), The Metabolic and Molecular Bases of Inherited Disease. vol. III, 8th edition, New York, 2001; cover.
Sears et al., "Toward Automated Synthesis of Oligosaccharides and Glycoproteins" Science 291:2344-2350 (Mar. 2001).
Seeberger et al., "Synthesis and medical applications of oligosaccharides" Nature 446(7139):1046-1051 (Apr. 2007).
Seeberger et al., "Automated synthesis of oligosaccharides as a basis for drug discovery" Nat. Rev. Drug Discov. 4(9):751-763 (2005).
Seto et al., "A model of the acid sphingomyelinase phosphoesterase domain based on its remote structual homolog purple acid phosphatase" Protein Sci. 13:3172-3186 (2004).
Shaffer, K.J. et al. (2006, e-pub Aug. 2, 2006), "☐-Glycosides of Hydroxyproline via na Umpolung Approach", American Chemical Society 8(18):3959-3962.
Shapiro et al., "Islet Transplantation in Seven Patients with Type■1 Diabetes Mellitus Using a Glucocorticoid Free Immunosuppressive Regimen" N. Engl. J. Med. 343(4)230-238 (Jul. 2000).
Shayman et al., "Inhibitors of Glucosylceramide Synthase" Meth. Enzymol. 311:373-387 (1999).
Shen et al., "Conjugation of poly-L-lysine to albumin and horseradish peroxidase: A novel method of enhancing the cellular uptake of proteins" Proc. Natl. Acad. Sci. USA 75:1872-1876 (1978).
Shull et al., "Enzyme Replacement in a Canine Model of Hurler Syndrome" Proc. Natl. Acad. Sci. USA 91:12937-12941 (1994).
Skolnick et al., "From genes to protein structure and function: Novel applications of computational approaches in the genomic era" TIBTECH 18:34-39 (Jan. 2000).
Slavik et al., "CD28/CTLA-4 and CD80/CD86 Families. Signaling and Function" Immunol. Res. 19(1):1-24 (1999).
Slodki, "Phosphate Linkages in Phosphomannans from Yeast" Biochim. Biophys. Acta 57:525-533 (1962).
Smallwood et al., "Different Substitutions at Conserved Amino Acids in Domains II and III in the Sendal I. RNA Polymerase Protein Inactivate Viral RNA Synthesis" Virology 304(1):135-145 (Dec. 2002).
Srinivasachar et al., "New Protein Cross-linking Reagents That Are Cleaved oy Mild Acid" Biochemistry 28:2501-2509 (1989).
Srivastava et al., "Synthesis of 6'-O-phosphorylated O-α-o-mannopyranosyl-(1----3)- and -(1----6)-α-o-mannopyranosides" Carbohydr. Res. 181:324-329 (1987).
Srivastava et al., "Synthesis of Phosphorylated Pentasaccharides Found on Asparagine-Linked Carbohydrate Chains of Lysosomal Enzymes" J. Org. Chem. 52:2869-2875 (1987).
Srivastava et al., "Synthesis of Phosphorylated Trimannosides Corresponding to End Groups of the High-mannose Chains of Lysosomal Enzymes" Carbohydr. Res. 161:195.210 (1987).
Srivastava et al., "Synthesis of the 6- and 6'-Phosphates of 8-Methoxycarbonyloctyl 2-O-α-o Mannopyranosyl-α-o-Mannopyranoside" Carbohydr. Res. 155:57-72 (1986).
Srivastava et al., "Synthesis of β-o-Mannopyranosides and Regioselective O-Alkylation of Dibutylstannylene Complexes" Tetrahedron Letters 20(35):3269-3272 (1979).
Sugawara, T. et al. (1992). "Synthesis of ω-(methoxycarbonyl)alkyl and 9-(methoxycarbonyl)-3,6-Dioxanonyl Glycopyranosides for the Preparation of Carbohydrate-Protein Conjugates", Carbohydrate Research 230:117-149.
Sukegawa-Hayasaka et al., "Effect of Hunter Disease (Mucopolysaccharidosis Type II) Mutations on Molecular Phenotypes of iduronate-2-Sulfatase: Enzymatic Activity, Protein Processing and Structural Analysis" J. Inherit. Metab. Dis. 29(6):755-761 (2006).
Takahashi et al., "Identification and Expression of Five Mutations in the Human Acid Sphingomyelinase Gene Causing Types A and B Niemann-Pick Disease" J. Biol. Chem. 267(18):12552-12558 (1992).
Takahashi et al., "Acid Sphingomyelinase: Relation of Lysine Residue on the Ratio of Intracellular to Secreted Enzyme Activity" Tokohu J. Exp. Med. 206:333-340 (2005).
Tanaka et al., "Novel Mutations, Including the Second Most Common in Japan, in the β-Hexosaminidase α Subunit Gene, and a Simple Screening of Japanese Patients with Tay-Sachs Disease" J. Hum. Genet. 44:91-95 (1999).
Tang et al., "Novel Approach to the Study of the Antigenicities and Receptor Functions of Carbohydrate Chains of Glycoproteins" Biochem. Biophys. Res. Commun. 132(2):474-480 (1985).
Taylor et al., "Uptake and Processing of Glycoproteins by Rat Hepatic Mannose Receptor" Am. J. Physiol. Endocrinol. Metab. 252.E690-E698 (1986).
Tolvanen et al., "In vitro attachment of mono- and oligosaccharide to surface glycoconjugates of intact cells" J. Biol. Chem. 261(20):9546-9551 (Jul. 1986).
Tomoda et al., "Binding specificity of o-mannose 6-phosphate receptor of rabbit alveolar macrophages" Carbohydr. Res., 213:37-46 (1991).
Tong et al., "Ligand Interactions of the Cation-independent Mannose 6-Phosphate Receptor" J. Biol. Chem. 254(14):7962-7969 (May 1969).
Torchin, "Drug Targeting" Eur. J. Pharm. Sci. 11(Suppl. 2):S81-S91 (2000).
Townsend et al., "Analysis of Glycoprotein Oligosaccharides Using High-pH Anion Exchange Chromatography" Glycobiol. 1(2):139-147 (1991).

(56) References Cited

OTHER PUBLICATIONS

Tsuji et al., "Signal Sequence and DNA-Mediated Expression of Human Lysosomal α-Galactosidase A" Eur. J. Biochem. 165:275-280 (1987).
Umpathysivam et al., "Determination of Acid α-Glucosidase Activity in Blood Spots as a Diagnostic Test for Pompe Disease" Clin Chem. 47(8):1378■1383 (2001).
U.S. Food and Drug Administration, Department of Health and Human Services Approval Letter to Genzyme Corporation regarding U.S. License No. 1596, dated Apr. 24, 2003. [online]: http://www.fda.gov/oder/foi/appletter/2003/agalgen042403L.htm, 4 pages.
U.S. Appl. No. 16/439,665, filed Jun. 12, 2019, by Zhu. (U.S. Patent Applications are not submitted herewith pursuant to the waiver of 37 C.F.R. § 1.98(a)(2)(iii) issued by the Office on Sep. 21, 2004).
U.S. Appl. No. 16/268,989, filed Feb. 6, 2019, by Zhu et al. (U.S. Patent Applications are not submitted herewith pursuant to the waiver of 37 C.F.R. § 1.98(a)(2)(iii) issued by the Office on Sep. 21, 2004).
U.S. Patent Application No. 16/048,176, filed May 27, 2018, by Stefano et al. (U.S. Patent Applications are not submitted herewith pursuant to the waiver of 37 C.F.R. § 1.98(a)(2)(iii) issued by the Office on Sep. 21, 2004).
U.S. Appl. No. 17/671,249, filed Feb. 14, 2022, by Robert et al. (U.S. Patent Applications are not submitted herewith pursuant to the waiver of 37 C.F.R. § 1.98(a)(2)(iii) issued by the Office on Sep. 21, 2004).
Valenzano et al., "Soluble Insulin-Like Growth Factor II/Mannose 6-Phosphate Receptor Carries Multiple High Molecular Weight Forms of Insulin-like Growth Factor II in Fetal Bovine Serum" J. Biol. Chem. 270:16441-16448 (Jul. 1996).
Van Der Ploeg et al., "Breakdown of Lysosomal Glycogen in Cultured Fibroblasts from Glycogenosis Type II Patients After Uptake of Acid α-Glucosidase" J. Neurolog. Sci. 79:327-336 (1987).
Van Der Ploeg et al., "Intravenous Administration of Phosphorylated Acid α-Glucosidase Leads to Uptake of Enzyme in Heart and Skeletal Muscle of Mice" J. Clin. Invest. 87:513-518 (1991).
Van Der Ploeg et al., "Prospect for Enzyme Therapy in Glycogenosis II Variants: A Study on Cultured Muscle Cells" J. Neurol. 235:392-396 (1988).
Van Der Ploeg et al., "Receptor-Mediated Uptake of Acid α-Glucosidase Corrects Lysosomal Glycogen Storage in Cultured Skeletal Muscle" Pediatr. Res. 24(1):90■94 (1988).
Van Diggelen et al., "A new fluorimetric enzyme assay for the diagnosis of Niemann-Pick A/B with specificity of natural sphingomyelinase substrate" J. Inherit. Metab. Dis. 28:733-741 (2005).
Van Heest et al., "Surgical Treatment of Carpal Turmel Syndrome and Trigger Digits in Children with Mucopolysaccharide Storage Disorders" J. Hand Surg. 23(2):236-243 (Mar. 1998).
Van Hove et al., "High-Level Production of Recombinant Human Lysosomal Acid α-Glucosidase in Chinese Hamster Ovary Cells which Targets to Heart Muscle and Corrects Glycogen Accumulation in Fibroblasts from Patients with Pompe Disease" Proc. Natl. Acad. Sci. USA 93:65-70 (Jan. 1996).
Van Rossenberg et al., "Improvement of Hepatocyte-Specific Gene Expression by a Targeted Colchicine Prodrug" ChemBioChem 4:633-639 (2003).
Varki et al., "Structural Studies of Phosphorylated High Mannose-type Oligosaccharides" J. Biol. Chem. 255:10647-10858 (1980).
Vilaseca et al., "Protein Conjugates of Defined Structure: Synthesis and Use of a New Carrier Molecule" Bioconj. Chem. 4:515-520 (1993).
Vogler et al., "Enzyme Replacement in Murine Mucopolysaccharidosis Type VII: Neuronal and Glial Response to β-Glucuronidase Requires Early Initiation of Enzyme Replacement Therapy" Pediatr. Res. 45(6):838-844 (1999).
Voskoboeva et al., "Four Novel Mutant Alleles of the Arylsulfatase B Gene in Two Patients with Intermediate Form of Mucopolysaccharidosis VI (Maroteaux-Lamy syndrome)" Hum. Genet. 93(3):259-264 (1994).

Voznyi et al., "A fluorimetric enzyme assay for the diagnosis of MPS II (Hunter disease)" J. Inherit. Metab. Dis. 24:675-680 (2001).
Wadhwa et al., "Receptor Mediated Glycotargeting" J. Drug Targeting 11(5):255-268 (2003).
Wagner et al., "Coupling of adenovirus to transferrin-polylysine/DNA complexes greatly enhances receptor-mediated gene delivery and expression of transfected genes" Proc. Natl. Acad. Sci. USA 89:6099-6103 (Jul. 1992).
Wang et al., "Addition of the keto functional group to the genetic code of *Escherichia coli*" PNAS 100(1):56-61 (Jan. 2003).
Wang et al., "Single-Chain Fv with manifold N-glycans as bifunctional scaffolds for immunomolecules" Protein Eng. 11(12):1277-1283 (1998).
Wender et al., "The design, synthesis, and evaluationof molecules that enable or enhance cellular uptake: Peptold molecular transporters" PNAS 97(24):13003-13008 (2000).
Wieder et al., "Enzyme Therapy: II. Effect of Covalent Attachment of Polyethylene Glycol on Biochemical Parameters and Immunological Determinants of β-Glucosidase and α-Galactosidase" J. Appl. Biochem. 5:337-347 (1983).
Wilchek et al., "Labeling Glycoconjugates with Hydrazide Reagents" Meth.. Enzymol. 138:429-442 (1987).
Wilcox et al., "Long-Term Safety and Efficacy of Enzyme Replacement Therapy for Fabry Disease" Am. J. Hum. Genet. 75:65-74 (2004).
Wilson et al., "Sequence of the Human iduronate 2-Sulfatase (IDS) Gene" Genomics 17:773-775 (1993).
Wilson et al., "Hunter syndrome: Isolation of an iduronate-2■sulfatase cDNA clone and analysis of patient DNA" Proc. Natl. Acad. Sci. USA 87:8531-8535 (Nov. 1990).
Wiseman et al., "Daclizumab: A Review of its Use in the Prevention of Acute Rejection in Renal Transplant Recipients" Drugs 58(6):1029-1042 (Dec. 1999).
Wraith et al., "Limitations of enzyme replacement therapy: Current and future" J. Inherit. Metab. Dis. 29:442-447 (2006).
Wraith, "Advances in the Treatment of Lysosomal Storage Disease" Dev. Med. Child Neurol. 43:639-646 (2001).
Wu et al., "Targeting Hepatocytes for Drug and Gene Delivery Emerging Novel Approaches and Applications" Frontiers in Bioscience 7:717-725 (Mar. 1, 2002).
Yamazaki et al., "Synthesis of α-o-Manp-(1--3)-[β-o-GlcpNAc-(1--4)]-[-α-o-Manp-(1 -- 6)]-β-o-Manp-(1-4)-[β-o-GlcpNAc-(1-4)-[α-L-Fucp-(1-6)]-o-GlcpNAc, a core glycoheptaose of a 'bisected' complex-type glycan of glycoproteins" Carb. Res. 201:31-50 (1990).
Yamazaki et al., "Endogenous Lectins as Targets for Drug Delivery" Adv. Drug Deliv. Rev. 43:225-244 (2000).
Yang et al., "Pedigree Analysis of α-L-Fucosidase Gene Mutations in Fucosidosis Family" Biochim. Biophys. Acta 1182(3):245-249 (Oct. 1993).
Ye, Z. et al. (May 17, 2006). "Receptor-Mediated Hepatic Uptake of M6P-BSA-Conjugated Triplex-Forming Oligonucleotides in Rats," Bioconjugate Chemistry 17(3):823-830.
Yoon et al., "Targeted gene correction of episomal DNA in mammalian cells mediated by a chimeric RNA-DNA oligonucleotide" Proc. Natl. Acad. Sci. USA 93:2071-2076 (Mar. 1996).
Young et al., Plasma Chilotriosidase Activity in Gaucher Disease Patients Who Have Been Treated Either by Bone Marrow Transplantation or by Enzyme Replacement Therapy with Alglucerase J. Inherit. Metab. Dis. 20(4):595-602 (Aug. 1997).
Yurkovetskiy et al., "Fully Degradable Hydrophilic Polyals for Protein Modification" Biomacromolecules 6:2648-2658 (2005).
Zalipsky et al., "Hydrazide Derivatives of Poly(ethylene glycol) and Their Bioconjugates" Poly(ethylene glycol) Chemistry and Biological Applications 680:318-341 (1997).
Zara et al., "A Carbohydrate-Directed Heterobifunctional Cross-Linking Reagent for the Synthesis of Immunoconjugates" Anal. Biochem. 194:156-162 (1991).
Zarate et al., "Lysosomal Storage Disease 3: Fabry's Disease" Lancet 372:1427-1435 (Oct. 2008).
Zhang et al., "Impact of Premature Stop Codons on mRNA Levels in Infantile Sandhoff Disease" Hum. Molec. Genet. 3(1):139-145 (Jan. 1994).

(56) References Cited

OTHER PUBLICATIONS

Zhang et al., "Linking Carbohydrates to Proteins Using N-(2,2-Dimethoxyethyl)-6-hydroxy Hexanamide" Tetrahedron 54:11783-11792 (1998).

Zhang et al., "Global Non-Viral Gene Transfer to the Primate Brain Following Intravenous Administration" Mol. Ther. 7:1-8 (2003).

Zhao et al., "Purification and Characterization of Recombinant Human α-N-Acetylglucominidase Secreted by Chinese Hamster Ovary Cells" Prot. Expression Purif. 19:202-211 (2000).

Zhou et al., "Mannose 6-Phosphate Quantilation in Glycoproteins Using High■pH Anion-Exchange Chromatography with Pulsed Amperometric Detection" Anal. Biochem. 306:163-170 (2002).

Zhou et al., "Strategies for Neoglycan Conjugation to Human Acid α-Glucosidase" Bioconj. Chem. 22:741-751 (2011).

Zhu et al., "Glycoengineered Acid α-Glucosidase with improved Efficacy at Correcting the Metabolic Aberrations and Motor Function Deficits in a Mouse Model of Pompe Disease" Mol. Ther. 17(6):954-963 (Jun. 2009).

Zhu et al., "Carbohydrate-remodeled acid α-glucosidase with higher affinity for the cation-independent mannose 6-phosphate receptor demonstrates improved delivery to muscles of Pompe mice" Biochem. J. 389:619-628 (2005).

Zhu et al., "Carbohydrate-remodeled acid α-glucosidase with higher affinity for the cation-independent mannose 6-phosphate receptor demonstrates improved delivery to muscles of Pompe mice" Manuscript for publication in Biochem J. Manuscript No. BJ20050384, 36 pages (Apr. 20, 2005).

Zhu et al., "Conjugation of Mannose 6-Phosphate containing Oligosaccharides to Acid α-Glucosidase Improves the Clearance of Glycogen in Pompe Mice" J. Biol. Chem. 279(48):50336-50341 (Nov. 2004).

Ziegler et al., "AAV2 Vector Harboring a Liver-Restricted Promoter Facilitates Sustained Expression of Therapeutic Levels of α-Galactosidase A and the Induction of Immune Tolerance in Fabry Mice" Mol. Ther. 9(2)231-240 (Feb. 2004).

Ziegler et al., "Correction of Enzymatic and Lysosomal Storage Defects in Fabry Mice by Adenovirus-Mediated Gene Transfer" Hum. Gene Ther. 10(10):1667-1682 (Jul. 1999).

Ziegler et al., "Correction of the Nonlinear Dose Response Improves the Viability of Adenoviral Vectors for Gene Therapy of Fabry Disease" Hum. Gene Ther. 13:935-945 (May 2002).

U.S. Appl. No. 17/162,541, filed Jan. 29, 2021 by Zhu et al. (U.S. Patent Applications are not submitted herewith pursuant to the waiver of 37 C.F.R. § 1.98(a)(2)(iii) issued by the Office on Sep. 21, 2004).

U.S. Appl. No. 17/224,535, filed Apr. 7, 2021, by Zhu et al. (U.S. Patent Applications are not submitted herewith pursuant to the waiver of 37 C.F.R. § 1.98(a)(2)(iii) issued by the Office on Sep. 21, 2004).

U.S. Appl. No. 18/379,110, filed Oct. 11, 2023, by Zhu et al. (U.S. Patent Applications are not submitted herewith pursuant to the waiver of 37 C.F.R. § 1.98(a)(2)(iii) issued by the Office on Sep. 21, 2004).

U.S. Appl. No. 18/637,271, filed Apr. 16, 2024, by Zhu et al. (U.S. Patent Applications are not submitted herewith pursuant to the waiver of 37 C.F.R. § 1.98(a)(2)(iii) issued by the Office on Sep. 21, 2004).

\* cited by examiner

Note: "Oxidized ◆" denotes oxidized sialic acid; "●" denotes galactose (residue MW: 162.1Da); "○" denotes mannose (residue MW: 162.1Da); "■" denotes GlcNAc (residue MW: 203.2Da); "AA" denotes anthranilic acid (residue MW: 120.1Da)

Total ion chromatograms (TIC) from normal phase HPLC analysis of PNGase F released native oligosaccharides from rhGAA and NeoGAA SAM6 prepared using 2 and 7.5 mM periodate.

1 Oligomannose 5
2 Oligomannose 6
3 Oxidized A1F, A1, A1-GlcNAc+Hex
4 Phosphorylated oligomannose 5&6
5 Bis-phosphorylated oligomannose 7
6 Monoconjugated A1F
7 Monoconjugated A1
8 Free glycan (cleavage at hydroxylamine oxygen)
9 Monoconjugated A2F +1 oxidized NANA
10 Monoconjugated A2 +1 oxidized NANA
11 Biconjugated A2F
12 Biconjugated A2

FIG. 15A
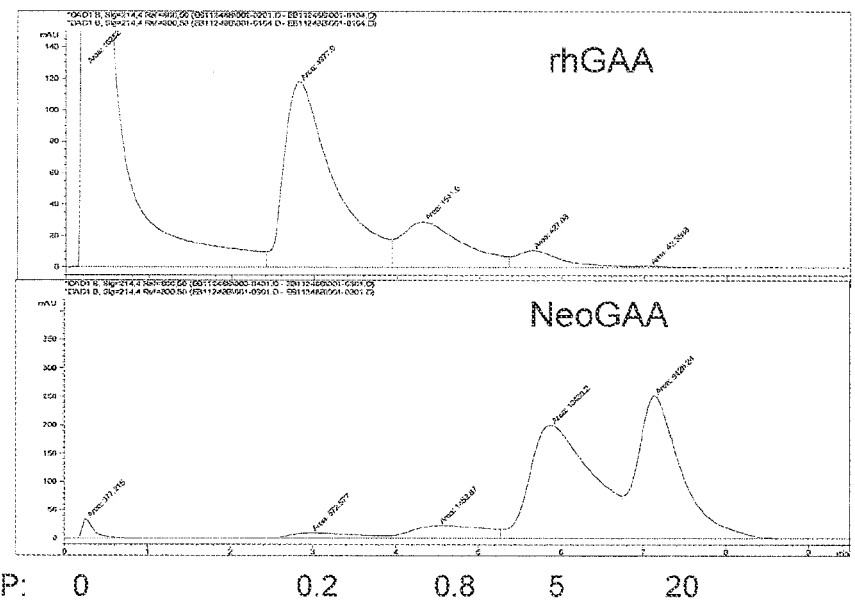
FIG. 15B
mM M6P:   0          0.2      0.8       5       20
FIG. 15C
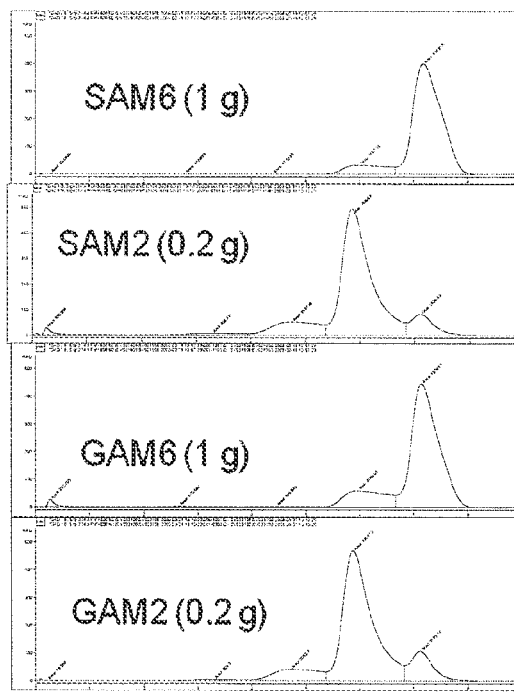

OLIGOSACCHARIDE-PROTEIN CONJUGATES

This application is a continuation of U.S. patent application Ser. No. 16/581,148, filed Sep. 24, 2019, which is a divisional of U.S. patent application Ser. No. 15/288,486, filed Oct. 7, 2016, now U.S. Pat. No. 10,464,962, which is a continuation of U.S. patent application Ser. No. 14/445,941, filed Jul. 29, 2014, now U.S. Pat. No. 9,493,498, which is a continuation of U.S. patent application Ser. No. 13/140,272, filed Aug. 25, 2011, which adopts the international filing date of Dec. 11, 2009, now U.S. Pat. No. 8,835,614, which is a national stage filing under 35 U.S.C. § 371 of International Application No. PCT/US2009/067775, filed Dec. 11, 2009, and which claims the benefit of priority of U.S. Provisional Application No. 61/122,851, filed Dec. 16, 2008, the disclosures of which are herein incorporated by reference in their entireties.

The invention relates generally to oligosaccharide-protein conjugates comprising particular oligosaccharides, and to compositions comprising such conjugates. The invention further relates to methods of treating lysosomal storage disorders using oligosaccharide-lysosomal enzyme conjugates.

Lysosomal storage disorders (LSDs) are a class of rare metabolic disorders comprising over forty genetic diseases involving a deficiency in the activity of lysosomal hydrolases. A hallmark feature of LSDs is the abnormal accumulation of lysosomal metabolites, which leads to the formation of large numbers of distended lysosomes.

LSDs can be treated by administration of the active version of the enzyme deficient in the subject, a process termed enzyme replacement therapy (ERT). The administered replacement enzyme bearing a terminal mannose-6-phosphate (M6P) is taken up by target cells through cell-surface-associated cation-independent M6P receptor (CI-MPR)-mediated endocytosis, and directed to the lysosome.

In general, poorly phosphorylated replacement enzymes are not efficiently internalized by the M6P receptor on cell surfaces, and therefore cannot be directed to the lysosome where they function. Consequently, a low degree of mannose phosphorylation can have a significant and deleterious effect on the therapeutic efficacy of a replacement enzyme.

Methods have been developed for increasing the M6P content of replacement enzymes. For example, U.S. Pat. Nos. 6,534,300; 6,670,165; and 6,861,242 describe the enzymatic phosphorylation of terminal mannose residues. In another example, U.S. Pat. No. 7,001,994 describes a method for coupling oligosaccharides comprising MOP with glycoproteins. A conjugate of the lysosomal enzyme acid α-glucosidase (GAA) with a bis-M6P oligosaccharide prepared by that method was found to be more effective in reducing skeletal and cardiac muscle glycogen than recombinant human GAA in a murine model of Pompe disease, an autosomal recessive muscular disease resulting from a metabolic deficiency of GAA, and characterized by the accumulation of lysosomal glycogen. Similarly, Zhu et al. describe coupling a synthetic bis-M6P oligosaccharide (Formula A) with GAA. Zhu et al., *Biochem. J.* 389:619-628 (2005). Formula A was designed from the natural, triantennary $Man_9$ core structure of N-linked glycans (Formula B) by removing one branch, shortening another branch, and phosphorylating the terminal mannose residues.

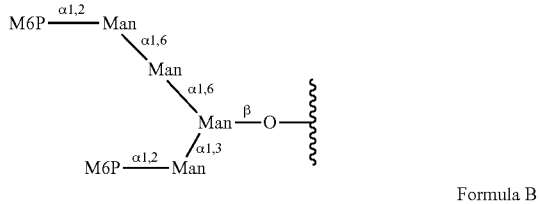

Formula A

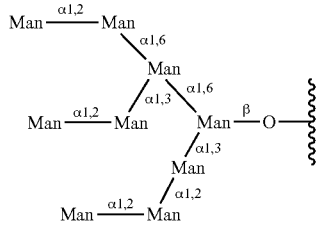

Formula B

The resulting conjugate bound to CI-MPR with increased affinity, was internalized more efficiently by L6 myoblasts, and had approximately normal enzymatic activity. In spite of this success, however, it remains important to identify novel oligosaccharides that may result in improved affinity for CI-MPR and/or more efficient cellular internalization when conjugated to lysosomal enzymes, while maintaining normal or near-normal enzymatic activity. Improved uptake alone, however, does not necessarily result in a better therapeutic outcome. Certain conjugation strategies and oligosaccharides result in conjugates with lower enzymatic activity. It is therefore desirable to identify oligosaccharides and conjugates that can improve therapeutic outcomes for subjects with LSDs.

In addition, certain oligosaccharides such as those shown in Formulas A and B can be difficult and expensive to synthesize. Furthermore, making β-linked saccharides in a stereoselective manner has been a difficult problem in carbohydrate chemistry. Alternate oligosaccharides and synthesis methods may be more practical for use on a commercial scale. An additional need exists for optimizing methods used to prepare oligosaccharide-protein conjugates. In particular, for therapeutic purposes, conjugate preparations should not be highly heterogeneous, as this may result in inconsistent biological function. Multiple aspects of the conjugates may affect therapeutic efficacy, including the oligosaccharides and linkers used, conjugation methods, purification methods, and formulations.

Accordingly, certain embodiments of the invention provide oligosaccharide-protein conjugates comprising (1) a protein and (2) an oligosaccharide of Formula I:

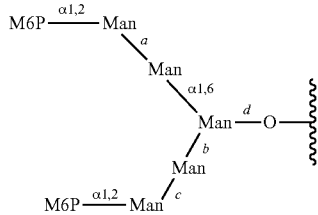

Formula I wherein:
a=α1,2; α1,3; α1,4; or α1,6;
b=α1,2; α1,3; or α1,4;

c=α1,2; α1,3; α1,4; or α1,6; and
d=α, β, or a mixture of α and β.

Other embodiments of the invention provide oligosaccharide-protein conjugates comprising (1) a protein and (2) an oligosaccharide of Formula II:

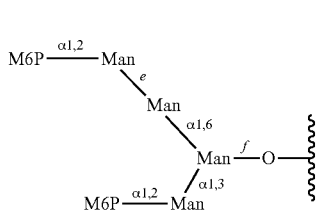

Formula II wherein:
e=α1,2; α1,3; α1,4; or α1,6 and
f=α, β, or a mixture of α and β,
with the proviso that f=α or a mixture of α and β when e=α1,6.

Still other embodiments of the invention provide oligosaccharide-protein conjugates comprising (1) a protein and (2) an oligosaccharide of Formula III:

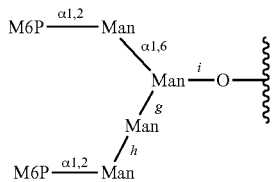

Formula III wherein:
g=α1,2; α1,3; or α1,4;
h=α1,2; α1,3; α1,4; or α1,6; and
i=α, β, or a mixture of α and β.

Additional embodiments of the invention provide oligosaccharide-protein conjugates comprising (1) a protein and (2) an oligosaccharide of Formula IV:

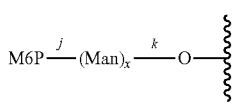

Formula IV wherein:
j is α1,2;
k is selected from α, β, and a mixture of α and β;
x is 1, 2, or 3; and
when x is 2 or 3, the linkage between each mannose is selected from α1,2; α1,3; α1,4; and α1,6.

Further embodiments provide oligosaccharide-protein conjugates comprising (1) a protein and (2) an oligosaccharide of Formula V:

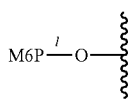

Formula V wherein:
l is selected from α, β, and a mixture of α and β.

Additional embodiments provide oligosaccharide-protein conjugates comprising (1) a protein and (2) an oligosaccharide of Formula VI:

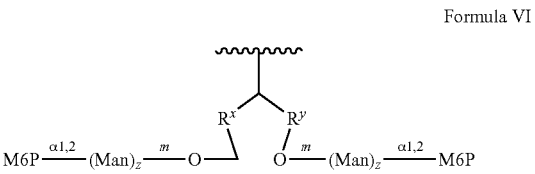

Formula VI wherein:
$R^x$ and $R^y$ are each independently chosen from polyethylene glycol and $C_1$-$C_{10}$ alkyl optionally substituted with oxo, nitro, halo, carboxyl, cyano, or lower alkyl, and optionally interrupted with one or more heteroatom selected from N, O, or S;
z is selected from 0, 1, 2, 3, or 4;
m is selected from α, β, and a mixture of α and β; and
when y is 2, 3, or 4, the linkage between each mannose is selected from α1,2; α1,3; α1,4; and α1,6.

In additional embodiments, the invention provides oligosaccharide-protein conjugates comprising (1) a protein and (2) an oligosaccharide of Formula A.

In certain embodiments, the conjugate comprises at least 2, 3, 4, or 5 moles of the oligosaccharide of Formula A per mole of the protein.

In some embodiments, the oligosaccharide-protein conjugates of the invention comprise a linker between the oligosaccharide and protein components of the conjugate.

The invention provides pharmaceutical compositions comprising oligosaccharide-protein conjugates of Formula I, II, III, IV, V, or VI and a filler, bulking agent, disintegrant, buffer, stabilizer, or excipient. The invention further provides methods of treating a lysosomal storage disorder such as, e.g., those disclosed in Table 1 infra, with an oligosaccharide-protein conjugate of Formula I, II, III, IV, V, or VI, or a pharmaceutical composition comprising such an oligosaccharide-protein conjugate. The lysosomal storage disorder may be chosen from, e.g., Fabry disease, Pompe disease, Niemann-Pick A disease, Niemann-Pick B disease, and mucopolysaccharidosis I. In further embodiments, the invention provides the use of an oligosaccharide-protein conjugate comprising (1) a protein and (2) an oligosaccharide of Formula I, II, III, IV, V, or VI in the manufacture of a medicament for treating a lysosomal storage disorder in a subject in need thereof.

Additional embodiments of the invention are discussed throughout this application. Other objects, features, and advantages of the present invention will become apparent from the following detailed description. Any embodiment discussed with respect to one aspect of the invention applies to other aspects of the invention as well and vice versa. The embodiments in the Example section are understood to be embodiments of the invention that are applicable to all aspects of the invention.

It should be understood, however, that the detailed description and the specific examples, while indicating specific embodiments of the invention, are given by way of illustration only, since various changes and modifications within the spirit and scope of the invention will become apparent to those skilled in the art from this application.

BRIEF DESCRIPTION OF THE FIGURES

FIG. 9A shows the amount of SAM2, SAM3, SAM4, Linear SAM4, αSAM6, and βSAM6 oligosaccharides conjugated with GAA in varying molar ratios. FIG. 9B shows the amount of hexasaccharide (glycan) conjugated with rhGAAs oxidized using different amounts of periodate.

FIG. 10A shows oxidation as monitored by monosaccharide composition analysis (oxidation inferred based upon the reduction in quantified monosaccharide amounts). FIG. 10B shows LTQ MS detection of AA-labeled SAM6 oligosaccharides in positive mode. FIGS. 10C and 10D show an MS/MS spectrum corresponding to AA-labeled oxidized oligosaccharides. FIG. 10E shows monosaccharide analysis of GAM conjugate titrated with various amount of GAO.

FIG. 13A Sensorgram showing association, dissociation. MOP elution, and regeneration phases for each sample injection, FIG. 13B Representative 4-parameter fit of sensorgram data for NeoGAA samples and rhGAA control sample. FIG. 13C M6P receptor affinity of NeoGAA samples prepared using 2 mM vs. 7.5 mM periodate, across different conjugation levels for each preparation.

FIGS. 15A, 15B, 15C, 15D, 15E, and 15F show elution of NeoGAA conjugates from a M6P receptor column. FIG. 15F shows Tissue Glycogen Levels in GAAKO Mice Following Administration of 4-Weekly doses of SAM6 Conjugates.

DESCRIPTION OF THE EMBODIMENTS

Figure 1:
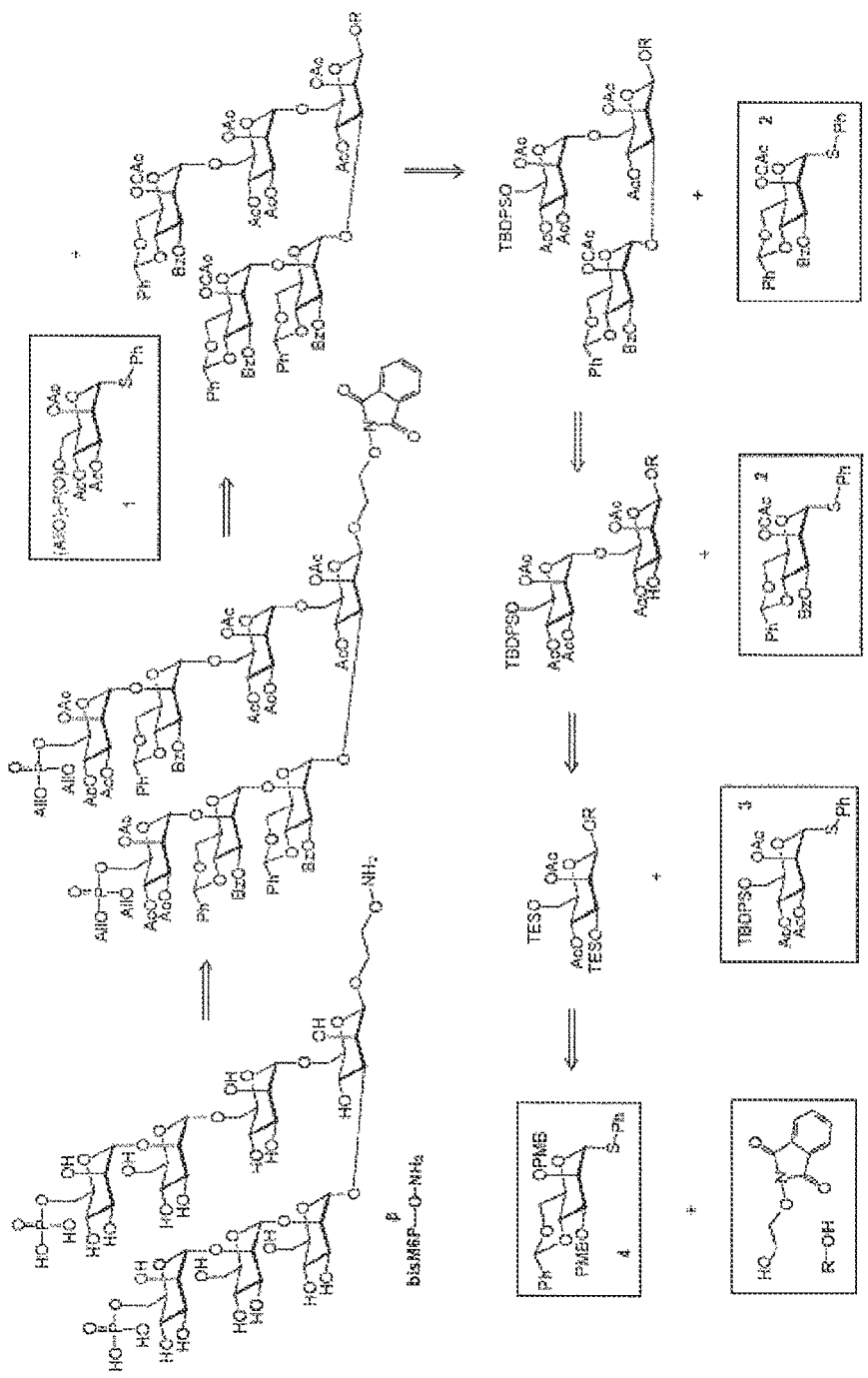
FIG. 1 depicts an exemplary retrosynthetic scheme setting forth the steps for synthesis of Oligosaccharide 82.
Figure 2:
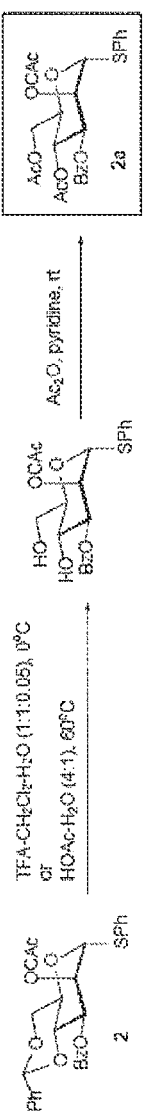
FIG. 2 depicts an exemplary synthesis of monosaccharide building block 2a that may be employed in the synthesis of oligosaccharides described herein.
Figure 3:
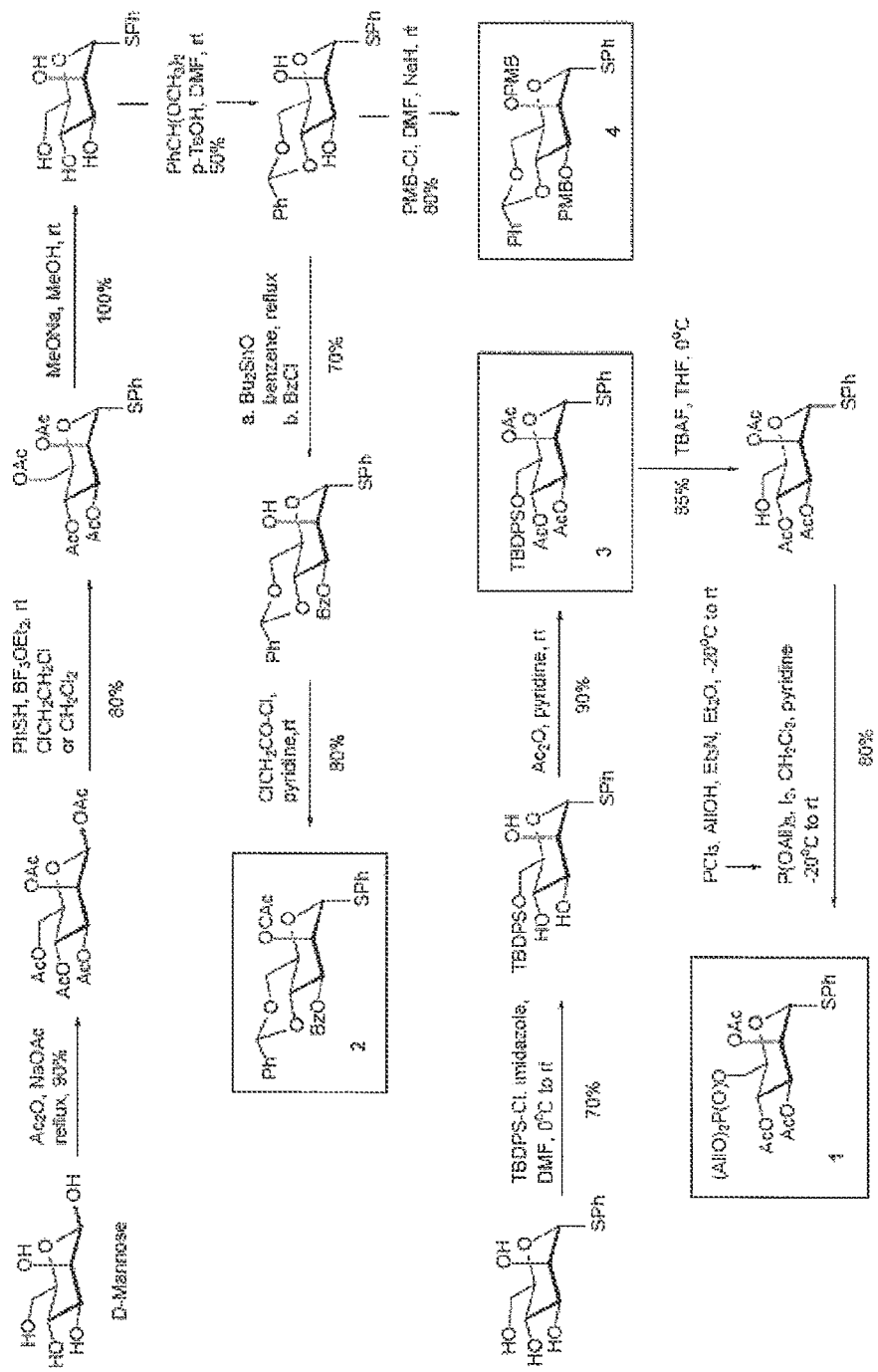
FIG. 3 depicts exemplary syntheses of monosaccharide building blocks 1, 2, 3, and 4 that may be employed in the synthesis of oligosaccharides described herein.
Figure 4:
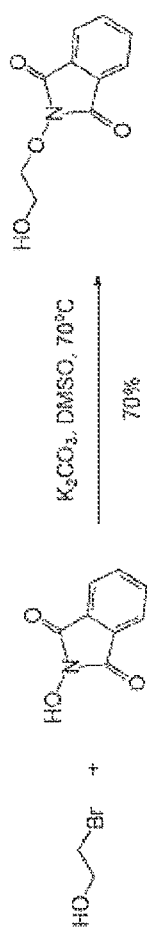
FIG. 4 depicts a synthetic scheme for the preparation of an ethylene linker.
Figure 5:
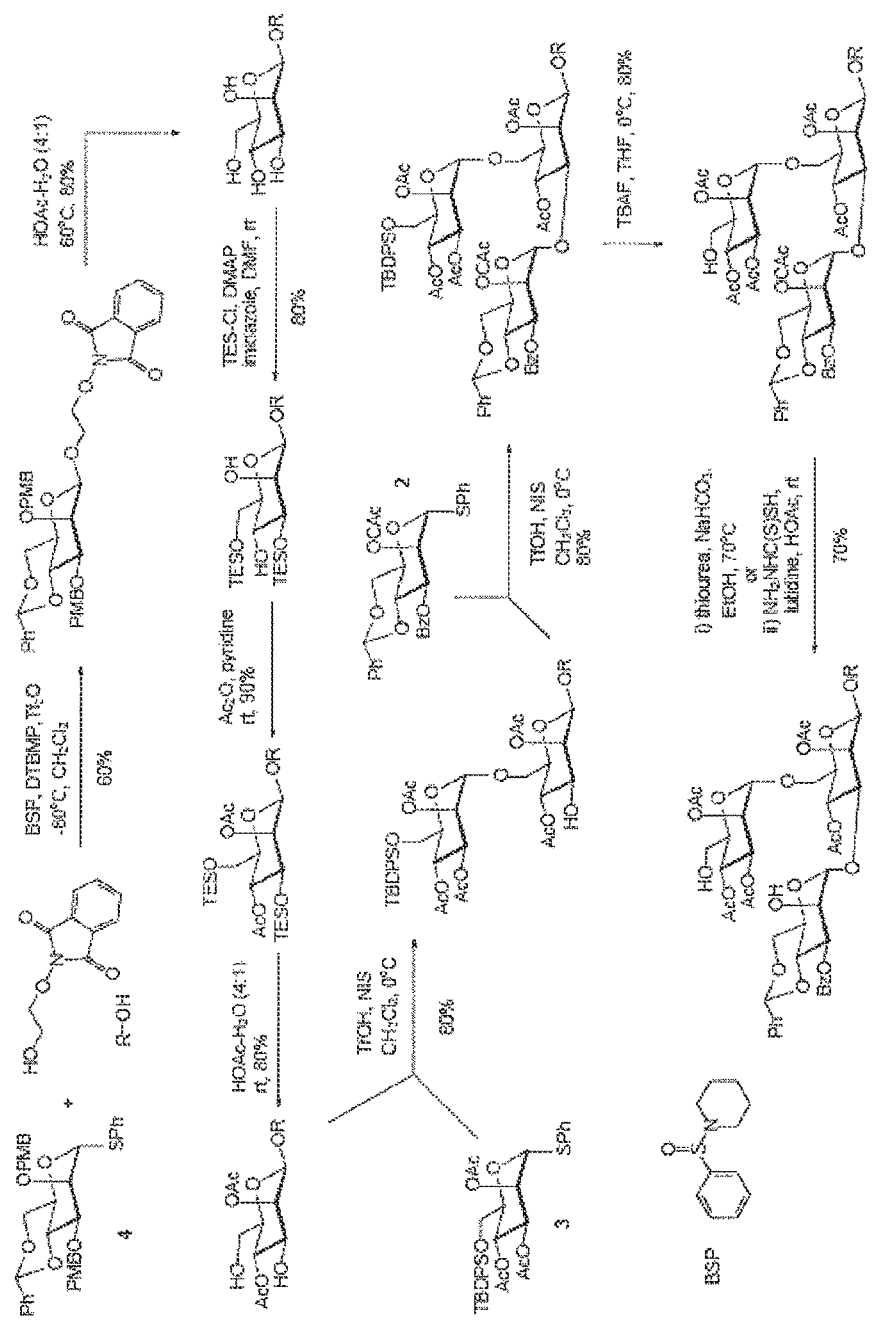
FIG. 5 depicts a synthetic scheme for the assembly of a trisaccharide precursor to Oligosaccharide 82 using building blocks 2, 3, and 4.
Figure 6:
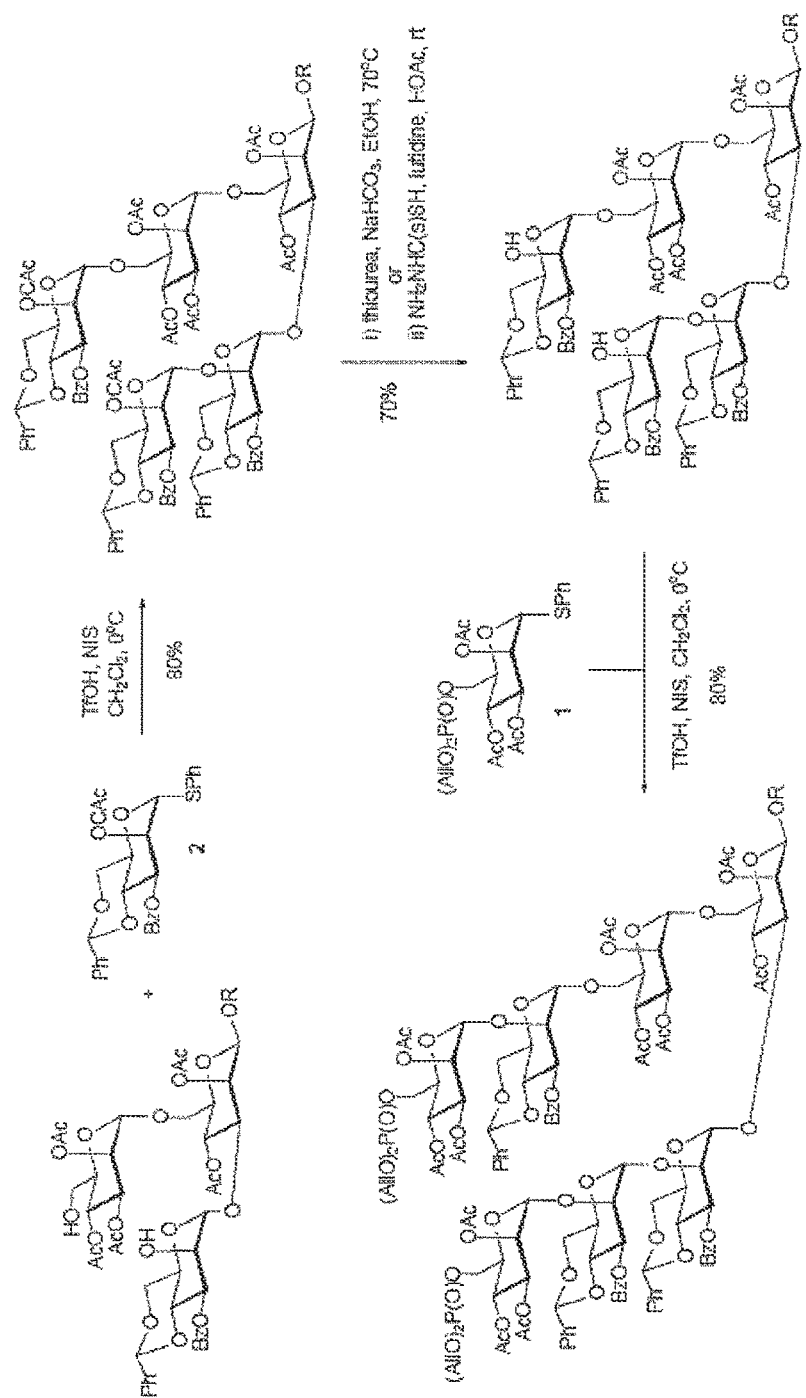
FIG. 6 depicts a synthetic scheme for the assembly of a protected heptasaccharide from the trisaccharide precursor described in FIG. 4.
Figure 7:
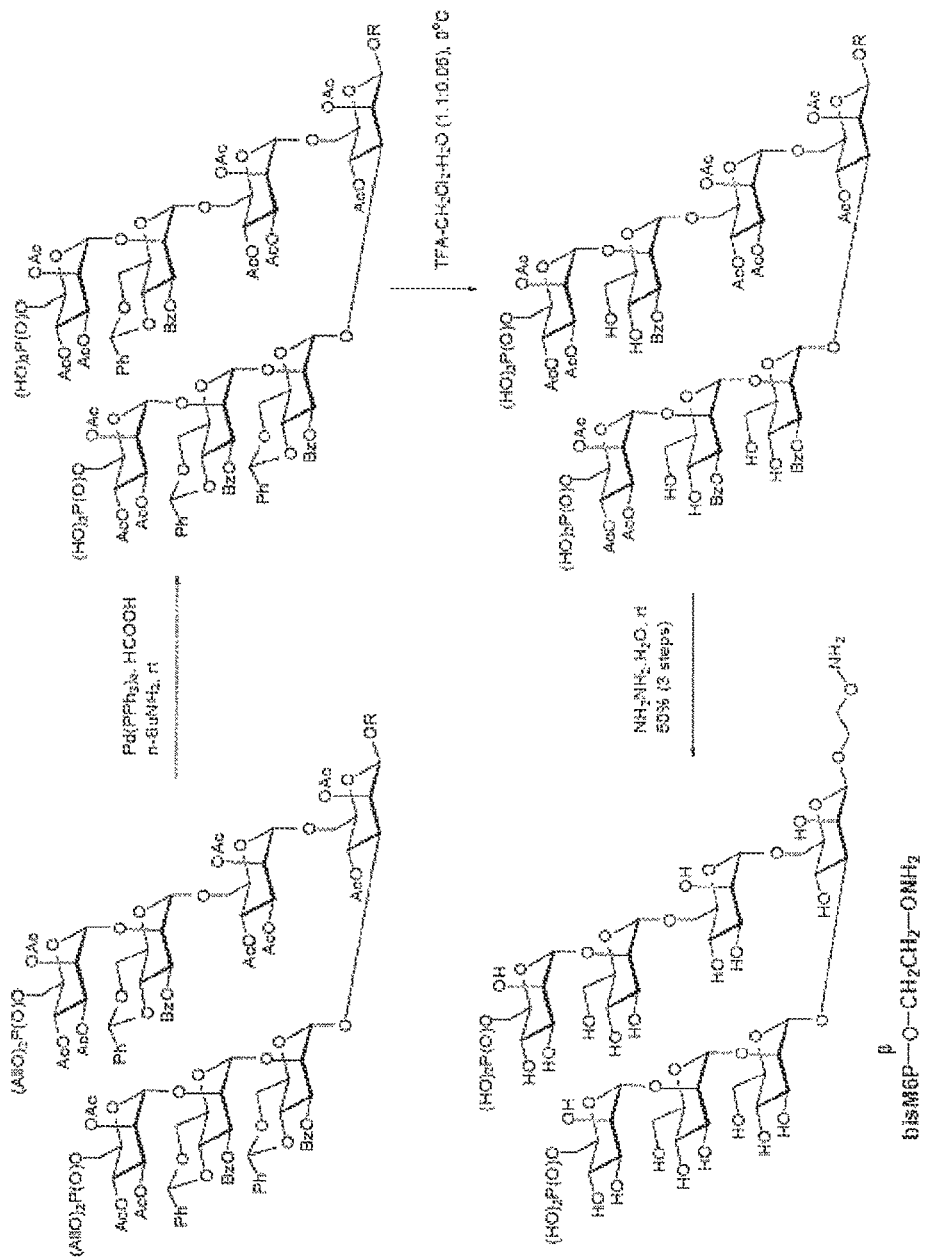
FIG. 7 depicts a synthetic scheme for deblocking the protected heptasaccharide described in FIG. 5, to yield Oligosaccharide 82.
Figure 8A:
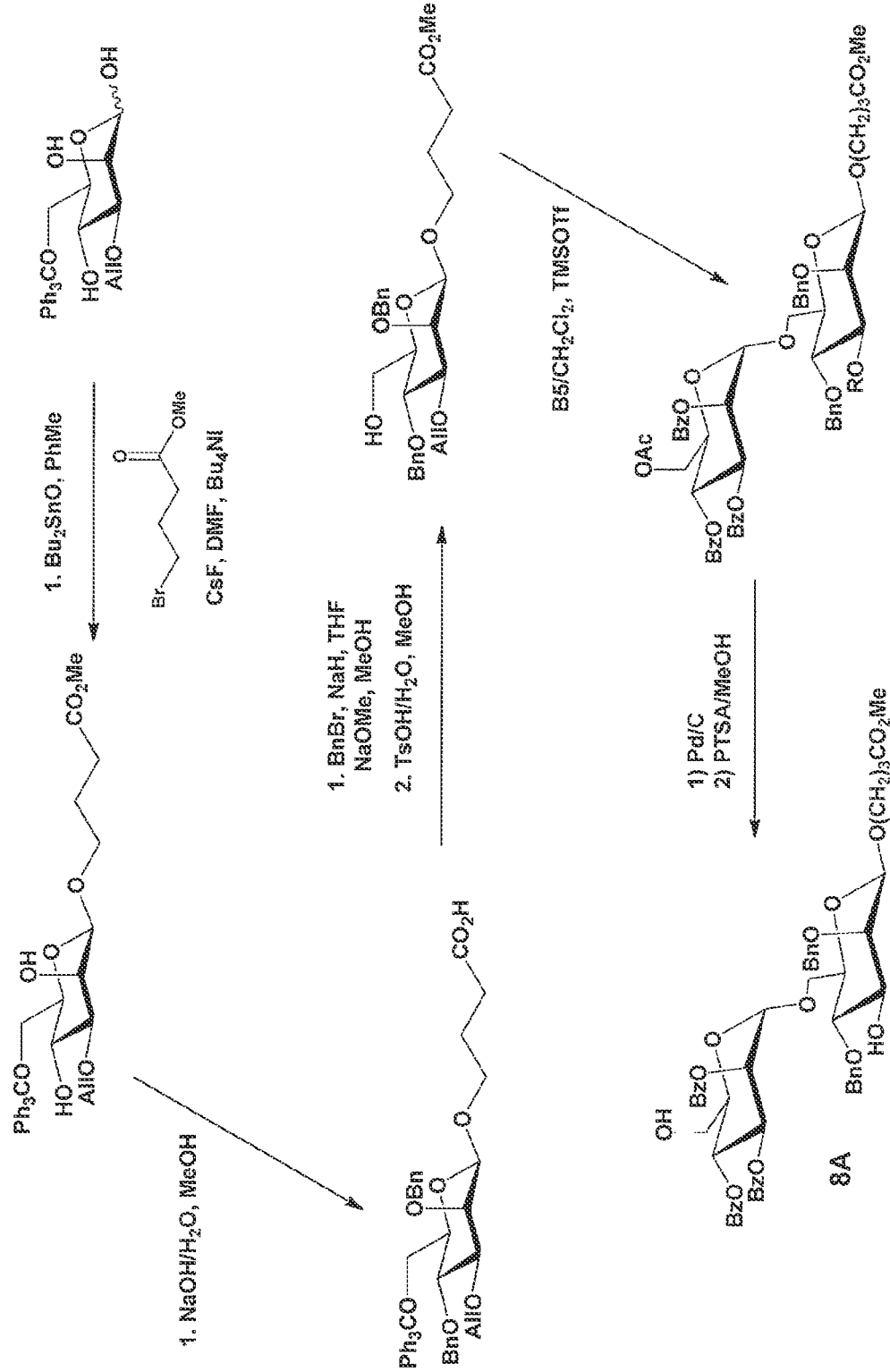
FIGS. 8A, 8B, 8C, 8D, and 8E depict a synthetic scheme for preparing a 3-linked hexasaccharide of Formula A using dibutyl tin to form a stereoselective intermediate, and an alternative form with a thiol-reactive group.
Figure 8B:
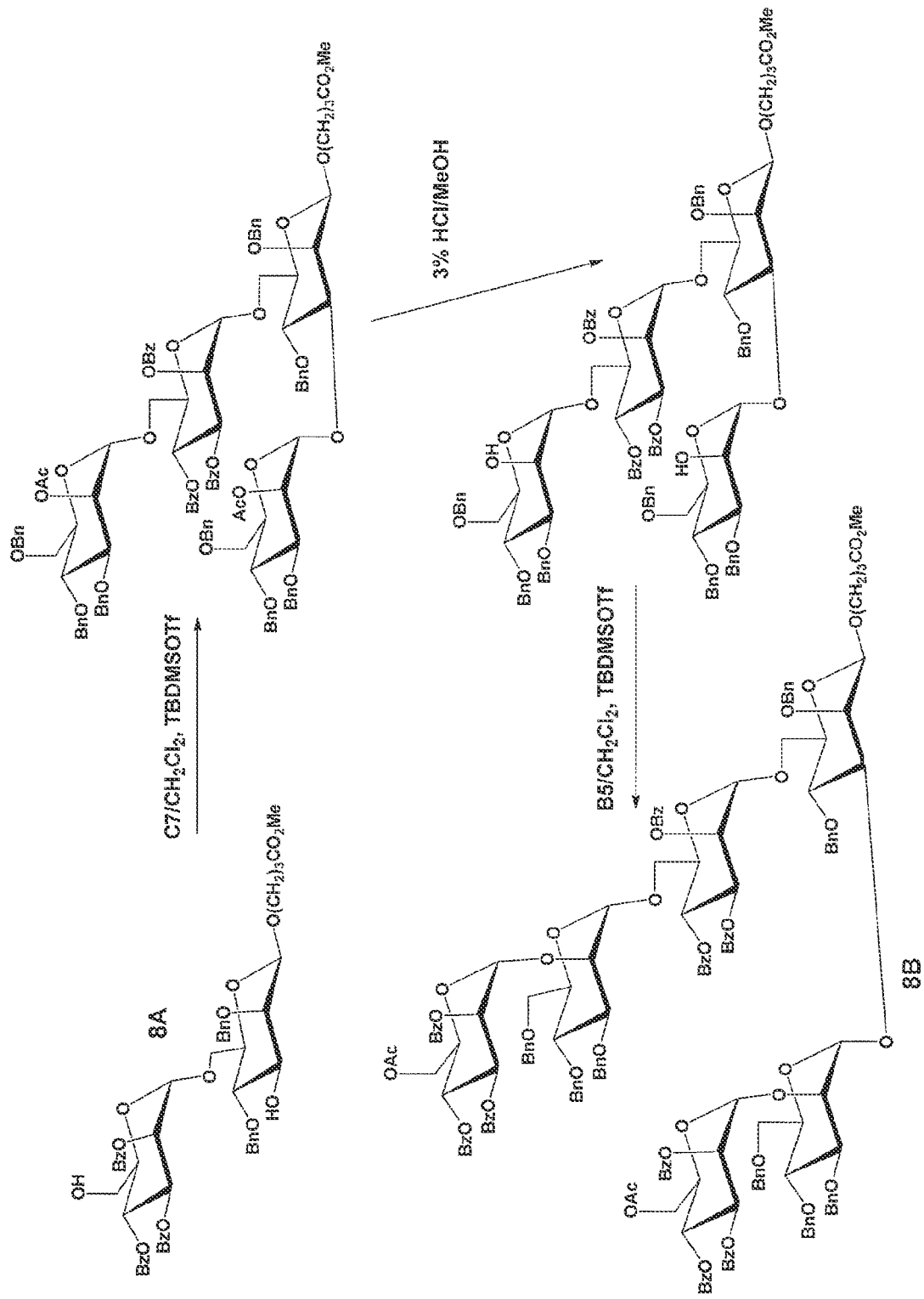
Figure 8C:
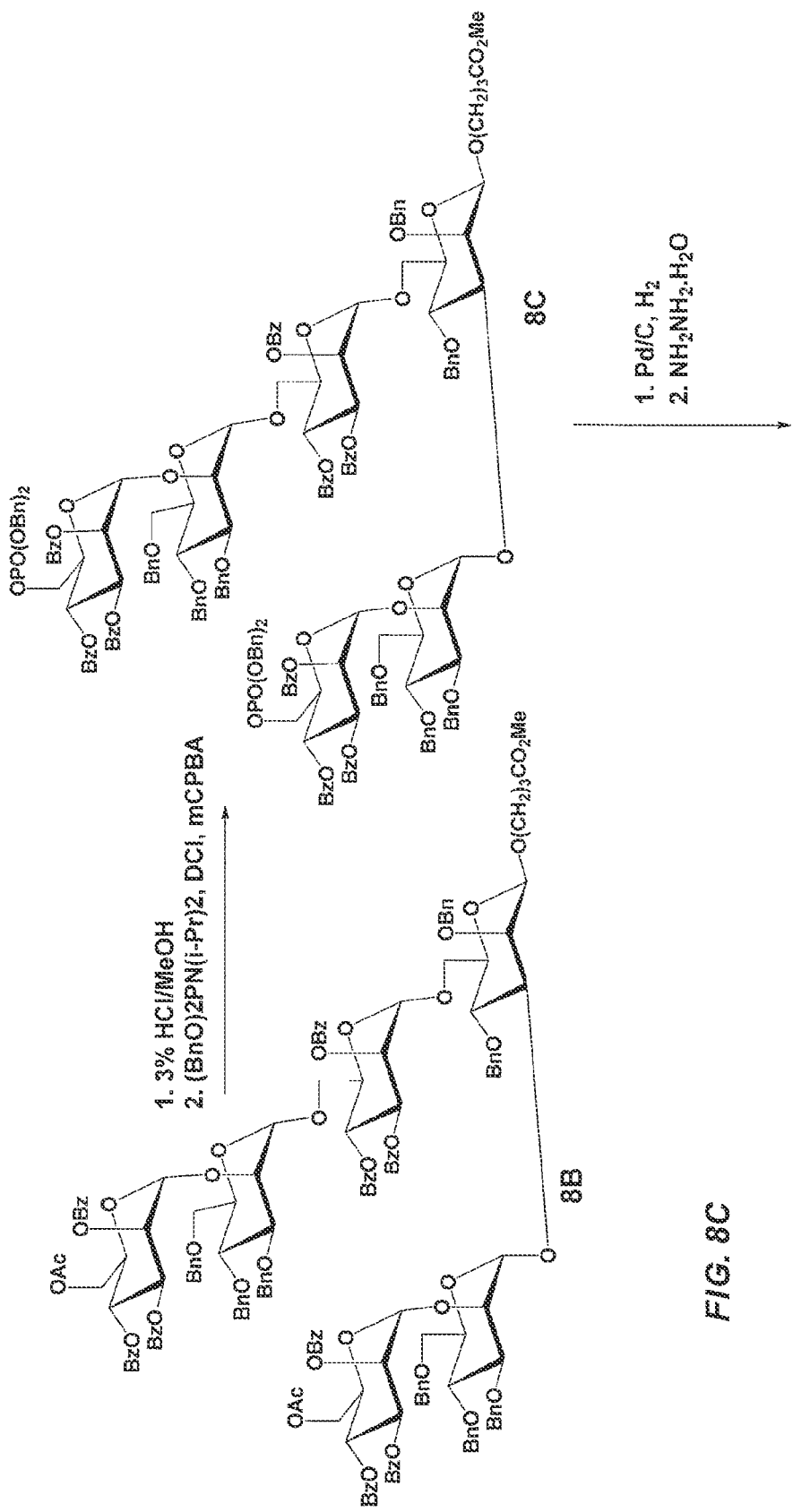
Figure 8D:
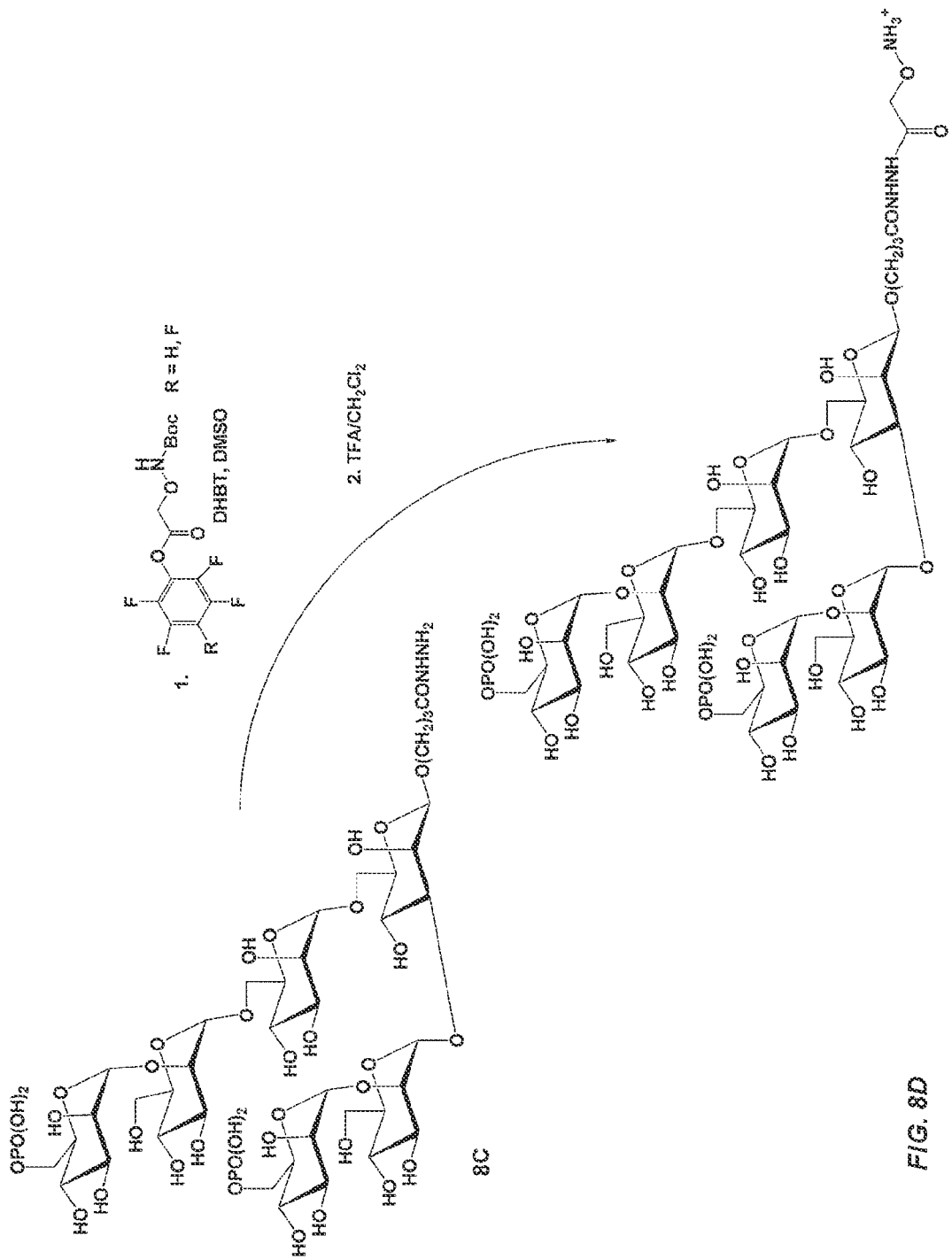
Figure 8E:
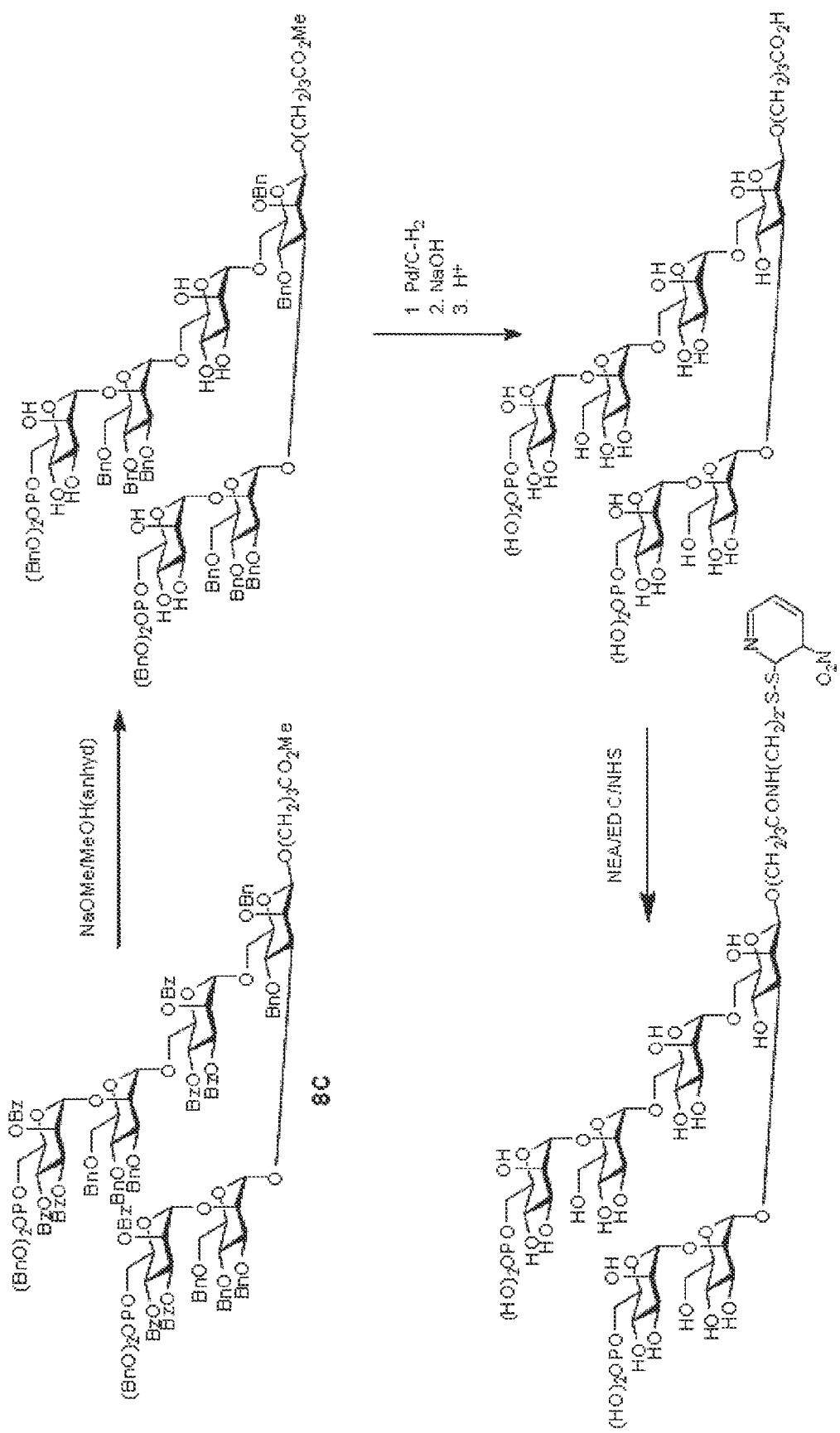

To assist in understanding the present invention, certain terms are first defined. Additional definitions are provided throughout the application.

As used in this specification and the appended claims, the singular forms "a," "an," and "the" include plural referents unless the cotenant clearly dictates otherwise. Thus, for example, reference to a method containing "a compound" includes a mixture of two or more compounds. The term "or" is generally employed in its sense including "and/or" unless the content clearly dictates otherwise.

I. Oligosaccharide-Protein Conjugates

In one embodiment, the invention provides oligosaccharide-protein conjugates, which may further comprise a linker. Exemplary oligosaccharides, proteins, linkers, conjugation methods, and conjugates are disclosed.

A. Oligosaccharide

The oligosaccharide may be chosen from biantennary oligosaccharide derivatives of Formula B or Formula VI, as depicted above, or linear oligosaccharide derivatives as shown in Formulas IV and V. Biantennary oligosaccharides, in general, have two terminal M6P residues, and may, in some embodiments, further comprise one or more penultimate M6P residues. Linear oligosaccharides have at least one M6P residue, and may comprise a terminal M6P residue. In general, the terminal M6P residues may be connected by an α1,2 linkage. (See Distler et al., *J. Biol. Chem.* 266: 21687-21692 (1991), observing that an α1,2 linkage at the terminal M6P resulted in greater binding to CI-MPR and the cation-dependent MPR (CD-MPR) than either α1,3 or α1,6 linkages.) In some embodiments the terminal M6P residues are connected, at their respective reducing ends, to the adjacent residue by an α1,2 linkage. In some embodiments, two terminal M6P residues are greater than 5, 10, 15, 20, 25, 30, 35, or 40 Å apart, as determined by, e.g., X-ray crystallography, NMR, and/or molecular modeling. For example, molecular modeling may be performed as described in Balaji et al., *Glycobiology* 4:497-515 (1994). In some embodiments, the oligosaccharide is chosen such that the terminal M6P residues have relatively little steric hindrance. In some embodiments, oligosaccharides in which the terminal M6P residues are relatively unhindered bind to CI-MPR with greater affinity than oligosaccharides in which the terminal M6P residues are hindered.

In general, the oligosaccharide will bind to CI-MPR. For example, the oligosaccharide may bind to CI-MPR with a dissociation constant less than, e.g., 500, 100, 50, 10, 5, 1, or 0.1 nM, or less than, e.g., 100, 50, 10, 5, 2, or 1 µM. The crystal structure of the N-terminal domains 1-3 of CI-MPR is known, in both ligand-bound and unbound forms. Olson et al., *J. Biol. Chem.* 279:34000-34009 (2004); Olson et al., *EMBO J.* 23:2019-2028 (2004). Further, the structurally related CD-MPR is also known in both ligand-bound and unbound forms. Olson et al., *J. Biol. Chem.* 274:29889-29886 (1999); Olson et al. *J. Biol. Chem.* 277:10156-10161 (2002). Accordingly, the skilled artisan would be able to use that receptor structural information to select an appropriate oligosaccharide.

The oligosaccharide may be chosen, for example, from any of the oligosaccharides of Formulae I, II, III, IV, V, or VI, as depicted above, including Oligosaccharides 1-127 described below. The oligosaccharides of Formulae I-III are formally derived from Formula B by removal of a branch, removal and/or substitution of a monosaccharide residue, and/or modification of the linkage (e.g., α1,2; α1,3; α1,4; or α1,6) between adjacent monosaccharide residues. In certain embodiments, the oligosaccharide may have, e.g., 1, 2, or 3 additional mannose residues in one or both arms, connected via an α1,2; α1,3; or α1,6 linkage, relative to any of Formulae I-VI.

The oligosaccharide may have, e.g., one, two or three M6P residues. The oligosaccharide may have, e.g., 1, 2, 3, 4, 5, 6, 7, 8, 9, or 10 monosaccharide residues in all. In other embodiments, the oligosaccharide may have 1, 2, 3, 4, 5, 6, 7, 8, 9, or 10 mannose residues, any of which may be phosphorylated or unphosphorylated.

In some embodiments, the oligosaccharide is chosen from Oligosaccharides 1-96, which are species of Formula I:

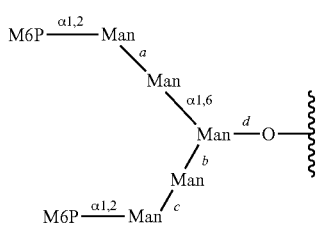

Formula I

| Oligosaccharide | a | b | c | d |
|---|---|---|---|---|
| 1 | α1,2 | α1,2 | α1,2 | α |
| 2 | α1,2 | α1,2 | α1,2 | β |
| 3 | α1,2 | α1,2 | α1,3 | α |
| 4 | α1,2 | α1,2 | α1,3 | β |
| 5 | α1,2 | α1,2 | α1,4 | α |
| 6 | α1,2 | α1,2 | α1,4 | β |
| 7 | α1,2 | α1,2 | α1,6 | α |
| 8 | α1,2 | α1,2 | α1,6 | β |
| 9 | α1,2 | α1,3 | α1,2 | α |
| 10 | α1,2 | α1,3 | α1,2 | β |
| 11 | α1,2 | α1,3 | α1,3 | α |
| 12 | α1,2 | α1,3 | α1,3 | β |
| 13 | α1,2 | α1,3 | α1,4 | α |
| 14 | α1,2 | α1,3 | α1,4 | β |
| 15 | α1,2 | α1,3 | α1,6 | α |
| 16 | α1,2 | α1,3 | α1,6 | β |
| 17 | α1,2 | α1,4 | α1,2 | α |
| 18 | α1,2 | α1,4 | α1,2 | β |
| 19 | α1,2 | α1,4 | α1,3 | α |
| 20 | α1,2 | α1,4 | α1,3 | β |
| 21 | α1,2 | α1,4 | α1,4 | α |
| 22 | α1,2 | α1,4 | α1,4 | β |
| 23 | α1,2 | α1,4 | α1,6 | α |
| 24 | α1,2 | α1,4 | α1,6 | β |
| 25 | α1,3 | α1,2 | α1,2 | α |
| 26 | α1,3 | α1,2 | α1,2 | β |
| 27 | α1,3 | α1,2 | α1,3 | α |
| 28 | α1,3 | α1,2 | α1,3 | β |
| 29 | α1,3 | α1,2 | α1,4 | α |
| 30 | α1,3 | α1,2 | α1,4 | β |
| 31 | α1,3 | α1,2 | α1,6 | α |
| 32 | α1,3 | α1,2 | α1,6 | β |
| 33 | α1,3 | α1,3 | α1,2 | α |
| 34 | α1,3 | α1,3 | α1,2 | β |
| 35 | α1,3 | α1,3 | α1,3 | α |
| 36 | α1,3 | α1,3 | α1,3 | β |
| 37 | α1,3 | α1,3 | α1,4 | α |
| 38 | α1,3 | α1,3 | α1,4 | β |
| 39 | α1,3 | α1,3 | α1,6 | α |
| 40 | α1,3 | α1,3 | α1,6 | β |
| 41 | α1,3 | α1,4 | α1,2 | α |
| 42 | α1,3 | α1,4 | α1,2 | β |
| 43 | α1,3 | α1,4 | α1,3 | α |
| 44 | α1,3 | α1,4 | α1,3 | β |
| 45 | α1,3 | α1,4 | α1,4 | α |
| 46 | α1,3 | α1,4 | α1,4 | β |
| 47 | α1,3 | α1,4 | α1,6 | α |
| 48 | α1,3 | α1,4 | α1,6 | β |
| 49 | α1,4 | α1,2 | α1,2 | α |
| 50 | α1,4 | α1,2 | α1,2 | β |
| 51 | α1,4 | α1,2 | α1,3 | α |
| 52 | α1,4 | α1,2 | α1,3 | β |
| 53 | α1,4 | α1,2 | α1,4 | α |
| 54 | α1,4 | α1,2 | α1,4 | β |
| 55 | α1,4 | α1,2 | α1,6 | α |
| 56 | α1,4 | α1,2 | α1,6 | β |
| 57 | α1,4 | α1,3 | α1,2 | α |
| 58 | α1,4 | α1,3 | α1,2 | β |
| 59 | α1,4 | α1,3 | α1,3 | α |
| 60 | α1,4 | α1,3 | α1,3 | β |
| 61 | α1,4 | α1,3 | α1,4 | α |
| 62 | α1,4 | α1,3 | α1,4 | β |
| 63 | α1,4 | α1,3 | α1,6 | α |
| 64 | α1,4 | α1,3 | α1,6 | β |
| 65 | α1,4 | α1,4 | α1,2 | α |
| 66 | α1,4 | α1,4 | α1,2 | β |
| 67 | α1,4 | α1,4 | α1,3 | α |
| 68 | α1,4 | α1,4 | α1,3 | β |
| 69 | α1,4 | α1,4 | α1,4 | α |
| 70 | α1,4 | α1,4 | α1,4 | β |
| 71 | α1,4 | α1,4 | α1,6 | α |
| 72 | α1,4 | α1,4 | α1,6 | β |
| 73 | α1,6 | α1,2 | α1,2 | α |
| 74 | α1,6 | α1,2 | α1,2 | β |
| 75 | α1,6 | α1,2 | α1,3 | α |
| 76 | α1,6 | α1,2 | α1,3 | β |
| 77 | α1,6 | α1,2 | α1,4 | α |
| 78 | α1,6 | α1,2 | α1,4 | β |
| 79 | α1,6 | α1,2 | α1,6 | α |
| 80 | α1,6 | α1,2 | α1,6 | β |
| 81 | α1,6 | α1,3 | α1,2 | α |
| 82 | α1,6 | α1,3 | α1,2 | β |
| 83 | α1,6 | α1,3 | α1,3 | α |
| 84 | α1,6 | α1,3 | α1,3 | β |
| 85 | α1,6 | α1,3 | α1,4 | α |
| 86 | α1,6 | α1,3 | α1,4 | β |
| 87 | α1,6 | α1,3 | α1,6 | α |
| 88 | α1,6 | α1,3 | α1,6 | β |
| 89 | α1,6 | α1,4 | α1,2 | α |
| 90 | α1,6 | α1,4 | α1,2 | β |
| 91 | α1,6 | α1,4 | α1,3 | α |
| 92 | α1,6 | α1,4 | α1,3 | β |
| 93 | α1,6 | α1,4 | α1,4 | α |
| 94 | α1,6 | α1,4 | α1,4 | β |
| 95 | α1,6 | α1,4 | α1,6 | α |
| 96 | α1,6 | α1,4 | α1,6 | β |

In some embodiments d is a mixture of α and β (i.e., the oligosaccharide is a mixture of, e.g., Oligosaccharides 1 and 2, 3 and 4, or 95 and 96).

In some embodiments, the oligosaccharide is chosen from Oligosaccharides 97-103, which are species of Formula II:

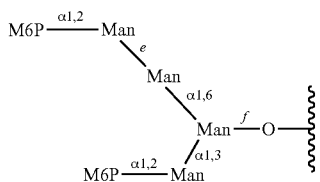

| Formula II | | |
|---|---|---|
| Oligosaccharide | e | f |
| 97 | α1,2 | α |
| 98 | α1,2 | β |
| 99 | α1,3 | α |
| 100 | α1,3 | β |
| 101 | α1,4 | α |
| 102 | α1,4 | β |
| 103 | α1,6 | α |
| Formula B | α1,6 | β |

In some embodiments f is a mixture of α and β (i.e., the oligosaccharide is a mixture of, e.g., Oligosaccharides 97 and 98, 99 and 100, or 101 and 102).

In some embodiments, the oligosaccharide is chosen from Oligosaccharides 104-127, which are species of Formula III:

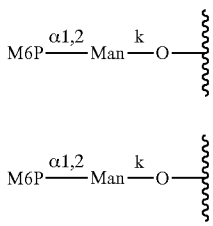

| Formula III | | | |
|---|---|---|---|
| Oligosaccharide | g | h | i |
| 104 | α1,2 | α1,2 | α |
| 105 | α1,2 | α1,2 | β |
| 106 | α1,2 | α1,3 | α |
| 107 | α1,2 | α1,3 | β |
| 108 | α1,2 | α1,4 | α |
| 109 | α1,2 | α1,4 | β |
| 110 | α1,2 | α1,6 | α |
| 111 | α1,2 | α1,6 | β |
| 112 | α1,3 | α1,2 | α |
| 113 | α1,3 | α1,2 | β |
| 114 | α1,3 | α1,3 | α |
| 115 | α1,3 | α1,3 | β |
| 116 | α1,3 | α1,4 | α |
| 117 | α1,3 | α1,4 | β |
| 118 | α1,3 | α1,6 | α |
| 119 | α1,3 | α1,6 | β |
| 120 | α1,4 | α1,2 | α |
| 121 | α1,4 | α1,2 | β |
| 122 | α1,4 | α1,3 | α |
| 123 | α1,4 | α1,3 | β |
| 124 | α1,4 | α1,4 | α |
| 125 | α1,4 | α1,4 | β |
| 126 | α1,4 | α1,6 | α |
| 127 | α1,4 | α1,6 | β |

In some embodiments i is a mixture of a and R (i.e., the oligosaccharide is a mixture of, e.g., Oligosaccharades 104 and 105, 106 and 107, or 126 and 127).

In some embodiments, the oligosaccharide is chosen from Oligosaccharides 128-133, which are species of Formula IV:

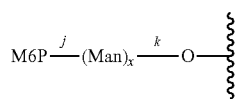

Formula IV

| Oligosaccharide | | k |
|---|---|---|
| 128 | 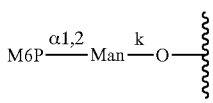 | α |
| 129 | 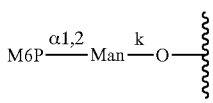 | β |
| 130 | 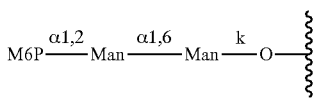 | α |
| 131 | 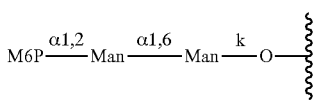 | β |
| 132 | 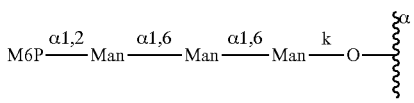 | α |
| 133 | 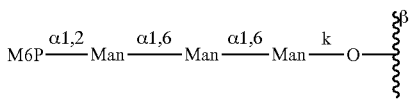 | β |

In some embodiments k is a mixture of α and β (i.e., the oligosaccharide is a mixture of, e.g., Oligosaccharides 128 and 129, 130 and 131, or 132 and 133).

In some embodiments, the oligosaccharide is chosen from Oligosaccharides 134 and 135, which are species of Formula V:

134

135

In some embodiments the oligosaccharide is a mixture of Oligosaccharides 134 and 135.

In some embodiments, the oligosaccharide is Oligosaccharide 136, which is a species of Formula VI:

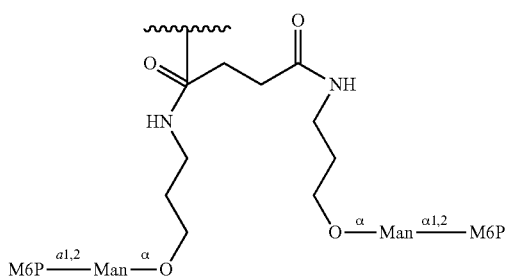

In some embodiments, the oligosaccharide may be isolated from a natural source. An oligosaccharide isolated from a natural source may be homogeneous or may be a heterogeneous mixture of related oligosaccharides.

In certain embodiments, the oligosaccharide is prepared by chemical and/or enzymatic synthesis. In some embodiments, an oligosaccharide may be prepared by chemical or enzymatic modification of an oligosaccharide isolated from a natural source ("semi-synthesis").

Oligosaccharides may be chemically and/or enzymatically synthesized as taught in, e.g., FIGS. 1-7, Osborn et al., *Oligosaccharides: Their Synthesis and Biological Roles*, Oxford University Press, 2000; Wang et al. (eds), *Synthesis of Carbohydrates through Biotechnology*, American Chemical Society, 2004; Seeberger, *Solid Support Oligosaccharide Synthesis and Combinatorial Carbohydrate Libraries*, Wiley-Interscience, 2001; Driguez et al., *Glycoscience: Synthesis of Oligosaccharides and Glycoconjugates*, Springer, 1999; Düffels et al., *Chem. Eur. J.* 6:1416-1430 (2000); Hojo et al., *Current Prot. Peptide Sci.* 1:23-48 (2000); Seeberger et al., *Nature* 446:1046-1051 (2007); Seeberger et al., *Nature Rev. Drug Discov.* 4:751-763 (2005); Srivastana et al., *Carbohydrate Res.* 161:195-210 (1987); and Hagihara et al., *Chem. Rec.* 6:290-302 (2006), and in U.S. Pat. Nos. 5,324,663; 6,156,547; 6,573,337; 6,723,843; 7,019,131; 7,160,517.

In some embodiments, an oligosaccharide may be synthesized by sequentially adding monosaccharides. In certain embodiments, monosaccharides can be added to a specific position (e.g., 2-O, 3-O, 4-O, or 6-O) of an existing saccharide by selective protection and deprotection. For example, oligosaccharide 82 may be synthesized as described in the retrosynthetic analysis in FIG. 1, and in the synthetic schemes set forth in FIGS. 2-7. In some embodiments, building block 2a may be substituted for building block 2 in the synthetic schemes of FIGS. 3, 5, and 6. If building block 2a is used, removal of the benzylidene group of building block 2 at the heptasaccharide stage may be avoided.

Mannose residues may be enzymatically phosphorylated as taught in, e.g., U.S. Pat. No. 6,905,856. In certain embodiments, 1, 2, or 3 of the M6P residues may be replaced by hydrolase-resistant M6P mimics such as, e.g., malonyl ethers, malonates, and phosphonates, as taught in Berkowitz et al., *Org. Lett.* 6:4921-4924 (2004).

In certain embodiments, a linker may be attached to a saccharide through an α or β linkage. In some embodiments, a β linkage can be formed by the methods described in Crich et al., *Tetrahedron*, 54:8321-8348 (1998); Kim et al, *J. Am. Chem. Soc.*, 130:8537-8547 (2008); Srivasta et al., *Tetrahedron Letters*, 35:3269-3272 (1979); Hodosi et al., *J. Am. Chem. Soc.*, 119:2335-2336 (1997); Nicolaou et al., *J. Am. Chem. Soc.*, 119:9057-9058 (1997). In one embodiment, a β linkage can be formed using a dibutyl tin oxide to form an intermediate that can be reacted with a linker containing an unactivated leaving group.

One embodiment provides a method of preparing a compound having the Formula VII:

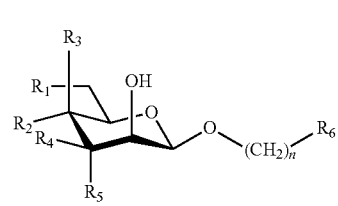

Formula VII wherein:
$R_1$ is chosen from hydrogen, hydroxyl, optionally substituted lower alkyl, phosphate, sulfate, —$OR_7$, a protecting group, and a saccharide;
$R_2$, $R_3$, $R_4$, and $R_5$ are each independently chosen from hydrogen, sulfate, hydroxyl, —$OR_8$, a protecting group and a saccharide;
$R_6$ is chosen from hydrogen, hydroxyl, carboxyl, alkoxycarbonyl, amino, amide, alkylamino, aminoalkyl, aminoxy, hydrazide, hydrazine, optionally substituted alkenyl and optionally substituted $C_2$-$C_6$ alkyl;
$R_7$ and $R_8$ are each independently chosen from acetyl and optionally substituted lower alkyl; and
n is an integer from 1 to 10;
comprising:
a) treating a compound having the Formula VIII:

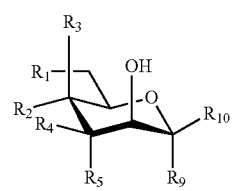

Formula VIII wherein:
$R_1$ through $R_5$ are as defined above; and
$R_9$ and $R_{10}$ are chosen from hydrogen and hydroxyl, such that
when one of $R_9$ and $R_{10}$ is hydroxyl, the other is hydrogen; with a compound having the Formula $R_{11}R_{12}(Sn=O)$ to form a compound having the Formula IX:

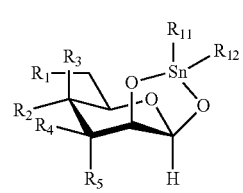

Formula IX wherein:
$R_1$ through $R_5$ are as defined above; and
$R_{11}$ and $R_{12}$ are each independently chosen from unsubstituted alkyl or $R_{11}$ and $R_{12}$, taken together, are chosen from unsubstituted alkylene;

and
b) treating the compound of Formula IX, optionally in the presence of a metal halide, with a compound having the Formula $R_6$—$(CH_2)_n$-L,
wherein:
$R_6$ and n are as defined above; and
L is a halogen; to form the compound of Formula VII.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Alkenyl" indicates an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In some embodiments, an alkenyl group has from 2 to 20 carbon atoms and in other embodiments, from 2 to 6 carbon atoms.

The term "substituted", as used herein, means that any one or more hydrogens on the designated atom or group is replaced with a selection from the indicated group, provided that the designated atom's normal valence is not exceeded. When a substituent is oxo (i.e., =O), 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The term "substituted alkyl", unless otherwise expressly defined, refers to alkyl wherein one or more hydrogen atoms are replaced by a substituent independently chosen from: —$R^a$, —$OR^b$, —$O(C_1$-$C_2$ alkyl)O— (e.g., methylenedioxy-), —$SR^b$, —$NR^bR^c$, halo, cyano, oxo, nitro, sulfate, phosphate, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, —$NR^cSO_2R^a$, ethylene glycol, and polyethylene glycol (PEG).

where $R^a$ is chosen from optionally substituted $C_1$-$C_6$ alkyl, optionally substituted aryl, and optionally substituted heteroaryl;

$R^b$ is chosen from hydrogen, —$NH_2$, —$NHR^c$, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group may be unsubstituted or independently substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ phenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

In some embodiments, $R_1$ is chosen from hydrogen, optionally substituted lower alkyl, phosphate, sulfate, —$OR_7$, a protecting group, and a saccharide. In additional embodiments, $R_2$, $R_3$, $R_4$, and $R_5$ are each independently chosen from hydrogen, sulfate, hydroxyl, —$OR_8$, a protecting group and a saccharide. In certain embodiments, $R_7$ and $R_8$ are each independently chosen from acetyl and optionally substituted lower alkyl. In some embodiments, any or all of $R_1$, $R_2$, $R_3$, $R_4$, and $R_5$ may be chosen from protecting groups that can be selectively removed, including benzyl, silyl, and trityl ethers, and esters other than acetate. In some embodiments, two of $R_1$ through $R_5$ taken together form a protecting group. In one embodiment, $R_1$ is chosen from —O-benzyl and —$OCPh_3$. In another embodiment, at least one of $R_2$ through $R_5$ is —O-benzyl. In some embodiments, $R_1$, $R_2$, and $R_4$ are each —O-benzyl. In a further embodiment, $R_1$ is —$OCPh_3$ and $R_4$ is —O-benzyl. In one embodiment, $R_{11}$ and $R_{12}$, taken together, form hexamethylene. In another embodiment, $R_{11}$ and $R_{12}$ are each isopropyl. In yet another embodiment, $R_{11}$ and $R_{12}$ are each hexyl.

In additional embodiments, the compound of Formula VIII is selected from optionally protected mannose, rhamnose, idose, and altrose. In one embodiment, the compound of Formula VIII is optionally protected mannose. In certain circumstances, the mannose may be protected at one or more of the C-3, C-4, or C-6 positions. In some instances, a single protecting group may be attached to two positions. For example, a benzylidene group may be used to protect both the C-4 and C-6 positions.

Generally, any protecting group on the sugar that is not strongly electrophilic or cross-reactive with compounds of Formula IX may be used. Suitable protecting groups include ethers such as optionally substituted benzyl ether, trityl ether, allyl ether, or silyl ether; esters such as optionally substituted acetate, benzoate, chloroacetate, pivalate, or levulinate; and acetals including benzylidene, isopropylidene, and butane diacetal, among others. In addition, protecting groups may be selected from carbamates and urethanes. In some embodiments, protecting groups may be selectively removed, such as, e.g., benzyl, silyl, and trityl ethers, and esters other than acetate. The positions and identities of the protecting groups may be varied depending on the desired final products. Additional protecting groups known to those of skill in the art may be used in accordance with the embodiments described herein.

In one embodiment, the compound of Formula VIII is treated with a compound having the Formula $R_{11}R_{12}$(Sn=O), wherein $R_{11}$ and $R_{12}$ are each independently chosen from unsubstituted alkyl, or $R_{11}$ and $R_{12}$, taken together, are chosen from unsubstituted alkylene. In some embodiments, $R_{11}$ and $R_{12}$ are butyl. In one embodiment, the compound having the Formula $R_{11}R_{12}$(Sn=O) is reacted with the compound of Formula VIII in a solvent such as toluene, benzene, dimethylformamide, isopropanol, methanol, or xylene. In some embodiments, the reaction is performed at elevated temperature, optionally under reflux, to form the compound of Formula IX. In some embodiments, the reaction mixture is heated to at least 40, 50, 60, 70, or 80° C. In additional embodiments, the compound having the Formula $R_{11}R_{12}$(Sn=O) is reacted with the compound of Formula VIII for at least 1, 2, 5, 10, 15, or 20 hours.

In one embodiment, the compound of Formula IX is treated with a compound having the Formula $R_6$—$(CH_2)_n$-L, optionally in the presence of a metal halide. In some embodiments, $R_6$ is chosen from hydrogen, hydroxyl, carboxyl, alkoxycarbonyl, amino, amide, alkylamino, aminoalkyl, aminoxy, hydrazide, hydrazine, optionally substituted alkenyl, and optionally substituted $C_2$-$C_6$ alkyl. In additional embodiments, n is an integer from 1 to 10. In certain embodiments, n is 2, 3, 4, 5, or 6, and $R_6$ is a $C_1$-$C_4$ alkoxycarbonyl. In one embodiment, n is 3, and $R_6$ is methoxycarbonyl. In some embodiments, L is a leaving group that is not activated. Examples of activated leaving groups include triflates, sulfonates, tosylates, and other similar groups. In some circumstances, a less reactive leaving group can be activated by neighboring groups such as allyl groups. In certain embodiments, Re does not contain a substituent that activates the leaving group. In some embodiments, L is bromide, chloride, or iodide. In one embodiment, L is bromide. In additional embodiments, the compound of Formula $R_6$—$(CH_2)_n$-L is methyl 4-bromobutyrate.

In one embodiment, the compound of Formula VIII is optionally protected mannose, and the compound of Formula $R_6$—$(CH_2)_n$-L is methyl 4-bromobutyrate. In another embodiment, the compound of Formula VIII is selected from 3,4,6-ti-O-benzyl-D-mannose and 3-O-allyl-6-O-trityl-D-mannose.

In some embodiments, the compound of Formula IX is treated with a compound having the Formula $R_6$—$(CH_2)_n$-L in the presence of a metal halide. Certain embodiments of metal halides include metal fluorides. In some embodiments, the metal fluoride is selected from cesium fluoride, sodium fluoride, calcium fluoride, magnesium fluoride, lithium fluoride, and potassium fluoride. In one embodiment, the metal fluoride is cesium fluoride. In some embodiments, the treatment of the compound of Formula IX with the compound of Formula $R_6$—$(CH_2)_n$-L further comprises the addition of tetraalkylammonium halide. In some instances, the tetraalkylammonium halide is tetrabutylammonium iodide. In additional embodiments, a metal halide can be used in the reaction. Examples of metal halides include alkali metal iodides such as sodium iodide.

In one embodiment, the compound of Formula IX can be combined with the compound of Formula $R_6$—$(CH_2)_n$-L in a polar aprotic solvent. Such solvents include dimethylformamide, dimethylacetamide, dimethylsulfoxide, nitromethane, hexamethylphosphoramide, N-methylpyrrolidone, acetone, acetonitrile, ethyl acetate, and methyl ethyl ketone, among others known to those of skill in the art.

In certain embodiments, the compound of Formula IX can be combined with the compound of Formula $R_6$—$(CH_2)_n$-L at room temperature. In other embodiments, the reactants are combined and heated to at least 50, 60, 70, or 80° C. to form a compound of Formula VII. In further embodiments, the mixture is heated for at least 1, 2, 5, 10, 15, or 20 hours.

In some embodiments, the methods described herein result in at least 50, 60, 70, 80, 90, 95, or 99% stereospecific product. In additional embodiments, the yield of stereospecific product is at least 50, 60, 70, 75, 80, 85, 90, 95, or 99% of the maximum possible yield. In certain embodiments, the ratio of beta- to alpha-linked product is at least 10:1, 20:1, 30:1, 40:1, 50:1, or 100:1.

In one embodiment, a compound of Formula VII can be prepared in a large scale. In some embodiments, "large scale" refers to the use of at least 50, 100, 500, or 1000 grams of a starting material, intermediate, or reagent. In additional embodiments, "large scale" includes the use of at least 10, 25, 50, 100, 250, or 500 kg of starting material, intermediate, or reagent.

An exemplary synthetic scheme for preparing a compound of Formula A using a dibutyl tin oxide reagent is shown in FIG. 8.

B. Protein

The oligosaccharide-protein conjugates described herein may comprise any pure protein, partially purified protein, or fragment thereof, including isolated proteins and recombinantly or synthetically produced proteins. The terms "pure," "purified," and "isolated" refer to a molecule that is substantially free of its natural environment. For instance, a pure protein is substantially free of cellular material and/or other proteins from the cell or tissue source from which it is derived. The term refers to preparations that are, for example, at least 70% to 80%, 80% to 90%, 90 to 95%; or at least 95%, 96%, 97%, 98%, 99%, or 100% (w/w) pure.

In other embodiments, the protein may be an enzyme that has optimal activity, as measured by an activity assay, at a pH ranging from 1-7, such as, e.g., 1-3, 2-5, 3-6, 4-5, 5-6, or 4-6. For example, the enzyme may have a pH optimum at a pH ranging from 4-6.

In same embodiments, the protein may be an enzyme that has an isoelectric point (p), ranging from 1 to 8, such as, e.g., from 1-3, 2-5, 3-8, 4-5, 5-6, 4-6, 5-8, 6-8, or 7-8. The μl of a protein may be may be measured using, e.g., isoelectric focusing gel electrophoresis.

In certain embodiments, the protein itself has at least one oligosaccharide (i.e., it is a glycoprotein). In particular embodiments, the protein is a therapeutic glycoprotein. For example, the therapeutic glycoprotein may be a lysosomal enzyme, including an ERT enzyme such as, e.g., one of the lysosomal hydrolases listed in Table 1. In certain embodiments, the lyosomal enzyme is chosen from, e.g., α-glucosidase (GAA), α-galactosidase A, acid sphingomyelinase, and α-L-iduronidase. In particular embodiments, the lyosomal enzyme is GAA.

TABLE 1

Examples of LSDs and Corresponding Lysosomal Hydrolases

| Lysosomal Storage Disorder | Defective Enzyme |
|---|---|
| Fabry | α-Galactosidase A |
| Farber | Acid ceramidase |
| Fucosidosis | Acid α-L-fucosidase |
| Gaucher types 1, 2, and 3 | Acid β-glucosidase |
| G$_{M1}$ gangliosidosis | Acid β-galactosidase |
| Hunter (Mucopolysaccharidosis (MPS) II) | Iduronate-2-sulfatase |
| Hurler-Scheie, Hurler, Scheie (MPS I) | α-L-Iduronidase |
| Krabbe | Galactocerebrosidase |
| α-Mannosidosis | Acid α-mannosidase |
| β-Mannosidosis | Acid β-mannosidase |
| Maroteaux-Lamy (MPS VI) | Arylsulfatase B |
| Metachromatic leukodystrophy | Arylsulfatase A |
| Morquio A (MPS IV) | N-Acetylgalactosamine-6-sulfate sulfatase (N-acetylgalactosamine-6-sulfatase) (galactose-6-sulfatase) |
| Morquio B (MPS IV) | Acid β-galactosidase |
| Niemann-Pick A and B | Acid sphingomyelinase |
| Pompe | Acid α-glucosidase (α-glucosidase) |
| Sandhoff | β-Hexosaminidase B |
| Sanfilippo A (MPS III) | Heparan N-sulfatase |
| Sanfilippo B (MPS III) | α-N-Acetylglucosaminidase |
| Sanfilippo C (MPS III) | Acetyl-CoA: α-glucosaminide N-acetyltransferase |
| Sanfilippo D (MPS III) | N-Acetylglucosamine-6-sulfate sulfatase |
| Schindler-Kanzaki | α-N-acetylgalactosaminidase |
| Sialidosis | Sialidase |
| Sly (MPS VII) | β-Glucuronidase |
| Tay-Sachs | β-Hexosaminidase A |

In some embodiments, the protein may be a glycoprotein having at least 1, 2, 3, 4, 5, or more N-linked or O-linked oligosaccharides. In other embodiments, the protein may have 1, 2, 3, 4, 5 or more consensus sites for N-linked or O-linked glycosylation, at least one of which is glycosylated.

In certain embodiments, the protein may be a ligand for a receptor. For example, in some embodiments the protein may be a glycoprotein that binds to a receptor that recognizes a sugar such as, e.g., mannose or mannose-6-phosphate. In particular embodiments, the glycoprotein may bind to, e.g., the asialoglycoprotein receptor, CI-MPR, CD-MPR, or the mannose receptor.

Suitable protein sequences are well known in the art. A skilled artisan can readily identify conserved regions and significant functional motif(s) by comparing related sequences, including, e.g., sequences from different species. Conserved amino acids are more likely to be important for activity; conversely, amino acids that are not conserved indicate regions of the polypeptide that are more likely to tolerate variation. Following those guidelines, the skilled artisan can identify functional variants through no more than routine effort. Further, where the crystal structure is known, a skilled artisan can examine the crystal structure and identify amino acids likely to be important for structure and/or function, and thus less tolerant to mutation. The skilled artisan would also be able to identify amino acids likely to tolerate variation. Moreover, the skilled artisan can evaluate possible mutations in light of known structure-function relationships.

For example, the sequence and structure of α-galactosidase are well known. See, e.g., Garman et al., *J. Mol. Biol.*, 337:319-335 (2004); Garman et al., *Mol. Genet. Metabol.*, 77:3-11 (2002); Matsuzawa et al., *Hum. Genet.* 117: 317-328 (2005). See also GenBank Accession No. X05790. In another example, the sequence of GAA is well known (see, e.g., Martiniuk et al., *Proc. Natl. Acad. Sci. USA* 83:9641-9644 (1986); Hoefsloot et al., *Biochem. J.* 272:493-497 (1990); Moreland et al., *J. Biol. Chem.* 280:6780-6791 (2005). See also GenBank Accession No. NM_000152. Further, the crystal structure of a homologous α-glycosidase from *E. coli* has been determined, and can provide structural insights into other α-glycosidases. See Lovering et al., *J. Biol. Chem.* 280:2105-2115 (2005). In a third example, the sequence of acid sphingomyelinase is well known (see, e.g., Lansmann et al., *Eur. J. Biochem.* 270:1076-1088 (2003)), as are key features of the acid sphingomyelinase sequence and structure. See, e.g., Seto et al., *Protein Sci.* 13:3172-3186 (2004); Qiu et al., *J. Biol. Chem.* 278:32744-32752 (2003); Takahashi et al., *Tokohu J. Exp. Med.* 206:333-340 (2005). See also GenBank Accession No. A1587087. In yet another example, the sequence of α-L-iduronidase is well known (see, e.g., Scott et al., *Proc. Natl. Acad. Sci USA* 88:9695-9699 (1991); Scott et al., *Genomics* 13:1311-1313 (1992)), as are key features of α-L-iduronidase. See, e.g., Scott et al., *Hum. Mutat.* 6:288-302 (1995); Rempel et al., *Mol. Genet. Metab.* 85:28-37 (2005); Durand et al., *Glycobiology* 7:277-284 (1997); Beesley et al., *Hum. Genet.* 109:503-511 (2001); Brooks et al., *Glycobiology* 11:741-750 (2001); Nieman et al., *Biochemistry* 42:8054-8065 (2003). In a further example, the sequence of iduronate-2-sulfatase is well known, as are disease-causing mutations. See, e.g., Flomen et al., *Hum. Mol. Genet.* 2:5-10 (1993); Roberts et al., *J. Med. Genet.* 26:309-313 (1989); Wilson et al., *Proc. Natl. Acad. Sci. USA* 87:8531-8535 (1990); Wilson et al., *Genomics* 17:773-775 (1993); Sukegwa-Hayasaka et al., *J. Inherit. Metab. Dis* 29:755-761 (2006) and references therein. The structure of iduronate-2-sulfatase has been modeled. See, e.g., Kim et al., *Hum. Mutat.* 21:193-201 (2003). In another example, the sequence and structure of N-acetylgalactosamine-4-sulfatase (arylsulfatase B) are known, as are disease-causing mutations. See, e.g., Litjens et al., *Hum. Mut.* 1:397-402 (1992); Peters et al., *J. Biol. Chem.* 265: 3374-3381 (1990); Schuchman et al., *Genomics* 6:149-158 (1990); Bond et al., *Structure* 15:277-289 (1997).

C. Linker

In certain embodiments, the oligosaccharide-protein conjugates of the invention comprise a linker between the oligosaccharide and protein components of the conjugate. In other embodiments, the conjugates do not include a linker. In embodiments comprising a linker, any suitable linker known to one of skill in the art may be used, so long as it does not interfere with the binding of the oligosaccharide to CI-MPR and/or block the activity (including, e.g., enzymatic activity) of the protein. For example, the linker may be one of the linkers disclosed in U.S. Pat. Nos. 4,671,958; 4,867,973; 5,691,154; 5,846,728; 6,472,506; 6,541,669; 7,141,676; 7,176,185; or 7,232,805 or in U.S. Patent Application Pub. No. 2006/0228348. In some embodiments, the linker is chosen from linkers disclosed in WO2008/089403.

In some embodiments, the linker can have the formula:

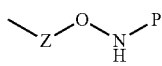

wherein Z is chosen from optionally substituted alkyl, alkenyl, alkynyl, aryl, ethylene glycol, polyethylene glycol (PEG) heteroaryl, and heterocyclyl, and P is chosen from hydrogen or an amino protecting group. As used herein, any chemical group on the aminooxy compound (such as, e.g., alkyl, alkenyl, alkynyl, aryl, heteroaryl, heterocyclyl, acyloxy, alkoxy, aryloxy, and heterocyclyloxy) may be substituted or unsubstituted, and may be interrupted by one or more heteroatoms or chemical groups, unless otherwise stated. Interrupting heteroatoms include nitrogen, oxygen, and sulfur. Substituents and interrupting chemical groups may be chosen from, e.g., acyl, acylamino, acyloxy, alkenyl, alkoxy, alkyl, alkynyl, amido, amino, aryl, aryloxy, azido, carbamoyl, carboalkoxy, carboxy, cyano, cycloalkyl, formyl, guanidino, halo, heteroaryl, heterocyclyl, hydroxy, iminoamino, nitro, oxo, phosphonamino, sulfinyl, sulfonamino, sulfonate, sulfonyl, thio, thioacylamino, thioureido, and ureido. The substituents may themselves be substituted or unsubstituted, and may be interrupted or terminated by one or more heteroatoms such as, e.g., nitrogen, sulfur, and oxygen.

In one embodiment, the linker can be formed by reaction with:

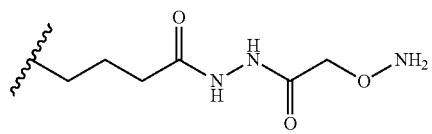 [SMILES: *CCCC(=O)NNC(=O)CON]

In additional embodiments, the linker can have the formula:

wherein Z and P are as defined above.

In another embodiment, the linker can contain a disulfide linkage. Disulfide linkers may be used to attach oligosaccharides to a protein backbone, for example through a cysteine. In one embodiment, the linker can comprise or be formed from reaction with:

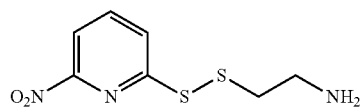 [SMILES: NCCSSc1cccc([N+](=O)[O-])n1]

In general, the linker may be of a suitable length such that it avoids steric hindrance between the oligosaccharide and the protein components of the conjugate, and does not interfere with the binding of the oligosaccharide to CI-MPR and/or with the activity (including, e.g., enzymatic activity) of the protein. For example, the linker may comprise 1-100, 1-60, 5-60, 5-40, 2-50, 2-20, 5-10, or 5-20 linear atoms, where the linker is attached to the protein and to the oligosaccharide by means of an ester, amide, hydrazone, oxime, semicarbazone, ether, thioether, phosphorothioate, phosphonate, thioester, and/or disulfide linkage. The remaining linear atoms in the linker are, e.g., chosen from carbon, oxygen, nitrogen and sulfur, any of which atoms optionally may be included in a carbocyclic, heterocyclic, aryl, or heteroaryl ring. The linear carbon atoms in the linker optionally can be substituted with a substituent chosen from halo, hydroxy, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido. A linear nitrogen atom in the linker may be optionally substituted with acyl, sulfonyl, alkyl, alkaryl, aryl, aralkyl, alkoxycarbonyl. A linear sulfur atom in the linker may optionally be oxidized.

In certain embodiments, the linker may be cleavable, as disclosed in, e.g., U.S. Patent Application Pub. No. 2006/0228348 and U.S. Pat. Nos. 4,867,973; 7,176,185; 7,232,805. In some embodiments, the linker may be cleavable under lysosomal conditions.

D. Methods of Preparing an Oligosaccharide-Protein Conjugate

The conjugates of the invention, such as, e.g., the conjugates comprising oligosaccharides of Formula I, II, III, IV, V, or VI may be prepared by any of the methods known to those of skill in the art. In any of those methods, a suitable linker may be present in either or both of the oligosaccharide and the protein. For example, the conjugates may be prepared as described in, e.g., Zhu et al., *Biochem. J.* 389:619-628 (2005); Zhu et al., *J. Biol. Chem.* 279:50336-50341 (2004); U.S. Pat. Nos. 5,153,312; 5,212,298; 5,280,113; 5,306,492; 5,521,290; 7,001,994; U.S. Provisional Patent Application No. 60/885,457, or 60/885,471.

In certain embodiments, the oligosaccharide may be conjugated to an amino acid of a protein, such as a cysteine or lysine. For example, the saccharide can be conjugated through a lysine by modifying the lysine residues in the protein with succinimidyl 4-formylbenzoate. Additionally, the saccharide may be conjugated through a lysine by modification of the lysines with Traut's reagent or linkers including disulfides such as N-succinimidyl-3-(2-pyridyldithio)propionate (SPDP) or protected thiols such as N-Succinimidyl-S-acetylthioacetate (SATA).

In additional embodiments, the oligosaccharide can be conjugated to a glycan on a glycoprotein. In one embodiment, the oligosaccharide may be conjugated to a sialic acid residue on a glycan. In other embodiments, the oligosaccharide may be conjugated to mannose, fucose, galactose, and/or sialic acid residues on a glycan. For conjugation through galactose, the glycoprotein may first be treated with sialidase to remove sialic acid residues, then treated with galactose oxidase prior to reaction with the oligosaccharide.

For example, the oligosaccharide-protein conjugate may be prepared by reaction of any functional group that may be present (including, e.g., an amine, a thiol, a carboxylic acid, a hydroxyl) and/or introduced into a protein with a suitable second functional group on an oligosaccharide. Methods for the introduction of functional groups are well known in the art. For example, a glycoprotein having at least one carbonyl group may be obtained by oxidation of that glycoprotein with, e.g., periodate (e.g., sodium periodate) or with galactose oxidase. In another example, a carbonyl group may be introduced by use of an expression system having an expanded genetic code, as described in, e.g., Wang et al., *Proc. Natl. Acad. Sci. USA* 100:56-61 (2003). See also, e.g., U.S. Patent Application Pub. No. 2006/0228348, which describes the introduction of reactive groups into a glycoprotein.

In some embodiments, the glycoprotein is oxidized with periodate prior to conjugation with an oligosaccharide modified with a linker containing a carbonyl-reactive group. Examples of carbonyl-reactive groups include aminoxy, hydrazine, or hydrazide, among others. In certain embodiments, the glycoprotein is oxidized with about 1, 2, 3, 4, 5, 7.5, 10, or 22.5 mM periodate. In certain embodiments, the glycoprotein is oxidized under conditions sufficient to oxidize sialic acid residues on the glycoprotein glycans, and minimize fucose and mannose oxidation. In exemplary embodiments, the periodate concentration used in less than about 2, 3, 4, or 5 mM. In one embodiment, the periodate is sodium periodate.

In certain embodiments, protein aggregates that form during conjugation can be removed using various chromatography methods. In one embodiment, hydrophobic interaction chromatography (HIC) may be employed. Examples of HIC columns include Butyl 650C and 650M, Hexyl 650C, Phenyl 6FF, Capto Octyl and Capto Phenyl. In other embodiments, aggregates may be removed by metal chelation chromatography, such as copper, nickel, cobalt, or mercury. In one embodiment, a copper column can be used in bind-and-elute or in flow-through mode. Exemplary elution buffers include glycine or imidazole. In some embodiments, aggregation is reduced by 10, 20, 30, 40, 50, 60, 70, 80, or 90%. In additional embodiments, the conjugate contains less than 0.5, 1, 1.5, 2, 2.5, or 3% aggregate.

E. Conjugates

The oligosaccharide and protein components of the conjugate may be, for example, any oligosaccharide and protein described herein. In certain embodiments, the oligosaccharide-protein conjugate is an oligosaccharide-glycoprotein conjugate. In some embodiments, the oligosaccharide-protein conjugate is an oligosaccharide-lysosomal enzyme conjugate.

In some embodiments, the conjugate comprises an oligosaccharide chosen from oligosaccharides of Formulae I-VI. In certain embodiments, the conjugate comprises an average of 1, 2, 3, 4, 5, 6, 7, 8, 9, 10, 11, 12, 13, 14, 15, 16, 17, 18, 19, 20 or 1-2, 1-3, 1-4, 1-6, 2-4, 2-10, 2-12, 4-6, 3-8, 5-6, 5-10, 5-15, 5-20, 10-15, 10-20, 12-15, 12-18, or 15-20 molecules of oligosaccharide per glycoprotein. In some embodiments, the conjugate comprises at least 4, 5, 6, 7, 8, 9, or 10 molecules of oligosaccharide per molecule of protein. In additional embodiments, the conjugate comprises at least 2, 3, 4, 5, 6, 7, 8, 9, or 10 moles of M6P per mole of protein.

In certain embodiments, the conjugate exhibits full activity (such as enzymatic activity), as compared to the unconjugated protein. In other embodiments, the conjugate may exhibit at least, e.g., 50, 60, 70, 75, 80, 85, 90, 92, 94, 95, 96, 97, 98, or 99% activity relative to the unconjugated protein. Assays for measuring activity, including enzymatic activity, are well known in the art. See, e.g., Eisenthal et al., *Enzyme Assays: A Practical Approach*, Oxford University Press: New York, 2002. Assays for measuring activity of lysosomal enzymes are described in, e.g., Li et al., *Clin. Chem.* 50:1785-1796 (2004); Civallero et al., *Clin. Chim. Acta* 372:98-102 (2006). An exemplary assay for measuring activity of GAA is described in Example 6. See also van Diggelen et al., *J. Inherit. Metab. Dis.* 28:733-741 (2005) (describing an assay for acid sphingomyelinase activity); Downing et al., *Plant Biotechnol.* 4:169-181 (2006) (describing an assay for α-L-iduronidase activity); Voznyi et al., *J. Inherit. Metab. Dis.* 24:675-80 (2001) (describing an assay for iduronate-2-sulfatase activity); Murray et al., *Mol. Genet. Metab.* 90:307-312 (2007) (describing an assay for α-galactosidase A activity); Brooks et al., *J. Inher. Metab. Dis.* 14:5-12 (1991) (describing an assay for N-acetylgalactosamine-4-sulfatase activity).

In certain embodiments, the conjugate is internalized more efficiently by a target cell (e.g., via CI-MPR-mediated endocytosis) than is the corresponding unconjugated protein. For example, the conjugate may be internalized more efficiently than the unconjugated protein by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200% (mol/mol) in a given time period. In other embodiments, at least 2, 3, 4, 5, 6, 7, 8, 9, 10, 20, 30, 40, 50, 100, or 1000 fold (mol/mol) as much of the conjugate may be internalized by a cell type of interest (such as, e.g., L6 myoblast cells or human Pompe fibroblast cells (NIGMS Human Genetic Cell Repository, Cat. No. GM20005) relative to the unconjugated protein, in a given time period. The referenced time period may be, for example, 10, 30, 45 minutes or 1, 2, 3, 5, 6, 12, 24, 48, or 72 hours, or more. In vitro uptake in L6 myoblast cells may be determined as described in, e.g., Example 6 and Zhu et al., *J. Biol. Chem.* 279:50336-50341 (2004).

In certain embodiments, the conjugate exhibits increased binding to CI-MPR relative to the unconjugated protein. For example, the conjugate may exhibit at least, e.g., 2, 3, 4, 5, 10, 20, 30, 40, 50, 100, 1,000, or 10,000-fold improved affinity to CI-MPR, relative to the unconjugated protein, as determined, e.g., by comparison of the association or dissociation constants of the conjugated and unconjugated protein. Binding to CI-MPR may be measured as described in, e.g., Example 5 and Zhu et al., *J. Biol. Chem.* 279:50336-50341 (2004).

In certain embodiments, the conjugate may exhibit no increase in uptake by the mannose receptor relative to the unconjugated protein, or less than 5, 10, 15, 20, 30, 40, or 50% uptake by the mannose receptor relative to the unconjugated protein. Uptake by the mannose receptor in rat alveolar macrophage cells may be determined in vitro as described in, e.g., Zhu et al., *Biochem. J.* 389:619-628 (2005).

In certain embodiments, the conjugate may exhibit, e.g., at least 2, 3, 4, 5, 10, 20, 30, 40, 50, 100, or 1000-fold reduction in the levels of an accumulated substrate of a metabolically defective enzyme in a suitable animal model. For example, reduction of glycogen levels in a Pompe mouse model may be measured as described in, e.g., Zhu et al., *J. Biol. Chem.* 279:50336-50341 (2004). Alternatively, a Pompe quail model described in, e.g., Kikuchi et al., *J. Clin. Invest.* 101:827-33 (1998), may be used. In another example, reduction of stored glycosaminoglycans in liver and spleen may be determined in a feline model of mucopolysaccharidosis I as described in Kakkis et al., *Mol. Genet. Metab.* 72:199-208 (2001). Further, reduction of globotriaosylceramide levels may be determined in a Fabry mouse model, as described in, e.g., Ioannou et al., *Am. J. Hum. Genet.* 68:14-25 (2001). In yet another example, reduction of sphingomyelin levels may be determined in murine model of types A and B Niemann-Pick disease, as described in, e.g., Horinouchi et al., *Nat. Genet.* 10:288-293 (1995).

II. Pharmaceutical Compositions

In some embodiments, the invention provides the use of an oligosaccharide-protein conjugate comprising (1) a protein and (2) an oligosaccharide of any of Formulae I-VI in the manufacture of a medicament for treating a lysosomal storage disorder in a subject in need thereof.

Pharmaceutical compositions described herein comprise an oligosaccharide-protein conjugate, as described supra, and at least one additive such as a filler, bulking agent, disintegrant, buffer, stabilizer, or excipient. In some embodiments, the pharmaceutical compositions of the invention comprise a conjugate comprising an oligosaccharide of any of Formulae I-VI and a lysosomal enzyme.

Standard pharmaceutical formulation techniques are well known to persons skilled in the art (see, e.g., 2005 *Physicians' Desk Reference®*, Thomson Healthcare: Montvale, NJ., 2004; *Remington: The Science and Practice of Pharmacy,* 20th ed., Gennado et al., Eds. Lippincott Williams & Wilkins: Philadelphia, PA, 2000). Suitable pharmaceutical additives include, e.g., mannitol, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The compositions may also contain pH buffering reagents and wetting or emulsifying agents. The compositions may or may not contain preservatives.

In some embodiments, pharmaceutical compositions comprising α-galactosidase A conjugates may comprise one or more excipients such as, e.g., mannitol, sodium phosphate monobasic monohydrate, and/or sodium phosphate dibasic heptahydrate. In some embodiments, pharmaceutical compositions comprising conjugates of α-glucosidase may comprise one or more of the following: mannitol, polysorbate 80, sodium phosphate dibasic heptahydrate, and sodium phosphate monobasic monohydrate. In another embodiment, pharmaceutical compositions comprising conjugates of α-glucosidase may comprise 10 mM Histidine pH 6.5 with up to 2% glycine, up to 2% mannitol, and up to 0.01% polysorbate 80.

The pharmaceutical composition may comprise any of the conjugates described herein either as the sole active compound or in combination with another compound, composition, or biological material. For example, the pharmaceutical composition may also comprise one or more small molecules useful for the treatment of a LSD and/or a side effect associated with the LSD. In some embodiments, the composition may comprise miglustat and/or one or more compounds described in, e.g., U.S. Patent Application Publication Nos. 2003/0050299, 2003/0153768; 2005/0222244; or 2005/0267094. In some embodiments, the pharmaceutical composition may also comprise one or more immunosuppressants.

The formulation of pharmaceutical compositions may vary depending on the intended route of administrations and other parameters (see, e.g., Rowe et al., *Handbook of Pharmaceutical Excipients,* 4th ed., APhA Publications, 2003.) In some embodiments, the composition may be a sterile, non-pyrogenic, white to off-white lyophilized cake or powder to be administered by intravenous injection upon reconstitution with Sterile Water for Injection, USP. In other embodiments, the composition may be sterile, non-pyrogenic solution.

Administration of a pharmaceutical composition described herein is not limited to any particular delivery system and may include, without limitation, parenteral (including subcutaneous, intravenous, intracranial, intramedullary, intraarticular, intramuscular, intrathecal, or intraperitoneal injection), transdermal, or oral (for example, in capsules, suspensions, or tablets). Administration to an individual may occur in a single dose or in repeat administrations, and in any of a variety of physiologically acceptable salt forms, and/or with an acceptable pharmaceutical carrier and/or additive as part of a pharmaceutical composition.

Pharmaceutically acceptable salts include, e.g., acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/disphosphate, polygalacturonate, salicylate, stearate, subacetate, succinate, sulfate, tannate, tartrate, and teoclate/triethiodide anions; benzathine, chloroprocaine, choline, diethanolamine, ethylenediamine, meglumine, and procaine (organic) cations; and aluminium, calcium, lithium, magnesium, potassium, sodium, and zinc (metallic) cations. Pharmaceutically acceptable salts also include those salts described in, e.g., Berge et al., *J. Pharm. Sci.* 66:1-19 (1977).

The conjugates described herein are administered in therapeutically effective amounts. Generally, a therapeutically effective amount may vary with the subject's age, general condition, and gender, as well as the severity of the medical condition in the subject. The dosage may be determined by a physician and adjusted, as necessary, to suit observed effects of the treatment. Toxicity and therapeutic efficacy of such compounds can be determined by standard pharmaceutical procedures in vitro and/or in vivo. The dose ratio between toxic and therapeutic effects is the therapeutic index (or therapeutic ratio), and can be expressed as the ratio $LD_{50}/ED_{50}$, where the $LD_{50}$ is the dose lethal to 50% of the population and the $ED_{50}$ is the dose therapeutically effective in 50% of the population. Conjugates of the invention may exhibit therapeutic indices of at least, e.g., 1, 1.5, 2, 3, 4, 5, 6, 7, 8, 9, 10, and 20.

The data obtained from in vitro assays and animal studies, for example, can be used in formulating a range of dosage for use in humans. The dosage of such compounds lies preferably within a range of circulating concentrations that include the $ED_{50}$ with low, little, or no toxicity. The dosage may vary within this range depending upon the dosage form employed and the route of administration utilized. The therapeutically effective dose of any conjugate can be estimated initially from in vitro assays. A dose may be formulated in animal models to achieve a circulating plasma concentration range that includes the $IC_{50}$ (i.e., the concentration of the test conjugate which achieves a half-maximal inhibition of symptoms) as determined in in vitro experiments. Levels in plasma may be measured, for example, by high performance liquid chromatography or by an appropriate enzymatic activity assay. The effects of any particular dosage can be monitored by a suitable bioassay of endpoints.

Unless otherwise indicated, conjugates may be administered at a dose of approximately from 1 μg/kg to 500 mg/kg, depending on the severity of the symptoms and the progression of the disease. For example, conjugates may be administered by slow intravenous infusion in an outpatient setting every, e.g., 1, 2, 3, 4, 5, 6, 7, 8, 9, 10, or more days, or by, e.g., weekly, biweekly, monthly, or bimonthly administration. The appropriate therapeutically effective dose of a compound is selected by a treating clinician and would range approximately from 1 μg/kg to 500 mg/kg, from 1 μg/kg to 10 mg/kg, from 1 μg/kg to 1 mg/kg, from 10 μg/kg to 1 mg/kg, from 10 μg/kg to 100 μg/kg, from 100 μg to 1 mg/kg, and from 500 μg/kg to 5 mg/kg. In some embodiments, the appropriate therapeutic dose is chosen from, e.g., 0.1, 0.25, 0.5, 0.75, 1, 5, 10, 15, 20, 30, 40, 50, 60, 70, and 100 mg/kg.

Conjugates comprising α-galactosidase A may be administered by intravenous infusion at a dose of, e.g., 1.0 mg/kg body weight every two weeks or four weeks at an infusion rate of, e.g., less than or equal to 10, 13, 15, 16, 17, 18, 19, 20, 21, 22, 23, 24, 25, 26, 27, 28, 29, 30, 31, 32, or 33 mg/hour). In another example, conjugates comprising α-glucosidase may be administered by intravenous injection at a dose of, e.g., 20 mg/kg or 40 mg/kg every two or four weeks, over approximately, e.g., 1, 2, 3, 4, 5, 6, 7, 8, 9, or 10 hours. In some embodiments, the rate of administration of α-glucosidase may be started at, e.g., 1 mg/kg/hr and then increased by, e.g., 2 mg/kg/hr every 30 minutes, after establishing subject tolerance to the infusion rate, until a maximum of, e.g., 7 mg/kg/hr. Conjugates comprising N-acetylgalactosamine-4-sulfatase may be administered by intravenous infusion at a dose of, e.g., 1.0 mg/kg body weight every week over approximately, e.g., 1, 2, 3, 4, 5, 6, 7, 8, 9, or 10 hours. Additionally, examples of specific dosages may be found in the *Physicians' Desk Reference®*.

III. Methods of Treating Lysosomal Storage Disorders

In some embodiments, the invention provides methods of treating lysosomal storage disorders, such as, e.g., those disclosed in Table 1. In some embodiments, the invention further provides methods of targeting proteins to the lysosome by conjugation with oligosaccharides comprising mannose-6-phosphate.

In certain embodiments, the methods comprise administering to a subject (where a subject includes, e.g., a mammal such as a human, cat, dog, mouse, or rat, or a bird such as, e.g., a quail) having a lysosomal storage disorder an oligosaccharide-protein conjugate of the invention in a therapeutically effective amount. The oligosaccharide-protein conjugate may be a conjugate of a glycoprotein, such as a lysosomal enzyme (e.g., a lysosomal enzyme listed in Table 1), with an oligosaccharide comprising mannose-6-phosphate, such as an oligosaccharide of any of Formulae I-VI. In one embodiment, the method comprises administering to a subject in need thereof a pharmaceutical composition comprising at least one of the conjugates of the invention.

In certain embodiments, the methods comprise administering conjugates comprising (1) a protein and (2) an oligosaccharide comprising mannose-6-phosphate, such as an oligosaccharide of any of Formulae I-VI with one or more other therapies. The one or more other therapies may be administered concurrently with (including concurrent administration as a combined formulation), before, or after the administration of the conjugates.

In some embodiments, the methods comprise treating a subject (before, after, or during treatment with a conjugate described herein) with an antipyretic, antihistamine, and/or immunosuppressant. In some embodiments, a subject may be treated with an antipyretic, antihistamine, and/or immunosuppressant prior to treatment with an oligosaccharide-glycoprotein conjugate in order to decrease or prevent infusion associated reactions. For example, subjects may be pretreated with one or more of acetaminophen, azathioprine, cyclophosphamide, cyclosporin A, diphenhydramine, methotrexate, mycophenolate mofetil, oral steroids, or rapamycin.

In some embodiments, the methods comprise treating subjects with one or more of acetaminophen, azathioprine, cyclophosphamide, cyclosporin A, diphenhydramine, methotrexate, mycophenolate mofetil, oral steroids, or rapamycin at or about, e.g., t=0 (the time of administration of the conjugate) and/or t=12, 24, 36, 48, 60, 72, 96, 120, and 144 hours for, e.g., the first 1, 2, 3, 4, 5, 6, 7, 8, 9, 10, or more incidences of treatment with a conjugate. For example, in some embodiments a subject with Fabry disease or Pompe disease may be treated with methotrexate (e.g., with 0.1, 0.2, 0.3, 0.4, 0.5, 0.6, 0.7, 0.8, 0.9, 1, 2, 3, 4, 5, 6, 8, 10, 12, 15, 25, 30, 35, 40, 50, 60, 70, 80 mg/kg methotrexate, or more) at or about, e.g., t=0, 24, and 48 hours for, e.g., the first 1, 2, 3, 4, 5, 6, 7, 8 weeks of treatment with a conjugate. In some embodiments, immune tolerance toward conjugates may be induced in a subject with a lysosomal storage disorder such as, e.g., mucopolysaccharidosis I, by treatment with cyclosporin A and azathioprine. For example, the subject may be treated with cyclosporine A and azathioprine as described in Kakkis et al., *Proc. Natl. Acad. Sci. U.S.A.* 101:829-834 (2004).

In some embodiments, the methods comprise treating a subject (before, after, or during treatment with a conjugate) with small molecule therapy and/or gene therapy, including small molecule therapy and gene therapy directed toward treatment of a lysosomal storage disorder. Small molecule therapy may comprise administration of miglustat and/or one or more compounds described in, e.g., U.S. Patent Application Pub. Nos. 2003/0050299, 2003/0153768; 2005/0222244; and 2005/0267094. Gene therapy may be performed as described in, e.g., U.S. Pat. Nos. 5,952,516; 6,066,626; 6,071,890; and 6,287,857; and U.S. Patent Application Pub. No. 2003/0087868.

The terms "treatment," "therapeutic method," and their cognates refer to both therapeutic treatment and prophylactic/preventative measures. Thus, those in need of treatment may include individuals already having a particular lysosomal storage disease as well as those at risk for the disease (i.e., those who are likely to ultimately acquire the disorder or certain symptoms of the disorder).

Therapeutic methods result in the prevention or amelioration of symptoms or an otherwise desired biological outcome, and may be evaluated by improved clinical signs or delayed onset of disease, increased activity of the metabolically defective enzyme, and/or decreased levels of the accumulated substrate of the metabolically defective enzyme.

In some embodiments, the methods comprise administering conjugates comprising (1) a lysosomal enzyme and (2) an oligosaccharide of any of Formulae I-VI to a subject, thereby increasing the deficient lysosomal enzyme activity in the subject by, e.g., at least 10%, 15%, 20%, 25%, 30%, 35%, 40%, 50%, 60%, 70%, 80%, 90%, or 100%, relative to endogenous activity. In some embodiments, the methods comprise administering conjugates comprising (1) a lysosomal enzyme and (2) an oligosaccharide of any of Formulae I-VI to a subject, thereby increasing the deficient enzymatic activity in the subject by, e.g., at least 2, 3, 4, 5, 6, 7, 8, 9, 10, 20, 30, 40, 50, 100, or 1000 fold, relative to endogenous activity The increased enzymatic activity may be determined by, e.g., a reduction in clinical symptoms or by an appropriate clinical or biological assay.

In some embodiments, the methods comprise administering conjugates of the invention comprising GAA to a subject, thereby treating Pompe disease (also known as acid α-glucosidase deficiency, acid maltase deficiency, glycogen storage disease type II, glycogenosis II, and lysosomal α-glucosidase deficiency). In certain embodiments, recombinant human GAA (rhGAA) is prepared in Chinese hamster ovary (CHO) cells. In additional embodiments, rhGAA may be conjugated with an oligosaccharide chosen from Oligosaccharide 103; a mixture of 103 and Formula A; Oligosaccharide 128, 129, 130, 131, 132, 133, or 136; and any combination thereof. In one embodiment, the oligosaccharide is chosen from Oligosaccharide 128 and 136. In additional embodiments, a conjugate containing at least 5 moles of Formula A per mole of GAA is administered to a patient.

In certain embodiments, the patient is an adult who has been diagnosed with Pompe disease. In other embodiments, the patient is an infant or a child.

Increased GAA activity may be determined by biochemical (see, e.g., Zhu et al., *J. Biol. Chem.* 279: 50336-50341 (2004)) or histological observation of reduced lysosomal glycogen accumulation in, e.g., cardiac myocytes, skeletal myocytes, or skin fibroblasts. GAA activity may also be assayed in, e.g., a muscle biopsy sample, in cultured skin fibroblasts, in lymphocytes, and in dried blood spots. Dried blood spot assays are described in e.g., Umpathysivam et al., *Clin. Chem.* 47:1378-1383 (2001) and Li et al., *Clin. Chem.* 50:1785-1796 (2004). Treatment of Pompe disease may also be assessed by, e.g., serum levels of creatinine kinase, gains in motor function (e.g., as assessed by the Alberta Infant Motor Scale), changes in left ventricular mass index as measured by echocardiogram, and cardiac electrical activity, as measured by electrocardiogram. Administration of GAA conjugates may also result in a reduction in one or more symptoms of Pompe disease such as cardiomegaly, cardiomyopathy, daytime somnolescence, exertional dyspnea, failure to thrive, feeding difficulties, "floppiness," gait abnormalities, headaches, hypotonia, organomegaly (e.g., enlargement of heart, tongue, liver), lordosis, loss of balance, lower back pain, morning headaches, muscle weakness, respiratory insufficiency, scapular winging, scoliosis, reduced deep tendon reflexes, sleep apnea, susceptibility to respiratory infections, and vomiting.

In other embodiments, the methods comprise administering conjugates comprising α-galactosidase A to a subject, thereby treating Fabry disease. Fabry disease, or Anderson-Fabry disease, is a rare, X-linked, lysosomal storage disorder marked by a deficiency of α-galactosidase A, and results in accumulation of globotriaosylceramide (GL3) and other neutral glycosphingolipids in the lysosomes of visceral tissues and endothelial, perithelial, and muscle cells. Accumulation of the neutral glycosphingolipids in the vasculature results in narrowing and dilatation of the blood vessels, and ultimately to ischemia and infarction.

Administration of conjugates of the invention comprising α-galactosidase A may result in a reduction in one or more clinical symptoms of Fabry disease including, e.g., acroparesthesia, angina, angiokeratoma, arrythmia, ataxia of gait, burning and/or tingling pain in the hands and feet, cataracts, cold intolerance, conduction abnormalities, corneal whorling, coronary artery disease, dementia, depression, diarrhea, dilated cardiac chambers, dizziness, cardiomegaly, cardiomyopathy, diplopia, dysarthria, fatigue, fever with elevated erythrocyte sedimentation rate, hearing problems, heart disease, heart valve problems, heat intolerance, hemiataxia, hemiparesis, hypohidrosis, impaired sweating, infarction, ischemia, joint pain, kidney disease, left ventricular hypertrophy, lenticular abnormalities, lenticular opacity, lipiduria, muscle weakness, myocardial infarction, nausea, nystagmus, pain (e.g., intense pain radiating throughout the body), polydipsia, proteinuria, post-prandial pain, renal failure, retinal abnormalities, ringing in ears, stomach pain, ST-T wave changes, stroke, uremia, valvular disease, vertigo, vomiting, and weakness. Administration of α-galactosidase A conjugates may result in increased α-galactosidase A activity in, e.g., plasma, tears, leukocytes, biopsied tissues, or cultured skin fibroblasts. Administration of α-galactosidase A conjugates may also result in a histologic finding of a reduction (e.g., of at least 10%) or lack of increase of birefringent lipid globules. It may also result in a decrease in lipid globules in urinary sediment, improved renal function as measured by serum creatinine levels or creatinine clearance, and reduced proteinuria. Administration of α-galactosidase A conjugates may also result in a reduction in GL3 inclusions in the capillary endothelium of the kidney, heart, and skin. Additional assays for measuring efficacy of treatment for Fabry disease can be found in, e.g., MacDermott et al., *J. Med. Genet.* 38:750-760 (2001).

In other embodiments, the methods comprise administering conjugates of the invention comprising acid sphingomyelinase to a subject, thereby treating Niemann-Pick A or Niemann-Pick B disease, or acid sphingomyelinase deficiency. Administration of acid sphingomyelinase conjugates may result in a reduction in one or more clinical symptoms of Niemann-Pick A or Niemann-Pick B disease including, e.g., abnormal cholesterol levels, abnormal lipid levels, ataxia, blood abnormalities, cherry red spots in the eye, frequent lung infections, growth retardation, hepatosplenomegaly, low numbers of platelets, lymphadenopathy, peripheral neuropathy, problems with lung function, shortness of breath, skin pigmentation changes, or xanthomas. In some embodiments, conjugates may be administered intracranially.

In other embodiments, the methods comprise administering conjugates of the invention comprising α-L-iduronidase to a subject, thereby treating mucopolysaccharidosis I (including, e.g., Hurler and Hurler-Scheie forms of MPS 1). Administration of α-L-iduronidase conjugates may result in a reduction in one or more clinical symptoms of MPS I including, e.g., aortic regurgitation, aortic stenosis, carpal tunnel syndrome, chronic rhinitis, conductive hearing loss, constipation, corneal clouding, developmental delay, diarrhea, distended abdomen, dorsolumbar kyphosis, gibbus deformity of the back, hepatosplenomegaly, hydrocephalus, inguinal hernia, kyphosis, mental retardation, mitral regurgitation, mitral stenosis, night-blindness, open-angle glaucoma, poor hand function, progressive arthropathy, recurrent respiratory infections, respiratory insufficiency, retinal degeneration, scoliosis, sensorineural hearing loss, severe back pain, rhinorrhea, sleep apnea, spinal cord compression, thenar atrophy, umbilical hernia, and upper airway complications.

In yet further embodiments, the methods comprise administering conjugates of the invention comprising iduronate-2-sulfatase to a subject, thereby treating mucopolysaccharidosis II (Hunter disease). Administration of iduronate-2-sulfatase conjugates may result in a reduction in one or more clinical symptoms of MPS II including, e.g., cardiac valvular disease, cardiopulmonary failure, carpal tunnel syndrome, chronic diarrhea, chronic papilledema, coarse facial features, corneal opacities, coronary artery narrowing, deafness, dysmorphism, dysostosis, ear infections, hearing impairment, hepatosplenomegaly, hydrocephalus, inguinal herniae, joint stiffness, kyphoscoliosis, mental retardation, myocardial disease, myocardial thickening, pulmonary hypertension, retinal dysfunction, skeletal abnormalities, umbilical herniae, upper respiratory tract infections, and valvular dysfunction.

In yet other embodiments, the methods comprise administering conjugates of the invention comprising N-acetylgalactosamine-4-sulfatase (arylsulfatase B) to a subject, thereby treating mucopolysaccharidosis VI (Maroteaux-Lamy syndrome). Administration of N-acetylgalactosamine-4-sulfatase conjugates may result in a reduction in one or more clinical symptoms of MPS VI including, e.g., blindness, cardiac abnormalities, cardiopulmonary disease, coarse facial features, corneal clouding, ear infections, growth retardation, hepatomegaly, hepatosplenomegaly, joint deformities, nerve entrapment syndromes, respiratory difficulties, skeletal deformities, spinal cord compression, splenomegaly, stiff joints, and upper-airway obstruction.

The foregoing and the following description are exemplary and explanatory only and are not restrictive of the invention, as claimed.

EXAMPLES

Example 1. General Procedures in Oligosaccharide Synthesis

A. Glycosylation

Glycosylation reactions were performed using standard methods by combining a donor saccharide and receptor saccharide. Briefly, donor and acceptor compounds were dissolved in anhydrous DCM under dry nitrogen in the presence of heat-activated 4 A molecular sieves unless indicated otherwise. The solution was cooled and held at 0° C. for ~30 mins, followed by the slow addition of TMSOTf (1 eq). Reactions were checked by TLC (silica gel) using hexanes/EtOAc and quenched with TEA or Hunig's base (1.05 eq). The mixtures were filtered and concentrated to syrups and purified by flash column chromatography using hexanes/EtOAc gradients unless indicated.

B. Acid-Catalyzed Deacetylation

In certain examples, acetylated compounds are deacetylated prior to glycosylation or other modifications such as phosphorylation. In the examples provided below, hydrogen chloride was generated by the addition of acetyl chloride to cold (0° C.) dry methanol. The concentrated solution was added to a 1:3 solution of the acetylated compound in DCM/methanol. The final concentration was 3% w/v with respect to the methanol component of the solution. Deacetylation reactions were run for: a) ~18 h for primary acetates and b) ~48-64 h for secondary acetates. Reactions were quenched with TEA or Hunig's base followed by an aqueous extraction from DCM or EtOAc unless indicated.

C. Phosphorylation

In some examples, saccharides are subject to site-specific phosphorylation. To a solution of the saccharide in dry acetonitrile at room temperature was added 5-methyltetrazole (3.4 eq), and the mixture was stirred for 30 mins under dry nitrogen. Dibenzyldiisopropylphosphoramidite (1.7 eq per OH group) was added and stirred until the reaction was complete (~60 mins). Reactions were checked by TLC (silica gel) using hexanes/EtOAc. The solution was cooled in ice/water for 15 mins and 30% w/v hydrogen peroxide (2 eq) added. After ~60 mins the reaction was complete, and excess saturated sodium thiosulphate was added. The mixture was concentrated to a gum, dissolved in EtOAc, washed with semi-saturated brine and dried over sodium sulphate. The residue was purified by flash column chromatography using hexanes/EtOAc gradients, unless otherwise indicated.

Example 2: Synthesis of Disaccharide Aminooxyacetamido Propyl 2-O-[6-O-phosphoryl-α-D-mannosyl]-α-D-mannoside (17)

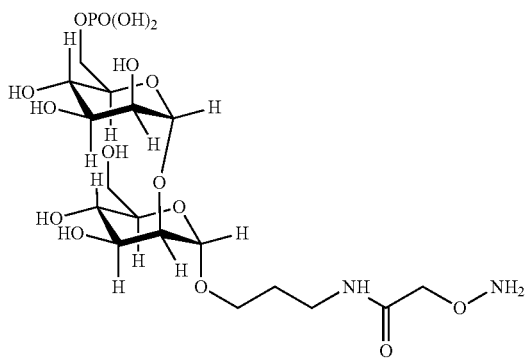

Allyl α-D-mannoside was prepared according to the method described in Pekar et al., *J. Org. Chem.* 66:7432 (2001). To allyl-α-D-mannoside (8.68 g, 39.4 mmol) in anhydrous methanol (100 mL) was added 2,3-butanedione (3.63 mL, 86.1 mmol), trimethylorthoformate (16 mL, 146 mmol) and 10-(+)-camphorsulphonic acid (1.37 g, 5.9 mmol). The mixture was heated under reflux for 9 h under dry nitrogen. The reaction mixture was quenched with TEA (1 mL) and concentrated to a red syrup and purified by silica gel flash column chromatography using EtOAc in hexanes 40-80%, affording allyl 3-O,4-O-[dimethoxybutan-2',3'-diyl]-α-D-mannoside 1 as a white solid (3.89 g, 29.4%).

Compound 1 (2.65 g, 8 mmol) was dissolved in dry pyridine (20 mL), the solution was cooled in an ice/water bath, and t-butyldiphenylsilyl chloride (2.28 mL, 8.7 mmol) was added. After 18 h, pyridine (20 mL) and acetic anhydride (1.6 mL, 16 mmol) were added, and the solution heated to 50° C. for 16 h, then concentrated to a syrup and stripped with toluene. The residue was dissolved in EtOAc (60 mL) and washed with 1M HCl (2×50 mL), saturated sodium bicarbonate (50 mL) and dried over sodium sulphate. The mixture was filtered and concentrated under vacuum and the solution was concentrated, affording allyl 2-O-acetyl-6-O-t-butyldiphenylsilyl-3-O,4-O[dimethoxybutan-2',3'-diyl]-α-D-mannoside 2 as a syrup (5.0 g).

Palladium (II) chloride (0.425 g, 2.4 mmol) was added to a solution of 2 (5.0 g, 8 mmol) in anhydrous methanol (25 mL), with stirring. After ~3 h the reaction was quenched with TEA (0.75 mL, 4.8 mmol). The methanol was removed under reduced pressure and the residue was purified by silica gel flash column chromatography using EtOAc in hexanes 10-50%, affording 2-O-acetyl-6-O-t-butyldiphenylsilyl-3-O,4-O[dimethoxybutan-2',3'-diyl]-α-D-mannoside 3 as a white foam (2.72 g, 59.2%).

Trichloroacetonitrile (1.75 mL, 17.4 mmol) and DBU (0.05 mL, 0.35 mmol) were added to a solution of 3 (1.0 g 1.74 mmol) in dry DCM (1 mL). After ~75 min, the solution was directly purified by silica gel flash column chromatography using EtOAc in hexanes (0 to 30%), affording 2-O-acetyl-6-O-t-butyldiphenylsilyl-3-O,4-O[dimethoxybutan-2',3'-diyl]-α-D-mannose trichloroacetimidate 4 as a white foam (0.98 g, 78.2%). Donor 4 (0.98 g, 1.36 mmol) and acceptor 3-N-benzyloxycarbonylaminopropanol (0.284 g, 1.36 mmol) were converted according to the general glycosylation procedure of Example 1, affording N-benzyloxycarbonylaminopropyl 2-O-acetyl-6-O-t-butyldiphenylsilyl-3-O,4-O[dimethoxybutan-2',3'-diyl]-α-D-mannoside 5 as a white foam (0.66 g, 64%).

To a solution of 5 (0.66 g, 0.87 mmol) in anhydrous methanol (5 mL) was added 25% w/v sodium methoxide in methanol (0.05 mL, 0.22 mmol). After ~1 h, the reaction was quenched with glacial acetic acid (0.025 mL) and concentrated to a syrup. The product was dissolved in DCM (10 mL), washed with semi-saturated brine (5 mL) and dried over sodium sulphate to give a white foam N-benzyloxycarbonylaminopropyl 6-O-t-butyldiphenylsilyl-3-O,4-O[dimethoxybutan-2',3'-diyl]-α-D-mannoside 6 (0.58 g, 92%).

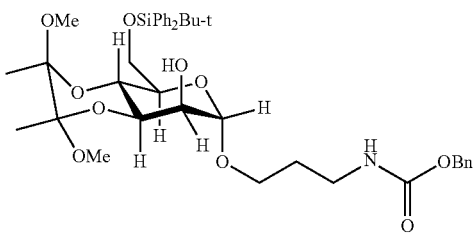

Allyl α-D-mannoside (3.15 g, 14.3 mmol) was dissolved in dry pyridine (20 mL) and cooled in an ice/water bath. t-Butyldiphenylsilylchloride (4.03 mL, 15.7 mmol) was added and the solution was allowed to come to room temperature. After stirring for 18 h, benzoyl chloride (5.93 mL, 51.5 mmol) was added, and after 24 h the reaction was quenched with water (3 mL) and stirred for 30 min. The solution was concentrated under vacuum and stripped with toluene (3×50 mL). The residue was dissolved in EtOAc (100 mL), washed with cold 1M HCl (50 mL), semi-saturated brine (50 mL), semi-saturated sodium hydrogen carbonate (50 mL), semi-saturated brine (50 mL) dried over sodium sulphate, filtered, and concentrated to a syrup. It was purified by silica gel flash column chromatography using EtOAc in hexanes 0-50%, affording allyl 2,3,4-tri-O-benzoyl-6-O-t-butyldiphenylsilyl-α-D-mannoside 7 as a white foam (8.62 g, 78.2%).

Glacial acetic acid (11.1 mL, 18.26 mmol) and 1M tetrabutylammonium fluoride (18.26 mL, 18.26 mmol) were added to a solution of 7 (12.77 g, 16.6 mmol) in dry THF (50 mL). At 80 mins, glacial acetic acid (0.15 mL, 2.5 mmol)) and 1M tetrabutylammonium fluoride (2.5 mL, 2.5 mmol) were added, followed at 90 mins by more glacial acetic acid (0.25 mL, 4.15 mmol)) and 1M tetrabutylammonium fluoride (4.15 mL, 4.15 mmol). After 2 h the solution was concentrated to half volume and diluted with EtOAc (150 mL). The solution was washed with semi-saturated brine (2×150 mL) and semi-saturated sodium bicarbonate (200 mL), concentrated, and the residue was purified by silica gel flash column chromatography with EtOAc in hexanes 10-50%, affording allyl 2,3,4-tri-O-benzoyl-α-D-mannoside 8 as a white foam (6.75 g, 76.4%). Compound 8 (6.75 g, y mmol) was converted according to the general procedure for phosphorylation affording allyl 2,3,4-tri-O-benzoyl-6-O-dibenzylphosphoryl-α-D-mannoside 9 as a white foam (9.52 g, 95%).

Palladium (II) chloride (0.638 g, 3.6 mmol) was added to a solution of 9 (9.52 g, 12.1 mmol) in dry methanol (50 mL). After ~5 h more palladium (II) (0.145 g) was added and the mixture was stored for 18 h. The solution was filtered, concentrated, and the residue was purified by silica gel flash column chromatography with EtOAc in hexanes 20-70%, affording 2,3,4-tri-O-benzoyl-6-O-dibenzylphosphoryl-α-D-mannose 10 as a white foam (3.8 g, 42.5%).

Trichloroacetonitrile (5.06 mL, 5.1 mmol) and DBU (0.15 mL, 1 mmol) were added to a solution of 10 (3.8 g) in dry DCM under dry nitrogen at 0° C. After ~90 mins, the solution was directly purified by silica gel flash column chromatography with EtOAc in hexanes 10-60%, affording 2,3,4-tri-O-benzoyl-6-O-dibenzylphosphoryl-α-D-mannoside trichloroacetimidate 11 as a white foam (3.3 g, 72.1%).

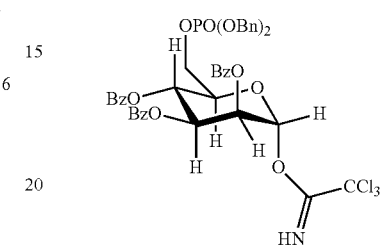

Donor 6 (2.62 g, 2.97 mmol) and acceptor 11 (1.92 g, 2.7 mmol) were converted according to the general glycosylation procedure of Example 1, affording N-benzyloxycarbonylaminopropyl 2-O-[2,3,4-tri-O-benzoyl-6-O-dibenzylphosphoryl-α-D-mannosyl]-6-O-t-butyldiphenylsilyl-3-O,4-O[dimethoxybutan-2',3'-diyl]-α-D-mannoside 12 as a white foam (1.27 g, 32.2%).

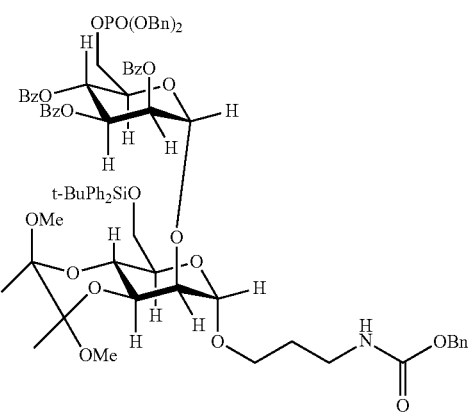

TFA/water 19:1 v/v (8.4 mL) was added to a solution of 12 (2.1 g, 1.44 mmol) in DCM (8 mL) cooled in an ice/water bath. After ~2 h the starting material was consumed as shown by TLC. Ethanol (25 mL) was added to the solution, then concentrated and stripped with ethanol (3×25 mL). The residue was dissolved in dry methanol (10 mL) and cooled in an ice/water bath. Acetyl chloride (0.4 mL) was added, affording a 3% w/v solution in HCl. The solution was allowed warm to room temp. After ~2 h the starting material was consumed as shown by TLC. The reaction was quenched with triethylamine (1 mL), concentrated, and the residue was purified by silica gel flash column chromatography with EtOAc in hexanes 30-100% to give 13 as a white foam (0.758 g, 47.9%). To 13 (0.758 g, 0.69 mmol) in anhydrous methanol (10 mL) was added 25% w/v sodium methoxide in methanol (0.15 mL). After ~1 h the starting material was consumed as shown by tlc. The reaction was quenched with 1M HCl, affording 14. To the solution was added glacial acetic acid (25 μL), wetted 10% Pd/C (0.1 g), and a hydrogen balloon was attached. After 6 h reaction the product charred with 5% sulphuric acid/EtOH but was not UV active. The mixture was filtered and concentrated to an oil, then dissolved in water (10 mL) and freeze dried to give 3-aminopropyl 2-O-[6-O-phosphoryl-α-D-mannosyl]-α-D-mannoside 15 (0.300 g, 91.3% from 13).

A solution of 0.1 M NaOH (0.2 mL) was added to a solution of 15 (0.1 g, 0.21 mmol) in water (8.5 mL), followed by N-t-butoxycarbonylaminooxyacetyl 2,3,5,6-tetrafluorophenylate (0.14 g, 0.42 mmol) in THF (8.5 mL). After 18 h the solution was adjusted to pH 4 with 2M HCl, and the solution was extracted with DCM (3×10 mL). The aqueous phase was freeze dried. affording N-t-butoxycarbonylaminooxyacetamidopropyl 2-O-[6-O-phosphoryl-α-D-mannosyl]-α-D-mannoside 16 (0.12 g). Compound 16 (0.12 g) was dissolved in TFA/DCM 1:1 (10 mL) and the solution was stirred for ~30 mins, then concentrated to an oil. It was dissolved in water (5 mL) and the product freeze dried, affording a solid (0.45 g). The solid was purified using Biogel® P2 and eluted with water to afford 17 (0.063 g).

Example 3: Synthesis of Trisaccharide (35)

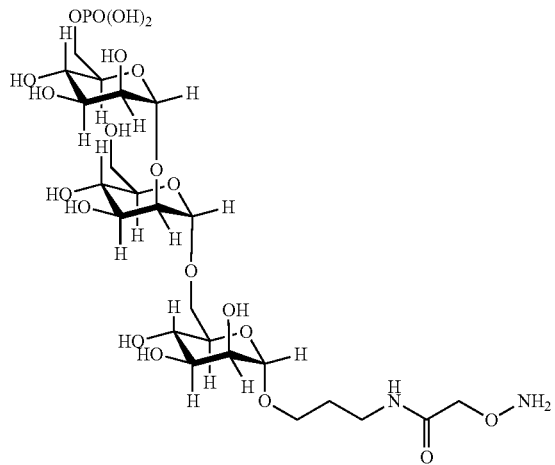

35

2-O-acetyl-3,4,6-tri-O-benzyl-α-D-mannose trichloroacetimidate 18 was prepared as described in Yamazaki et al., *Carb. Res.* 201:31 (1990).

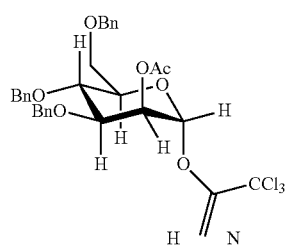

18

6-O-acetyl-3,4,6-tri-O-benzoyl-α-D-mannose trichloroacetimidate 19 was prepared as described in Heng et al., *J. Carb. Chem.* 20:285 (2001).

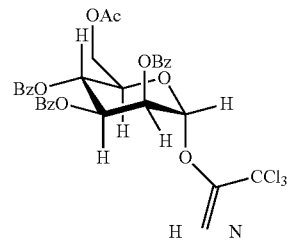

19

Donor 19 (5.0 g, 7.4 mmol) and acceptor N-9-fluorenylmethylcarbonylamino propanol (2.41 g, 8.1 mmol) were converted according to the general glycosylation procedure affording N-9-fluorenylmethylcarbonylaminopropyl 6-O-acetyl-2,3,4-tri-O-benzoyl-α-D-mannoside 29 as a white foam (4.0 g, 66.4%).

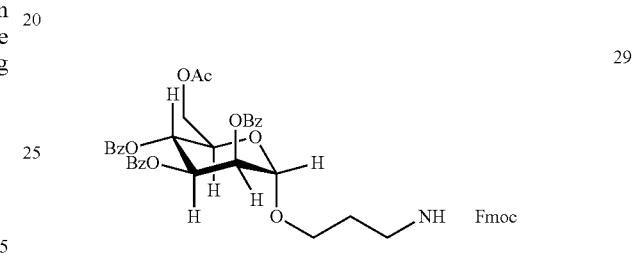

29

Compound 29 (4.0 g, 4.9 mmol) was converted according to the general procedure for acid catalysed deacetylation of secondary acetates (b) affording N-9-fluorenylmethylcarbonylaminopropyl 2,3,4-tri-O-benzoyl-α-D-mannoside 30 as a white foam (3.3 g, 87.3%). Donor 18 (3.27 g, 5.16 mmol) and acceptor 30 (3.3 g, 4.3 mmol) were converted according to the general glycosylation procedure affording N-9-fluorenylmethylcarbonylaminopropyl 6-O-[2-O-acetyl-3,4,6-tri-O-benzylmannosyl]-2,3,4-tri-O-benzoyl-α-D-mannoside 31 as a white foam (4.94 g, 92.7%).

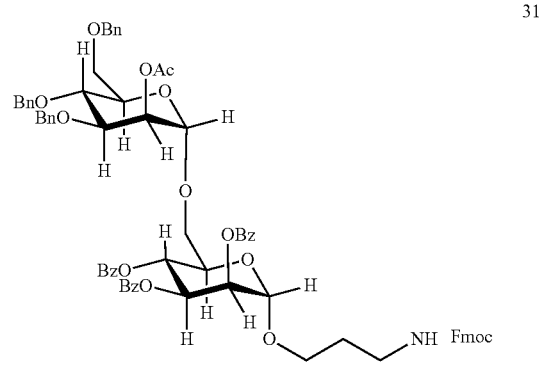

31

Compound 31 (4.94 g, 3.96 mmol) was converted according to the general procedure for acid catalysed deacetylation of secondary acetates (b) affording N-9-fluorenylmethylcarbonylaminopropyl 6-O-[3,4,6-ti-O-benzylmannosyl]-2,3,4-tri-O-benzoyl-α-D-mannoside 32 as a white foam (1.73 g, 36%). Compound 11 was prepared according to the method of Example 2. Donor 11 (3.37 g, 3.74 mmol) and acceptor 32 (1.73 g, 1.44 mmol) were converted according to the general glycosylation procedure affording 33 as a white foam (1.2 g, 43.1%).

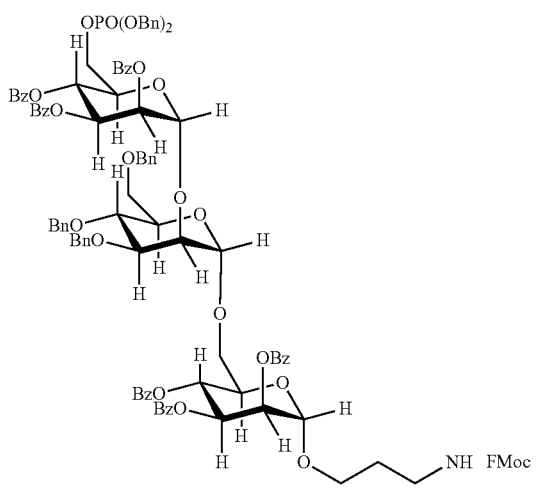

33

To a solution of 33 (1.2 g, 0.62 mmol) in anhydrous THF (10 mL) was added dodecylthiol (1.48 mL, 6.2 mmol) and Diazabicycloundec-7-ene (DBU) (0.093 mL, 0.62 mmol). After ~18 h the starting material was consumed as shown by tlc. The solution was concentrated to a syrup and purified by silica gel flash column chromatography using methanol in DCM 0-20%. To the product was added methanol/water 1:1 (20 mL) and acetic acid (25 µL) and Pd/C (0.1 g) and a balloon of hydrogen was attached. After 18 h the solution was filtered through Celite and concentrated to a white foam. The foam was dissolved in dry methanol (10 mL) and 25% w/v sodium methoxide in methanol (0.15 mL,) after 6 h the solution was concentrated taken in water (10 mL) and washed with DCM (10 mL). The aqueous phase was freeze dried affording aminopropyl 6-O-([α-D-mannosyl]-2-O-[6-O-phosphoryl-α-D-mannosyl])-α-D-mannoside 34 (0.27 g, 63.5% from 33) as the disodium salt.

To a solution of 34 (0.17 g, 0.3 mmol) in water/DMSO 1:1 (10 mL) then N-t-butoxycarbonylamino-oxyacetyl 2,3,5,6-tetrafluorophenylate (0.34 g, 1.14 mmol) in DMSO (2 mL) and 3-Hydroxy-1,2,3-benzotrazin-4(3H)-one (DHBT) (0.09 g, 0.6 mmol) in DMSO (1 mL) were added. After 24 h the solution was purified on sephadex size exclusion resin. Fractions were checked on silica gel plates by charring and selected fractions pooled and freeze dried affording a solid. It was dissolved in TFA/DCM (8 mL) and was stirred for 60 mins and then concentrated to an oil. Water (5 mL) was added and the product was purified on sephadex size exclusion resin. Fractions were checked on silica gel plates by charring and selected fractions pooled and freeze dried affording 35 (0.033 g, 16.4% from 34).

Example 4: Synthesis of Tetrasaccharides

A. Aminooxyacetamido 1,5-di-3-amidoorooyl [2-O-[6-O-phosphoryl-α-D-mannosyl]-α-D-mannosyl] glutamate (28)

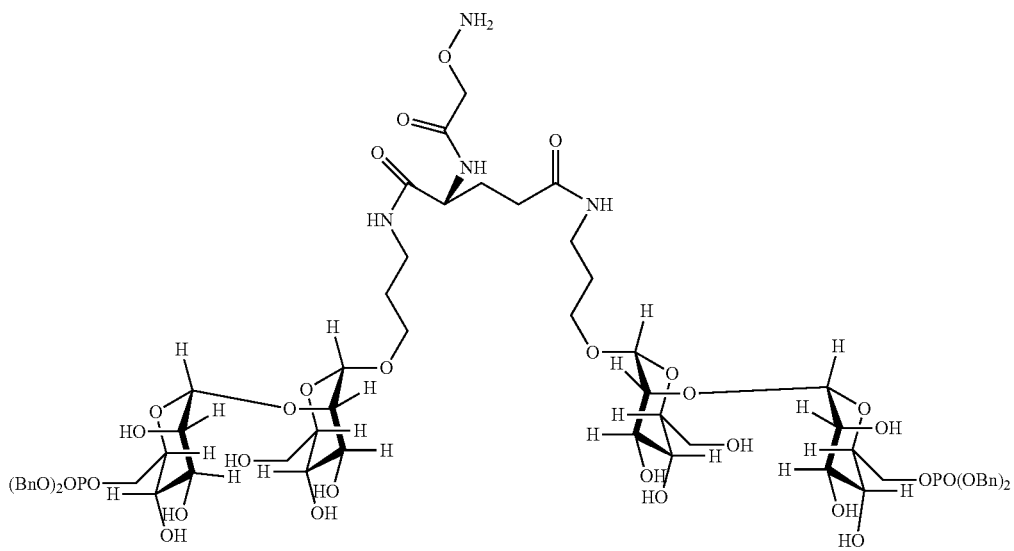

28

Compound 19 was prepared according to the method described in Example 3. Donor 19 (15.49 g, 24.3 mmol) and acceptor 3-N-9-fluorenylmethoxycarbonylaminopropanol (8.7 g, 29.19 mmol) were converted according to the general glycosylation procedure affording N-9-fluorenylmethoxycarbonylaminopropyl 2-O-acetyl-3,4,6-tri-O-benzyl-α-D-mannoside 20 as a white foam (10.55 g, 55%).

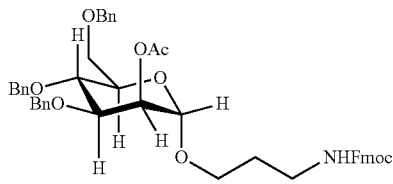

Acetyl chloride (4.8 mL, 63 mmol) was added dropwise to a solution of 20 (10.5 g, y mmol) in dry DCM (50 mL) and anhydrous methanol (100 mL) over ~30 mins, affording a 2.3% w/v solution of HCl in methanol. After ~18 h the reaction was quenched with Hunig's base (9.81 mL, 63 mmol) and an additional 1.5 mL was added. The solution was concentrated to a syrup, stripped with chloroform (2×50 mL), dissolved in DCM (100 mL) and washed with semi-saturated saline (100 mL) and dried over sodium sulphate. The solution was concentrated and purified by silica gel flash column chromatography with EtOAc in hexanes 0-100% to give a white foam N-9-fluorenylmethoxycarbonylaminopropyl 3,4,6-tri-O-benzyl-α-D-mannoside 21 (6.11 g, 61.2%). Donor 21 (6.11 g, 13.4 mmol) and acceptor 11 (7.1 g, 7.9 mmol) were converted according to the general glycosylation procedure affording N-9-fluorenylmethoxycarbonylaminopropyl 2-O-[6-O-dibenzylphosphoryl-2,3,4-tri-O-benzoyl-α-D-mannosyl]-3,4,6-tri-O-benzyl-α-D-mannoside 22 as a white foam (5.8 g, 50.1%).

To a solution of 22 (5.8 g, 3.96 mmol) in anhydrous THF (75 mL) was added dodecylthiol (9.53 mL, 40 mmol) and DBU (0.6 mL, 4 mmol). After ~4 h the reaction was quenched with methanolic HCl (5.6 mL, 8 mmol) and concentrated to a syrup. The product triturated with diethyl ether affording 3-aminopropyl 2-O-[2,3,4-tri-O-benzoyl-α-D-mannosyl]-3,4,6-tri-O-benzyl-α-D-mannoside hydrochloride 23 as a gum (3.77 g, 74.5%).

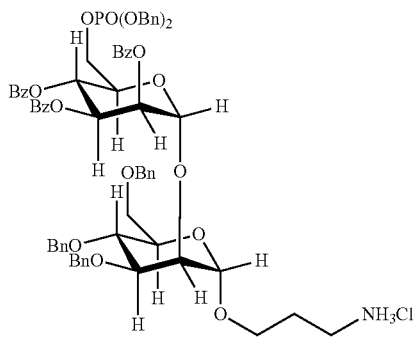

To a solution of 23 (3.77 g, 2.95 mmol) in dry acetonitrile (50 mL) was added N-benzyloxycarbonyl glutamic acid (0.3661 g, 1.3 mmol), N-hydroxybenzotriazole (HOBt) (0.4 g, 2.95 mmol), DBU (4.6 mL, 4 mmol), and 1-ethyl-3-[3-dimethylaminopropyl]carbodiimide (EDC) (0.75 g, 8.85 mmol). After 16 h Hünig's base (0.25 mL) was added followed by more EDC (0.75 g, 8.85 mmol). After 21 h the solution was concentrated to a syrup and purified by silica gel flash column chromatography using 10% 2-propanol in DCM against DCM 0-50% affording N-benzyloxycarbonylamino 1,5-di-[3-amidopropyl 2-O-[2,3,4-tri-O-benzoyl-6-O-dibenzylphosphoryl-α-D-mannosyl]-3,4,6-tri-O-benzyl-α-D-mannosyl]glutamate 24 as a white foam (0.97 g, 11.2%).

To a solution of 24 (0.912 g, 0.33 mmol) in anhydrous DCM (20 mL) and methanol (25 mL) was added 25% w/v sodium methoxide in methanol (0.09 mL, 0.41 mmol). After ~6.5 h the reaction was quenched with 1M HCl (0.41 mL, 0.41 mmol) and concentrated to a syrup and purified by silica gel flash column chromatography using 10% 2-propanol in DCM against DCM 0-100%, affording N-benzyloxycarbonylamino 1,5-di-3-amidopropyl [2-O-[6-O-dibenzylphosphoryl-α-D-mannosyl]-3,4,6-tri-O-benzyl-α-D-mannosyl]glutamate 25 (0.306 g, 44.4%).

To a stirred solution of 25 (0.3 g, 0.144 mmol) in THF/water 2:1 v/v (75 mL), wetted 10% Pd/C (0.052 g) and a hydrogen balloon was attached. After 16 h glacial acetic acid (25 μL) was added, and a fresh hydrogen balloon attached. After 6 h more 10% Pd/C (0.04 g) was added and more hydrogen. After 18 h fresh 5% Pc/C (0.05 g) was added and more hydrogen. After 24 h the product charred with 5% sulphuric acid/EtOH but was not UV active. The mixture was filtered through celite, and the pad washed and concentrated to ~30% to remove the THF, then freeze dried to give 1,5-di-3-amidopropyl [2-O-[6-O-phosphoryl-α-D-mannosyl]-α-D-mannosyl]glutamate 26 (0.121 g, 77.9%).

N-t-butoxycarbonylaminooxyacetyl 2,3,5,6-tetrafluorophenylate (0.19 g, 0.57 mmol) in DMSO (1 mL) and 3,4-Dihydro-3-hydroxy-4-oxo-1,2,3-benzotriazine (DHBT) (0.052 g, 0.3 mmol) in DMSO (1 mL) were added to a solution of 26 (0.16 g, 0.15 mmol) in water/DMSO 1:1 (7.5 mL). After 18 h the solution was purified on sephadex size exclusion resin. Fractions were checked on silica gel plates by charring and selected fractions pooled and freeze dried, affording N-t-butoxycarbonylaminooxyacetamido 1,5-di-3-amidopropyl [2-O-[6-O-phosphoryl-α-D-mannosyl]-α-D-mannosyl]glutamate 27 (0.095 g, 42.1%). To compound 27 was added TFA/DCM 1:1 (8 mL) and the mixture was stirred for until dissolved (~60 mins), then concentrated to an oil. Water (10 mL) was added and the product was purified on sephadex size exclusion resin. Fractions were checked on silica gel plates by charring and selected fractions pooled and freeze dried affording 28 (0.048 g, 54.2%).

B. Aminooxyacetamidopropyl 6-O-([α-D-mannosyl]-6-O-[α-D-mannosyl]-2-O-[6-O-phosphoryl-α-D-mannosyl])-α-D-mannoside (47)

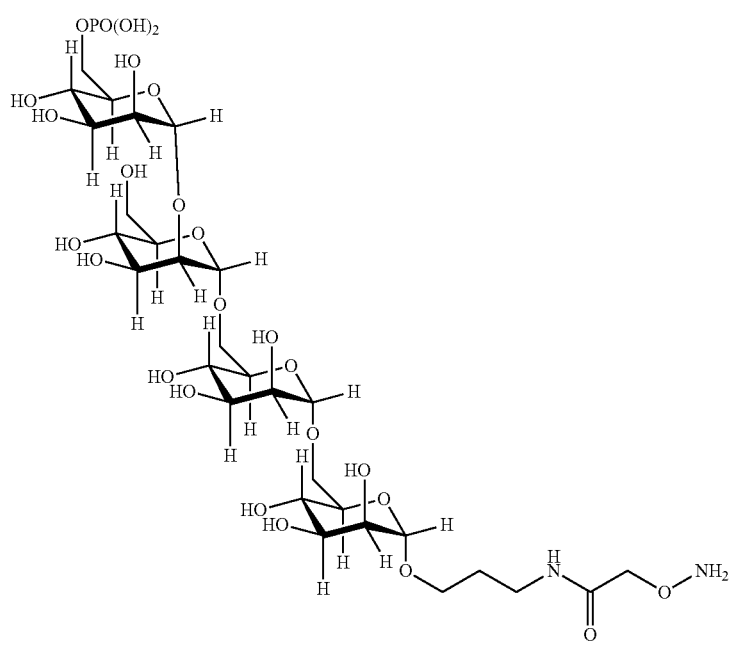

47

Compound 11 was prepared as described in Example 2. Donor 11 (5.0 g, 7.4 mmol) and acceptor 3-N-benzyloxycarbonylaminopropanol (1.93 g, 9.25 mmol) were converted according to the general glycosylation procedure of Example 1, affording a white foam. The product was converted according to the general procedure for acid catalyzed deacetylation of primary acetates, affording N-benzyloxycarbonylaminopropyl 2,3,4-tri-O-benzoyl-α-D-mannoside 36 as a white foam.

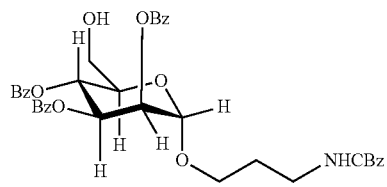

36

Donor 19 (4.47 g, 6.6 mmol) and acceptor 36 (3.6 g, 5.3 mmol) were converted according to the general glycosylation procedure of Example 1, affording N-benzyloxycarbonylaminopropyl 6-O-([6-O-acetyl-2,3,4-tri-O-benzoyl-α-D-mannosyl])-2,3,4-ti-O-benzoyl-α-D-mannoside 37 as a white foam (3.8 g, 63.3%). Compound 37 (3.8 g, 3.17 mmol) was converted according to the general procedure for acid catalysed deacetylation of primary acetates, affording N-benzyloxycarbonylaminopropyl 6-O-[2,3,4-tri-O-benzoyl-α-D-mannosyl]-2,3,4-tri-O-benzoyl-α-D-mannoside 38 as a white foam (3.5 g, 95.3%).

Compound 18 was prepared according to the method described in Yamazaki et al., Carb. Res. 201:31 (1990). Donor 18 (2.41 g, 3.75 mmol) and acceptor 38 (3.5 g, 3 mmol) were converted according to the general glycosylation procedure of Example 1, affording N-benzyloxycarbonylaminopropyl 6-O-([2,3,4-tri-O-benzoyl-α-D-mannosyl]-6-O-[2-O-acetyl-3,4,6-tri-O-benzyl-α-D-mannosyl])-2,3,4-tri-O-benzoyl-α-D-mannoside 39 as an oil (5.63 g). Compound 39 (5.83 g) was converted according to the general procedure for acid catalysed deacetylation of secondary acetates (see Example 1), affording N-benzyloxycarbonyl-aminopropyl 6-O-([2,3,4-tri-O-benzoyl-α-D-mannosyl]-6-O-[3,4,6-tri-O-benzyl-α-D-mannosyl])-2,3,4-tri-O-benzoyl-α-D-mannoside 40 as a white foam (2.0 g, 41.9% from 38). Donor 19 (1.07 g, 1.63 mmol) and acceptor 41 (2.0 g, 1.3 mmol) were converted according to the general glycosylation procedure, affording N-benzyloxycarbonylaminopropyl 6-O-([2,3,4-tri-O-benzoyl-α-D-mannosyl]-6-O-[3,4,6-tri-O-benzyl-α-D-mannosyl]-2-O-[6-O-acetyl-2,3,4-tri-O-benzoyl-α-D-mannosyl])-2,3,4-tri-O-benzoyl-α-D-mannoside 42 as a white foam (1.4 g, 50.8%). Compound 42 (1.4 g, 0.066 mmol) was converted according to the general procedure for acid catalysed deacetylation of primary acetates, affording N-benzyloxycarbonyl-aminopropyl 6-O-([2,3,4-tri-O-benzoyl-α-D-mannosyl]-6-O-[3,4,6-tri-O-benzyl-α-D-mannosyl]-2-O-[2,3,4-tri-O-benzoyl-α-D-mannosyl])-2,3,4-tri-O-benzoyl-α-D-mannoside 43 as a white foam (1.0 g, 80%). Compound 43 (1.0 g, 0.048 mmol) was converted according to the general procedure for phosphorylation affording N-benzyloxycarbonylaminopropyl 6-O-([2,3,4-tri-O-benzoyl-α-D-mannosyl]-6-O-[3,4,6-tri-O-benzyl-α-D-mannosyl]-2-O-[6-O-dibenzylphosphoryl-2,3,4-tri-O-benzoyl-α-D-mannosyl])-2,3,4-tri-O-benzoyl-α-D-mannoside 44 as a white foam (0.9 g, 80.7%).

44

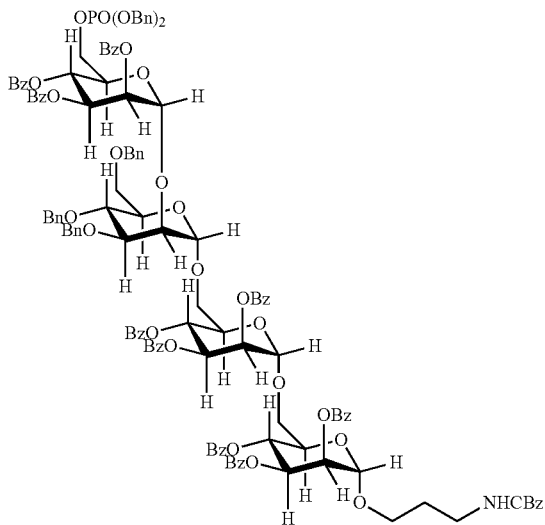

To a solution of 44 (0.9 g, 0.039 mmol) in anhydrous methanol (20 mL) was added 25% w/v sodium methoxide in methanol (0.09 mL, 0.4 mmol). After ~7 h, the reaction was quenched with 1M HCl (0.5 mL), 10% Pd/C (0.2 g), and water (10 mL). The mixture was held under hydrogen with a balloon for 24 h. The mixture was filtered with through celite and washed with EtOAc (20 mL). The solution was freeze dried to give a white solid N-benzyloxycarbonyl-aminopropyl 6-O-([α-D-mannosyl]-6-O-[3,4,6-ti-O-benzyl-α-D-mannosyl]-2-O-[6-O-dibenzylphosphoryl-α-D-mannosyl])-α-D-mannoside 45 (0.23 g, 74.7% from 44).

N-t-butoxycarbonylaminooxyacetyl 2,3,5,6-tetrafluorophenylate (0.375 g, 1.14 mmol) in DMSO (2 mL) and DHBT (0.1 g, 0.6 mmol) in DMSO (1 mL) were added to a solution of 45 (0.23 g, 0.3 mmol) in water/DMSO 1:1 (10 mL). After 24 h the solution was purified on sephadex size exclusion resin. Fractions were checked on silica gel plates by charring, and selected fractions pooled and freeze dried. The product was reacylated in water/DMSO 1:1 (10 mL) using N-t-butoxycarbonylaminooxyacetyl 2,3,5,6-tetrafluorophenylate (0.375 g, 1.14 mmol) in DMSO (2 mL) and DHBT (0.1 g, 0.6 mmol) in DMSO (1 mL). After 24 h the solution was purified on sephadex size exclusion resin, and the fractions pooled and freeze dried, affording N-t-butoxycarbonylaminooxyacetamidopropyl 6-O-([α-D-mannosyl]-6-O-[α-D-mannosyl]-2-O-[6-O-phosphoryl-α-D-mannosyl])-α-D-mannoside 46 (0.11 g, 37.5%). Compound 46 was dissolved in TFA/DCM (8 mL) was added. The solution was stirred for 60 mins and then concentrated to an oil. Water (5 mL) was added and the product was purified on sephadex size exclusion resin. Fractions were checked on silica gel plates by charring, and selected fractions pooled and freeze dried, affording 47 (0.07 g, 70.7%).

Example 5: Synthesis of β-Linked Hexasaccharide

A. Methylcrotonyl 3,4,6-tri-O-benzyl-β-D-mannoside (51)

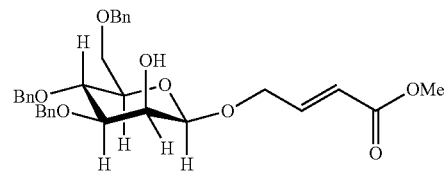

51

2-O-acetyl-3,4,6-tri-O-benzyl-α-D-mannose was prepared as described in Mayer et al., Eur J. Org. Chem. 10:2563 (1999). 25% w/v sodium methoxide in methanol (0.5 mL) was added to a solution of 2-O-acetyl-3,4,6-tri-O-benzyl-α-D-mannose (8.0 g, 23.3 mmol) in anhydrous methanol (50 mL). After ~2 hours the starting material was consumed as shown by thin layer chromatography (TLC). The reaction was quenched with Amberlite IR120 (H+) resin, filtered, and concentrated to a syrup to give 3,4,6-tri-O-benzyl-α-D-mannose 50 (6.67 g, 99%). To compound 50 was added toluene (150 mL) followed by dibutyltin oxide (3.88 g, 16.28 mmol), and the mixture was heated under reflux for 3 h using a Dean-Stark condenser. The resulting solution was cooled, concentrated to a syrup, and dissolved in dry DMF (50 mL). Cesium fluoride (2.28 g, 12.1 mmol), tetrabutylammonium iodide (5.47 g, 14.8 mmol), and methyl 4-bromocrotonate (2.46 mL, 22.2 mmol, tech grade) were added to the mixture and heated to ~60° C. for 18 hours. The mixture was allowed to cool and the solid filtered off. It was diluted with isopropyl ether/EtOAc 3.7:1 (380 mL) and washed with semi-saturated sodium thiosulphate (240 mL). The aqueous phase was extracted with isopropyl ether/EtOAc 3.7:1 (2×190 mL) and the organic layers pooled and concentrated. The syrup was stripped with isopropanol (2×25 mL), and purified by flash column chromatography using a EtOAc in hexanes 0-50% to afford 51 as a syrup (4.58 g, 56.4%). 13C-NMR (100 MHz) $^1J_{1C,1H}$ (100 MHz),157 Hz (β<160 Hz, α>170 Hz)

B. Methylbutyryl 3,4,6-tri-O-benzyl-β-D-mannoside (52)

Compound 50 was prepared as described in Example 2. To compound 50 (9.4 g, 21 mmol) was added toluene (200 mL) followed by dibutyltin oxide (5.49 g, 22 mmol), and the mixture was heated under reflux for 23 h using a Dean-Stark condenser. The resulting solution was cooled, concentrated to a syrup and dissolved in dry DMF (100 mL). Methyl 4-bromobutyrate (4.23 mL, 32 mmol), tetrabutylammonium iodide (1.94 g, 5.25 mmol), and cesium fluoride (3.91 g, 25.5 mmol) were added and the mixture was heated to 60° C. for 2 h, followed by 18 h at ambient temperature. The mixture was allowed to cool and filtered through celite and washed with EtOAc (50 mL). It was concentrated to a gum, stripped with toluene (3×40 mL), absorbed onto silica and purified by flash column chromatography using a EtOAc in hexanes 0-70% to afford 52 as an oil (9.11 g, 78.6%). 13C-NMR (100 MHz) $^1J_{1C,1H}$ (100 MHz),157.2 Hz (β<160 Hz, α>170 Hz). No α-linked product was observed.

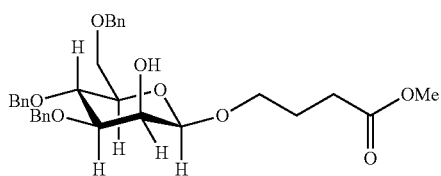

52

C. Methylbutyryl 2-O-[6-O-phosphoryl-α-D-mannosyl]-β-D-mannoside (57)

Compound 52 was prepared as described in Example 2, and 6-O-acetyl-3,4,6-tri-O-benzoyl-α-D-mannose trichloroacetimidate 19 was made according to the method of Heng et al., *J. Carb. Chem.* 20:285 (2001). Donor 19 (4.29 g, 6.36 mmol) and acceptor 52 (2.9 g, 5.3 mmol) were converted according to the general glycosylation procedure of Example 1, affording methylbutyryl 2-O-[6-O-acetyl-2,3,4-tri-O-benzoyl-α-D-mannosyl]-3,4,6-tri-O-benzyl-β-D-mannoside 53 as a white foam (4.41 g, 78.5%). Compound 53 (4.41 g, 4.1 mmol) was converted according to the general procedure for acid catalysed deacetylation of primary acetates described in Example 1, affording methylbutyryl 2-O-[2,3,4-tri-O-benzoyl-α-D-mannosyl]-3,4,6-tri-O-benzyl-β-D-mannoside 54 as a white foam (2.25 g, 53.7%). Compound 54 (2.25 g, 2.2 mmol) was converted according to the general procedure for phosphorylation of Example 1, affording methylbutyryl 2-O-[2,3,4-tri-O-benzoyl-6-O-dibenzylphosphoryl-α-D-mannosyl]-3,4,6-tri-O-benzyl-β-D-mannoside 55 as a white foam (2.2 g, 77.7%).

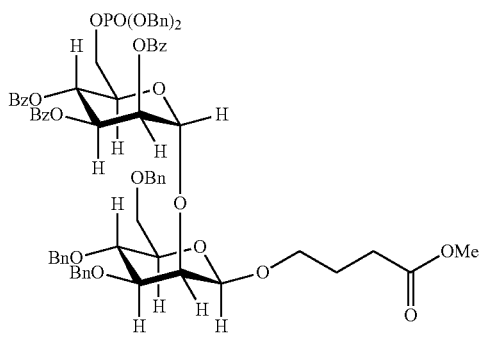

55

To deprotect 55, 25% w/v sodium methoxide in methanol (0.2 mL) was added to a solution of 55 (2.2 g, 1.7 mmol) in anhydrous methanol (20 mL). After ~24 h the starting material was consumed as shown by TLC. The reaction was quenched with Amberlite IR120 (H+) and concentrated to a syrup. The solution was concentrated and purified by silica gel flash column chromatography to give methylbutyryl 2-O-[6-O-dibenzylphosphoryl-α-D-mannosyl]-3,4,6-tri-O-benzyl-(0-D-mannoside 56 as white foam (1.10 g, 67%).

To a stirred solution of 56 (1.10 g, 1.15 mmol) in THF/water (20 mL) was added glacial acetic acid (25 μL), wetted 10% Pd/C (0.1 g) and a hydrogen balloon was attached. After 24 h reaction the product charred with 5% sulphuric acid/EtOH but was not seen under UV. The mixture was filtered through celite and the pad washed with water (20 mL). The solution was concentrated and dried under vacuum to give methylbutyryl 2-O-[6-O-phosphoryl-α-D-mannosyl]-R-D-mannoside 57 (0.6 g, 98%).

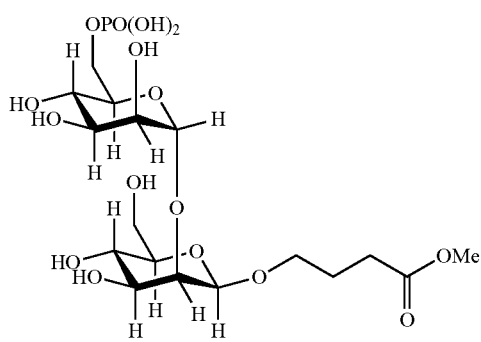

57

D. Aminooxyacetamidohydrazidobutyl 2-O-[6-O-phosphoryl-α-D-mannosyl]-β-D-mannoside (60)

Hydrazine hydrate (0.44 mL, 5.75 mmol) was added to 57 (0.6 g, 1.15 mmol) in methanol (20 mL), with stirring. After 30 mins, water (5 mL) was added and the solution was stirred for 18 h. More hydrazine (0.44 mL, 5.75 mmol) was added and the mixture stirred for 120 h. The solution was concentrated to ~25% volume, stripped with water (2×10 mL), and the product was freeze dried, affording hydrazidobutyl 2-O-[6-O-phosphoryl-α-D-mannosyl]-β-D-mannoside 58 as an off white solid (0.6 g, 99%).

To 58 (0.2 g, 0.38 mmol) in DMSO/water 1:1 (10 mL) was added a solution of N-t-butoxycarbonylaminooxyacetyl 2,3,5,6-tetrafluorophenylate (0.49 g, 1.52 mmol) in DMSO (2 mL) and DHBT (0.125 g, 0.76 mmol) in DMSO (2 mL). After 18 h the solution purified on sephadex size exclusion resin. Fractions were checked on silica gel plates by charring, and selected fractions pooled and freeze dried, affording N-t-butoxycarbonylamino-oxyacetamidohydrazidobutyl 2-O-[6-O-phosphoryl-α-D-mannosyl]-β-D-mannoside 59 as an off white solid (0.1 g, 37.8%). Compound 59 was dissolved in TFA/DCM 1:1 (8 mL). The solution was stirred for ~60 mins and then concentrated to an oil. Water (10 mL) was added and the product was purified on sephadex size exclusion resin. Fractions were checked on silica gel plates by charring, and selected fractions were pooled and freeze dried, affording 60 as an off-white solid (0.045 g, 52.5%).

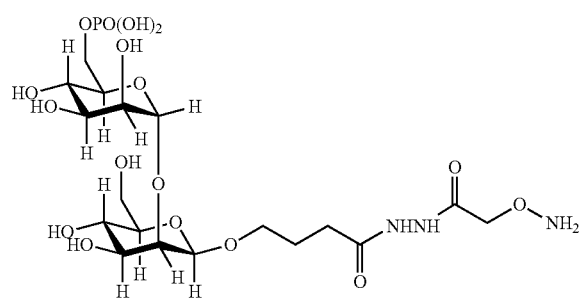

60

E. Large Scale Synthesis of Methylbutyryl 3-O-allyl-6-O-trityl-β-D-mannoside (64)

A solution of 50.0 kg (128.09 mol) d-mannose pentaacetate in 100 L CH$_2$Cl$_2$ was treated with 26.8 kg (243.2 mol, 1.90 eq.) thiophenol and 27.3 kg (192.3 mol, 1.50 eq.) borontrifluoride diethyletherate and the resulting solution was stirred at 22° C. for 40 h, whereupon the reaction was judged to be complete by HPLC analysis. 115 L 5N aqueous NaOH was then carefully introduced to the stirred reaction vessel, the phases separated and the organic phase washed once more with 46 L 5N NaOH. The CH$_2$Cl$_2$ was removed by distillation under reduced pressure and the residue was redissolved in 100 kg isopropanol at 60° C. Upon cooling to 9° C. the product F1 crystallised and could be isolated by filtration followed by washing with isopropanol to furnish 35.8 kg (63%).

35.80 kg of F1 (88.28 mol) was suspended in 143 kg of MeOH at 22° C. and treated with 0.73 kg 30% methanolic sodium methoxide solution (4.05 mol, 0.046 eq.) whereupon a clear solution was obtained. After the reaction was judged to be complete by TLC analysis, 0.49 kg acetic acid (8.14 mol, 0.09 eq.) was added and the solvent removed under reduced pressure. The residue was suspended in toluene, again concentrated under reduced pressure, and finally treated with acetone whereupon the product phenyl-α-D-thiomannoside was crystallised. After filtration, washing and drying a yield of 19.65 kg (89%) was obtained.

Phenyl-α-D-thiomannoside (19.25 kg, 70.69 mol) in pyridine (43.8 kg) was added to a solution of triphenylmethylchloride (19.7 kg, 70.66 mol) in toluene (89 kg) at 40° C. and stirred for 22 h. After the reaction was judged to be complete by HPLC analysis, the solvent was distilled off under reduced pressure, the residue taken up in toluene, and re-concentrated. After dilution with more toluene, the solution was washed once with water. The product was precipitated by adding the toluene solution to a mixture of hexane (840 L) and diisopropylether (250 L) to furnish, after filtration and drying, phenyl 6-O-trityl-1-thio-α-D-mannoside 61 (32.30 kg, 89%).

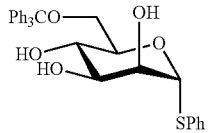

61

A mixture of 61 (30.0 kg, 58.29 mol) and dibutyltin oxide (20.3 kg, 81.5 mol) in toluene (500 kg) was heated at reflux for 2 hours until no further water separated from the condensed solvent vapours. The solution was cooled to 40° C. and DMF (34 kg) was added. Approximately half of the total solvent was distilled off under reduced pressure, whereupon DMF (216 kg) was added and the solution was again concentrated to approximately half of its volume. More DMF (250 kg) was added, followed by cesium fluoride (8.9 kg, 58.59 mol), tetrabutylammonium iodide (23.6 kg, 63.89 mol) in DMF (65 kg), and allyl bromide (21.1 kg, 174.4 mol). The resultant mixture was stirred at 50° C. for 15 h. After the reaction was judged to be complete by HPLC analysis, the solids were removed from the reaction mixture by filtration and the filtrate was treated with a mixture of diisopropylether (136 kg) and ethyl acetate (30 kg) followed by 10% w/w aqueous sodium thiosulphate solution (300 kg). After separation of the phases, the lower phase was re-extracted 4 times with a mixture of diisopropylether (136 kg) and ethyl acetate (30 kg), and the combined upper phases were washed three times with water (150 kg). The upper phase was concentrated under reduced pressure and the residue dissolved in ethanol (160 kg) at 75° C. Upon cooling to 0° C., the product crystallized and could be isolated by filtration. After washing and drying of the filter cake, phenyl 3-O-allyl-6-O-trityl-1-thio-α-D-mannoside 62 (15 kg, 46%) was obtained.

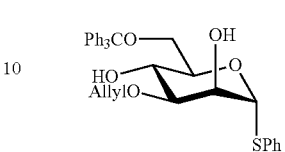

62

A solution of 62 (12.5 kg, 22.53 mol) in a mixture of THF (63 kg) and pyridine (18 kg, 227.5 mol) was treated with a solution of toluenesulfonic acid monohydrate (16.7 kg, 87.79 mol) in water (10.7 kg), followed by a solution of N-chlorosuccinimide (9.6 kg, 71.89 mol) in a mixture of water (17 kg) and THF (83 kg) at 15° C. The resultant mixture was warmed to 22° C. and stirred for 3 h. After the reaction was judged to be complete by HPLC analysis, a solution of sodium thiosulfate (4.6 kg, 29.11 mol) in water (15 kg) was added to the reaction mixture. The phases were separated, the upper phase concentrated under reduced pressure, and the residue taken up in toluene and again concentrated. The residue was redissolved in ethyl acetate, washed with water, and then with 16% w/w aqueous sodium chloride solution. After evaporation of the ethyl acetate, the crude product was purified by column chromatography over 52 kg silica gel, and eluted with a gradient of 3-10% v/v ethyl acetate in toluene to furnish 3-O-allyl-6-O-trityl-α-D-mannose 63 (7.7 kg, 73%).

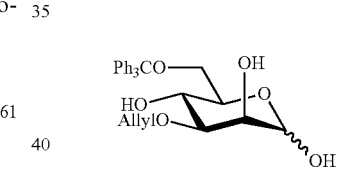

63

A mixture of 63 (7.7 kg, 16.65 mol) and dibutyltin oxide (4.56 kg, 18.32 mol) in methanol (61 kg) was heated at reflux until a turbid solution was obtained, and then for an additional 1 h. The solution was cooled to 25° C. and approximately half of the total solvent was distilled off under reduced pressure, whereupon DMF (33 kg) was added and the solution was again concentrated to approximately half of its volume. More DMF (15 kg) was added followed by cesium fluoride (2.53 kg, 16.65 mol), tetrabutylammonium iodide (6.15 kg, 16.65 mol) in DMF (17 kg) and methyl 4-bromobutyrate (4.52 kg, 24.97 mol). The resultant mixture was stirred at 80° C. for 5 h. The solids were removed from the reaction mixture by filtration, and the filtrate was treated with a mixture of diisopropylether (41 kg), ethyl acetate (14 kg), and 10% w/w aqueous sodium thiosulphate solution (77 kg). After separation of the phases, the lower phase was re-extracted with a mixture of diisopropylether (41 kg) and ethyl acetate (51 kg), and the combined upper phases were washed with water (39 kg). The upper phase was concentrated under reduced pressure and the residue dissolved in methanol (35 kg).

To improve the reaction yield, the linkage reaction process was repeated. The dissolved residue was again concentrated under reduced pressure, then diluted with methanol (122 kg). Methanol (60 L) was again distilled off, the resultant solution was treated with dibutyltin oxide (2.28 kg, 9.16 mol), and the mixture was heated to reflux for 2 h. The solution was cooled to 29° C., and approximately half of the total solvent was distilled off under reduced pressure, whereupon DMF (37 kg) was added and the solution was again concentrated to approximately half of its volume. More DMF (15 kg) was added followed by cesium fluoride (1.26 kg, 8.29 mol), tetrabutylammonium iodide (3.7 kg, 10.02 mol) in DMF (17 kg), and methyl 4-bromobutyrate (3.06 kg, 16.90 mol) and the resultant mixture was stirred at 80° C. for 2 h. After the reaction was judged to be complete by HPLC analysis, the solids were removed from the reaction mixture by filtration, and the filtrate was treated with a mixture of diisopropylether (25 kg), ethyl acetate (32 kg) and 10% w/w aqueous sodium thiosulphate solution (77 kg). After separation of the phases, the lower phase was re-extracted with a mixture of diisopropylether (25 kg) and ethyl acetate (32 kg), and the combined upper phases were washed with water (39 kg). The solution was concentrated under reduced pressure and the residue was redissolved in toluene (43 kg), and finally concentrated to a final volume of approximately 30 L. The crude methyl ester of 64 was then purified by column chromatography on 50 kg silica gel, and eluted with a gradient of 5%-30% v/v ethyl acetate in toluene.

A solution of the purified methyl ester in methanol (50 kg) was treated with a mixture of 30% w/w aqueous sodium hydroxide (3.29 kg) and methanol (7.7 kg) and the resultant solution stirred for 14 h. After the reaction was judged to be complete by HPLC analysis, the reaction mixture was treated with a mixture of diisopropylether (41 kg) and ethyl acetate (14 kg), followed by water (77 kg). The biphasic mixture was passed through a 1.2 μm filter cartridge and the phases were separated. The lower phase was treated with a mixture of diisopropylether (41 kg) and ethyl acetate (14 kg), and the pH of the lower phase lowered to 4.5-5 by the addition of a 5% w/w aqueous solution of citric acid (38 L). The phases were separated and the lower phase was extracted with a mixture of diisopropylether (41 kg) and ethyl acetate (14 kg). The combined upper phases were washed with water (39 kg) and then concentrated under reduced pressure. The residue was mixed with diisopropylether (39 kg) and solvent partially concentrated to give a final volume of approximately 20 L, whereupon the product crystallised and could be isolated by filtration. After washing the filter-cake and drying, (3-O-allyl-6-O-trityl-s-D-mannosyl)-4-butanoic acid 64 (4.7 kg, 51.5%) was obtained.

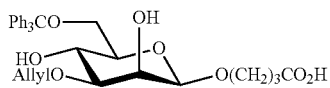

64

F. Large Scale Synthesis of Tetrasaccharide Intermediate (69)

Compound 64 was prepared according to the methods of Part E. The protecting groups of 64 were modified prior to further glycosylation reactions. A solution of 64 (4.25 kg, 7.75 mol) in THF (14 kg) was carefully added to a stirred slurry of 60% sodium hydride dispersion (1.55 kg, 38.75 mol) in THF (45 kg) and the resultant suspension was stirred until hydrogen evolution had ceased. A suspension of tetrabutylammonium iodide (0.29 kg, 0.78 mol) in THF (2 kg) was introduced to the reaction vessel followed by benzyl bromide (9.2 kg, 53.79 mol). The mixture was stirred at 22° C. for 46 h, then at 30° C. for 12 h and at 35° C. for 48 h. When the reaction was judged to be complete by HPLC analysis, the mixture was cooled to 0° C. and anhydrous methanol (0.7 kg, 21.87 mol) followed by 30% w/w methanolic sodium methoxide (2.1 kg, 11.66 mol) were carefully introduced. Acetic acid (1.4 kg) followed by triethylamine (9.4 kg, 92.89 mol) were then charged and the mixture was stirred for 18 h. To the resultant suspension were added water (31 kg) and the two phases were separated. The upper phase was concentrated under reduced pressure, the residue taken up in toluene and concentrated again to final volume of approximately 20 L. The crude product was purified by column chromatography on 42 kg silica gel eluting with a gradient of 5-15% ethyl acetate in hexane to afford methylbutyryl 3-O-allyl-2,4-di-O-benzyl-6-O-trityl-β-D-mannoside 65 (4.4 kg, 77%) as a solution in ethyl acetate.

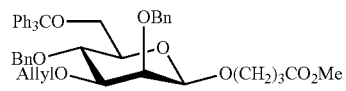

65

To a solution of 65 (4.4 kg, 5.92 mol) in methanol (19 kg) at 37° C. was added a solution of toluenesulphonic acid monohydrate (0.9 kg, 4.73 mol) in methanol (6.3 kg) and the resultant mixture stirred for 1 h. When the reaction was judged to be complete to HPLC analysis, triethylamine (1.5 kg, 14.82 mol) was charged and the solution was concentrated under reduced pressure. Toluene (28 kg was then added and the solution was washed with water (32 kg). The phases were separated and the upper phase was concentrated under reduced pressure. The crude product was purified by silica gel chromatography on silica gel (32 kg), eluting with a gradient of 9%, then 17%, then 50% v/v ethyl acetate in toluene to afford methylbutyryl 3-O-allyl-2,4-di-O-benzyl-s-D-mannoside 66 (2.67 kg, 90%) as a solution in toluene.

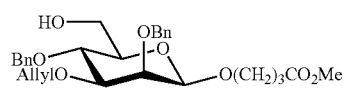

66

3.73 kg (5.49 mol, 1.10 eq.) 19 and 2.50 kg (4.99 mol) 66 were dissolved in 34 kg dry toluene from which ~10 L was evaporated under reduced pressure. The solution was then cooled to 0° C. and treated, dropwise, with 22 g (0.099 mol, 0.02 eq.) TMSOTf so that the reaction temperature remained <5° C., and stirred at 0° C. for 1 h after the end of the addition. When the reaction was judged to be complete by HPLC analysis, the mixture was neutralised by the addition of 30 g (0.296 mol, 0.06 eq.) $Et_3N$. Hexane (22 L) was added and the resultant suspension was filtered and the filtrate was washed with 33 L water and concentrated under reduced pressure. The residue was taken up in 10 L toluene and again concentrated, and the process repeated twice more. Column-chromatographic purification of the crude product on 50 kg silica gel, and eluting with a gradient of 9-13% v/v EtOAc in hexane:toluene 1:1 furnished 4.23 kg, 83%, compound 67 as a solution in toluene.

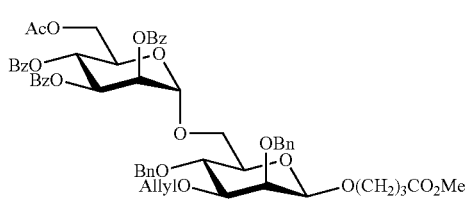

67

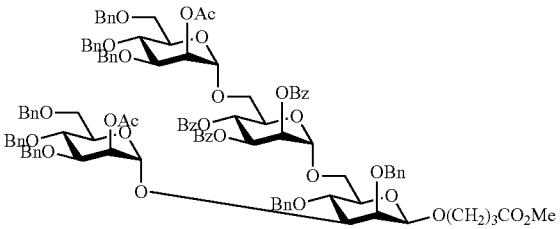

69

G. Synthesis of Protected Hexasaccharide (73)

To a solution of 4.23 kg (4.16 mol) of 67 in 5.6 L $CH_2Cl_2$ and 40 L MeOH was added 0.72 kg 10% Pd/C followed by a solution of 0.12 kg (0.63 mmol, 0.15 eq.) toluenesulfonic acid monohydrate and the mixture was stirred at 22° C. for 24 h. When the reaction was judged to be complete by HPLC analysis the palladium/carbon was removed by filtration and the filtrate was used without further purification in the next step.

To the filtrate was added a solution of 2.97 kg (15.6 mol, 3.75 eq.) toluenesulfonic acid in 4 L MeOH and the resultant mixture was stirred for 16 h at 22° C. When the reaction was judged to be complete by HPLC analysis, the mixture was cooled to 0° C. and neutralised by the addition of 1.64 kg (16.2 mol, 3.89 eq.) triethylamine. The solution was concentrated under reduced pressure and the residue partitioned between 82 L MTBE and 32 L water. The organic phase was concentrated under reduced pressure, diluted with 10 L toluene and reconcentrated. This procedure was repeated twice more. Column-chromatographic purification of the crude product on 38 kg silica gel, eluting with a gradient of 23-26% v/v EtOAc in hexane:toluene 1:1 furnished 2.59 kg compound 68 (67% from 67) as a solution in toluene.

Tetrasaccharide intermediate 69 was prepared according to the methods described in Example 7. To a solution of 9.7 g (5.15 mmol) 69 in 60 ml $CH_2Cl_2$ was added 100 ml MeOH followed by, dropwise, 27 ml of a 5.7 N solution of HCl in 1,4-dioxane (0.154 mol, 30 eq.), so that the temperature of the mixture remained below 30° C. The reaction mixture was then stirred at 22° C. for 40 h. When the reaction was judged to be complete by HPLC analysis, 32 ml (22.9 mmol, 44.7 eq.) triethylamine was added cautiously so that the temperature of the mixture remained below 25° C. Water (250 ml) and toluene (200 ml) were added, the mixture was shaken, and the phases were separated. The lower phase was re-extracted with 50 ml toluene, the combined upper phases were washed with 50 ml water, and concentrated under reduced pressure. The crude product was purified by column chromatography on 100 g silica gel, eluting with a gradient of 30-50% v/v EtOAc in hexane to give methylbutyryl 3-O-([3,4,6-tri-O-benzyl-α-D-mannosyl])-(6-O-[2,3,4-tri-O-benzoyl-α-D-mannosyl]-6-O-[3,4,6-tri-O-benzyl-α-D-mannosyl])-2,4-di-O-benzyl-β-D-mannoside 70 (6.35 g, 69%).

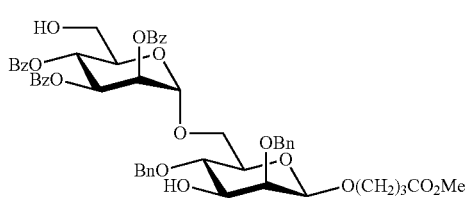

68

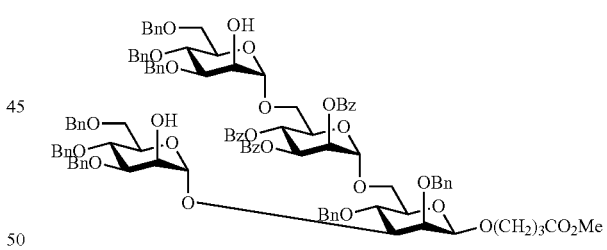

70

A solution of 2.90 kg (3.10 mol) of 68 and 5.24 kg (8.23 mol, 2.65 eq.) 18 in 30 kg dry toluene at 0° C. was treated with 0.049 kg (0.185 mol, 0.06 eq.) TBDMSOTf and stirred at 0° C. for 4 h. When the reaction was judged to be complete by HPLC analysis, 0.104 kg (1.03 mol, 0.128 eq.) triethylamine was added followed by 33 L hexane. The resultant suspension was filtered and the filtrate washed with 28 L water and then with 28 L 5% aqueous $Na_2CO_3$. The toluene phase was concentrated under reduced pressure and the crude product was purified by column chromatography on 58 kg silica gel, eluting with a gradient of 9-20% v/v EtOAc in hexane:toluene 1:1 furnished 4.40 kg of tetrasaccharide intermediate 69 (75%) as a solution in toluene.

A solution of 1.0 g (0.56 mmol) of 70 and 0.95 g (1.40 mmol, 2.5 eq.) 19 in 9 ml dry toluene at 0° C. was treated with 0.02 g (0.075 mmol, 0.14 eq.) TBDMSOTf and stirred at 0° C. for 1 h. When the reaction was judged to be complete by HPLC analysis, 22 ml (0.158 mmol, 0.28 eq.) triethylamine was added. The resultant mixture was washed twice with 10 ml water concentrated under reduced pressure. Purification of the crude product by column chromatography on 15 g silica gel, eluting with a gradient of 15-25% v/v EtOAc in hexane:toluene 1:1 furnished 1.75 g compound methylbutyryl 3-O-([3,4,6-tri-O-benzyl-α-D-mannosyl]-2-O-[6-O-acetyl-2,3,4-tri-O-benzoyl-α-D-mannosyl])-(6-O-[2,3,4-tri-O-benzoyl-α-D-mannosyl]-6-O-[3,4,6-tri-O-benzyl-α-D-mannosyl]-2-O-[6-O-acetyl-2,3,4-tri-O-benzoyl-α-D-mannosyl])-2,4-di-O-benzoyl-β-D-mannoside 71 as an oil containing residual toluene.

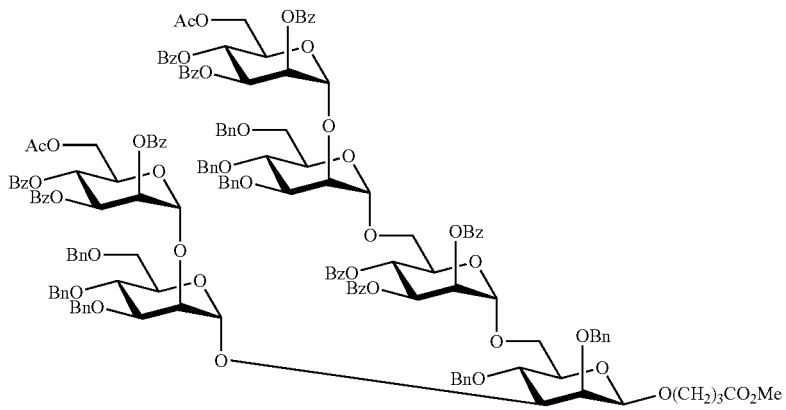

71

A solution of 10.0 g (3.5 mmol) 71 in 40 ml 1,4-dioxane was treated with 60 ml MeOH, followed by 3.25 g (14.0 mmol, 4 eq.) (+)-camphorsulfonic acid, and the resulting solution was stirred for 100 h at 22° C. When the reaction was judged to be complete by HPLC analysis, 3 ml (21.5 mmol, 6.2 eq.) triethylamine was added and the solvent was removed under reduced pressure. The residue was dissolved in 200 ml MTBE and shaken with 200 ml $H_2O$. The phases were separated and the upper phase was concentrated under reduced pressure. Chromatographic purification of the crude product on 114 g silica gel, and eluting with a gradient of 14-25% v/v EtOAc in toluene furnished 8.24 g methylbutyryl 3-O-([3,4,6-tri-O-benzyl-α-D-mannosyl]-2-O-[2,3,4-tri-O-benzoyl-α-D-mannosyl])-(6-O-[2,3,4-ti-O-benzoyl-α-D-mannosyl]-6-O-[3,4,6-tri-O-benzyl-α-D-mannosyl]-2-O-[2,3,4-tri-O-benzoyl-α-D-mannosyl])-2,4-di-O-benzoyl-β-D-mannoside 72 as an oil containing residual toluene.

complete by TLC analysis, 0.5 ml water was added and the solution was stirred for 15 min. Water (9.5 ml) and 10 ml MTBE was added and the resulting mixture was shaken, the phases separated, and the lower phase was shaken with 10 ml MTBE. The upper phases were combined and concentrated under reduced pressure to give a colourless oil. This residue was dissolved in $CH_2Cl_2$, cooled to −20° C., and treated with 0.247 g (1.13 mmol, 3.2 eq.) 70% 3-chloroperbenzoic acid. After the reaction was judged to be complete by TLC analysis, 10 ml of 10% aqueous sodium thiosulfate was added and the mixture was warmed to 23° C. The lower phase was separated, shaken with 10 ml water and concentrated under reduced pressure. The crude product was purified by column chromatography on 19 g silica gel, and eluting with a gradient of 25-50% v/v EtOAc in hexane, to furnish 0.83 g (72%) methylbutyryl 3-O-([3,4,6-tri-O-benzyl-α-D-mannosyl]-2-O-[6-O-dibenzylphosphoryl-2,3,4-

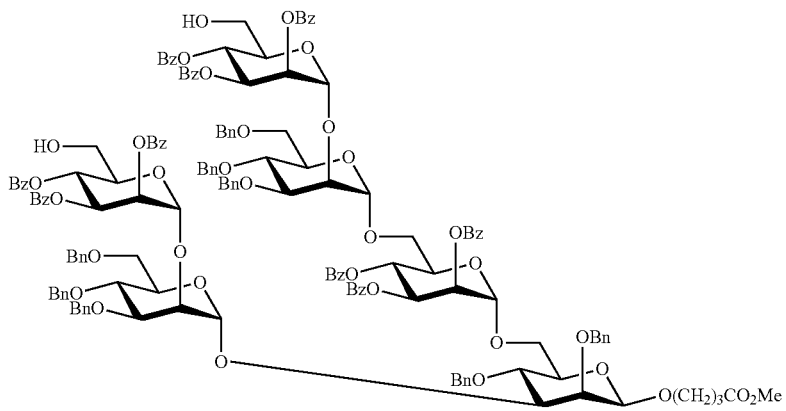

72

To a solution of 0.965 g (0.35 mmol) 72 in 4 g dry acetonitrile was added 0.083 g (0.70 mmol, 2 eq.) 4,5-dicyanoimidazole followed by 0.315 g (0.91 mmol, 2.6 eq.) dibenzyl diisopropylphosphoramidite, and the mixture was stirred at 23° C. for 1 h. When the reaction was judged to be tri-O-benzoyl-α-D-mannosyl])-(6-O-[2,3,4-tri-O-benzoyl-α-D-mannosyl]-6-O-[3,4,6-tri-O-benzyl-α-D-mannosyl]-2-O-[6-O-dibenzylphosphoryl-2,3,4-tri-O-benzoyl-α-D-mannosyl])-2,4-di-O-benzoyl-β-D-mannoside 73 as a colourless oil.

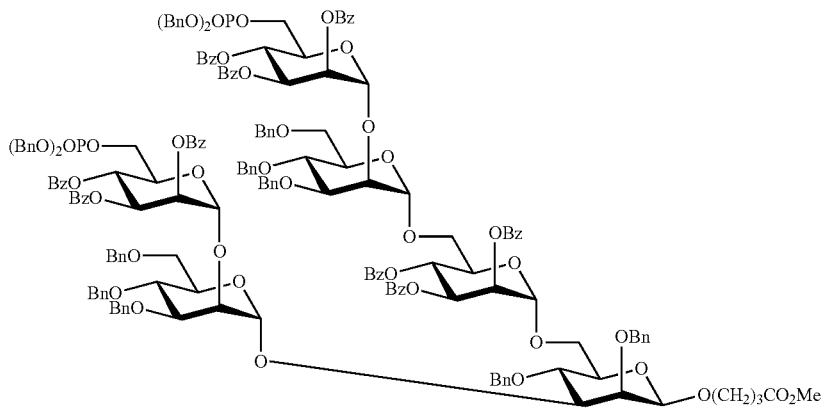

73

H. Synthesis of Aminooxyacetamidohydrazido 3-O-([α-D-mannosyl]-2-O-[6-O-phosphoryl-α-D-mannosyl])-(6-O-[α-D-mannosyl]-6-O-[α-D-mannosyl]-2-O-[6-O-phosphoryl-α-D-mannosyl])-β-D-mannoside (77)

Compound 73 was prepared according to the methods described in Example 8. Glacial acetic acid (100 μL) was added to 73 (64 g, 19.6 mmol) in methanol/THF 1:1 (600 mL), and the product was hydrogenated using a H-Cube® over 20% Pd(OH)$_2$/C at 50° C., 50 bar H$_2$ pressure and at a flow rate of 6 mL/min with recirculation over the catalyst. After 20 h the reaction was essentially complete by TLC, and the solution was concentrated to afford 74 as a foam (39.88 g, 93%).

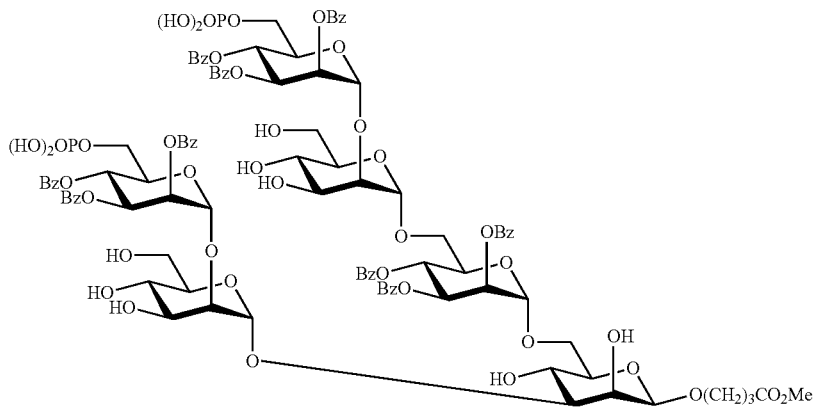

74

Methanol (180 mL) was added to 74 (33.8 g, 15.5 mmol) with stirring until dissolved, and the solution was cooled in an ice/water bath for 15 mins. To the solution was added 64% hydrazine monohydrate (94 ml, 1.24 mol), with stirring. After 30 mins, water (120 mL) was added and the solution was allowed to come to room temperature and stored for 18 h. The solution was concentrated to ~100 mL and stripped with water (2×100 mL), and the final solution was adjusted to ~180 mL with water. The solution was extracted with DCM (2×100 mL) and then 3 portions of 60 mL were separated on a sephadex size exclusion column. Fractions containing the purest material were pooled and freeze dried affording 75 (15.5 g, 80%).

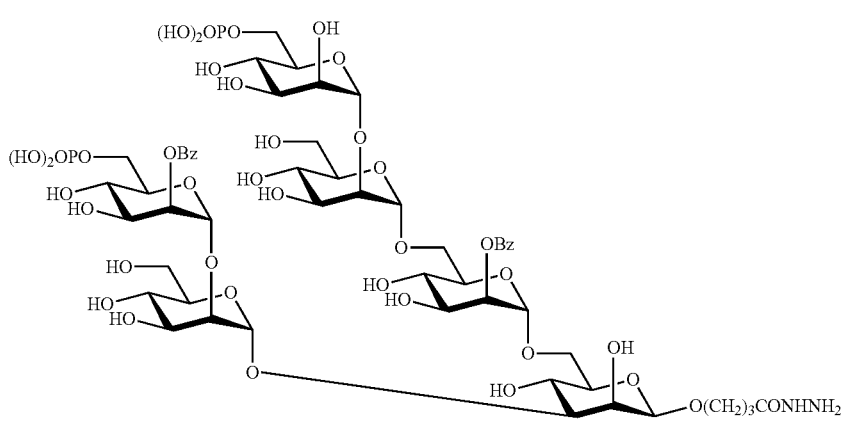

75

DMSO (20 mL) was added slowly to 75 (2.5 g, 2.0 mmol) in water (30 mL), then N-t-butoxycarbonylaminooxyacetyl 2,3,5,6-tetrafluorophenylate (2.58 g, 7.6 mmol) in DMSO (6 mL) and DHBT (0.65 g, 4 mmol) in DMSO (4 mL) were added. After 18 h the solution was purified on sephadex size exclusion resin. Fractions were checked on silica gel plates by charring, and selected fractions were pooled and freeze dried, affording N-t-butoxycarbonylaminooxyacetamidohydrazidobutyryl 3-O-([α-D-mannosyl]-2-O-[6-O-phosphoryl-α-D-mannosyl])-(6-O-[α-D-mannosyl]-6-O-[α-D-mannosyl]-2-O-[6-O-phosphoryl-α-D-mannosyl])-β-D-mannoside 76 (2.57 g, 90%). DCM (30 mL), then TFA (16 mL), were added to compound 76 (2.57 g, 1.8 mmol). The mixture was stirred until dissolved (~60 mins) and then concentrated to an oil. Water (20 mL) was added and the product was purified on sephadex size exclusion resin. Fractions were checked on silica gel plates by charring and selected fractions pooled and freeze dried, affording 77 (1.6 g, 67.1%).

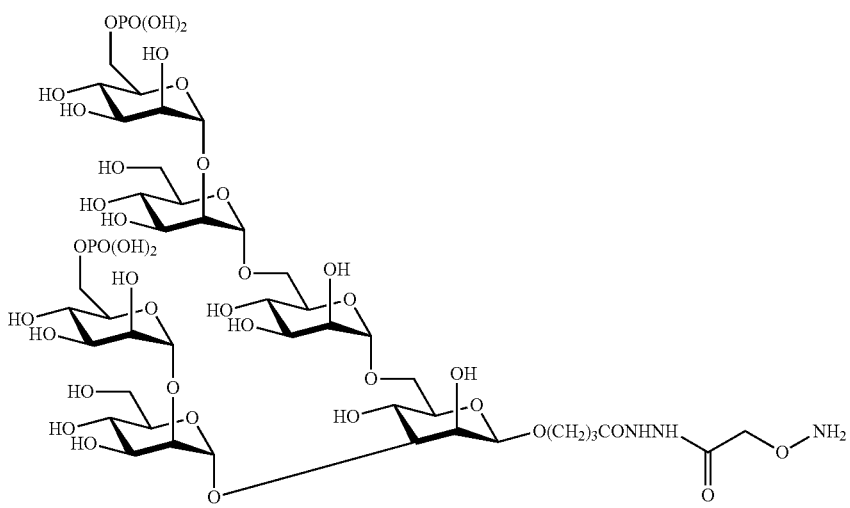

77

Example 6: Synthesis of Hexasaccharide with Disulfide Linker

A. Preparation of Hexasaccharide in Free Acid Form

Anhydrous MeOH is added to compound 73 followed by NaOMe and incubated for 4-18 h. The reaction is quenched with glacial acetic acid and the solution concentrated to a syrup to afford 78.

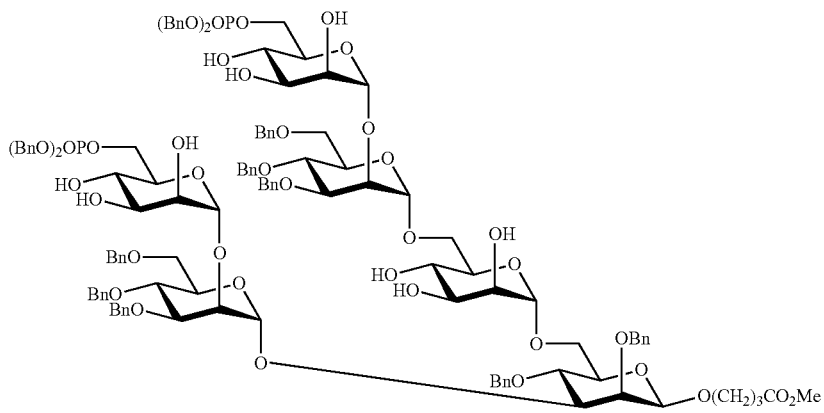

78

Compound 78 is dissolved in THF/methanol 1:1 and hydrogenated Pd/C—$H_2$. The solution is concentrated to a solid and dissolved in water, saponified with aqueous NaOH, the pH adjusted to ~4 and purified on Sephadex G-10 to afford the free acid 81.

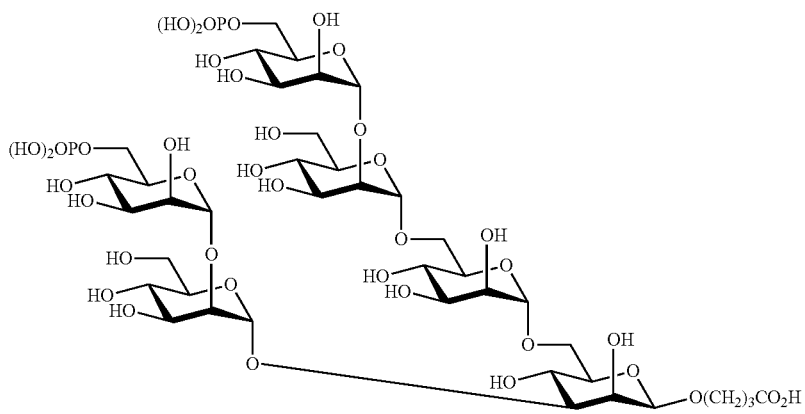

81

B. Attachment of Disulfide Linker

A crude fraction of compound 81 prepared by a different method (obtained from Biomira) was converted to the triethylamine (TEA) salt by mixing with excess TEA followed by chromatography on Superdex Peptide (GE Healthcare) using 30% acetonitrile, 0.1% TEA bicarbonate as a mobile phase. Pooled fractions were lyophilized and conjugated with NEA in a reaction containing glycan:NEA:EDAC:NHS:HOBt:TEA (1:1:1.5:1:1:1 mol:mol) incubated overnight with gentle shaking. A portion (0.5 mg) product was chromatographed on Superdex Peptide as before and lyophilized to afford 82 (0.28 mg).

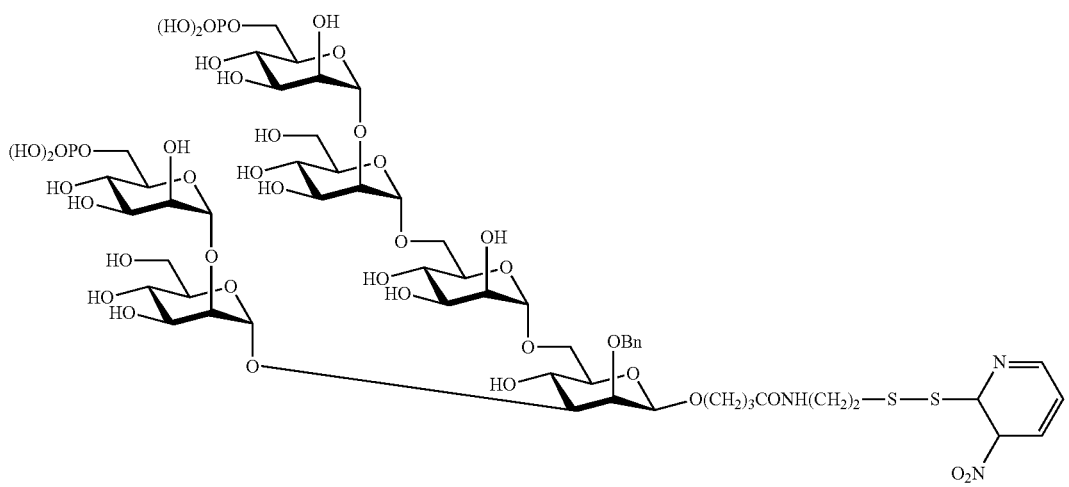

82

Example 7: Synthesis of α-Glucosidase Conjugates and Oxidation Optimization

A. Conjugation

Oligosaccharides were conjugated to recombinant human acid α-glucosidase (rhGAA) to form NeoGAAs. Conjugates with oligosaccharides primarily attached through sialic acid residues on rhGAA are named "SAM", while those attached through galactose residues are named "GAM."

NeoGAA βSAM6 was prepared essentially as described by Zhu et al., Biochem J, 389(Pt 3): 619-628 (2005). The sample of rhGAA used for the experiment was found by monosaccharide composition analysis to have ~5.2 moles sialic acid/mole protein. Briefly, rhGAA (Genzyme Corp.) at 5 mg/mL was buffer-exchanged into 100 mM sodium acetate pH 5.6, then reacted with sodium periodate (2, 7.5, or 22.5 mM) on ice in the dark for 30 minutes. The reaction was quenched by addition of glycerol to 2% (vol/vol). The oxidized rhGAA was buffer-exchanged to remove small molecular weight by-products from the oxidation reaction, and conjugated with Compound 77 (0-120-fold molar ratio vs. protein, as shown in FIG. 9) at 37° C. for 6 hrs. All the conjugates were buffer-exchanged into 25 mM sodium phosphate pH 6.25, containing 2% mannitol and 0.005% Tween-80.

Similar NeoGAA conjugates were prepared with SAM2 (Compound 17, Example 2), SAM3 (Compound 35, Example 3), SAM4 (Compound 28, Example 4A), Linear SAM4 (Compound 47, Example 4B), and αSAM6 (Oligosaccharide 103), using 7.5 mM periodate and varying molar ratios of oligosaccharide to rhGAA.

Alternate conjugation methods were also performed. Specifically, hexasaccharide with either an aminoxy, hydrazide or thiol-reactive linker was attached to rhGAA through Cys374, lysines, sialic acids, or galactose residues.

The lysine conjugation was performed by modifying lysine residues in rhGAA with succinimidyl 4-formylbenzoate (SFB; Solulink Corp.), followed by conjugation with the oligosaccharide. Briefly, the rhGAA was first buffer-exchanged into 50 mM sodium phosphate, pH 7.2, containing 150 mM sodium chloride. The buffered rhGAA was then treated with freshly prepared (SFB) at 20:1 molar ratio of SFB to GAA. The mixture was incubated at room temperature for 30 min before it was buffer-exchanged into 100 mM sodium acetate, pH 5.5, for conjugation to the hydrazide hexasaccharide at room temperature for 2 hrs, or the GAA modified with SFB was buffer-exchanged into 100 mM sodium acetate, pH 5.6, for conjugation to aminoxy hexasaccharide at 37° C. for 6 hrs.

Cysteine-based conjugation was performed by reaction with the thiol-reactive NEA-hexasaccharide 82 (Example 6 I). NEA-modified hexasaccharide 82 was reconstituted in water and incubated with rhGAA (15:1 molar ratio of neoglycan to rhGAA) in 50 mM sodium phosphate and 50 mM hydroxylamine pH7.2 for 2 hrs at 25° C. The pH was adjusted to 6.2 with 50 mM sodium phosphate pH 4.1 and the incubation continued overnight. The product was purified by centrifugal diafiltration against 25 mM sodium phosphate pH 6.2. Less than 1 mol:mol M6P was introduced.

While direct conjugation through Cys374 was unsuccessful, a homobifunctional thiol-specific reagent, 1,4-di-(3'-[2-pyridyldithio]-propionamido) butane (DPDPB) with spacer arm of 19.9 Å, was tested to provide a more solvent-accessible thiol group at position 374 before conjugation with the oligosaccharide. A 60-fold molar excess of DPDPB was reacted with rhGAA in the presence of either 10% DMSO or 10% propanol as cosolvents. This elicited strong aggregation as detected by light scattering. Reaction in the presence of 20% acetonitrile also showed aggregation, but an absorbance at 344 nm of an ultrafiltrate of the reaction mixture consistent with quantitative modification of the cysteine. A reduction in the acetonitrile concentration to 10% reduced the amount of aggregation but yielded a lower extent of modification.

An alternative thiol-based approach was performed by introduction of thiol groups at lysine residues. Protected thiols were introduced onto the lysine residues by reaction of the enzyme with a 100-fold molar excess of SATA-dPEG4-NHS (Quanta Biodesign) in sodium phosphate pH 6.2 for 4 hrs at 25° C. and purified by overnight dialysis against the same buffer. The purified product was then reacted with NEA-oligosaccharide 82 under the conditions described above for the cysteine-based conjugation to afford a lysine-thiol conjugate. This showed an ~10-fold increase in the Man-6 P content (~5 glycans conjugated)

The stability of lysine conjugates with hydrazide was evaluated at 37° C. for up to 14 days by measuring the intact protein molecular weight and M6P content. The conjugate is not stable, as more than 50% of the neoglycan was lost over 14 days. Aminoxy conjugates through lysine were prepared using 0, 16.6, 25, 33, and 40 molar excess of hexasaccharide to rhGAA, as described above. The conjugation was saturable at 16.6-fold molar excess, although only ~31% (or 5 neoglycan conjugated) of total lysines were conjugated. High aggregation level was also observed in several preparations. A PEGylated version of SFB was tested, with no reduction in aggregation.

Galactose conjugation (GAM) was performed by first pretreating rhGAA with sialidase from *Clostridium perfringens* at 20 mU/mg at 37° C. for 6 hrs in 25 mM sodium phosphate, pH 6.25, containing 2% mannitol and 0.005% Tween-80. After desialylation, the protein was treated with galactose oxidase (GAO) at 1-10 µg/mg and catalase (Sigma) at 2 U/mg in the same buffer at 37° C. overnight before re-purifying using Poros 50D (anion-exchange) chromatography to remove neuraminidase and catalase. The product treated with both enzymes was diluted with equal volume of $dH_2O$, then applied to the Poros 50D column, which was pre-equilibrated with 10 mM sodium phosphate buffer, pH 6.9. After the column was washed with 10 mM sodium acetate buffer, pH 5.0, the rhGAA was eluted with 150 mM sodium acetate buffer, pH 5.0, and conjugated with the aminoxy hexasaccharide at various molar ratios at 37° C. for 6 hrs.

GAM conjugation was saturated at 16.6-fold molar excess of hexasaccharide to GAA, with ~6-7 glycans conjugated. Aggregation levels were low. No sialic acid was detected after desialylation, while little galactose was found after galactose oxidase treatment. In some cases, 20-30% of galactose residues were over-oxidized, producing galacturonic acid, which does not conjugate to oligosaccharides. GAO was titrated, showing that above 1 µg/mg, GAO decreased glycan conjugation. There was a clear increase in the amount of galacturonic acid over-oxidation product above 2 µg/mg GAO. The maximal amount of conjugation was achieved at 1-2 µg GAO per mg rhGAA (FIG. 10E—Monosaccharides, including Man-6 P, Gal, GalA content of GAM conjugate after titrated with GAO. High conjugation observed as Man-6 P content in the protein when 0.5 to 2 ug GAO/mg GAA used. Either lower galactose or higher GalA generated when lower or higher GAO used.

The amount of bis-M6P hexasaccharide glycan conjugated to NeoGAA was quantified by M6P content analysis and MALDI-TOF. For M6P quantitation, samples were buffer exchanged using Amicon 4, 50,000 MWCO centrifugal filter units with 5 rounds of filtration to remove any potential excess glycan. Eighty micrograms of each of rhGAA or NeoGAA sample were hydrolyzed in 6.75 M TFA for 1.5 hours at 100° C. Samples were cooled, dried in a Speed Vac and reconstituted in 200 µL of distilled water. The reconstituted samples were again dried in a Speed Vac and reconstituted with 200 µL 50 mM citrate pH 2.0. The samples were filtered through S Mini H cartridges (Sartorius), which were equilibrated in sodium citrate pH 2.0, to remove impurities from the hydrolysate. Ribose-5-phosphate was added as an internal standard to all samples and standards. 50 µL of the hydrolysate was injected onto a Dionex HPLC and analyzed by high pH anion exchange chromatography with pulsed amperometric detection (HPAEC-PAD). Quantitation was carried out with a standard curve constructed with hydrolyzed standards of M6P. The extent of conjugation was then calculated based on the known molar ratio of 2 moles of M6P per mole of glycan.

MALDI-TOF MS analysis was performed using a Voyager DE-PRO mass spectrometer in linear mode. A 1:5 dilution into 0.1% Formic Acid in water was performed on all samples and standards followed by a 1:1 dilution into saturated sinnapinnic acid in 50% Acetonitrile/0.1% TFA. One µL of this mixture was applied to a target. The sample, reference and BSA calibration control were analyzed in triplicate. Two-point calibration was performed using the (M+H)+ and dimer ions of BSA. The extent of conjugation of each NeoGAA sample was estimated based on the difference in molecular weights between the sample and an oxidized rhGAA control (no glycan added), given a measured glycan molecular weight of 1323 g/mole.

Figure 9A:
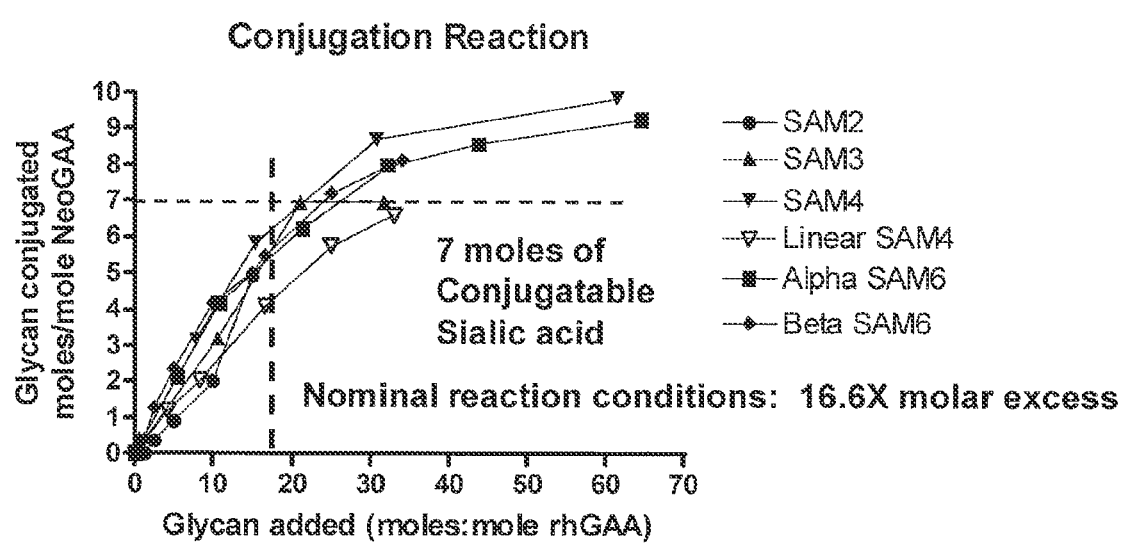
FIGS. 9A and 9B show the effect of oxidation level on conjugatability of NeoGAA βSAM6.

FIG. 9A shows the results of experiments using the di-, tri-, tetra-, and hexasaccharide conjugates described above.

Figure 9B:
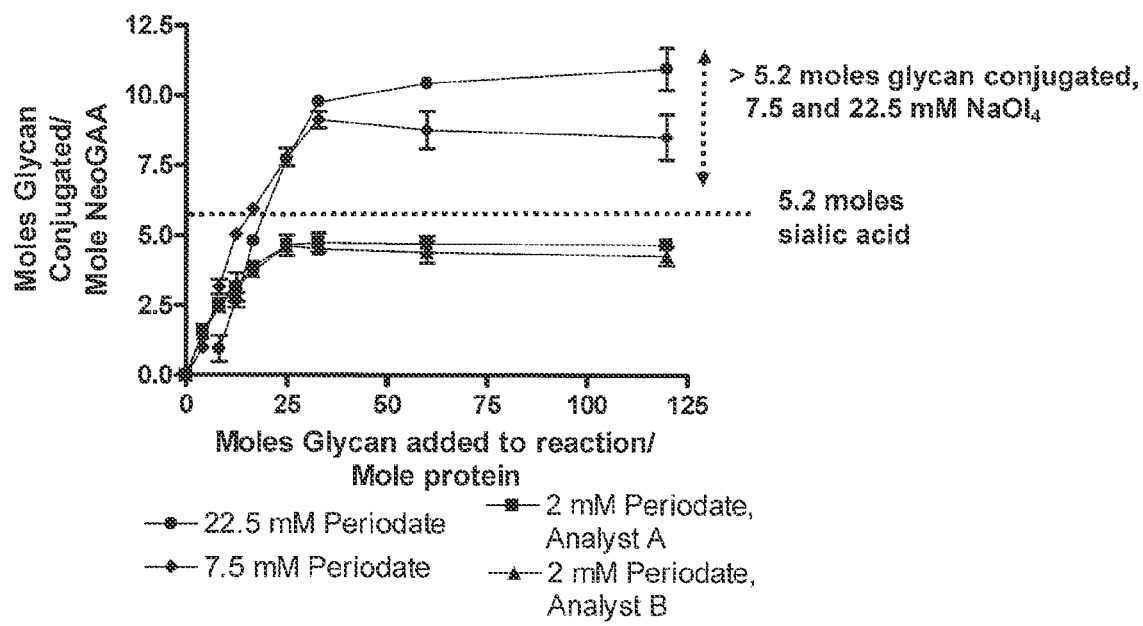
Figure 9B:
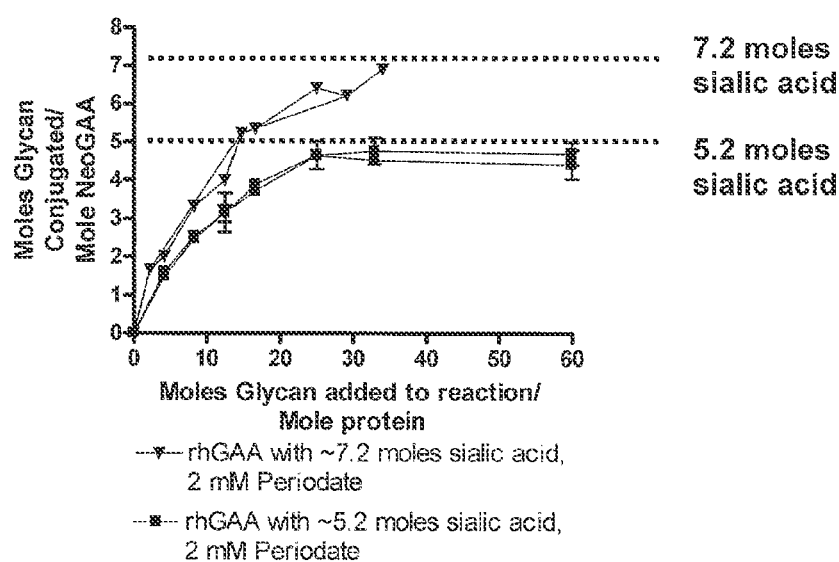

FIG. 9B provides results of βSAM6 conjugates prepared with different amounts of periodate. The levels of oligosaccharide needed to achieve saturation of the conjugation reaction were proportional to the amount of periodate used during the oxidation step (FIG. 9B, top panel). With 2 mM periodate, a sample of rhGAA with ~5.2 moles sialic acid reached saturation at approximately a 25-fold molar excess of hexasaccharide vs. protein (4.8-fold molar excess vs. sialic acid). With 7.5 mM periodate, saturation was achieved at 33-fold molar excess of glycan. Saturation was approached, but not achieved for rhGAA oxidized with 22.5 mM periodate, with 120-fold molar excess of glycan. The maximum levels of conjugation achieved were also different for samples prepared with different levels of periodate. With 7.5 and 22.5 mM periodate, approximately 8.5 and 10.5 moles of glycan/mole of protein were incorporated, respectively. Following oxidation with 2 mM periodate, the level of conjugation achievable was approximately 5 moles of glycan/mole protein, which is similar to the number of sialic acid residues in the starting material.

The glycan titration experiment was repeated with 2 mM periodate using rhGAA with a starting sialic acid level of ~7.2 moles/mole protein (FIG. 9B, bottom panel). A conjugation level of approximately 7 moles of glycan/mole protein was achieved at ≥33-fold molar excess of glycan to protein (~4.6-fold molar excess compared to sialic acid).

B. Aggregation Reduction

Certain conjugation methods result in protein aggregation. Two methods for aggregation reduction in neoGAA have been developed: 1) hydrophobic Interaction chromatography (HIC) using a variety of HIC chromatography media and 2) metal chelation.

A 3 g batch of NeoGAA was prepared and used to evaluate HIC and copper columns for aggregation removal. The HIC columns evaluated in flow-through mode were: Butyl 650C and 650M, Hexyl 650C, Phenyl 6FF, Capto Octyl and Capto Phenyl. Hexyl and Capto Phenyl gave comparable results with recoveries of 87.5% and 90.4%, and aggregate reduction from 3.2% (initial level) to 1.4%, and 3.9% (initial) to 1.6%, respectively. See Table 2.

TABLE 2

Removing aggregates from conjugated GAA
(3.2% agg) using HIC column (8° C.)

| Column | mg neoGAA loaded/ml resin (mg/ml) | [NaOAc] of wash buffer mM | Recovery (%) | Aggregation (%) |
|---|---|---|---|---|
| Butyl 650C | 21.1 | 100 | 98.1 | 3.3 |
| Phenyl 6FF | 18.1 | 100 | 94.3 | 1.6 |
| Hexyl 650C | 8.7 | 100 | 78.2 | 1.0 |
|  |  | 10 | 91.4 | 1.5 |
| Hexyl 650C | 21.4 | 100 | 87.5 | 1.4 |
| Capto Phenyl | 12.4 | 100 | 84.7 | 1.1 |
|  |  | 50 | 92.3 | 1.3 |
| Butyl 650M | 15.7 | 100 | 92.5 | 1.9 |
| Capto Octyl | 8.5 | 100 | 95.6 | 1.8 |

Conditions for operation of copper chelate columns (GE or Tosoh) were also established either in flow-through or bind-elute mode. A 7 ml metal chelating FF column (I.D., 7 ml) charged with copper was first evaluated in the bind-and-elute mode with 10 mg/ml conjugated GAA loaded. 87% NeoGAA was recovered with 1.2% aggregates when the column is eluted with 175 mM glycine, 100 mM acetate, pH 5.5 as the elution buffer at RT. At 8° C., higher than 175 mM glycine was required to elute the column for satisfactory recovery. In flow-through mode (Table 3), good recovery of 92% was achieved with aggregate reduced from 3.2 to 1.2% using 150 mM glycine, 100 mM acetate, pH 5.5 as the elution buffer.

TABLE 3

Removing aggregates from conjugated GAA (3.2% agg) using copper 6FF column (RT, Ft mode)

| mg neoGAA loaded/ml resin (mg/ml) | [glycine] in the load mM | [glycine] of elution buffer mM | Recovery (%) | Aggr. (%) |
|---|---|---|---|---|
| 36.6 | 0 | 125 | 76.5 | 1.1 |
| 10 | 50 | 175 | 80.8 | 1.0 |
| 10 | 150 | 150 | 79.6 | 1.3 |
| 10 | 100 | 175 | 84.7 | 0.9 |
| 30 | 100 | 150 | 92.0 | 1.2 |
| 30 | 50 | 150 | 92.3 | 1.3 |

Imidazole (7.5, 8, and 10 mM) was also tried as the elution buffer for the metal chelating 6FF column. About 8 mM imidazole was needed to elute the column. Because imidazole does not elute copper from the column, it was not necessary to condition the column or make a clear space with EDTA on the top of the column. A column capacity of 15 mg/ml NeoGAA was achieved.

Toso AF-chelate 650M column charged with copper was also evaluated. In bind-and-elute mode, a column capacity of 15 mg/ml was achieved, with 94.1% elution and 1.2% aggregate using 8 mM glycine. In flow-through mode, 33.6 mg/ml capacity was achieved. 90.6% recovery with 1.2% aggregate was obtained with 50 mM glycine in the elution buffer.

C. Analysis of Oligosaccharides

According to these experiments, the use of >2 mM periodate resulted in incorporation of NeoGAA glycan which exceeded the starting level of sialic acid in the protein, indicating that non-sialic acid moieties were being oxidized. To determine the levels of oxidation at other carbohydrate sites by periodate, a series of periodate titration experiments were performed, monitoring the levels of other monosaccharide residues.

For determination of sialic acid content, samples were subjected to acid hydrolysis using 0.5 M formic acid at 80° C. for one hour. The released sialic acid was analyzed by high pH anion exchange chromatography coupled with pulsed amperometric detection (HPAEC-PAD) on a Dionex CarboPac PA1 column using a 50-180 mM sodium acetate gradient in 100 mM sodium hydroxide over 20 minutes. The results are expressed as moles of sialic acid (NANA or NGNA)/mole of rhGAA or NeoGAA, and were determined from standard curves of authentic commercially available sialic acid standards.

The levels of neutral monosaccharides, including fucose, galactose, GlcNAc, and mannose, were determined by hydrolyzing 100 µg of rhGAA or NeoGAA in 1 M TFA at 110° C. for 2 hours. Following hydrolysis, tubes were cooled on ice, centrifuged for 1 minute at 10,000 rpm and evaporated to dryness by Speed Vac. The released monosaccharides were resuspended in 250 µL water, vortexed and filtered using Millipore Ultrafree-MC filter tubes (10,000 MWCO). Released monosaccharides were analyzed by high pH anion exchange chromatography using pulsed amperometric detection (HPAEC-PAD) on a CarboPac PA1 column. Quantitation was performed using standard curves of monosaccharides hydrolyzed in the same manner.

Figure 10A:
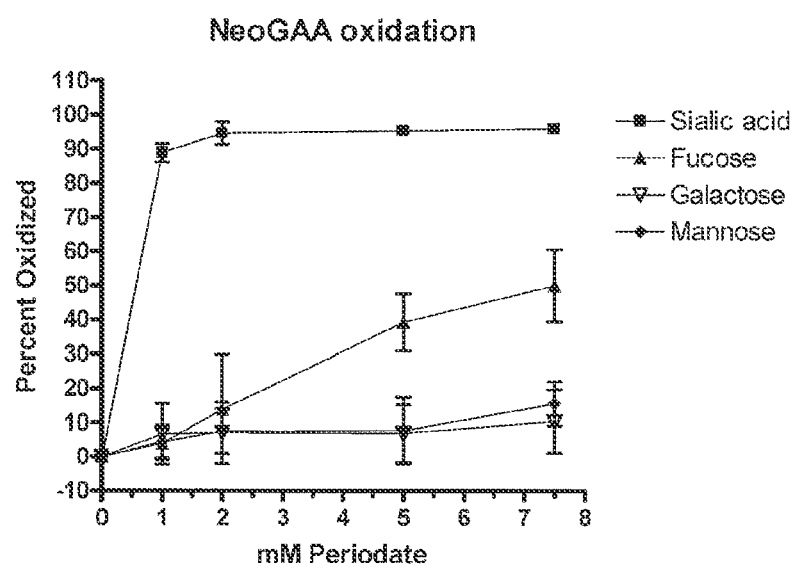
FIGS. 10A, 10B, 10C, 10D, and 10E show oxidation of sialic acid, fucose, galactose, and mannose with varying amounts of periodate.

The results of the above experiments are shown in FIG. 10A. The results suggested that sialic acid is the most-susceptible of the monosaccharides to oxidation. Low levels of fucose destruction were detectable at 2 mM periodate, and the amounts were more measurable and reproducible at ≥5 mM. Slight oxidation of mannose was detectable only at ≥7.5 mM periodate.

To confirm the presence of oxidized sialic acid, fucose, and mannose, fragmentation mass spectrometry was performed on oligosaccharides released from rhGAA oxidized using 7.5 mM periodate. The N-linked oligosaccharides in rhGAA and NeoGAA were released using overnight digestion with PNGase F in 50 mM sodium phosphate pH 7.0 and 10 mM B-mercaptoethanol. The released oligosaccharides were cleaned by bio-dialysis (MWCO 500 Da) with several changes of water. The dialyzed samples were dried in a speed-vac concentrator and reconstituted with 110 µL of 10 mM ammonium formate pH 4.0 in 50% acetonitrile and 50% water. The samples were analyzed using a TSK Gel Amide-80 column (100 µL injection onto a 2×100 mm, 5 µm particle size) with in-line MS detection (QStar quadrupole time-of-flight, LCT Premier time-of-flight, and LTQ linear ion trap instruments) in an acetonitrile-water gradient and 10 mM ammonium formate pH 4.0.

For oligosaccharide structure analysis, oligosaccharides were dried and fluorescently labeled using anthranilic acid (AA). AA-labeled oligosaccharides were resolved by normal phase HPLC on a TSK gel amide 80 column with fluorescence detection using an acetonitrile/water gradient. MS fragmentation analysis was performed in-line using an LTQ XL linear ion trap mass spectrometer in positive ion mode. Spectra were scanned from 400 to 2,000 m/z, with normalized collision energy set at 35 (default, unless noted in the text) and activation Q was set at 0.25.

Sialic Acid:

Complete oxidation of sialic acid (at both the C7,8 and C8,9 bonds) would result in a 62 Dalton reduction in mass. Oxidation of fucose and mannose would initially lead to a 2 Dalton reduction (oxidation of the C2,3 or C3,4 bonds), followed by 30 Dalton reduction upon oxidation of remaining vicinal diols. Reductive amination of carbohydrate aldehydes with AA results in a loss of oxygen, with a net addition of 121.1 Daltons molecular weight per addition of AA. Theoretical and observed molecular weight changes of rhGAA oligosaccharides following oxidation of sialic acid, fucose, and mannose are shown in Table 4.

TABLE 4

Summary of targeted ions of AA-labeled SAM6 oligosaccharides for ms2 and ms3 analysis "1+" and "2+"corresponds to the singly charged and doubly charged positive species, respectively. "2-" and "3-"corresponds to the doubly charged- and triply charged negative species, respectively

| Oxidation Detected | Oligosaccharide structures examined | Theoretical mass (Da) | Observed Precursor ions of MS2 (m/z) | Observed Precursor ions of MS3 (m/z) |
|---|---|---|---|---|
| Sialic acid oxidation (1 Ox. sialic acid + 2 AA) | Monosial., Biant. (A1) | 2111 | 1057(2+) | 716, 1032, 1235, 1397, 1585, 1747 |
|  | Monosial, Bianten., core fucosylated (A1F) | 2258 | 1130(2+) | 716, 878, 1178, 1381, 1543, 1893 |
|  | Bisial., Biant. (A2) | 2462 | 1232(2+) | — |
|  | Bisial, Bianten., core fucosylated (A2F) | 2608 | 1305(2+) | — |
| Mannose oxidation (1 Ox. mannose + 3 AA) | Oligomannose 5 | 1595.5 | 1596.5(1+) | 1194, 1395 |
|  | Oligomannose 6 | 1758 | 1758(1+) | 1356, 1547 |
| Fucose oxidation (1 Ox S.A. + Ox. Fucose + 4AA) | Monosial, Bianten., core fucosylated (A1F) | 2498 | 1250(2+) | 716, 1397, 1621, 1783 |
|  | Bisial, Bianten., core fucosylated (A2F) | 2848 | 1426(2+) | — |

Several ions corresponding to oxidized and AA-derivatization oxidized sialic acid, fucose, and mannose oligosaccharide species were observed. In addition to derivatization at reducing GlcNAc of all released oligosaccharides, AA was derivatized in proportion to the number of reactive aldehyde species present, ie, in a 1:1 ratio with oxidized sialic acid and in a 2:1 ratio per oxidized mannose and fucose.

Figure 10B:
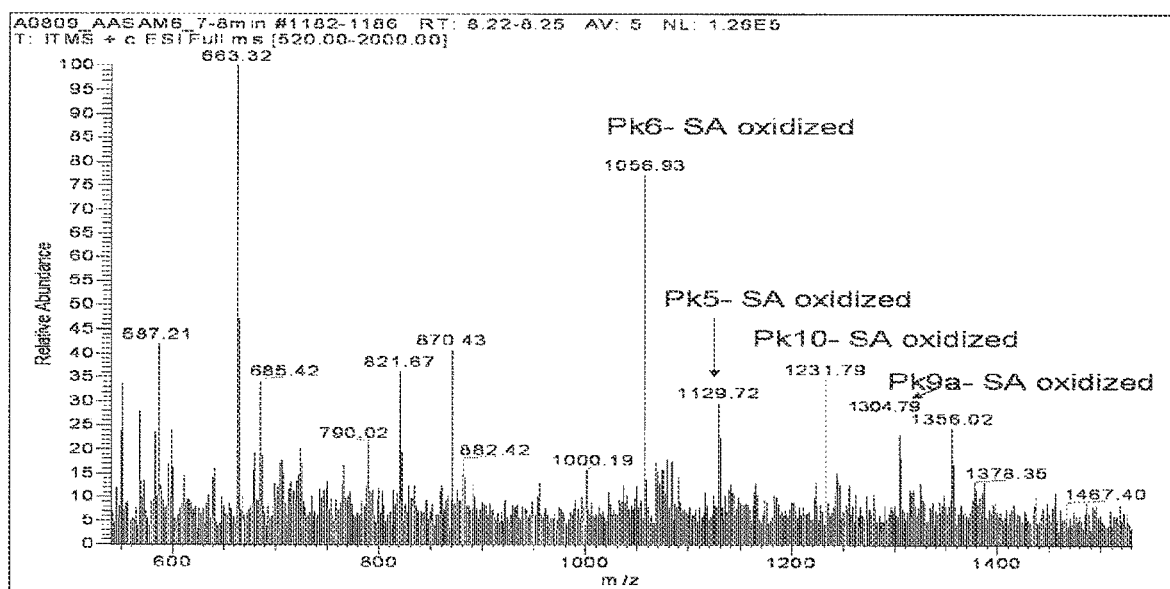
Figure 10C:
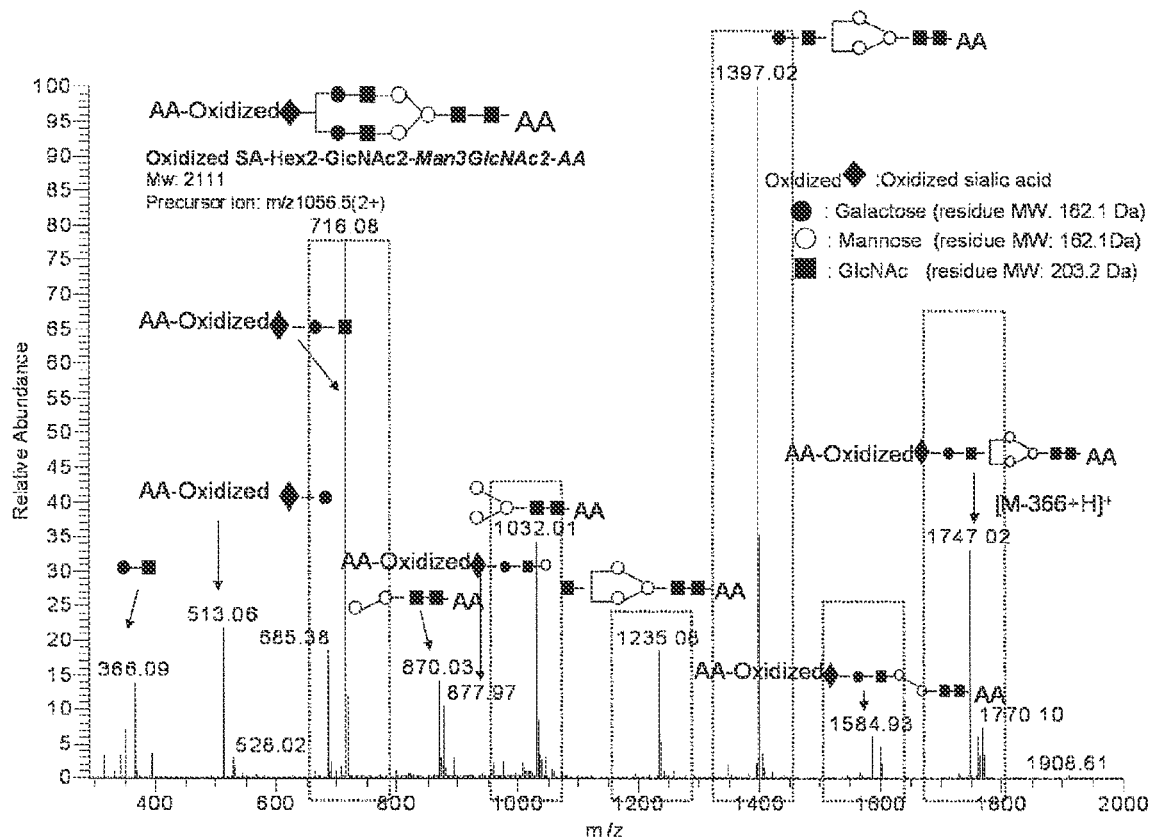

The mass spectrum of FIG. 10B shows detection of 4 ions corresponding to rhGAA oligosaccharides with oxidation and AA-derivatization at C7 of sialic acid. Two ions of interest to sialic acid oxidation (m/z 1057 and 1130) were selected for further, MS/MS fragmentation analysis. The fragmentation pattern of m/z 1057 is shown in FIG. 10C, with each ion annotated with hypothesized identities. The fragmentation ions m/z 716, 1032, 1235, 1397, 1584, and 1747 were selected for MS3 analysis. The $MS^3$ spectra matched with the hypothesized oligosaccharide structure containing oxidized and AA-labeled sialic acid on the terminus of a biantennary glycan. In particular, release of a fragment of m/z 351 confirmed the attachment of AA to a C7 form of sialic acid. In all samples analyzed, only the C7 form of oxidized sialic acid was observed; no evidence for the presence of sialic acid oxidized at C8 was observed.

Fucose Oxidation:

Table 5 lists the theoretical and observed masses of AA-derivatized, oxidized A1F and A2F.

TABLE 5

Theoretical and observed masses of AA-derivatized A1F and A2F, following oxidation of 1 fucose residue with periodate. "2+" corresponds to the doubly-charged positive ion species. The theoretical masses are based on conjugation of 4 AA molecules per A1F oligosaccharide, and 5 AA molecules per A2F

| Derivatized Oligosaccharide | Theoretical Mass (Da)* | Detected ions (m/z) |
|---|---|---|
| A1F, with AA-labeled and oxidized sialic acid and fucose | 2498.1 | 1250.4 (2+) |
| A2F, with AA-labeled and oxidized sialic acid and fucose | 2848.3 | 1426.0 (2+) |

Figure 10D:
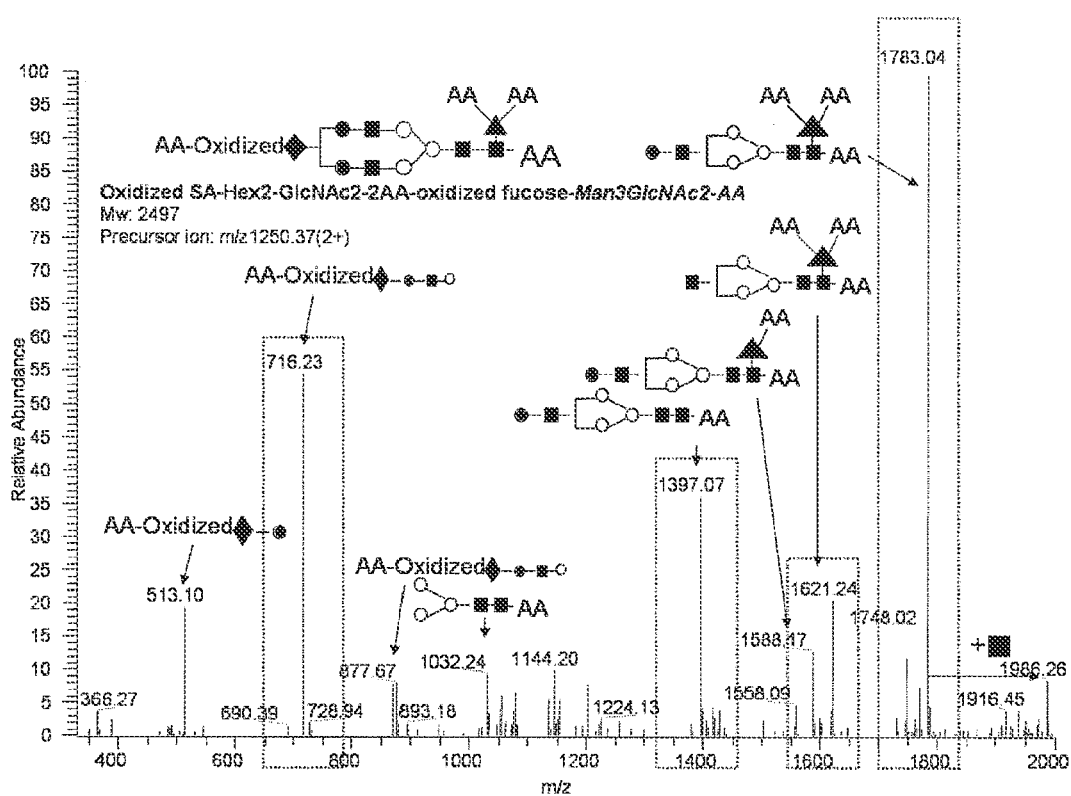
Figure 10E:
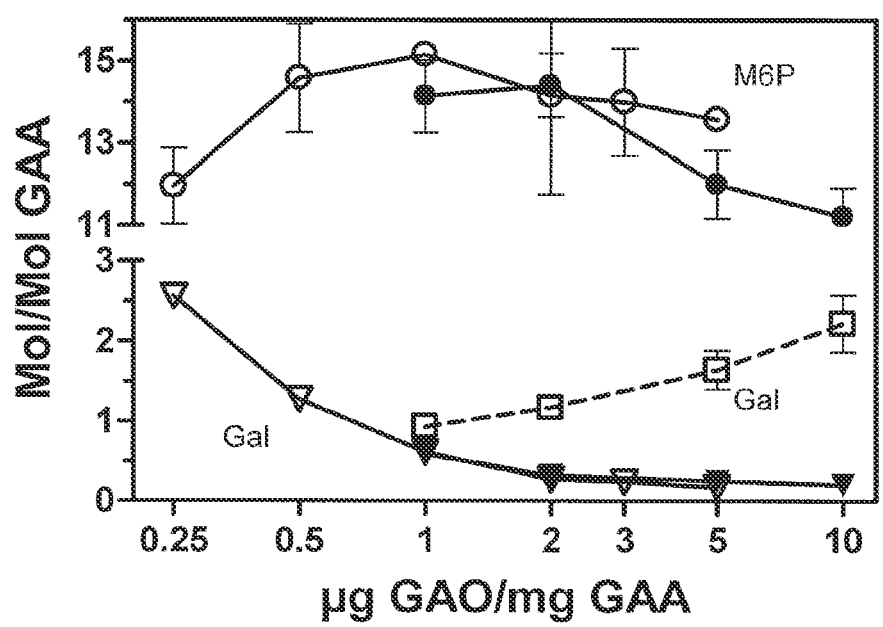

The fragmentation pattern of parent ion m/z 1250.4 is shown in FIG. 10D, and is consistent with what would be expected for an AA-labeled monosialylated monoantennary core fucosylated oligosaccharide which contains oxidized sialic acid and oxidized fucose. Major fragment ions m/z 716, 1397, 1621, and 1783 were observed. These ions were selected for $MS^3$ analysis to confirm the hypothesized identities. In the $MS^3$ spectra of m/z 1621 and 1783, ion fragmentation patterns were observed with a loss of 195 Daltons from the parent ions (to 1426 and 1588 from parent ions 1621 and 1783, respectively). This molecular weight change is consistent with cleavage between the C1 and oxygen atoms of oxidized fucose, resulting in the loss of the derivatized anthranilic acid attached to C4. In addition, further fragmentation and loss of the second derivatized anthranilic acid bound to C3 was observed as a loss of 386 Daltons from the parent ions (1235 and 1397 m/z, from parent ions 1621 and 1783, respectively).

The MS fragmentation pattern of oxidized rhGAA oligosaccharide A1F showed derivatization of C3,4 in fucose with anthranilic acid, confirming that periodate oxidation occurred. No evidence for C2-C3 bond oxidation was observed. Conjugation of Bis-M6P hexasaccharide glycan to oxidized rhGAA resulted in a net addition of 1305.3 Daltons during the condensation reaction.

To confirm the identities of conjugated oligosaccharide structures, high mass accuracy MS analysis of native, released oligosaccharides was performed. Oligosaccharides from rhGAA and NeoGAA SAM6 prepared with 2 and 7.5 mM periodate were released using PNGase F, resolved by normal-phase HPLC (TSK gel amide-80 column) in an acetonitrile-water gradient with 10 mM ammonium formate pH 4.0. Mass spectrometry detection of glycans was performed in-line, in negative ion mode, using QStar or LCT time-of-flight mass spectrometers.

The following table provides a summary of native N-linked oligosaccharide peak identities from rhGAA oxidized with 2 and 7.5 mM periodate, and in SAM6 prepared with 2 and 7.5 mM periodate, based on high-accuracy MS/TOF analysis. "Ox" refers to the number of sites of oxidation, "Conj" to the number of Bis-M6P hexasaccharide glycans conjugated. Theoretical masses are calculated from monoisotopic molecular weights of theoretical oligosaccharide structures, and theoretical and observed m/z for the corresponding charge states are shown.

| Base structure | Oligo | Theor. Mw (mono) | Theor. m/z (2−) | Theor. m/z (3−) | Theor. m/z (4−) | 2 mM periodate-treated SAM6 Observed Mw | 7.5 mM periodate-treated SAM6 Observed Mw | 2 mM periodate-treated GAA Observed Mw | 7.5 mM periodate-treated GAA Observed Mw |
|---|---|---|---|---|---|---|---|---|---|
| Man5 | Native | 1234.43 | 616.21 | | | 1233.45(1−) | 1233.45(1−) | 1233.45(1−) | 1233.45(1−) |
| | 1 Ox Mannose | 1232.42 | 615.20 | | | N/D | N/D | 1231.44(1−) | 1231.40(1−) |
| | 2 Ox Mannose | 1230.40 | 614.19 | | | N/D | N/D | 1229.45(1−) | 1229.45(1−) |
| | 1 Ox Mannose + 1 Conj | 2537.75 | 1267.87 | 844.91 | 633.43 | 1267.91(2−) | 1267.91(2−) | N/D | N/D |
| | 2 Ox Mannose + 1 Conj | 2535.73 | 1266.86 | 844.24 | 632.93 | N/D | N/D | N/D | N/D |
| | 1 Ox Mannose + 2 Conj | 3843.08 | 1920.53 | 1280.02 | 959.76 | N/D | 1280.01(3−) | N/D | N/D |
| | 2 Ox Mannose + 2 Conj | 3841.06 | 1919.52 | 1279.35 | 959.26 | N/D | 1279.41(2−) | N/D | N/D |
| | 2 Ox Mannose + 3 Conj | 5146.39 | 2572.19 | 1714.46 | 1285.59 | N/D | N/D | N/D | N/D |
| Man6 | Native | 1396.49 | 697.24 | | | 1395.49(1−); 697.26(2−) | 1395.49(1−); 697.26(2−) | 1395.49(1−); 697.24(2−) | 1395.47(1−) 697.26(2−) |
| | 1 Ox Mannose | 1394.47 | 696.23 | | | N/D | N/D | 1393.47(1−); 696.23(2−) | 1393.47(1−); 696.27(2−) |
| | 2 Ox Mannose | 1392.46 | 695.22 | | | N/D | N/D | N/D | 1391.44(1−); 695.24(2−) |
| | 1 Ox Mannose + 1 Conj | 2699.80 | 1348.89 | 898.93 | 673.94 | 1348.88(2−) | 1348.88(2−) | N/D | N/D |
| | 2 Ox Mannose + 1 Conj | 2697.78 | 1347.88 | 898.25 | 673.44 | N/D | N/D | N/D | N/D |
| | 1 Ox Mannose + 2 Conj | 4005.13 | 2001.56 | 1334.04 | 1000.27 | 2001.48(2−); 1333.99(3−) | 2001.48(2−); 1334.04(3−) | N/D | N/D |
| | 2 Ox Mannose + 2 Conj | 4003.11 | 2000.55 | 1333.36 | 999.77 | N/D | 1333.45(3−) | N/D | N/D |
| | 2 Ox Mannose + 3 Conj | 5308.44 | 2653.21 | 1768.47 | 1326.10 | N/D | N/D | N/D | N/D |
| NA2 | Native | 1640.59 | 819.29 | | | 1639.55(1−); 819.33(2−) | 1639.55(1−); 819.33(2−) | 1639.55(1−); 819.33(2−) | 1639.55(1−); 819.33(2−) |
| | 1 Ox Gal/Man | 1638.58 | 818.28 | | | N/D | N/D | N/D | 818.30(2−) |
| | 2 Ox Gal/Man | 1636.56 | 817.27 | | | N/D | N/D | N/D | N/D |
| | 3 Ox Gal/Man | 1634.55 | 816.26 | | | N/D | N/D | N/D | N/D |
| | 4 Ox Gal/Man | 1632.53 | 815.26 | | | N/D | N/D | N/D | N/D |
| | 1 Ox Gal/Man + 1 Conj | 2943.91 | 1470.95 | 980.29 | 734.97 | N/D | N/D | N/D | N/D |
| | 2 Ox Gal/Man + 1 Conj | 2941.89 | 1469.94 | 979.62 | 734.46 | N/D | N/D | N/D | N/D |
| | 1 Ox Gal/Man + 2 Conj | 4249.24 | 2123.61 | 1415.40 | 1061.30 | N/D | 1415.42(3−) | N/D | N/D |
| | 2 Ox Gal/Man + 2 Conj | 4247.22 | 2122.60 | 1414.73 | 1060.80 | N/D | N/D | N/D | N/D |
| | 2 Ox Gal/Man + 3 Conj | 5552.55 | 2775.27 | 1849.84 | 1387.13 | N/D | N/D | N/D | N/D |
| NA2F | Native | 1786.65 | 892.32 | | | 892.34(2−) | 892.34(2−) | 892.34(2−) | 892.34(2−) |
| | 1 Ox Gal/Man/Fuc | 1784.63 | 891.31 | | | N/D | N/D | 891.36(2−) | 891.31(2−) |
| | 2 Ox Gal/Man/Fuc | 1782.62 | 890.30 | | | N/D | N/D | N/D | 890.33(2−) |
| | 3 Ox Gal/Man/Fuc | 1780.60 | 889.29 | | | N/D | N/D | N/D | N/D |
| | 4 Ox Gal/Man/Fuc | 1778.59 | 888.29 | | | N/D | N/D | N/D | N/D |
| | 1 Ox Gal/Man/Fuc + 1 Conj | 3089.96 | 1543.97 | 1028.98 | 771.48 | N/D | N/D | N/D | N/D |
| | 1 Ox Gal/Man/Fuc + 2 Conj | 4395.29 | 2196.64 | 1464.09 | 1097.82 | 1464.06(3−) | 1464.06(3−) | N/D | N/D |
| | 2 Ox Gal/Man/Fuc + 2 Conj | 4393.28 | 2195.63 | 1463.42 | 1097.31 | N/D | N/D | N/D | N/D |
| | 3 Ox Gal/Man/Fuc + 2 Conj | 4391.26 | 2194.62 | 1462.75 | 1096.81 | N/D | N/D | N/D | N/D |
| | 3 Ox Gal/Man/Fuc + 3 Conj | 5696.59 | 2847.29 | 1897.86 | 1423.14 | N/D | N/D | N/D | N/D |
| A1 | Native | 1931.69 | 964.84 | | | N/D | N/D | N/D | N/D |
| | Ox Sialic acid | 1869.65 | 933.82 | | | 933.84(2−) | 933.84(2−) | 933.84(2−) | 933.84(2−) |
| | Ox Sialic acid + 1 Ox Gal/Man | 1867.64 | 932.81 | | | N/D | N/D | N/D | N/D |
| | Ox Sialic acid + 2 Ox Gal/Man | 1865.62 | 931.80 | | | N/D | N/D | N/D | N/D |
| | Ox Sialic acid + 3 Ox Gal/Man | 1863.60 | 930.79 | | | N/D | N/D | N/D | N/D |
| | Ox Sialic acid + 4 Ox Gal/Man | 1861.59 | 929.79 | | | N/D | N/D | N/D | N/D |
| | Ox Sialic acid + 1 Conj | 3174.98 | 1586.48 | 1057.32 | 792.74 | 1586.49(2−); 1057.31(3−) | 1586.49(2−); 1057.31(3−) | N/D | N/D |
| | Ox Sialic acid + 1 Ox Gal/Man + 1 Conj | 3172.96 | 1585.47 | 1056.65 | 792.23 | N/D | N/D | N/D | N/D |

| Base structure | Oligo | Theor. Mw (mono) | Theor. m/z (2−) | Theor. m/z (3−) | Theor. m/z (4−) | 2 mM periodate-treated SAM6 Observed Mw | 7.5 mM periodate-treated SAM6 Observed Mw | 2 mM periodate-treated GAA Observed Mw | 7.5 mM periodate-treated GAA Observed Mw |
|---|---|---|---|---|---|---|---|---|---|
| | Ox Sialic acid + 1 Ox Gal/Man + 2 Conj | 4478.29 | 2238.14 | 1491.76 | 1118.57 | N/D | 1491.73(3−) | N/D | N/D |
| | Ox Sialic acid + 2 Ox Gal/Man/Fuc + 2 Conj | 4476.28 | 2237.13 | 1491.08 | 1118.06 | N/D | N/D | N/D | N/D |
| | Ox Sialic acid + 3 Ox Gal/Man/Fuc + 2 Conj | 4474.26 | 2236.12 | 1490.41 | 1117.56 | N/D | N/D | N/D | N/D |
| | Ox Sialic acid + 1 Ox Gal/Man + 3 Conj | 5783.62 | 2890.80 | 1926.87 | 1444.90 | N/D | 1926.86(3−); 1444.89(4−) | N/D | N/D |
| | Ox Sialic acid + 2 Ox Gal/Man/Fuc + 3 Conj | 5781.61 | 2889.80 | 1926.19 | 1444.39 | N/D | N/D | N/D | N/D |
| A1F | Native | 2077.75 | 1037.87 | 691.57 | 518.43 | N/D | N/D | N/D | N/D |
| | Ox Sialic acid | 2015.71 | 1006.85 | 670.90 | 502.92 | 1006.88(2−) | 1006.82(2−) | 1006.88(2−) | 1006.88(2−) |
| | Ox Sialic acid + 1 Ox Gal/Man/Fuc | 2013.69 | 1005.84 | 670.22 | 502.42 | N/D | 1005.82(2−) | 1005.88(2−) | 1005.88(2−) |
| | Ox Sialic acid + 2 Ox Gal/Man/Fuc | 2011.68 | 1004.83 | 669.55 | 501.91 | N/D | N/D | N/D | 1004.83(2−) |
| | Ox Sialic acid + 3 Ox Gal/Man/Fuc | 2009.66 | 1003.82 | 668.88 | 501.41 | N/D | N/D | N/D | N/D |
| | Ox Sialic acid + 4 Ox Gal/Man/Fuc | 2007.65 | 1002.82 | 668.21 | 500.90 | N/D | N/D | N/D | N/D |
| | Ox Sialic acid + 1 Conj | 3321.04 | 1659.51 | 1106.00 | 829.25 | 1659.56(2−); 1106.02(3−) | 1659.51(2−); 1106.03(3−) | N/D | N/D |
| | Ox Sialic acid + 1 Ox Gal/Man + 1 Conj | 3319.02 | 1658.50 | 1105.33 | 828.75 | N/D | 1658.50(2−) | N/D | N/D |
| | Ox Sialic acid + 1 Ox Gal/Man/Fuc + 2 Conj | 4624.35 | 2311.17 | 1540.44 | 1155.08 | 1540.45(3−) | 1540.45(3−) | N/D | N/D |
| | Ox Sialic acid + 1 Ox Gal/Man/Fuc + 3 Conj | 5929.68 | 2963.83 | 1975.55 | 1481.41 | N/D | 1481.40(4−) | N/D | N/D |
| A2 | Native | 2222.78 | 1110.38 | 739.92 | 554.69 | N/D | N/D | N/D | N/D |
| | 1 Ox Sialic acid | 2160.75 | 1079.37 | 719.24 | 539.18 | N/D | N/D | N/D | N/D |
| | 2 Ox Sialic acid | 2098.71 | 1048.35 | 698.56 | 523.67 | N/D | 1048.33(2−) | 1048.36(2−) | N/D |
| | 2 Ox Sialic acid + 1 Ox Gal/Man | 2096.69 | 1047.34 | 697.89 | 523.17 | N/D | N/D | N/D | N/D |
| | 2 Ox Sialic acid + 2 Ox Gal/Man | 2094.68 | 1046.33 | 697.22 | 522.66 | N/D | N/D | N/D | N/D |
| | 2 Ox Sialic acid + 3 Ox Gal/Man | 2092.66 | 1045.32 | 696.55 | 522.16 | N/D | N/D | N/D | N/D |
| | 2 Ox Sialic acid + 4 Ox Gal/Man | 2090.65 | 1044.32 | 695.87 | 521.65 | N/D | N/D | N/D | N/D |
| | 2 Ox Sialic acid + 1 Conj | 3404.04 | 1701.01 | 1133.67 | 850.00 | N/D | 1700.98(2−); 1133.67(3−) | N/D | N/D |
| | 2 Ox Sialic acid + 2 Conj | 4709.37 | 2353.68 | 1568.78 | 1176.33 | 1568.77(3−) | 1568.77(3−) | N/D | N/D |
| | 2 Ox Sialic acid + 1 Ox Gal/Man + 1 Conj | 3402.02 | 1700.00 | 1133.00 | 849.50 | N/D | N/D | N/D | N/D |
| | 2 Ox Sialic acid + 1 Ox Gal/Man + 2 Conj | 4707.35 | 2352.67 | 1568.11 | 1175.83 | N/D | N/D | N/D | N/D |
| | 2 Ox Sialic acid + 2 Ox Gal/Man/Fuc + 2 Conj | 4705.34 | 2351.66 | 1567.44 | 1175.33 | N/D | N/D | N/D | N/D |
| | 2 Ox Sialic acid + 3 Ox Gal/Man/Fuc + 2 Conj | 4703.32 | 2350.65 | 1566.77 | 1174.82 | N/D | N/D | N/D | N/D |
| | 2 Ox Sialic acid + 1 Ox Gal/Man + 3 Conj | 6012.66 | 3005.33 | 2003.22 | 1502.16 | N/D | N/D | N/D | N/D |
| A2F | Native | 2368.84 | 1183.41 | 788.61 | 591.20 | N/D | N/D | N/D | N/D |
| | 1 Ox Sialic acid | 2306.80 | 1152.39 | 767.93 | 575.69 | N/D | N/D | N/D | N/D |
| | 2 Ox Sialic acid | 2244.77 | 1121.38 | 747.25 | 560.18 | N/D | 1121.36(2−) | 1121.38(2−) | 1121.38(2−) |
| | 2 Ox Sialic acid + 1 Ox Gal/Man/Fuc | 2242.75 | 1120.37 | 746.58 | 559.68 | N/D | 1120.36(2−) | N/D | 1120.36(2−) |
| | 2 Ox Sialic acid + 2 Ox Gal/Man/Fuc | 2240.74 | 1119.36 | 745.90 | 559.18 | N/D | N/D | N/D | N/D |

-continued

| Base structure | Oligo | Theor. Mw (mono) | Theor. m/z (2−) | Theor. m/z (3−) | Theor. m/z (4−) | 2 mM periodate-treated SAM6 Observed Mw | 7.5 mM periodate-treated SAM6 Observed Mw | 2 mM periodate-treated GAA Observed Mw | 7.5 mM periodate-treated GAA Observed Mw |
|---|---|---|---|---|---|---|---|---|---|
| | 2 Ox Sialic acid + 3 Ox Gal/Man/Fuc | 2238.72 | 1118.35 | 745.23 | 558.67 | N/D | N/D | N/D | N/D |
| | 2 Ox Sialic acid + 4 Ox Gal/Man/Fuc | 2236.71 | 1117.34 | 744.56 | 558.17 | N/D | N/D | N/D | N/D |
| | 2 Ox Sialic acid+ 1 Conj | 3550.10 | 1774.04 | 1182.36 | 886.52 | 1182.33(3−) | 1774.00(2−); 1182.33(3−) | N/D | N/D |
| | 2 Ox Sialic acid+ 2 Conj | 4855.43 | 2426.71 | 1617.47 | 1212.85 | 1617.47(3−) | 1617.44(3−) | N/D | N/D |
| | 2 Ox Sialic acid + 1 Ox Gal/Man/Fuc + 2 Conj | 4851.40 | 2424.69 | 1616.12 | 1211.84 | N/D | 1616.77(3−) | N/D | N/D |
| | 2 Ox Sialic acid + 2 Ox Gal/Man/Fuc + 2 Conj | 4849.38 | 2423.68 | 1615.45 | 1211.34 | N/D | N/D | N/D | N/D |
| | 2 Ox Sialic acid + 1 Ox Gal/Man/Fuc + 3 Conj | 6158.74 | 3078.36 | 2051.91 | 1538.68 | N/D | 2051.89(3−); 1538.66(4−) | N/D | N/D |
| | 2 Ox Sialic acid + 1 Ox Gal/Man/Fuc + 4 Conj | 7624.11 | 3811.05 | 2540.36 | 1905.02 | N/D | N/D | N/D | N/D |

Mass accuracy of >20 ppm was observed for all oligosaccharide species. The MS results were consistent with monosaccharide composition analysis which showed that oxidation of sialic acid is complete at ≥1 mM periodate. Some oxidation of mannose and fucose was also apparent. Ions corresponding to conjugation of 1 and 2 moles of glycan per oxidized mannose and/or fucose were observed, suggesting that both aldehyde species of each are reactive toward glycan, as was observed for AA.

Some conjugation of high mannose structures (oligomannose 5 and 6) was detected in both the 2 and 7.5 mM periodate-treated material. In the material conjugated with 2 mM periodate, 0 or 1 conjugated glycans were observed in the A1 (monosialylated) species, while ions corresponding to 0, 1, 2, and 3 conjugated glycans were observed in the A1 species in the 7.5 mM SAM6. This result implies that with 7.5 mM periodate (but not 2 mM), some oxidation and conjugation of core mannose and/or galactose residues occurred in the A1 structures.

For the A2 and A2F species (bisialylated, biantennary, ±fucose), both mono- and bi-conjugated species were observed in the 2 and 7.5 mM periodate samples. Evidence of tri-conjugation with oxidized mannose was observed only in the 7.5 mM periodate-treated sample, and not in the 2 mM treatment, consistent with conjugation through fucose at elevated periodate concentration.

Figure 11A:
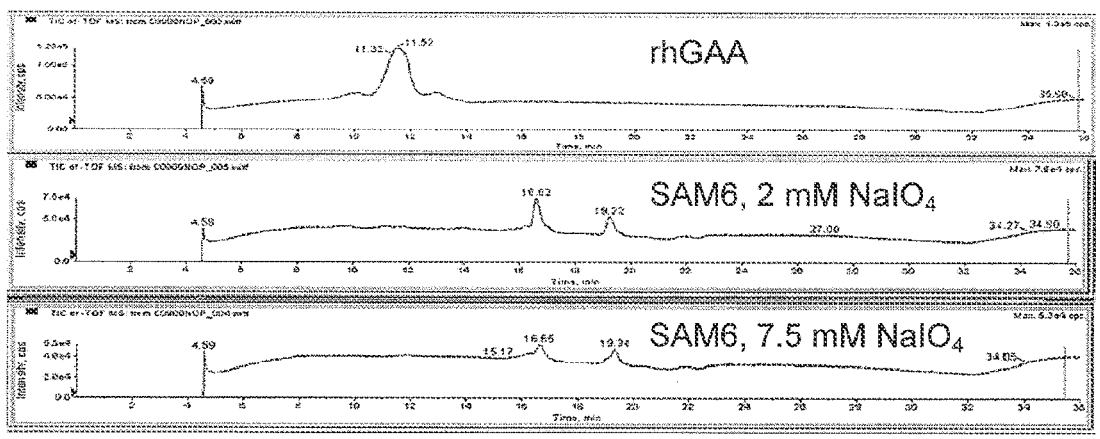
FIGS. 11A, 11B, and 11C show HPLC analysis of oligosaccharides released from rhGAA and NeoGAA.

FIG. 11A shows HPLC analysis of oligosaccharides released from rhGAA and NeoGAA. For the rhGAA control, the majority of the N-linked oligosaccharide species eluted between 11-13 minutes, a region corresponding to oligosaccharides with no phosphorylation or conjugation. For the NeoGAA oligosaccharides, bi-conjugated oligosaccharide species eluted between 19-20 minute, mono-conjugated oligosaccharide species eluted between 15-18 minutes, and oxidized/unmodified oligosaccharides eluted between 10-13 minutes. In the SAM6 sample made with 7.5 mM periodate, approximately half of the oligosaccharides were found to elute in the region corresponding to bi-conjugated species, while roughly ⅓ of the oligosaccharides from the 2 mM periodate-treated samples were bi-conjugated. The elution profiles of these samples are consistent with their conjugation levels (~7 and 9 moles glycan conjugated/mole NeoGAA for 2 and 7.5 mM periodate generated SAM6, respectively) as measured by MALDI-TOF and mannose-6-phosphate content analyses.

To provide better visualization and qualitative comparison of oligosaccharide structures present, released oligosaccharides were analyzed by high pH anion exchange chromatography with pulsed amperometric detection (HPAEC-PAD). Samples were analyzed by HPAEC-PAD on a Dionex CarboPac PA100 column using a sodium acetate gradient in 100 mM sodium hydroxide. Oligosaccharide peak identities were confirmed by off-line fraction collection, dialysis vs. water, and analysis by normal phase HPLC with in-line MS analysis.

Figure 11B:
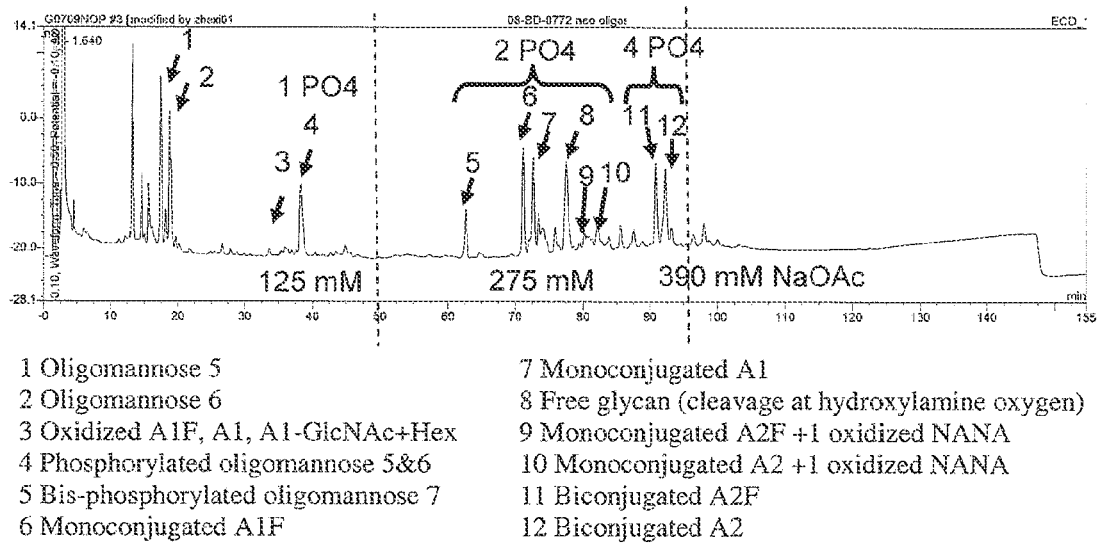
Figure 11C:
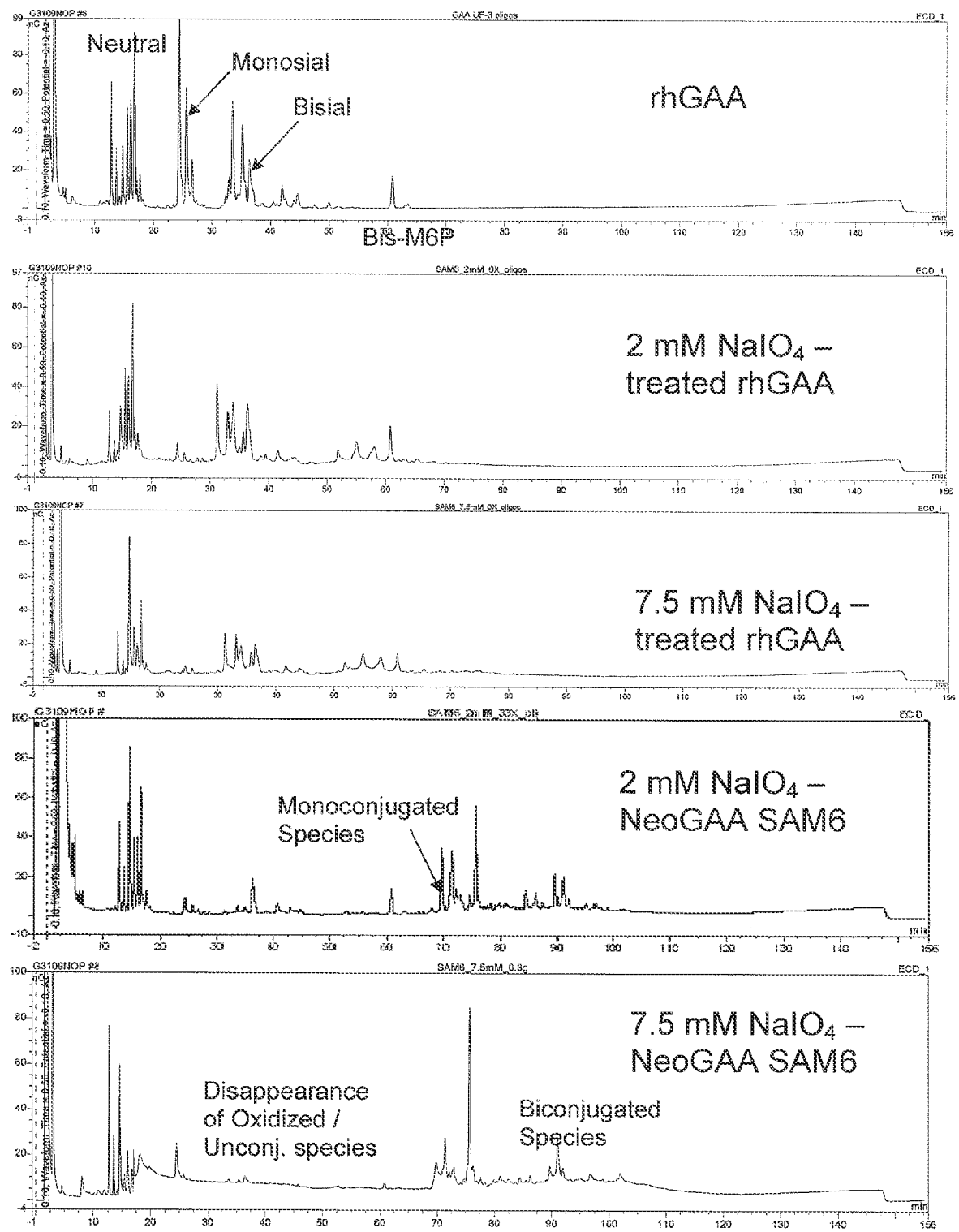

FIG. 11B shows a representative HPAEC-PAD profile with identification of peaks (as determined by MS). FIG. 11C shows oligosaccharide profiling by HPAEC-PAD of the 2 and 7.5 mM periodate-treated rhGAA and NeoGAA SAM6 samples.

D. Analysis of rhGAA Protein Backbone Following Treatment with Periodate

Figure 12:
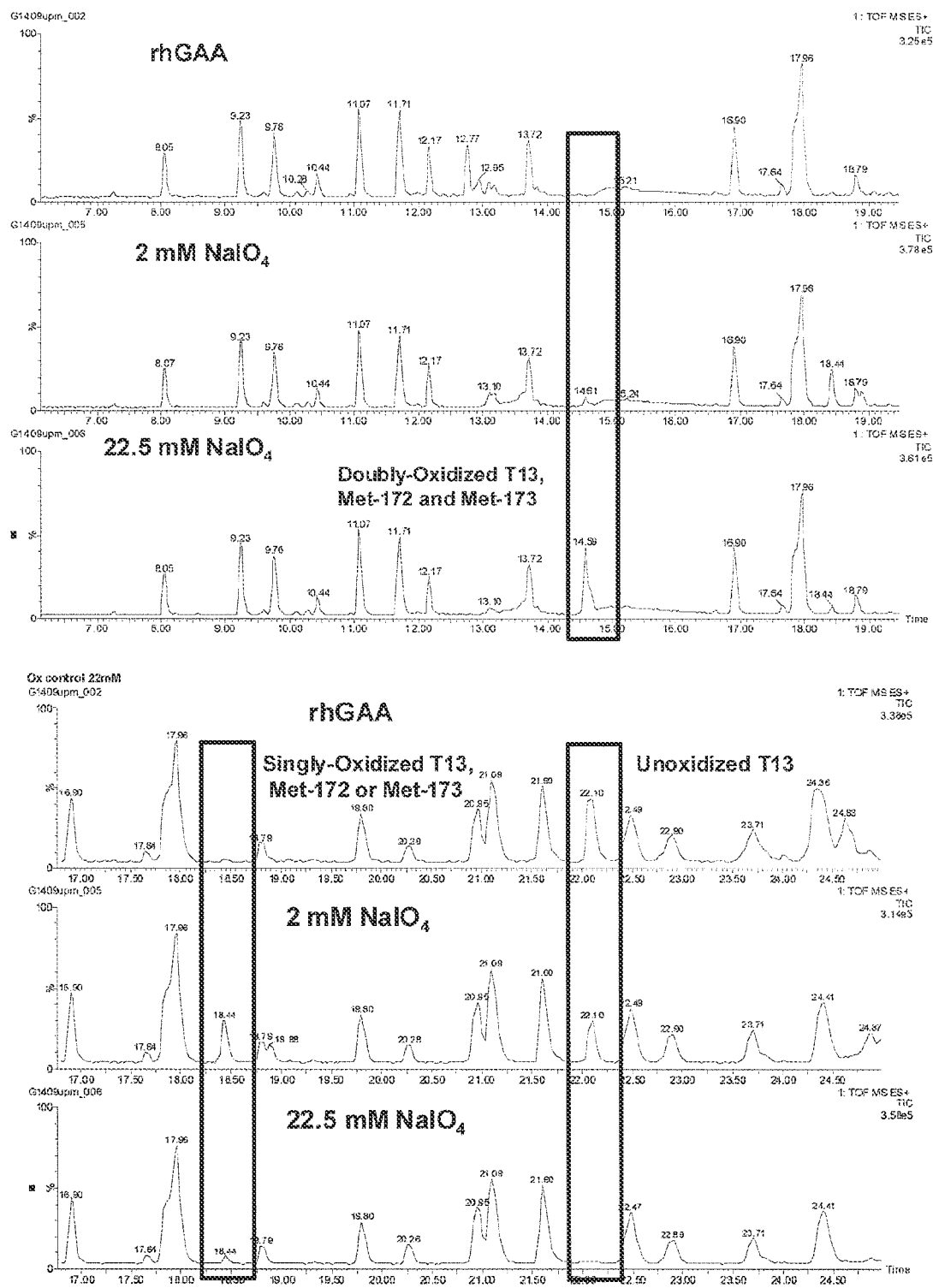
FIG. 12 shows peptide mapping LC/MS analysis of rhGAA treated with 2- and 22.5 mM periodate. Highlighted in the boxes are the elution positions of unoxidized, and singly- and doubly-oxidized tryptic peptide T13 (containing methionines 172 and 173).

To survey the potential modification of the protein backbone of NeoGAA, peptide mapping LC/MS was performed. NeoGAA SAM6 produced using 0, 2, 7.5, and 22.5 mM periodate was prepared using trypsin, and analyzed by reversed phase HPLC with an LCT time-of-flight mass spectrometer. Potential peptide modifications, such as oxidation at cysteine, methionine, tryptophan, tyrosine, and histidine residues, as well as deamidation of asparagine, were evaluated using BioPharmalynx software. The only significant modification detected was oxidation of methionine at several different sites. The levels of oxidation at peptide T13 (containing methionine 172 and 173) following treatment with 0, 2, and 22.5 mM periodate is illustrated in FIG. 12.

Significant levels of oxidation were found at methionine residues 122, 172, and 173. Oxidation at these methionine residues was confirmed by LC/MS/MS analysis. A low level of oxidation was also observed to occur in a periodatedependent manner at methionine 363. In an attempt to minimize periodate oxidation, periodate concentrations were titrated to levels between 1 and 7.5 mM, with oxidation at the most-susceptible site (peptide T13) monitored by LC/MS. Significant levels of methionine oxidation were observed at periodate concentrations of greater than 1 mM, suggesting that methionines in rhGAA are as susceptible to oxidation as sialic acid residues.

During GAM conjugation, galactose oxidation by GAO resulted in ~26% oxidation of Met172/173. When catalase was included in the oxidation reaction at 2 and 50 units/mg GAA, the methionine oxidation was eliminated.

Example 8: In Vitro Characterization of GAA Conjugates

NeoGAA SAM2 was prepared as described in Example 7, using Compound 17 from Example 2 and 7.5 mM periodate. A galactose-conjugated NeoGAA GAM2 was prepared by treating rhGAA with galactose oxidase prior to conjugation with disaccharide 17. Similarly, trisaccharide NeoGAA SAM3 (Compound 35, Example 3), tetrasaccharide NeoGAAs SAM4 (Compound 28, Example 4A) and Linear SAM4 (Compound 47, Example 4B) were also prepared. In addition, hexasaccharide NeoGAA βSAM6 was prepared with Compound 77 as described in Example 7, using 2 and 7.5 mM periodate. Additional hexasaccharide conjugates αSAM6 (α linkage, conjugated through sialic acid residues) and GAM6 (conjugated through galactose residues) were also prepared.

A. Specific Activity

Activity analysis was performed by monitoring the rate of hydrolysis of the synthetic substrate p-nitrophenyl-D-α-glucopyranoside (p-NP), as catalyzed by rhGAA and NeoGAA. The released chromophore is measured by absorbance at 400 nm under alkaline conditions. One unit of activity is defined as the amount of enzyme required to hydrolyze one µmol of p-nitrophenyl-D-α-glucopyranoside to p-nitrophenol per minute at 37° C. under the defined assay conditions.

Figure 13A:
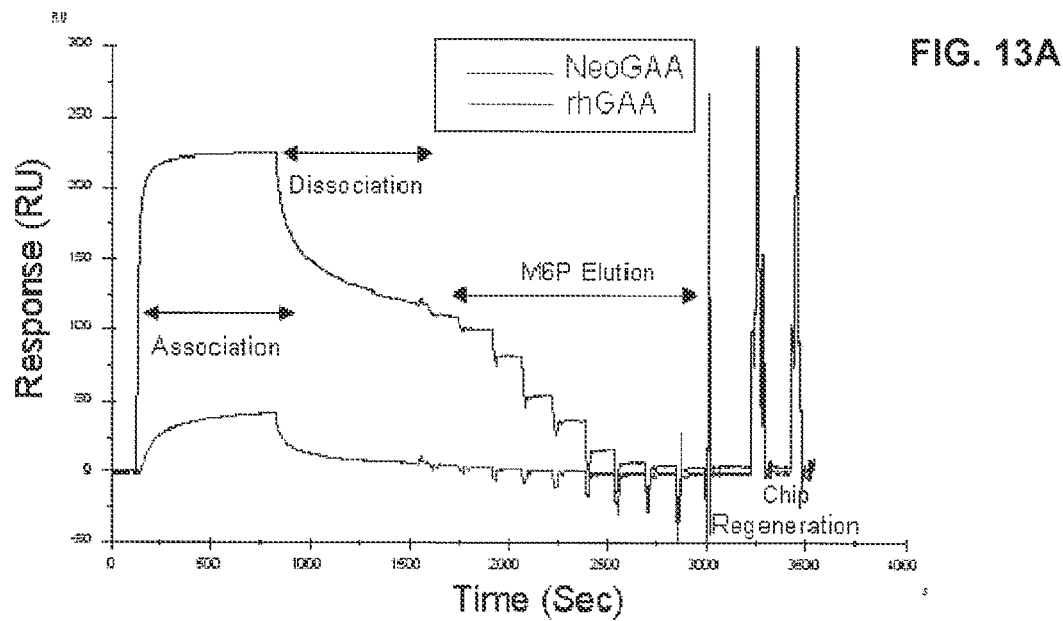
FIGS. 13A, 13B, and 13C show Biacore binding analysis of NeoGAA and rhGAA to sCIMPR.
Figure 13B:
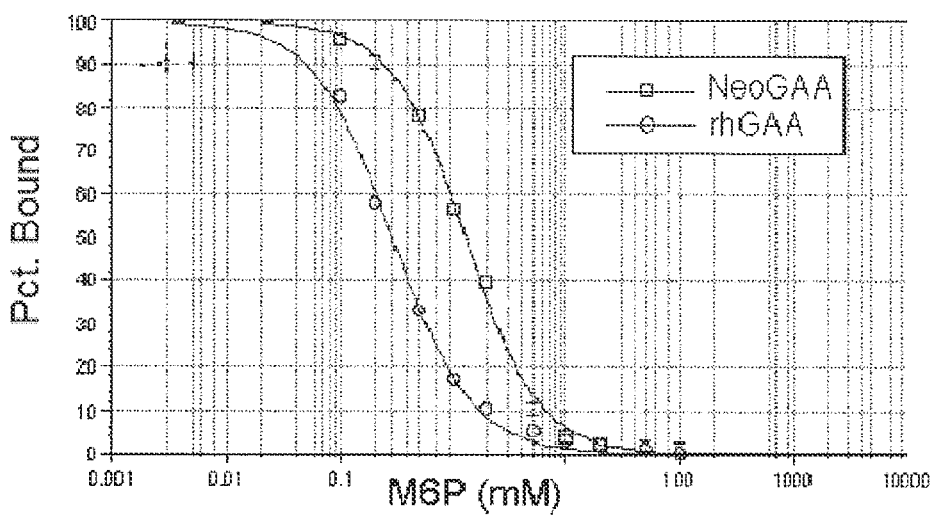
Figure 13C:
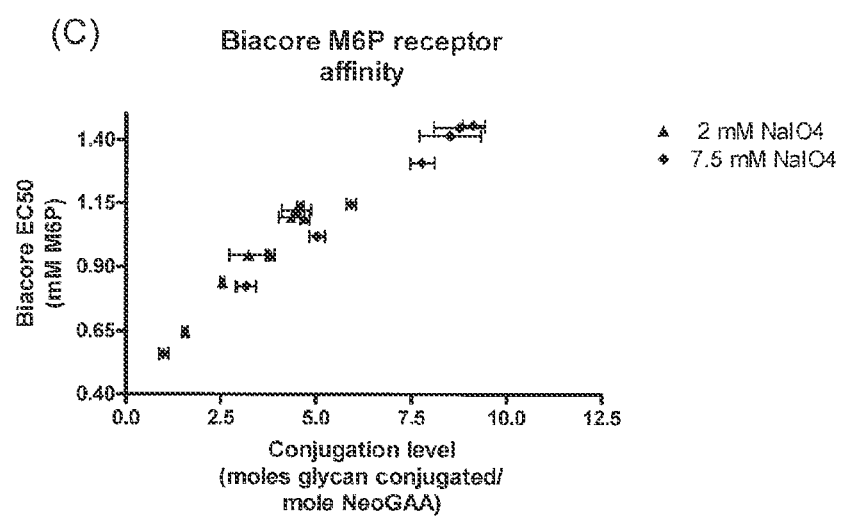

The specific activities of NeoGAAs SAM2, SAM3, SAM4, Linear SAM4, αSAM6, and βSAM6 are shown in FIG. 13. In addition, specific activity of conjugates prepared using the SAM method vs. the GAM method were evaluated. There was an inverse correlation (p<0.001) between the number of M6P per GAA and the specific activity of the NeoGAA conjugates prepared at small and large scale, and 16.6-fold molar excess of oligosaccharide/GAA. Loss of GAA activity was also observed with increasing amounts of M6P content on SAM or GAM conjugates in separate experiments in which NeoGAA concentrations were titrated during conjugation (from 2.5 to 33-fold molar excess of oligosaccharide). For SAM with 49-81% GAA activity (compared to control), the various NeoGAAs contained 6-8 molecules of oligosaccharide per protein. GAM conjugates had 67-92% activity, and 4-6 oligosaccharides per protein.

B. M6P Receptor Binding

The functional effects of conjugation were evaluated by monitoring the binding of NeoGAA to the soluble cation independent mannose-6-phosphate receptor (sCIMPR) by Biacore and M6P receptor column affinity HPLC, and by uptake in L6 myoblast cells. sCIMPR, as purified from bovine serum, contains extracellular domains A-X, while lacking the transmembrane portion.

For Biacore analysis, sCIMPR was amine-coupled to a CM-5 chip, 10 µg/mL of NeoGAA sample was loaded onto the surface and eluted with increasing concentrations of mannose-6-phosphate. Affinity was quantified as the concentration of M6P needed to displace 50% of NeoGAA bound (EC50). The method was used to monitor the effects of conjugation and oxidation on receptor affinity.

Figure 14:
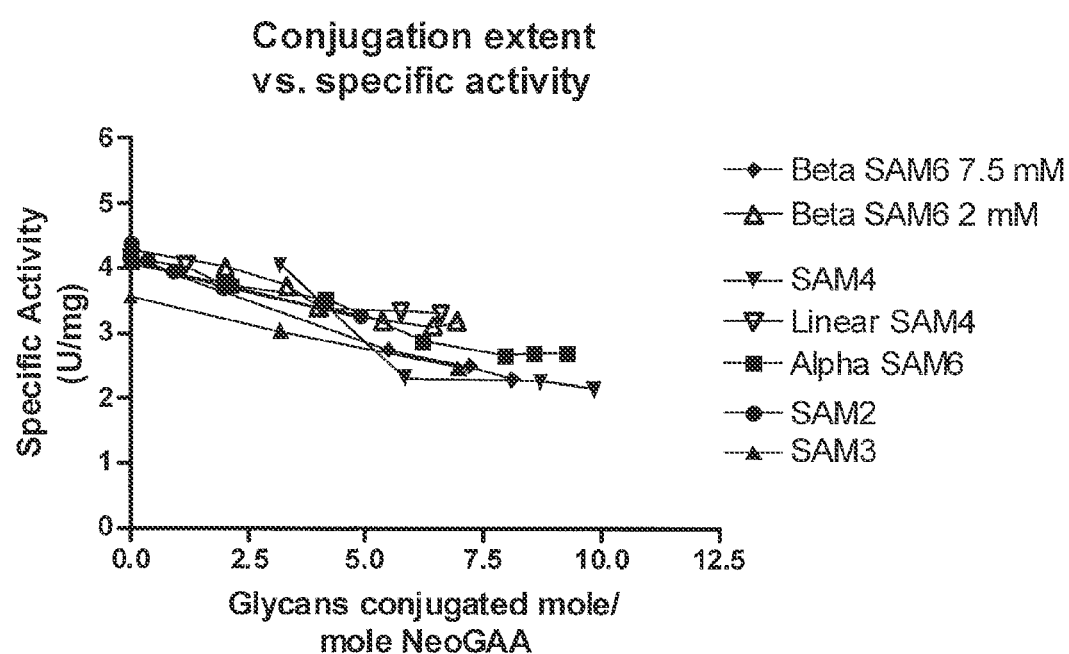
FIG. 14 shows the specific activity of various NeoGAA conjugates

FIG. 14 shows results of the Biacore analysis. Injection of 10 µg/mL NeoGAA onto a sCIMPR-immobilized Biacore chip led to a response increase of ~250 RU, while the same amount of rhGAA caused ~100 RU deflection. In addition, approximately 10-fold greater M6P concentration was required to elute NeoGAA than rhGAA (EC50 values of approximately 0.1 vs. 1.0 mM for rhGAA and NeoGAA, respectively). There was a linear relationship (r-squared>0.95) between the EC50 values and the level of conjugation for NeoGAA prepared using 2 and 7.5 mM periodate. Across the ranges of conjugation examined (1.6-4.7 moles glycan/mole NeoGAA for 2 mM periodate preparation, and 1.0-8.5 moles glycan/mole for the 7.5 mM NaIO$_4$ preparation), the effect of conjugation level on binding affinities were similar for NeoGAA prepared with 2 and 7.5 mM periodate.

Figure 15D:
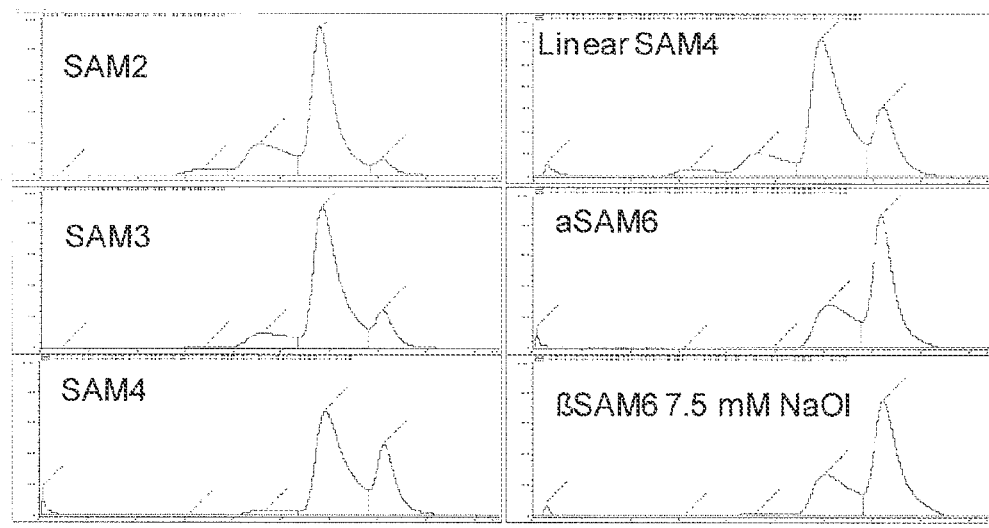

M6P receptor binding was evaluated by HPLC using a M6P receptor column prepared by immobilizing sCIMPR on a Poros EP resin, which is then packed into an analytical HPLC column. rhGAA and NeoGAA were eluted using 0.25, 0.85, 5, and 20 mM M6P (FIGS. 15 A and B). In one experiment, SAM2 and GAM2 were compared to βSAM6 and GAM6 (FIG. 15C). SAM6 and GAM6 required 20 mM M6P before the majority of the material is eluted (>95% of the conjugate bound to the column). SAM2 and GAM2 bound less tightly, with the majority eluting at 5 mM M6P (>95% bound to the column).

In addition, NeoGAA conjugates SAM2, SAM3, SAM4, Linear SAM4, and αSAM6 were evaluated for M6P receptor binding (FIG. 15 D). The majority of SAM2, SAM3, and both SAM4 conjugates eluted with 5 mM M6P, while both SAM6 conjugates required 20 mM M6P.

Figure 15E:
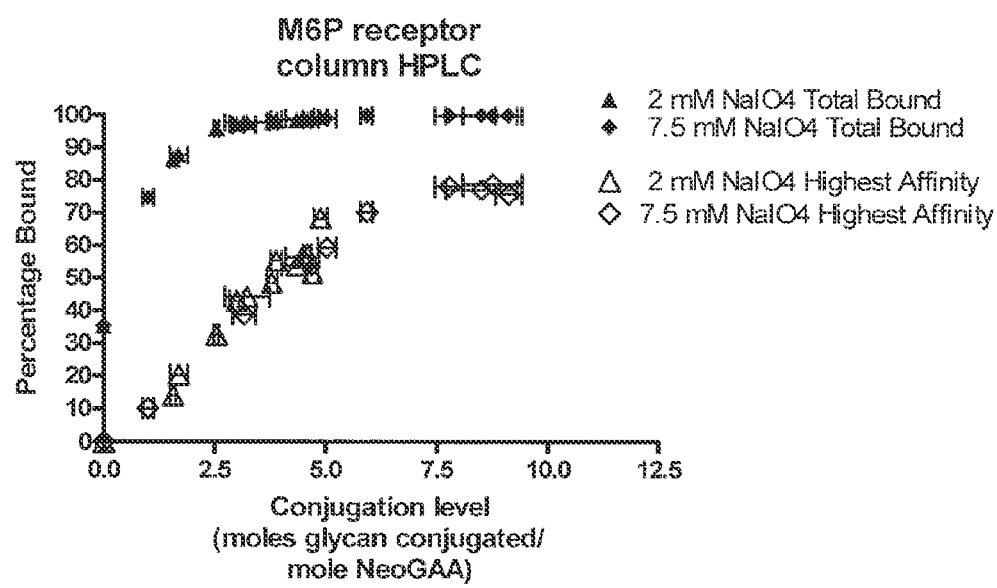

NeoGAA conjugates with varying amounts of conjugation were evaluated (FIG. 15E). The percentage of NeoGAA in the bound fraction was consistently >95% for those preparations with >2.0 moles glycan per mole NeoGAA conjugated. In the few fractions which had lower conjugation levels (1.0-1.7 moles glycan), the bound fraction was between 75-90%. M6P column profiles for NeoGAA also showed higher amounts of high-affinity species than in rhGAA. Specifically, the majority of the bound rhGAA was eluted with 0.2 mM M6P, while 20 mM M6P was required to elute NeoGAA from the column. The overall effects of conjugation level on the percentages of high affinity species was similar between the 2.0 and 7.5 mM periodate treatments.

Figure 15F:
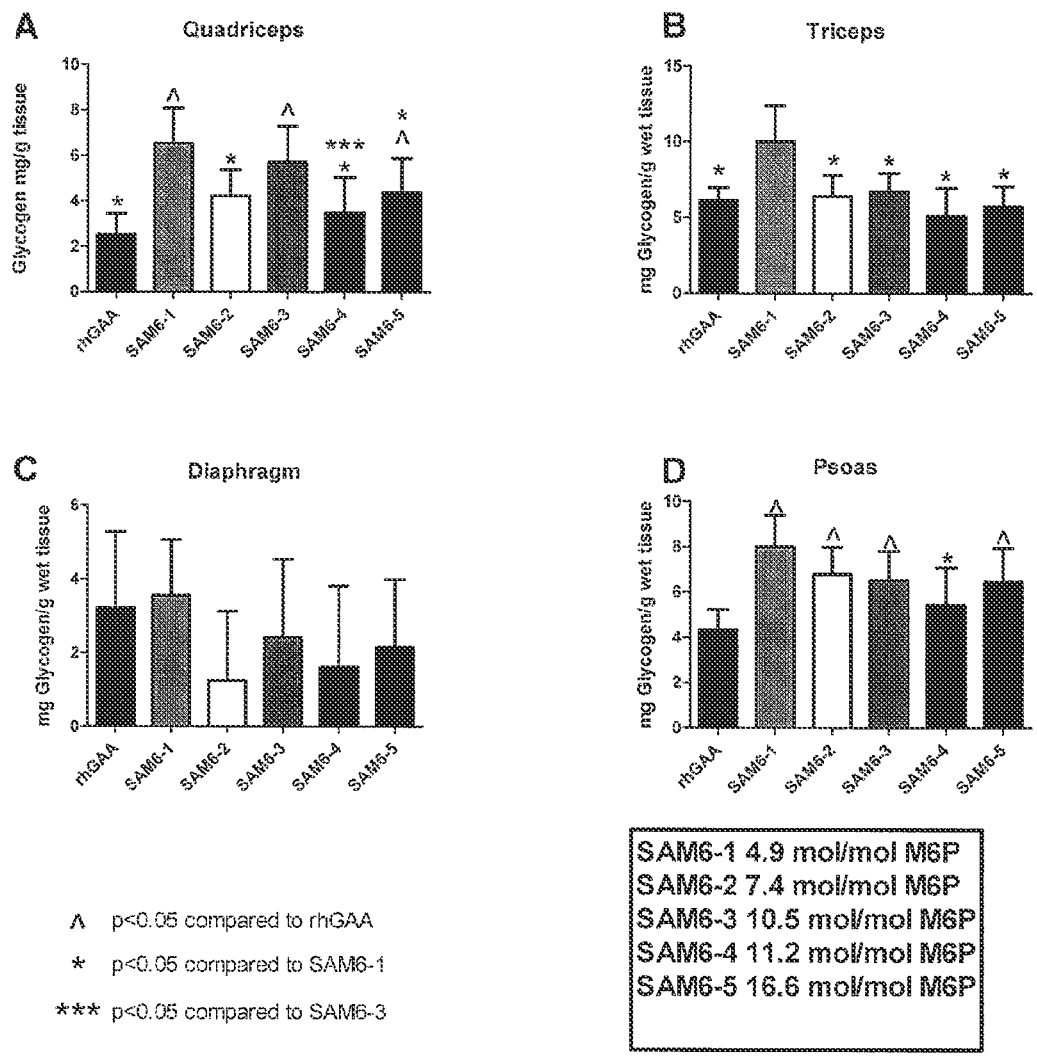

FIG. 15F shows the effects of varying amount of M6P. SAM6 conjugates contained the following amount of M6P: SAM6-1 (4.9 mol M6P/mol rhGAA), SAM6-2 (7.4 mol M6P/mol rhGAA), SAM6-3 (10.5 mol M6P/mol rhGAA), SAM6-4 (11.2 mol M6P/mol rhGAA), and SAM6-5 (16.6 mol M6P/mol rhGAA). Statistical significance is indicated by ^, * and *** and represents p<0.05 compared to 100 mg/kg rhGAA, SAM6-1 and SAM6-3 respectively.

C. Internalization by L6 Myoblasts

An L6 myoblast uptake assay was performed as described in Zhu et al., *J. Biol. Chem.* 279:50336-50341 (2004), to demonstrate targeting of rhGAA and NeoGAA to myoblasts via the cation independent mannose-6-phosphate receptor (CIMPR) pathway. In the L6 myoblast uptake assay, rhGAA and NeoGAA were added +/−5 mM M6P to media in wells containing L6 myoblasts, and incubated for a pre-determined overnight. After incubation, the cells were lysed and assayed for activity using 4-MU glucoside substrate, and for protein concentration via a micro-BCA assay, to generate an enzyme dose response curve.

Figure 16:
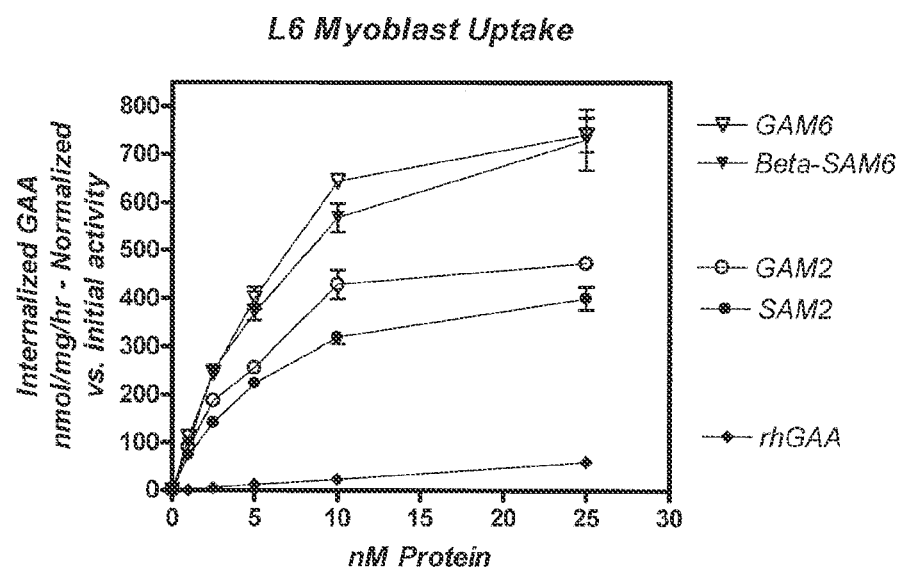
FIG. 16 shows results from a L6 myoblast uptake assay, demonstrating internalization of various NeoGAA conjugates.
Figure 16:
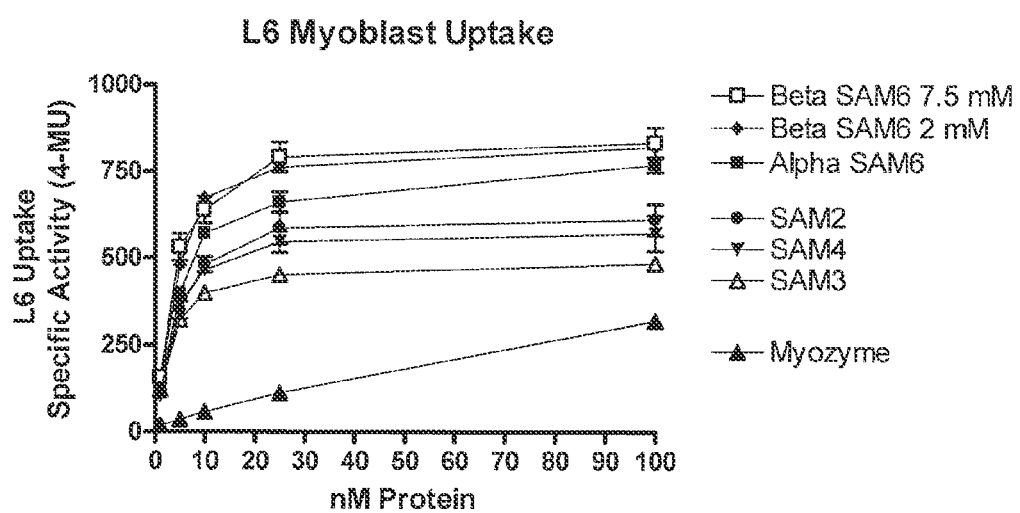

Results of the L6 myoblast uptake assay are shown in FIG. 16. SAM2 and GAM2 conjugates showed significantly higher uptake than unmodified rhGAA, but not as high as the bis-phosphorylated SAM6 or GAM6 conjugates (FIG. 16, top panel). Uptake of NeoGAAs SAM2, SAM3, SAM4, Linear SAM4, and αSAM6 were also tested (FIG. 16, bottom panel). In a similar experiment, the lysine-thiol conjugate of Example 7 produced an ~8-fold increase in uptake.

Example 9: In Vivo Effects of New GAA Conjugates

In vivo effects of certain NeoGAA conjugates were investigated in a GAA knockout mouse model described in Raben et al. *J. Biol. Chem.* 273(30):19086-92 (1998). Groups of six mice each were treated once weekly for four weeks as follows:

| Group | GAA | Dose (mg/kg) |
|---|---|---|
| 1 | Vehicle (repeated with each of SAM2, SAM4, and SAM6 experiments) | — |
| 2 | Myozyme (repeated with each of SAM2, SAM4, and SAM6 experiments) | 20 |
| 3 | Myozyme (repeated with each of SAM2, SAM4, and SAM6 experiments) | 100 |
| 4 | SAM2 | 4 |
| 5 | SAM2 | 20 |
| 6 | SAM4 | 4 |
| 7 | SAM4 | 20 |
| 8 | αSAM6 | 4 |
| 9 | αSAM6 | 20 |
| 10 | βSAM6 (7.5 mM periodate) | 4 |
| 11 | βSAM6 (7.5 mM periodate) | 20 |
| 12 | βSAM6 (2 mM periodate) | 4 |
| 13 | βSAM6 (2 mM periodate) | 20 |

Figure 17:
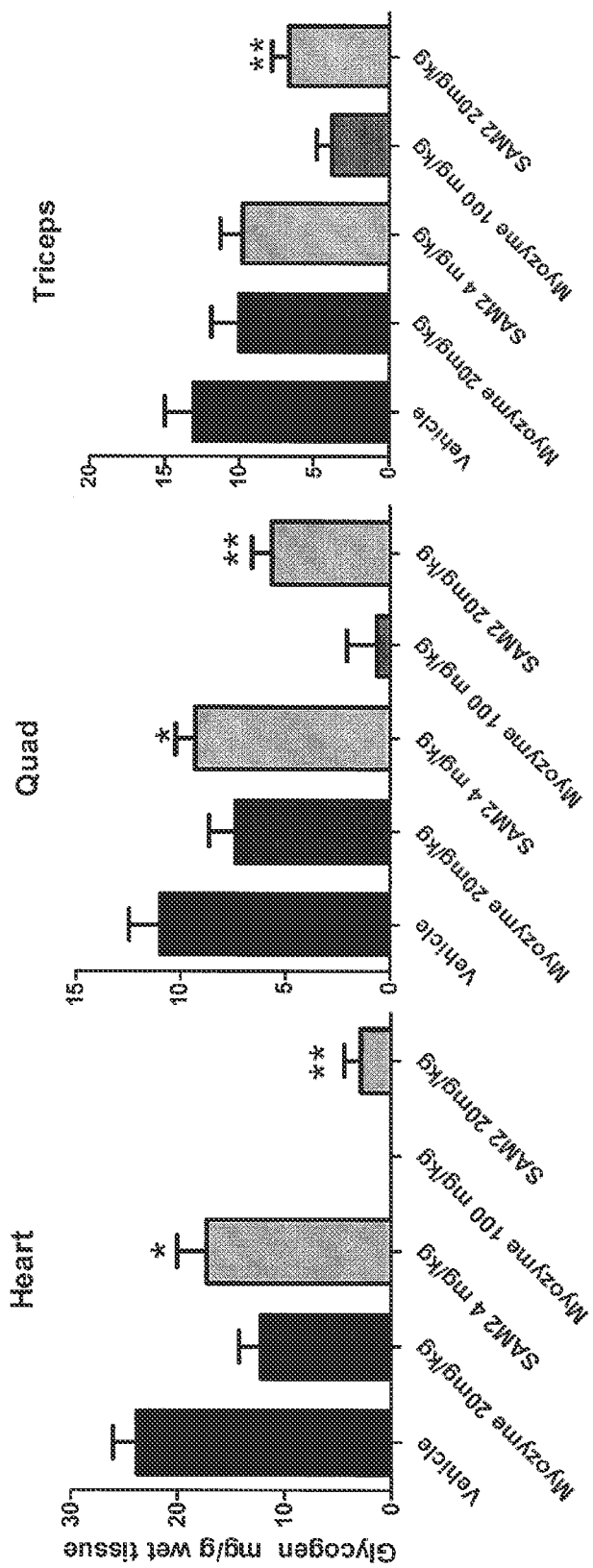
FIG. 17 shows glycogen clearance from the heart, quadriceps, and triceps of GAA knockout mice after treatment with SAM2.
Figure 18:
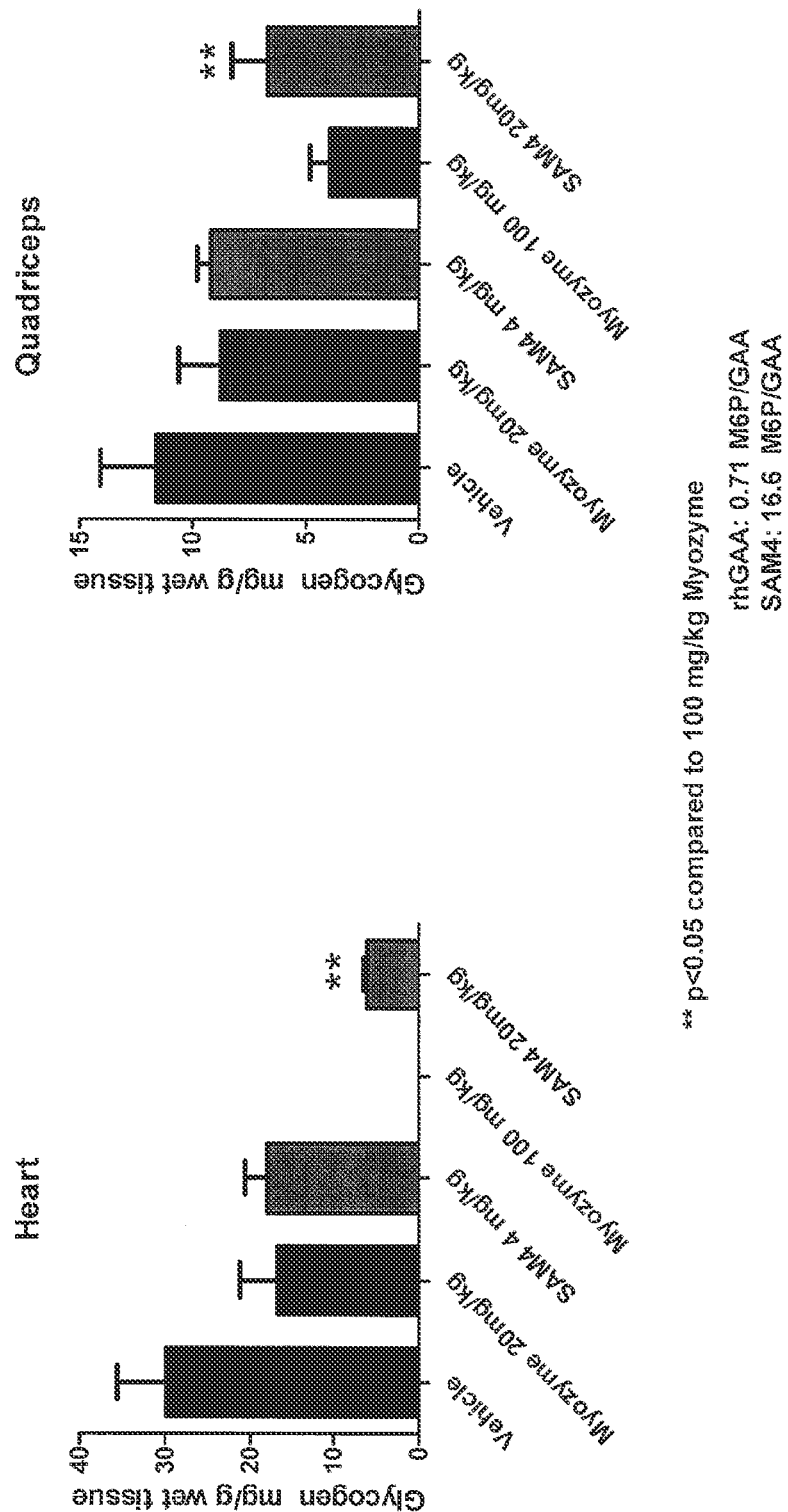
FIG. 18 snows glycogen clearance from the heart and quadriceps of GAA knockout mice after treatment with SAM4.
Figure 19:
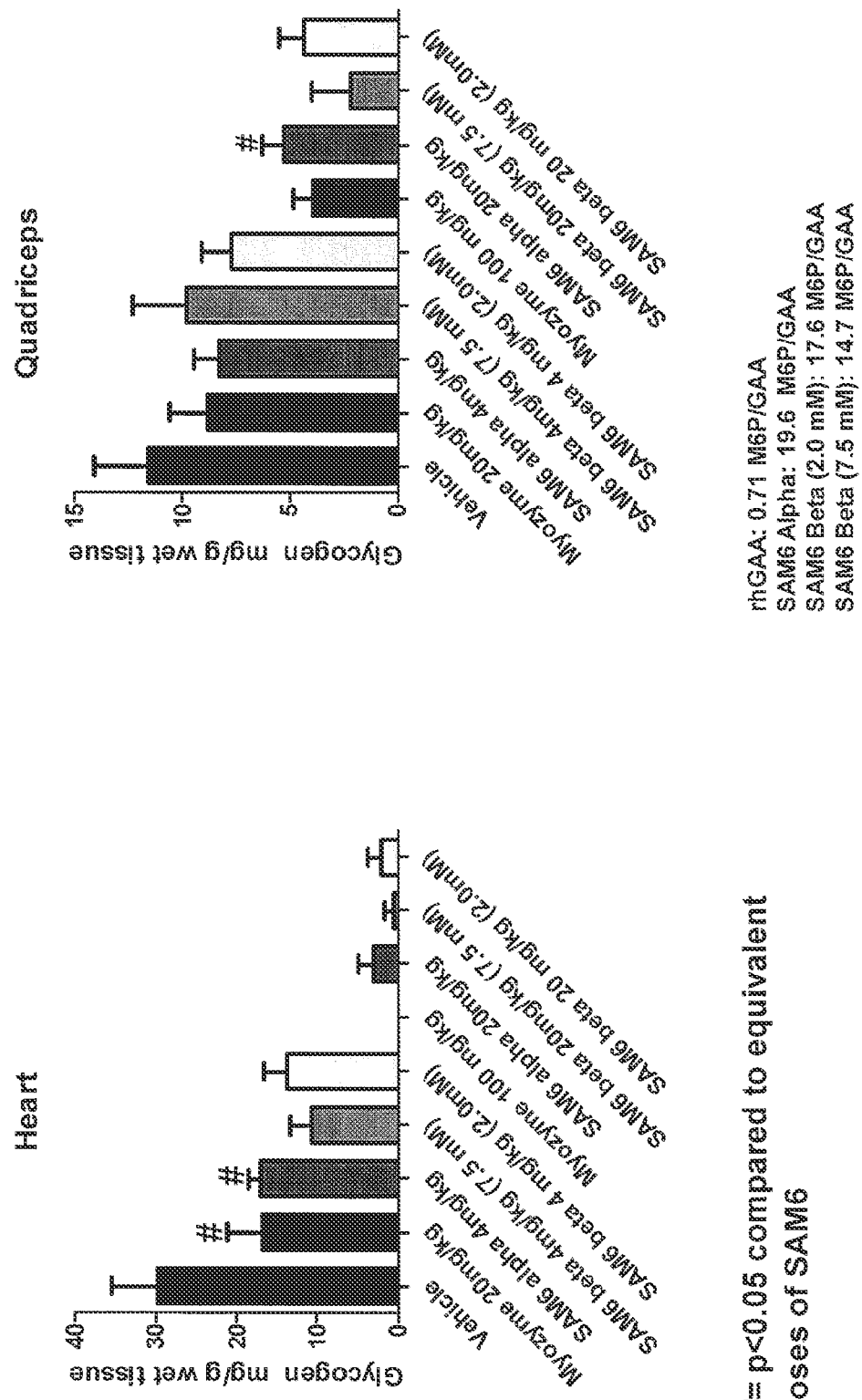
FIG. 19 shows glycogen clearance from the heart and quadriceps of GAA knockout mice after treatment with SAM).

Samples were collected from heart, quadriceps, and triceps, and measured for tissue glycogen content. Results for the SAM2, SAM4, and SAM6 animals are shown in FIGS. 17, 18, and 19, respectively. The experiment was repeated with groups of 12 animals using SAM6 conjugates, confirming that SAM6 conjugates were more than five-fold more potent than unmodified rhGAA.

Figure 20A:
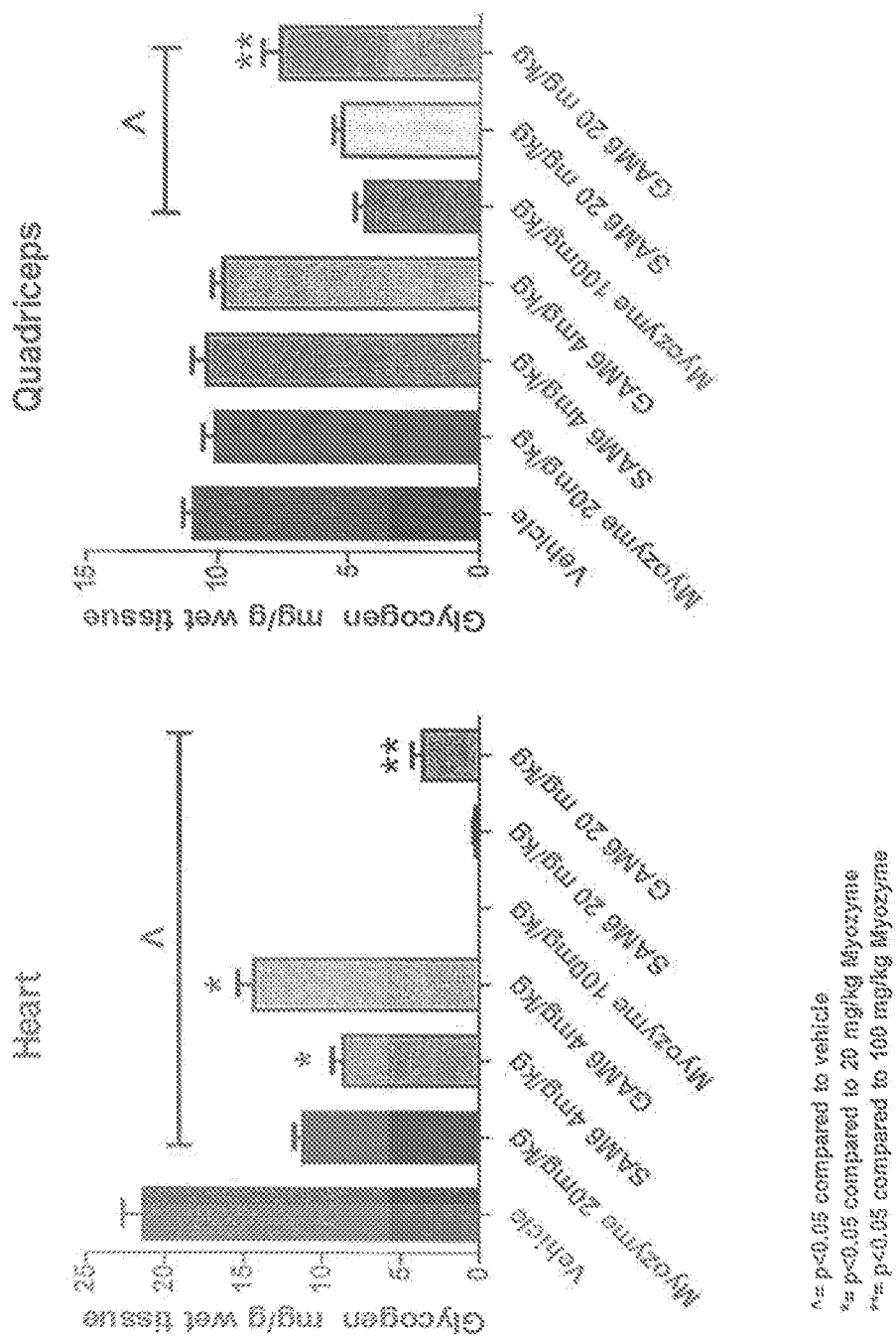
FIGS. 20A and 20B show glycogen clearance from the heart and quadriceps of GAA knockout mice after treatment with SAM6 and GAM6.
Figure 20B:
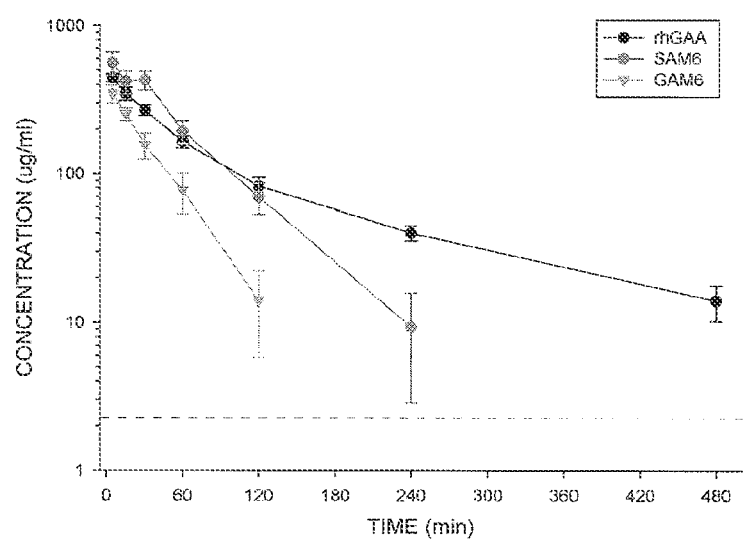

SAM and GAM hexasaccharide conjugates were also compared using groups of six mice receiving vehicle, 20, 60, or 100 mg/kg of rhGAA or 4, 12. or 20 mg/kg SAM6 or GAM6 once a week for four weeks. Heart, quadriceps, triceps diaphragm, and psoas were harvested and analyzed for glycogen content. FIG. 20 shows the results of this study. Pharmacokinetic and pharmacodynamic studies: Thirty GAA knock out mice (15 males and 15 females), 3-6 months of age, were obtained form Charles River Laboratories, Wilmington, MA Each dose group contained 5 males and 5 females. Animals were grouped housed and maintained at 25° C. humidity with a 12 hour light/dark cycle. All animals had free access to food (PicoLab® Rodent Diet 20) and water. Animals were randomly divided into 3 dose groups of 5 males and 5 females/group for a total of 10 mice per dose group. Groups received a single intravenous administration of rhGAA, GAM and SAM conjugates at 20 mg/kg. Blood samples for pharmacokinetic analysis were collected at 5, 15, 30, 60, 120, 240, and 480 minutes post dose via the retro-orbital plexus in conscious mice. rhGAA concentrations in serum were determined using the GAA activity assay. Results are shown in FIG. 20B.

Example 10: Synthesis of a Conjugate of Acid Sphingomyelinase

Recombinant human acid sphingomyelinase (rhASM) expressed in a baculovirus expression system or in Chinese hamster ovary cells has a C-terminal cysteine with a free thiol group. See Lansmann et al., *Eur. J. Biochem.* 270:1076-1088 (2003); Qiu et al, *J. Biol. Chem.* 278:32744-32752 (2003). rhASM may be coupled, through that free thiol group, with any of Oligosaccharides 1-127, wherein the oligosaccharide comprises a linker and a thiol-reactive group, according to the method described in U.S. Provisional Patent Application No. 60/885,457 or Example 6.

Example 11: Synthesis of a Conjugate of α-L-Iduronidase

α-L-Iduronidase is coupled with any of oligosaccharides 1-127, wherein the oligosaccharide comprises a linker comprising a propionaldehyde reactive group, according to the method described in Lee et al., *Pharm. Res.* 20:818-825 (2003). α-L-Iduronidase and oligosaccharide are coupled, in the presence of sodium cyanoborohydride as a reducing agent, at room temperature, pH 5.5, for 1 day. Small molecules are then removed from the reaction mixture by dialysis or diafiltration.

All references cited herein are incorporated herein by reference in their entirety. To the extent publications and patents or patent applications incorporated by reference contradict the invention contained in the specification, the specification will supersede any contradictory material.

All numbers expressing quantities of ingredients, reaction conditions, and so forth used in the specification and claims are to be understood as being modified in all instances by the term "about," wherein about signifies, e.g., ±5%. Accordingly, unless indicated to the contrary, the numerical parameters set forth in the specification and attached claims are approximations that may vary depending upon the desired properties sought to be obtained by the present invention. At the very least, without any intent to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. A pharmaceutical composition comprising an oligosaccharide-protein conjugate and an excipient comprising about 10 mM histidine pH 6.5, about 2% glycine, about 2% mannitol and about 0.01% polysorbate 80, wherein the oligosaccharide-protein conjugate comprises: (1) a protein, wherein the protein is acid a-glucosidase, and (2) an oligosaccharide of Formula A:

Formula A

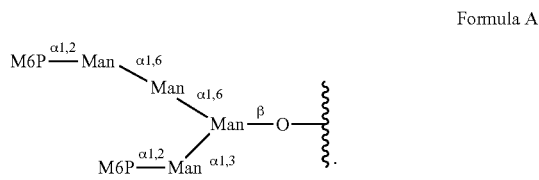

2. The pharmaceutical composition of claim 1, wherein the oligosaccharide-protein conjugate further comprises a linker between the protein and the oligosaccharide of Formula A.

3. The pharmaceutical composition of claim 2, wherein the linker comprises a reactive group for conjugation of the linker to the protein, wherein the reactive group is an aminooxy, hydrazide, or thiol group.

4. The pharmaceutical composition of claim 1, wherein the oligosaccharide-protein conjugate comprises an oligosaccharide-linker having the structure of:

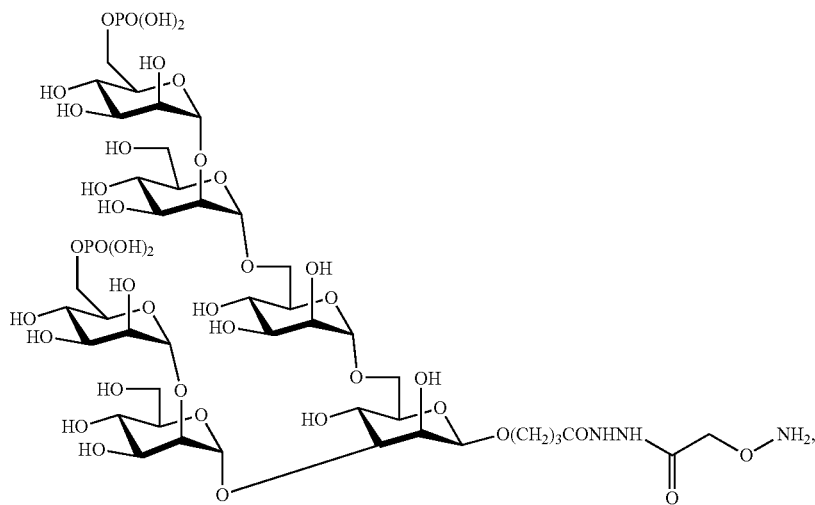

wherein the protein is conjugated to the linker through the aminooxy group of the linker.

5. The pharmaceutical composition of claim 1, wherein the pharmaceutical composition has been reconstituted from a lyophilized powder.

* * * * *